United States Patent
Crawley et al.

(10) Patent No.: US 11,760,802 B2
(45) Date of Patent: Sep. 19, 2023

(54) ILT3-BINDING AGENTS AND METHODS OF USE THEREOF

(71) Applicant: NGM Biopharmaceuticals, Inc., South San Francisco, CA (US)

(72) Inventors: Suzanne Christine Crawley, Brisbane, CA (US); Jer-Yuan Hsu, San Bruno, CA (US); Daniel David Kaplan, San Mateo, CA (US); Betty Chan Li, Millbrae, CA (US); Vicky Yi-Bing Lin, Cupertino, CA (US); Seth Malmersjö, Menlo Park, CA (US); Kevin James Paavola, San Francisco, CA (US); Julie Michelle Roda, Pacifica, CA (US); Yan Wang, Foster City, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 168 days.

(21) Appl. No.: 17/125,734

(22) Filed: Dec. 17, 2020

(65) Prior Publication Data

US 2021/0221887 A1 Jul. 22, 2021

Related U.S. Application Data

(60) Provisional application No. 62/950,434, filed on Dec. 19, 2019.

(51) Int. Cl.
| | | |
|---|---|---|
| *C07K 16/28* | (2006.01) | |
| *A61P 35/00* | (2006.01) | |
| *A61K 39/00* | (2006.01) | |

(52) U.S. Cl.
CPC .... *C07K 16/2803* (2013.01); *A61K 2039/505* (2013.01); *C07K 2317/565* (2013.01)

(58) Field of Classification Search
CPC ........ A61K 2039/505; C07K 2317/565; C07K 2317/33; C07K 16/2803; C07K 2317/76; A61P 35/00
See application file for complete search history.

(56) References Cited

U.S. PATENT DOCUMENTS

| | | | |
|---|---|---|---|
| 7,777,008 | B2 | 8/2010 | Ponath et al. |
| 7,834,157 | B2 | 11/2010 | Cosman |
| 9,696,312 | B2 | 7/2017 | Suciu-Foca et al. |
| 10,428,143 | B2 | 10/2019 | Krummel et al. |
| 2004/0241167 | A1 | 12/2004 | Suciu-Foca et al. |
| 2007/0041982 | A1 | 2/2007 | Ponath et al. |
| 2007/0166318 | A1 | 7/2007 | Macina et al. |
| 2009/0202544 | A1 | 8/2009 | Suciu-Foca et al. |
| 2009/0226457 | A1 | 9/2009 | Cosman |
| 2009/0280109 | A1 | 11/2009 | Suciu-Foca et al. |
| 2011/0034675 | A1 | 2/2011 | Ponath et al. |
| 2015/0110714 | A1 | 4/2015 | Suciu-Foca et al. |
| 2015/0139986 | A1 | 5/2015 | Ponath et al. |
| 2015/0174203 | A1 | 6/2015 | Chen et al. |
| 2016/0244525 | A1 | 8/2016 | Yin et al. |
| 2017/0291946 | A1 | 10/2017 | Krummel et al. |
| 2017/0327591 | A1 | 11/2017 | Suciu-Foca et al. |
| 2018/0086829 | A1 | 3/2018 | Zhang et al. |
| 2018/0177847 | A1 | 6/2018 | Chen et al. |
| 2018/0201676 | A1 | 7/2018 | Blaser et al. |
| 2019/0153093 | A1 | 5/2019 | Meehl et al. |
| 2019/0241655 | A1 | 8/2019 | Cua et al. |
| 2019/0255107 | A1 | 8/2019 | Kuchroo et al. |
| 2022/0324950 | A1 | 10/2022 | Takai et al. |

FOREIGN PATENT DOCUMENTS

| | | |
|---|---|---|
| EP | 2041180 | 1/2014 |
| EP | 1907001 | 7/2015 |
| EP | 2937360 | 10/2015 |
| EP | 3265113 | 1/2018 |
| JP | S63-219393 A | 9/1988 |
| JP | 2018-025554 A | 2/2018 |
| JP | 2008-514621 A | 5/2018 |
| WO | WO 2003/000199 | 1/2003 |
| WO | WO 2006/036813 A2 | 4/2006 |
| WO | WO 2014/055897 | 4/2014 |
| WO | WO 2014/116846 | 7/2014 |
| WO | WO 2014/179664 | 11/2014 |
| WO | WO 2016/144728 | 9/2016 |
| WO | WO 2017/069958 | 4/2017 |
| WO | WO 2018/067991 | 4/2018 |
| WO | WO 2018/089300 | 5/2018 |
| WO | WO 2018/148494 | 8/2018 |
| WO | WO 2018/234367 A1 | 12/2018 |
| WO | WO 2019/099597 | 5/2019 |
| WO | WO 2019/144052 | 7/2019 |

(Continued)

OTHER PUBLICATIONS

Kussie et al. A single engineered amino acid substitution changes antibody fine specificity.J Immunol. Jan. 1, 1994;152(1):146-52. (Year: 1994).*
Wu et al. Humanization of a murine monoclonal antibody by simultaneous optimization of framework and CDR residues. J Mol Biol. Nov. 19, 1999;294(1):151-62. (Year: 1999).*
Rudikoff S et al. Single amino acid substitution altering antigen-binding specificity. Proc Natl Acad Sci USA. Mar. 1982;79(6):1979-83. (Year: 1982).*
Almagro JC, Fransson J. Humanization of antibodies. Front Biosci. Jan. 1, 2008;13:1619-33. (Year: 2008).*
Chen et al. Enhancement and destruction of antibody function by somatic mutation: unequal occurrence is controlled by V gene combinatorial associations.EMBO J.Jun. 15, 1995; 14(12): 2784-94.(Year:1995) (Year: 1995) (Year: 1995).*
U.S. Appl. No. 10/428,143, filed Oct. 1, 2019, Kmmmel et al.

(Continued)

*Primary Examiner* — Aurora M Fontainhas
*Assistant Examiner* — Jennifer A Benavides
(74) *Attorney, Agent, or Firm* — Jones Day

(57) ABSTRACT

The present disclosure provides binding agents, such as antibodies, that specifically bind ILT3, including human ILT3, as well as compositions comprising the binding agents, and methods of their use. The disclosure also provides related polynucleotides and vectors encoding the binding agents and cells comprising the binding agents.

53 Claims, 28 Drawing Sheets

Specification includes a Sequence Listing.

(56) References Cited

FOREIGN PATENT DOCUMENTS

| WO | WO 2019/185792 A1 | 10/2019 |
| WO | WO 2021/029318 A1 | 2/2021 |

OTHER PUBLICATIONS

Brandish et al., "Antibodies to ILT3 (LILRB4) abrogate myeloid immunosuppression and combine with PD1 blockade to enable T cell activation and function," Journal for ImmunoTherapy of Cancer, 2019, 7(Suppl 1):283, p. 137.
Celia et al., "A novel inhibitory receptor (ILT3) expressed on monocytes, macrophages, and dendritic cells involved in antigen processing," J Exp. Med, 1997, 185(10):1743-1751.
Deng et al., "A motif in LILRB2 critical for Angpt12 binding and activation," Blood, 2014, 124(6):924-935.
Deng et al., "LILRB4 signalling in leukaemia cells mediates T cell suppression and tumour infiltration," Nature, 2018, 562(7728):605-609.
Gribskov et al., "Sigma factors from *E. coli*, *B. subtilis*, phage SP01, and phage T4 are homologous proteins," Nucl. Acids Res., 1986, 14(6):6745-6763.
Lefranc et al., "IMGT unique numbering for immunoglobulin and T cell receptor variable domains and Ig superfamily V-like domains," Dev. Comp, Immunol., 2003, 27(1):55-77.
Lu et al., "Leukocyte Ig-like receptor B4 (LILRB4) is a potent inhibitor of FcgammaRI-mediated monocyte activation via dephosphorylation of multiple kinases," J Biol Chem, 2009, 284(5):34839-34848.
NCBI Reference Sequence. XP_015297198, "leukocyte immunoglobulin-like receptor subfamily B member 4 isoform X1 [Macaca fascicularis]," Jan. 25, 2016, 2 pages.
International Search Report and Written Opinion in International Appln. No. PCT/US2020/065642, dated, Apr. 6, 2021, 26 pages.
Penna et al., "Expression of the inhibitory receptor ILT3 on dendritic cells is dispensable for induction of CD4+Foxp3+ regulatory T cells by 1,25-dihydroxyvitamin D3," Blood, Nov. 2005, 106(10):3490-7.
Resources.mdsystems.com, [online], "Human LILRB4/CD85k/ILT3 Antibody," Feb. 7, 2018, retrieved on Apr. 16, 2021, retrieved from URL<Human LILRB4/CD85k/ILT3 Antibody>, 1 page.
Stahl et al., "The tripartite CNTF receptor complex: activation and signaling involves components shared with other cytokines," J Neurobiol., 1994, 25(11):1454-1466.
UniProt Accession No. P02751, "RecName: Full=Fibronectin; Short=FN; AltName: Full=Cold-insoluble globulin; Short=CIG; Contains: RecName: Full=Anastellin; Contains: RecName: Full=Ugl-Y1; Contains: RecName: Full=Ugl-Y2; Contains: RecName: Full=Ugl-Y3; Flags: Precursor," Dec. 5, 2018, 40 pages.
UniProt Accession No. P26992, "RecName: Full=Ciliary neurotrophic factor receptor subunit alpha; Short=CNTF receptor subunit alpha; Short=CNTFR-alpha; Flags: Precursor," Dec. 5, 2018, 5 pages.
UniProt Accession No. Q8NHJ6, "RecName: Full=Leukocyte immunoglobulin-like receptor subfamily B member 4; AltName: Full=CD85 antigen-like family member K; AltName: Full=Immunoglobulin-like transcript 3; Short=ILT-3; AltName: Full=Leukocyte immunoglobulin-like receptor 5; Short=LIR-5; AltNam . . . ," Sep. 12, 2018, 7 pages.
Xu et al., "ILT3.Fc-CD166 Interaction Induces Inactivation of p70 S6 Kinase and Inhibits Tumor Cell Growth," J Immunol., 2018, 200(3):1207-1219.
Carsons, 1987, "High Levels of Fibronectin Fragments in the Plasma of a Patient with Active Systemic Lupus Erythematosus," The Journal of Rheumatology, 14(5):1052-1054.
International Searching Authority, English translation of International Search Report and Written Opinion for International Patent Application No. PCT/JP2020/030175, Publication No. WO2021029318 A1, dated Sep. 24, 2020 (13 pages).
International Searching Authority, International Search Report and Written Opinion for PCT International Application No. PCT/US2020/065642, Publication No. WO2021127200, dated Apr. 6, 2021 (21 pages).
Meng et al., 2009, "Characterisation of fibronectin-mediated FAK signalling pathways in lung cancer cell migration and invasion," British Journal of Cancer, 101(2):327-334.
Mori et al., 2007, "Analysis of differentiation regulation mechanism of human osteoclast cells by LILRB4", The Journal of Japanese Orthopaedic Surgical Society, 81(8):S980, 1-Pf-2 (in Japanese with machine English translation).
Mori et al., 2008, "Inhibitory Immunoglobulin-Like Receptors LILRB and PIR-B Negatively Regulate Osteoclast Development,:" J. Immunol., 181(7):4742-4751.
Przybysz et al., 2013, "Fibronectin molecular status determination useful to differentiate between rheumatoid arthritis and systemic lupus erythematosus patients," Rheumatol Int., 33(1):37-43 (Epub 2012).
Przybysz et al., 2007, "Synovial fibronectin fragmentation and domain expressions in relation to rheumatoid arthritis progression," Rheumatology, 46(7):1071-1075.
Sekiguchi et al., 1983, "Differences in domain structure between pericellular matrix and plasma fibronectins as revealed by domain-specific antibodies combined with limited proteolysis and S-cyanylation: A preliminary note.," Biochemical and Biophysical Research Communications, 116(2):534-540.
Xu et al., 2018, "ILT3.Fc-CD166 Interaction Induces Inactivation of p70 S6 Kinase and Inhibits Tumor Cell Growth," The Journal of Immunology, 200(3):1207-1219 and Supplemental Material (15 pages).
Gui et al., 2019, "Disrupting LILRB4/APOE interaction by an efficacious humanized 3 antibody reverses T-cell suppression and blocks AML development", Cancer Immunol Res 1(8):1244-1257.
Paavola et al., 2021, "The Fibronectin-ILT3 Interaction Functions as a Stromal Checkpoint that Suppresses Myeloid Cells", Cancer Immunology Research 9:1283-1297.
Wong et al., 2019, "Gp49B is a pathogenic marker for autoantibody-producing plasma cells in lupus-prone BXSB/Yaa mice", International Immunology 31(6):397-406.

* cited by examiner

SEQUENCE LISTING

<160> NUMBER OF SEQ ID NOS: 164

<210> SEQ ID NO 1
<211> LENGTH: 448
<212> TYPE: PRT
<213> ORGANISM: Homo sapiens

<400> SEQUENCE: 1

```
Met Ile Pro Thr Phe Thr Ala Leu Leu Cys Leu Gly Leu Ser Leu Gly
1               5                   10                  15

Pro Arg Thr His Met Gln Ala Gly Pro Leu Pro Lys Pro Thr Leu Trp
            20                  25                  30

Ala Glu Pro Gly Ser Val Ile Ser Trp Gly Asn Ser Val Thr Ile Trp
        35                  40                  45

Cys Gln Gly Thr Leu Glu Ala Arg Glu Tyr Arg Leu Asp Lys Glu Glu
    50                  55                  60

Ser Pro Ala Pro Trp Asp Arg Gln Asn Pro Leu Glu Pro Lys Asn Lys
65                  70                  75                  80

Ala Arg Phe Ser Ile Pro Ser Met Thr Glu Asp Tyr Ala Gly Arg Tyr
                85                  90                  95

Arg Cys Tyr Tyr Arg Ser Pro Val Gly Trp Ser Gln Pro Ser Asp Pro
            100                 105                 110

Leu Glu Leu Val Met Thr Gly Ala Tyr Ser Lys Pro Thr Leu Ser Ala
        115                 120                 125

Leu Pro Ser Pro Leu Val Thr Ser Gly Lys Ser Val Thr Leu Leu Cys
    130                 135                 140

Gln Ser Arg Ser Pro Met Asp Thr Phe Leu Leu Ile Lys Glu Arg Ala
145                 150                 155                 160

Ala His Pro Leu Leu His Leu Arg Ser Glu His Gly Ala Gln Gln His
                165                 170                 175

Gln Ala Glu Phe Pro Met Ser Pro Val Thr Ser Val His Gly Gly Thr
            180                 185                 190

Tyr Arg Cys Phe Ser Ser His Gly Phe Ser His Tyr Leu Leu Ser His
        195                 200                 205

Pro Ser Asp Pro Leu Glu Leu Ile Val Ser Gly Ser Leu Glu Asp Pro
    210                 215                 220

Arg Pro Ser Pro Thr Arg Ser Val Ser Thr Ala Ala Gly Pro Glu Asp
225                 230                 235                 240

Gln Pro Leu Met Pro Thr Gly Ser Val Pro His Ser Gly Leu Arg Arg
                245                 250                 255

His Trp Glu Val Leu Ile Gly Val Leu Val Val Ser Ile Leu Leu Leu
            260                 265                 270

Ser Leu Leu Leu Phe Leu Leu Leu Gln His Trp Arg Gln Gly Lys His
        275                 280                 285

Arg Thr Leu Ala Gln Arg Gln Ala Asp Phe Gln Arg Pro Pro Gly Ala
    290                 295                 300

Ala Glu Pro Glu Pro Lys Asp Gly Gly Leu Gln Arg Arg Ser Ser Pro
```

```
305                 310                 315                 320
Ala Ala Asp Val Gln Gly Glu Asn Phe Cys Ala Ala Val Lys Asn Thr
                325                 330                 335

Gln Pro Glu Asp Gly Val Glu Met Asp Thr Arg Gln Ser Pro His Asp
                340                 345                 350

Glu Asp Pro Gln Ala Val Thr Tyr Ala Lys Val Lys His Ser Arg Pro
                355                 360                 365

Arg Arg Glu Met Ala Ser Pro Ser Pro Leu Ser Gly Glu Phe Leu
370                 375                 380

Asp Thr Lys Asp Arg Gln Ala Glu Glu Asp Arg Gln Met Asp Thr Glu
385                 390                 395                 400

Ala Ala Ala Ser Glu Ala Pro Gln Asp Val Thr Tyr Ala Gln Leu His
                405                 410                 415

Ser Phe Thr Leu Arg Gln Lys Ala Thr Glu Pro Pro Ser Gln Glu
                420                 425                 430

Gly Ala Ser Pro Ala Glu Pro Ser Val Tyr Ala Thr Leu Ala Ile His
                435                 440                 445

<210> SEQ ID NO 2
<211> LENGTH: 427
<212> TYPE: PRT
<213> ORGANISM: Homo sapiens

<400> SEQUENCE: 2

Gln Ala Gly Pro Leu Pro Lys Pro Thr Leu Trp Ala Glu Pro Gly Ser
1               5                   10                  15

Val Ile Ser Trp Gly Asn Ser Val Thr Ile Trp Cys Gln Gly Thr Leu
                20                  25                  30

Glu Ala Arg Glu Tyr Arg Leu Asp Lys Glu Glu Ser Pro Ala Pro Trp
                35                  40                  45

Asp Arg Gln Asn Pro Leu Glu Pro Lys Asn Lys Ala Arg Phe Ser Ile
                50                  55                  60

Pro Ser Met Thr Glu Asp Tyr Ala Gly Arg Tyr Arg Cys Tyr Tyr Arg
65                  70                  75                  80

Ser Pro Val Gly Trp Ser Gln Pro Ser Asp Pro Leu Glu Leu Val Met
                85                  90                  95

Thr Gly Ala Tyr Ser Lys Pro Thr Leu Ser Ala Leu Pro Ser Pro Leu
                100                 105                 110

Val Thr Ser Gly Lys Ser Val Thr Leu Leu Cys Gln Ser Arg Ser Pro
                115                 120                 125

Met Asp Thr Phe Leu Leu Ile Lys Glu Arg Ala Ala His Pro Leu Leu
                130                 135                 140

His Leu Arg Ser Glu His Gly Ala Gln Gln His Gln Ala Glu Phe Pro
145                 150                 155                 160

Met Ser Pro Val Thr Ser Val His Gly Gly Thr Tyr Arg Cys Phe Ser
                165                 170                 175

Ser His Gly Phe Ser His Tyr Leu Leu Ser His Pro Ser Asp Pro Leu
                180                 185                 190

Glu Leu Ile Val Ser Gly Ser Leu Glu Asp Pro Arg Pro Ser Pro Thr
                195                 200                 205

Arg Ser Val Ser Thr Ala Ala Gly Pro Glu Asp Gln Pro Leu Met Pro
                210                 215                 220

Thr Gly Ser Val Pro His Ser Gly Leu Arg Arg His Trp Glu Val Leu
225                 230                 235                 240
```

```
Ile Gly Val Leu Val Ser Ile Leu Leu Ser Leu Leu Phe
            245                 250             255

Leu Leu Leu Gln His Trp Arg Gln Gly Lys His Arg Thr Leu Ala Gln
        260                 265                 270

Arg Gln Ala Asp Phe Gln Arg Pro Gly Ala Ala Glu Pro Glu Pro
            275                 280             285

Lys Asp Gly Gly Leu Gln Arg Arg Ser Ser Pro Ala Ala Asp Val Gln
290                 295                 300

Gly Glu Asn Phe Cys Ala Ala Val Lys Asn Thr Gln Pro Glu Asp Gly
305                 310                 315                 320

Val Glu Met Asp Thr Arg Gln Ser Pro His Asp Glu Asp Pro Gln Ala
            325                 330                 335

Val Thr Tyr Ala Lys Val Lys His Ser Arg Pro Arg Arg Glu Met Ala
            340                 345                 350

Ser Pro Pro Ser Pro Leu Ser Gly Glu Phe Leu Asp Thr Lys Asp Arg
            355                 360                 365

Gln Ala Glu Glu Asp Arg Gln Met Asp Thr Glu Ala Ala Ala Ser Glu
        370                 375                 380

Ala Pro Gln Asp Val Thr Tyr Ala Gln Leu His Ser Phe Thr Leu Arg
385                 390                 395                 400

Gln Lys Ala Thr Glu Pro Pro Pro Ser Gln Glu Gly Ala Ser Pro Ala
            405                 410                 415

Glu Pro Ser Val Tyr Ala Thr Leu Ala Ile His
            420                 425

<210> SEQ ID NO 3
<211> LENGTH: 238
<212> TYPE: PRT
<213> ORGANISM: Homo sapiens

<400> SEQUENCE: 3

Gln Ala Gly Pro Leu Pro Lys Pro Thr Leu Trp Ala Glu Pro Gly Ser
1               5                   10                  15

Val Ile Ser Trp Gly Asn Ser Val Thr Ile Trp Cys Gln Gly Thr Leu
            20                  25                  30

Glu Ala Arg Glu Tyr Arg Leu Asp Lys Glu Glu Ser Pro Ala Pro Trp
        35                  40                  45

Asp Arg Gln Asn Pro Leu Glu Pro Lys Asn Lys Ala Arg Phe Ser Ile
    50                  55                  60

Pro Ser Met Thr Glu Asp Tyr Ala Gly Arg Tyr Arg Cys Tyr Tyr Arg
65                  70                  75                  80

Ser Pro Val Gly Trp Ser Gln Pro Ser Asp Pro Leu Glu Leu Val Met
                85                  90                  95

Thr Gly Ala Tyr Ser Lys Pro Thr Leu Ser Ala Leu Pro Ser Pro Leu
            100                 105                 110

Val Thr Ser Gly Lys Ser Val Thr Leu Leu Cys Gln Ser Arg Ser Pro
        115                 120                 125

Met Asp Thr Phe Leu Leu Ile Lys Glu Arg Ala Ala His Pro Leu Leu
    130                 135                 140

His Leu Arg Ser Glu His Gly Ala Gln Gln His Gln Ala Glu Phe Pro
145                 150                 155                 160

Met Ser Pro Val Thr Ser Val His Gly Gly Thr Tyr Arg Cys Phe Ser
                165                 170                 175

Ser His Gly Phe Ser His Tyr Leu Leu Ser His Pro Ser Asp Pro Leu
            180                 185                 190
```

```
Glu Leu Ile Val Ser Gly Ser Leu Glu Asp Pro Arg Pro Ser Pro Thr
        195                 200                 205

Arg Ser Val Ser Thr Ala Ala Gly Pro Glu Asp Gln Pro Leu Met Pro
    210                 215                 220

Thr Gly Ser Val Pro His Ser Gly Leu Arg Arg His Trp Glu
225                 230                 235

<210> SEQ ID NO 4
<211> LENGTH: 92
<212> TYPE: PRT
<213> ORGANISM: Homo sapiens

<400> SEQUENCE: 4

Pro Lys Pro Thr Leu Trp Ala Glu Pro Gly Ser Val Ile Ser Trp Gly
1               5                   10                  15

Asn Ser Val Thr Ile Trp Cys Gln Gly Thr Leu Glu Ala Arg Glu Tyr
            20                  25                  30

Arg Leu Asp Lys Glu Glu Ser Pro Ala Pro Trp Asp Arg Gln Asn Pro
        35                  40                  45

Leu Glu Pro Lys Asn Lys Ala Arg Phe Ser Ile Pro Ser Met Thr Glu
50                  55                  60

Asp Tyr Ala Gly Arg Tyr Arg Cys Tyr Tyr Arg Ser Pro Val Gly Trp
65                  70                  75                  80

Ser Gln Pro Ser Asp Pro Leu Glu Leu Val Met Thr
                85                  90

<210> SEQ ID NO 5
<211> LENGTH: 95
<212> TYPE: PRT
<213> ORGANISM: Homo sapiens

<400> SEQUENCE: 5

Pro Thr Leu Ser Ala Leu Pro Ser Pro Leu Val Thr Ser Gly Lys Ser
1               5                   10                  15

Val Thr Leu Leu Cys Gln Ser Arg Ser Pro Met Asp Thr Phe Leu Leu
            20                  25                  30

Ile Lys Glu Arg Ala Ala His Pro Leu Leu His Leu Arg Ser Glu His
        35                  40                  45

Gly Ala Gln Gln His Gln Ala Glu Phe Pro Met Ser Pro Val Thr Ser
50                  55                  60

Val His Gly Gly Thr Tyr Arg Cys Phe Ser Ser His Gly Phe Ser His
65                  70                  75                  80

Tyr Leu Leu Ser His Pro Ser Asp Pro Leu Glu Leu Ile Val Ser
                85                  90                  95

<210> SEQ ID NO 6
<211> LENGTH: 448
<212> TYPE: PRT
<213> ORGANISM: Macaca fascicularis

<400> SEQUENCE: 6

Met Thr Pro Pro Leu Thr Val Leu Phe Cys Leu Gly Leu Ser Leu Gly
1               5                   10                  15

Pro Arg Thr Cys Val Gln Ala Gly Pro Leu Pro Lys Pro Thr Val Trp
            20                  25                  30

Ala Glu Pro Gly Ser Val Ile Ser Trp Gly Ser Pro Val Thr Ile Trp
        35                  40                  45
```

Cys Gln Gly Thr Leu Asp Ala Gln Glu Tyr His Leu Asp Lys Glu Gly
 50                  55                  60

Ser Pro Ala Pro Trp Asp Thr Gln Asn Pro Leu Glu Pro Arg Asn Lys
 65                  70                  75                  80

Ala Lys Phe Ser Ile Pro Ser Met Thr Gln His Tyr Ala Gly Arg Tyr
                 85                  90                  95

Arg Cys Tyr Tyr His Ser His Pro Asp Trp Ser Glu Asp Ser Asp Pro
                100                 105                 110

Leu Asp Leu Val Met Thr Gly Ala Tyr Ser Lys Pro Ile Leu Ser Val
            115                 120                 125

Leu Pro Ser Pro Leu Val Thr Ser Gly Glu Ser Val Thr Leu Leu Cys
130                 135                 140

Gln Ser Gln Ser Pro Met Asp Thr Phe Leu Leu Phe Lys Glu Gly Ala
145                 150                 155                 160

Ala His Pro Leu Pro Arg Leu Arg Ser Gln His Gly Ala Gln Leu His
                165                 170                 175

Trp Ala Glu Phe Pro Met Gly Pro Val Thr Ser Val His Gly Gly Thr
                180                 185                 190

Tyr Arg Cys Ile Ser Ser Arg Ser Phe Ser His Tyr Leu Leu Ser Arg
            195                 200                 205

Pro Ser Asp Pro Val Glu Leu Thr Val Leu Gly Ser Leu Glu Ser Pro
210                 215                 220

Ser Pro Ser Pro Thr Arg Ser Ile Ser Ala Ala Gly Pro Glu Asp
225                 230                 235                 240

Gln Ser Leu Met Pro Thr Gly Ser Asp Pro Gln Ser Gly Leu Arg Arg
                245                 250                 255

His Trp Glu Val Leu Ile Gly Val Leu Val Val Ser Ile Leu Leu Leu
            260                 265                 270

Ser Leu Val Phe Phe Leu Leu Leu Gln His Trp Arg Gln Gly Lys His
275                 280                 285

Arg Thr Ser Ala Gln Arg Gln Ala Asp Phe Gln Arg Pro Pro Gly Ala
            290                 295                 300

Ala Glu Pro Glu Pro Lys Asp Gly Gly Leu Gln Arg Arg Ser Arg Pro
305                 310                 315                 320

Ala Ala Asp Val Gln Gly Glu Asn Pro Asn Ala Ala Met Lys Asp Thr
                325                 330                 335

Gln Pro Glu Asp Gly Val Glu Leu Asp Ser Arg Gln Arg Pro His Asp
                340                 345                 350

Glu Asp Pro Gln Ala Val Thr Tyr Ala Arg Val Lys His Ser Gly Pro
            355                 360                 365

Arg Arg Glu Met Ala Ser Pro Pro Ser Pro Leu Ser Glu Glu Phe Leu
370                 375                 380

Asp Thr Lys Asp Thr Gln Ala Glu Glu Asp Arg Gln Met Asp Thr Gln
385                 390                 395                 400

Ala Ala Thr Ser Glu Ala Pro Gln Asp Val Thr Tyr Ala Gln Leu Gln
                405                 410                 415

Ser Leu Thr Leu Arg Arg Glu Ala Thr Glu Pro Pro Pro Gln Lys
            420                 425                 430

Arg Glu Pro Ser Ala Glu Pro Ser Val Tyr Ala Thr Leu Ala Ile His
            435                 440                 445

<210> SEQ ID NO 7
<211> LENGTH: 427
<212> TYPE: PRT

<213> ORGANISM: Macaca fascicularis

<400> SEQUENCE: 7

```
Gln Ala Gly Pro Leu Pro Lys Pro Thr Val Trp Ala Glu Pro Gly Ser
1               5                   10                  15

Val Ile Ser Trp Gly Ser Pro Val Thr Ile Trp Cys Gln Gly Thr Leu
            20                  25                  30

Asp Ala Gln Glu Tyr His Leu Asp Lys Glu Gly Ser Pro Ala Pro Trp
        35                  40                  45

Asp Thr Gln Asn Pro Leu Glu Pro Arg Asn Lys Ala Lys Phe Ser Ile
    50                  55                  60

Pro Ser Met Thr Gln His Tyr Ala Gly Arg Tyr Arg Cys Tyr Tyr His
65                  70                  75                  80

Ser His Pro Asp Trp Ser Glu Asp Ser Asp Pro Leu Asp Leu Val Met
                85                  90                  95

Thr Gly Ala Tyr Ser Lys Pro Ile Leu Ser Val Leu Pro Ser Pro Leu
            100                 105                 110

Val Thr Ser Gly Glu Ser Val Thr Leu Leu Cys Gln Ser Gln Ser Pro
        115                 120                 125

Met Asp Thr Phe Leu Leu Phe Lys Glu Gly Ala Ala His Pro Leu Pro
    130                 135                 140

Arg Leu Arg Ser Gln His Gly Ala Gln Leu His Trp Ala Glu Phe Pro
145                 150                 155                 160

Met Gly Pro Val Thr Ser Val His Gly Gly Thr Tyr Arg Cys Ile Ser
                165                 170                 175

Ser Arg Ser Phe Ser His Tyr Leu Leu Ser Arg Pro Ser Asp Pro Val
            180                 185                 190

Glu Leu Thr Val Leu Gly Ser Leu Glu Ser Pro Ser Pro Ser Pro Thr
        195                 200                 205

Arg Ser Ile Ser Ala Ala Gly Pro Glu Asp Gln Ser Leu Met Pro
    210                 215                 220

Thr Gly Ser Asp Pro Gln Ser Gly Leu Arg Arg His Trp Glu Val Leu
225                 230                 235                 240

Ile Gly Val Leu Val Ser Ile Leu Leu Ser Leu Val Phe Phe
                245                 250                 255

Leu Leu Leu Gln His Trp Arg Gln Gly Lys His Arg Thr Ser Ala Gln
            260                 265                 270

Arg Gln Ala Asp Phe Gln Arg Pro Gly Ala Ala Glu Pro Glu Pro
    275                 280                 285

Lys Asp Gly Gly Leu Gln Arg Arg Ser Arg Pro Ala Ala Asp Val Gln
290                 295                 300

Gly Glu Asn Pro Asn Ala Ala Met Lys Asp Thr Gln Pro Glu Asp Gly
305                 310                 315                 320

Val Glu Leu Asp Ser Arg Gln Arg Pro His Asp Glu Asp Pro Gln Ala
                325                 330                 335

Val Thr Tyr Ala Arg Val Lys His Ser Gly Pro Arg Arg Glu Met Ala
            340                 345                 350

Ser Pro Pro Ser Pro Leu Ser Glu Glu Phe Leu Asp Thr Lys Asp Thr
        355                 360                 365

Gln Ala Glu Glu Asp Arg Gln Met Asp Thr Gln Ala Ala Thr Ser Glu
    370                 375                 380

Ala Pro Gln Asp Val Thr Tyr Ala Gln Leu Gln Ser Leu Thr Leu Arg
385                 390                 395                 400
```

```
Arg Glu Ala Thr Glu Pro Pro Pro Gln Lys Arg Glu Pro Ser Ala
            405                 410                 415

Glu Pro Ser Val Tyr Ala Thr Leu Ala Ile His
            420                 425

<210> SEQ ID NO 8
<211> LENGTH: 238
<212> TYPE: PRT
<213> ORGANISM: Macaca fascicularis

<400> SEQUENCE: 8

Gln Ala Gly Pro Leu Pro Lys Pro Thr Val Trp Ala Glu Pro Gly Ser
1               5                   10                  15

Val Ile Ser Trp Gly Ser Pro Val Thr Ile Trp Cys Gln Gly Thr Leu
            20                  25                  30

Asp Ala Gln Glu Tyr His Leu Asp Lys Glu Gly Ser Pro Ala Pro Trp
        35                  40                  45

Asp Thr Gln Asn Pro Leu Glu Pro Arg Asn Lys Ala Lys Phe Ser Ile
    50                  55                  60

Pro Ser Met Thr Gln His Tyr Ala Gly Arg Tyr Arg Cys Tyr Tyr His
65                  70                  75                  80

Ser His Pro Asp Trp Ser Glu Asp Ser Asp Pro Leu Asp Leu Val Met
                85                  90                  95

Thr Gly Ala Tyr Ser Lys Pro Ile Leu Ser Val Leu Pro Ser Pro Leu
            100                 105                 110

Val Thr Ser Gly Glu Ser Val Thr Leu Leu Cys Gln Ser Gln Ser Pro
        115                 120                 125

Met Asp Thr Phe Leu Leu Phe Lys Glu Gly Ala Ala His Pro Leu Pro
    130                 135                 140

Arg Leu Arg Ser Gln His Gly Ala Gln Leu His Trp Ala Glu Phe Pro
145                 150                 155                 160

Met Gly Pro Val Thr Ser Val His Gly Gly Thr Tyr Arg Cys Ile Ser
                165                 170                 175

Ser Arg Ser Phe Ser His Tyr Leu Leu Ser Arg Pro Ser Asp Pro Val
            180                 185                 190

Glu Leu Thr Val Leu Gly Ser Leu Glu Ser Pro Ser Pro Ser Pro Thr
        195                 200                 205

Arg Ser Ile Ser Ala Ala Gly Pro Glu Asp Gln Ser Leu Met Pro
    210                 215                 220

Thr Gly Ser Asp Pro Gln Ser Gly Leu Arg Arg His Trp Glu
225                 230                 235

<210> SEQ ID NO 9
<211> LENGTH: 92
<212> TYPE: PRT
<213> ORGANISM: Macaca fascicularis

<400> SEQUENCE: 9

Pro Lys Pro Thr Val Trp Ala Glu Pro Gly Ser Val Ile Ser Trp Gly
1               5                   10                  15

Ser Pro Val Thr Ile Trp Cys Gln Gly Thr Leu Asp Ala Gln Glu Tyr
            20                  25                  30

His Leu Asp Lys Glu Gly Ser Pro Ala Pro Trp Asp Thr Gln Asn Pro
        35                  40                  45

Leu Glu Pro Arg Asn Lys Ala Lys Phe Ser Ile Pro Ser Met Thr Gln
    50                  55                  60
```

His Tyr Ala Gly Arg Tyr Arg Cys Tyr Tyr His Ser His Pro Asp Trp
65                  70                  75                  80

Ser Glu Asp Ser Asp Pro Leu Asp Leu Val Met Thr
                85                  90

<210> SEQ ID NO 10
<211> LENGTH: 95
<212> TYPE: PRT
<213> ORGANISM: Macaca fascicularis

<400> SEQUENCE: 10

Pro Ile Leu Ser Val Leu Pro Ser Pro Leu Thr Ser Gly Glu Ser
1               5                   10                  15

Val Thr Leu Leu Cys Gln Ser Gln Ser Pro Met Asp Thr Phe Leu Leu
                20                  25                  30

Phe Lys Glu Gly Ala Ala His Pro Leu Pro Arg Leu Arg Ser Gln His
                35                  40                  45

Gly Ala Gln Leu His Trp Ala Glu Phe Pro Met Gly Pro Val Thr Ser
            50                  55                  60

Val His Gly Gly Thr Tyr Arg Cys Ile Ser Ser Arg Ser Phe Ser His
65                  70                  75                  80

Tyr Leu Leu Ser Arg Pro Ser Asp Pro Val Glu Leu Thr Val Leu
                85                  90                  95

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Phe Ser Leu Thr Ser Tyr Gly Val His
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Ile Trp Pro Gly Gly Thr Ile Asn Tyr Asn Ser Ala Leu Met Ser
1               5                   10                  15

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Lys Tyr Asp Gly Gly Trp Phe Ala Tyr
1               5                   10

<210> SEQ ID NO 14
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 14

Lys Ala Ser Gln Asn Val Arg Thr Ala Val Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Ala Ser Asn Arg His Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Gln His Leu Asn Tyr Pro Leu Thr
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Phe Ser Leu Thr Ser Tyr
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Pro Gly Gly Thr
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Ile Trp Pro Gly Gly Thr Ile Asn
1               5
```

```
<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Tyr Gly Val His
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Ser Tyr Gly Val His
1               5

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Leu Gly Val Ile Trp Pro Gly Gly Thr Ile Asn
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ser Asp Lys Tyr Asp Gly Gly Trp Phe Ala
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Thr Ala Val Ala Trp Tyr
1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 25

Ala Leu Ile Tyr Leu Ala Ser Asn Arg His
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Gln His Leu Asn Tyr Pro Leu
1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Phe Thr Phe Ser Ser Tyr Gly Met Ser
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Ile Ser Gly Gly Gly Ser Tyr Thr Asn Tyr Pro Asp Ser Val Lys
1               5                   10                  15

Gly

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Glu Trp Arg Met Thr Leu Tyr Ala Met Asp Tyr
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ala Ser Glu Ser Val Asp Ser Tyr Gly Asn Ser Phe Met His
1               5                   10                  15

<210> SEQ ID NO 31
```

```
<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Thr Ser Asn Leu Glu Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln Asn Asn Glu Asp Pro Phe Thr
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Phe Thr Phe Ser Ser Tyr
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Gly Gly Gly Ser Tyr
1               5

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Ile Ser Gly Gly Gly Ser Tyr Thr Asn
1               5                   10

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36
```

```
Ser Tyr Gly Met Ser
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Ser Tyr Gly Met Ser
1               5

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Val Ala Thr Ile Ser Gly Gly Gly Ser Tyr Thr Asn
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Arg Arg Glu Trp Arg Met Thr Leu Tyr Ala Met Asp
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Ser Tyr Gly Asn Ser Phe Met His Trp Tyr
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Leu Ile Tyr Leu Thr Ser Asn Leu Glu
1               5                   10

<210> SEQ ID NO 42
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 42

Gln Gln Asn Asn Glu Asp Pro Phe
1               5

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Tyr Thr Phe Thr Asp Tyr Asn Met Asp
1               5                   10

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Ile Tyr Pro Asn Asn Gly Gly Thr Gly Tyr Asn Gln Lys Phe Asn
1               5                   10                  15

Ser

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Pro Tyr Tyr Asp Tyr Val Gly Ser Tyr Ala Met Asp Tyr
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Ala Ser Ser Ser Val Ser Ser Ser Tyr Leu His
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Thr Ser Asn Leu Ala Ser
1               5
```

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His Gln Tyr His Arg Ser Pro Arg Thr
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Tyr Thr Phe Thr Asp Tyr
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Tyr Pro Asn Asn Gly Gly
1               5

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Tyr Ile Tyr Pro Asn Asn Gly Gly Thr Gly
1               5                   10

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Tyr Asn Met Asp
1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Asp Tyr Asn Met Asp
1               5

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Trp Ile Gly Tyr Ile Tyr Pro Asn Asn Gly Gly Thr Gly
1               5                   10

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Ser Ser Pro Tyr Tyr Asp Tyr Val Gly Ser Tyr Ala Met Asp
1               5                   10                  15

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Ser Ser Tyr Leu His Trp Tyr
1               5

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Trp Ile Tyr Ser Thr Ser Asn Leu Ala
1               5                   10

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

His Gln Tyr His Arg Ser Pro Arg
1               5

<210> SEQ ID NO 59
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Tyr Ile Tyr Pro Ser Asn Gly Gly Thr Gly Tyr Asn Gln Lys Phe Lys
1               5                   10                  15
Ser

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Val Pro Tyr Tyr Asp Tyr Leu Tyr Tyr Tyr Ala Met Asp Tyr
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Ala Ser Ser Ser Val Ser Phe Met His
1               5                   10

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Thr Ser Asn Leu Ala Ser
1               5

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gln Trp Ser Thr Asn Pro Tyr Met Tyr Thr
1               5                   10

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64
```

Tyr Pro Ser Asn Gly Gly
1               5

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Ile Tyr Pro Ser Asn Gly Gly Thr Gly
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Trp Ile Gly Tyr Ile Tyr Pro Ser Asn Gly Gly Thr Gly
1               5                   10

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Arg Val Pro Tyr Tyr Asp Tyr Leu Tyr Tyr Tyr Ala Met Asp
1               5                   10                  15

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Phe Met His Trp Tyr
1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Pro Trp Ile Tyr Ala Thr Ser Asn Leu Ala
1               5                   10

<210> SEQ ID NO 70
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 70

Gln Gln Trp Ser Thr Asn Pro Tyr Met Tyr
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Phe Thr Phe Ser Asp Tyr Gly Met His
1               5                   10

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Tyr Ile Phe Ser Gly Ser Ser Thr Ile Tyr Tyr Ala Asp Thr Val Lys
1               5                   10                  15

Gly

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Asp Gly Arg Gly Ala Met Asp Tyr
1               5

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Ala Ser Gln Asp Ile Ser Lys Phe Leu Asn
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Tyr Thr Ser Arg Leu His Ser
```

```
<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Gln Gly Asn Thr Leu Pro Trp Thr
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Phe Thr Phe Ser Asp Tyr
1               5

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Phe Ser Gly Ser Ser Thr
1               5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Tyr Ile Phe Ser Gly Ser Ser Thr Ile Tyr
1               5                   10

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Tyr Gly Met His
1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                         peptide

<400> SEQUENCE: 81

Ser Asp Tyr Gly Met His
1               5

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Trp Val Ala Tyr Ile Phe Ser Gly Ser Ser Thr Ile Tyr
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Arg Ala Asp Gly Arg Gly Ala Met Asp
1               5                   10

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Lys Phe Leu Asn Trp Tyr
1               5

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Leu Ile Tyr Tyr Thr Ser Arg Leu His
1               5                   10

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Gln Gly Asn Thr Leu Pro Trp
1               5

<210> SEQ ID NO 87
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Ile Ser Ser Gly Gly Thr Tyr Thr Phe Tyr Pro Asp Ser Val Lys
1               5                   10                  15
Gly

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Gly Trp Leu Leu His Tyr Tyr Ala Met Asp Tyr
1               5                   10

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Pro Ser Glu Ser Val Asp Ser Phe Gly Asn Ser Phe Met His
1               5                   10                  15

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Leu Ser Ser Lys Leu Glu Ser
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Gln His Asn Glu Asp Pro Phe Thr
1               5

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 92

Ser Ser Gly Gly Thr Tyr
1               5

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Ile Ser Ser Gly Gly Thr Tyr Thr Phe
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Trp Val Ala Thr Ile Ser Ser Gly Gly Thr Tyr Thr Phe
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ala Arg Arg Gly Trp Leu Leu His Tyr Tyr Ala Met Asp
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asp Ser Phe Gly Asn Ser Phe Met His Trp Phe
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Leu Leu Ile Tyr Leu Ser Ser Lys Leu Glu
1               5                   10

<210> SEQ ID NO 98
<211> LENGTH: 8
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 98

Gln Gln His Asn Glu Asp Pro Phe
1               5

<210> SEQ ID NO 99
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Tyr Ile Ser Thr Gly Ile Ile Thr Val Tyr Tyr Ala Asp Thr Val Lys
1               5                   10                  15

Gly

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Ala Ser Gln Asp Ile Ser Asn Phe Leu Asn
1               5                   10

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Thr Gly Ile Ile Thr
1               5

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Tyr Ile Ser Thr Gly Ile Ile Thr Val Tyr
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

```
Trp Val Ala Tyr Ile Ser Thr Gly Ile Ile Thr Val Tyr
1               5                   10
```

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

```
Ser Asn Phe Leu Asn Trp Tyr
1               5
```

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

```
Arg Glu Trp Arg Tyr Thr Leu Tyr Ala Met Asp Tyr
1               5                   10
```

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

```
Arg Ala Ser Glu Ser Val Glu Ser Tyr Gly Ser Ser Phe Met His
1               5                   10                  15
```

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Ala Arg Arg Glu Trp Arg Tyr Thr Leu Tyr Ala Met Asp
1               5                   10
```

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

```
Glu Ser Tyr Gly Ser Ser Phe Met His Trp Tyr
1               5                   10
```

<210> SEQ ID NO 109
<211> LENGTH: 118
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 109

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Pro Gly Gly Thr Ile Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Met Tyr Tyr Cys Ala
                85                  90                  95

Ser Asp Lys Tyr Asp Gly Gly Trp Phe Ala Tyr Trp Gly Gln Gly Thr
            100                 105                 110

Leu Val Thr Val Ser Ala
        115

<210> SEQ ID NO 110
<211> LENGTH: 107
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 110

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Glu Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Ser Leu Ser Ile Ser Asn Val Gln Ser
65                  70                  75                  80

Glu Asp Leu Ala Asp Tyr Phe Cys Leu Gln His Leu Asn Tyr Pro Leu
                85                  90                  95

Thr Phe Gly Ser Gly Thr Lys Leu Glu Ile Lys
            100                 105

<210> SEQ ID NO 111
<211> LENGTH: 121
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 111

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val

```
            35                  40                  45

Ala Thr Ile Ser Gly Gly Ser Tyr Thr Asn Tyr Pro Asp Ser Val
        50                  55                  60

Lys Gly Arg Leu Thr Ile Ser Arg Asp Asn Ala Lys Lys Asn Leu Tyr
65                  70                  75                  80

Leu Glu Met Ser Ser Leu Arg Ser Glu Asp Thr Ala Leu Tyr Tyr Cys
                85                  90                  95

Ala Arg Arg Glu Trp Arg Met Thr Leu Tyr Ala Met Asp Tyr Trp Gly
            100                 105                 110

Gln Gly Thr Ser Val Thr Val Ser Ser
            115                 120

<210> SEQ ID NO 112
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Ala Pro
        35                  40                  45

Lys Leu Leu Ile Tyr Leu Thr Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Phe Thr Phe Gly Ser Gly Thr Lys Leu Glu Ile Lys
            100                 105                 110

<210> SEQ ID NO 113
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Tyr Ile Tyr Pro Asn Asn Gly Gly Thr Gly Tyr Asn Gln Lys Phe
    50                  55                  60

Asn Ser Lys Ala Thr Leu Thr Val Asp Lys Ser Ser Thr Ala Tyr
65                  70                  75                  80

Met Glu Leu His Ser Leu Thr Ser Glu Asp Ser Ala Val Tyr Tyr Cys
                85                  90                  95

Ala Ser Ser Pro Tyr Tyr Asp Tyr Val Gly Ser Tyr Ala Met Asp Tyr
```

```
                       100                 105                 110

Trp Gly Gln Gly Thr Ser Val Thr Val Ser Ser
        115                 120

<210> SEQ ID NO 114
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Arg Thr Phe Gly Gly Gly Thr Lys Leu Glu Ile Lys
            100                 105

<210> SEQ ID NO 115
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Tyr Ile Tyr Pro Ser Asn Gly Gly Thr Gly Tyr Asn Gln Lys Phe
    50                  55                  60

Lys Ser Lys Ala Thr Leu Thr Val Asp Lys Ser Ser Asn Thr Ala Tyr
65                  70                  75                  80

Met Glu Leu His Ser Leu Thr Ser Glu Asp Ser Ala Val Tyr Tyr Cys
                85                  90                  95

Ala Arg Val Pro Tyr Tyr Asp Tyr Leu Tyr Tyr Ala Met Asp Tyr
            100                 105                 110

Trp Gly Gln Gly Thr Ser Val Thr Val Ser Ser
        115                 120

<210> SEQ ID NO 116
<211> LENGTH: 108
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 116

```
Gln Ile Val Leu Ser Gln Ser Pro Ala Ile Leu Ser Ala Ser Pro Gly
1               5                   10                  15

Glu Lys Val Thr Met Ala Cys Arg Ala Ser Ser Val Ser Phe Met
            20                  25                  30

His Trp Tyr Gln Gln Lys Pro Gly Ser Ser Pro Gln Pro Trp Ile Tyr
            35                  40                  45

Ala Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Thr Asn Pro Tyr Met
                85                  90                  95

Tyr Thr Phe Gly Gly Gly Thr Lys Leu Glu Ile Lys
            100                 105
```

<210> SEQ ID NO 117
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
            35                  40                  45

Ala Tyr Ile Phe Ser Gly Ser Ser Thr Ile Tyr Tyr Ala Asp Thr Val
        50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ala Asp Gly Arg Gly Ala Met Asp Tyr Trp Gly Gln Gly Thr
            100                 105                 110

Ser Val Thr Val Ser Ser
        115
```

<210> SEQ ID NO 118
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Asp Val Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Phe
            20                  25                  30

Leu Asn Trp Tyr Gln Gln Lys Pro Asp Gly Thr Val Lys Leu Leu Ile
            35                  40                  45
```

```
Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Asp Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105
```

<210> SEQ ID NO 119
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Glu Val Gln Leu Val Glu Ser Gly Gly Asp Leu Met Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Thr Phe Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Arg Gly Trp Leu Leu His Tyr Tyr Ala Met Asp Tyr Trp Gly
            100                 105                 110

Gln Gly Thr Ser Val Thr Val Ser Ser
        115                 120
```

<210> SEQ ID NO 120
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Asn Ile Val Leu Thr Gln Ser Pro Ala Ser Leu Ala Val Ser Leu Gly
1               5                   10                  15

Gln Arg Ala Thr Ile Ser Cys Arg Pro Ser Glu Ser Val Asp Ser Phe
            20                  25                  30

Gly Asn Ser Phe Met His Trp Phe Gln Gln Lys Pro Gly Gln Pro Pro
        35                  40                  45

Lys Leu Leu Ile Tyr Leu Ser Ser Lys Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln His Asn
                85                  90                  95

Glu Asp Pro Phe Thr Phe Gly Ser Gly Thr Lys Leu Glu Ile Lys
            100                 105                 110
```

```
<210> SEQ ID NO 121
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Val Gln Val Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Thr Gly Ile Ile Thr Val Tyr Tyr Ala Asp Thr Val
    50                  55                  60

Lys Gly Arg Phe Thr Met Ser Arg Asp Asn Ala Lys Asn Thr Leu Phe
65                  70                  75                  80

Leu Gln Met Thr Ser Leu Arg Ser Glu Asp Thr Ala Ile Tyr Tyr Cys
                85                  90                  95

Ala Arg Ala Asp Gly Arg Gly Ala Met Asp Tyr Trp Gly Gln Gly Thr
            100                 105                 110

Ser Val Ile Val Ser Ser
        115

<210> SEQ ID NO 122
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Phe
            20                  25                  30

Leu Asn Trp Tyr Gln Gln Lys Pro Asp Gly Thr Val Thr Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 123
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Ser Gly Gly Ser Tyr Thr Asn Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Glu Trp Arg Tyr Thr Leu Tyr Ala Met Asp Tyr Trp Gly
            100                 105                 110

Gln Gly Thr Thr Val Thr Val Ser Ser
            115                 120

<210> SEQ ID NO 124
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Asp Ile Gln Leu Thr Gln Ser Pro Ser Phe Leu Ser Ala Ser Val Gly
1               5                   10                  15

Asp Arg Val Thr Ile Thr Cys Arg Ala Ser Glu Ser Val Glu Ser Tyr
            20                  25                  30

Gly Ser Ser Phe Met His Trp Tyr Gln Gln Lys Pro Gly Lys Ala Pro
        35                  40                  45

Lys Leu Leu Ile Tyr Leu Thr Ser Asn Leu Glu Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Phe Thr Phe Gly Gly Gly Thr Lys Leu Glu Ile Lys
            100                 105                 110

<210> SEQ ID NO 125
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Gly Met Ser Trp Val Arg Gln Ala Pro Gly
    50                  55                  60

```
Lys Gly Leu Glu Trp Val Ala Thr Ile Ser Gly Gly Ser Tyr Thr
 65                  70                  75                  80

Asn Tyr Pro Asp Ser Val Lys Gly Arg Phe Thr Ile Ser Arg Asp Asn
                 85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Arg Glu Trp Arg Tyr Thr Leu Tyr
            115                 120                 125

Ala Met Asp Tyr Trp Gly Gln Gly Thr Thr Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Gly Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470
```

```
<210> SEQ ID NO 126
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Ser Gly Gly Ser Tyr Thr Asn Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Glu Trp Arg Tyr Thr Leu Tyr Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Gly Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450

<210> SEQ ID NO 127
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Asp Met Arg Val Pro Ala Gln Leu Leu Gly Leu Leu Leu Leu Trp
1               5                   10                  15

Leu Arg Gly Ala Arg Cys Asp Ile Gln Leu Thr Gln Ser Pro Ser Phe
                20                  25                  30

Leu Ser Ala Ser Val Gly Asp Arg Val Thr Ile Thr Cys Arg Ala Ser
            35                  40                  45

Glu Ser Val Glu Ser Tyr Gly Ser Ser Phe Met His Trp Tyr Gln Gln
50                  55                  60

Lys Pro Gly Lys Ala Pro Lys Leu Leu Ile Tyr Leu Thr Ser Asn Leu
65                  70                  75                  80

Glu Ser Gly Val Pro Ser Arg Phe Ser Gly Ser Gly Ser Gly Thr Glu
                85                  90                  95

Phe Thr Leu Thr Ile Ser Ser Leu Gln Pro Glu Asp Phe Ala Thr Tyr
            100                 105                 110

Tyr Cys Gln Gln Asn Asn Glu Asp Pro Phe Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 128
<211> LENGTH: 218
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 128

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Glu Ser Val Glu Ser Tyr
            20                  25                  30

Gly Ser Ser Phe Met His Trp Tyr Gln Gln Lys Pro Gly Lys Ala Pro
        35                  40                  45

Lys Leu Leu Ile Tyr Leu Thr Ser Asn Leu Glu Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Phe Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 129
<211> LENGTH: 330
<212> TYPE: PRT
<213> ORGANISM: Homo sapiens

<400> SEQUENCE: 129

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 130
<211> LENGTH: 330
<212> TYPE: PRT
<213> ORGANISM: Homo sapiens

<400> SEQUENCE: 130

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Ala Leu Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
            165                 170                 175
Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 131
<211> LENGTH: 330
<212> TYPE: PRT
<213> ORGANISM: Homo sapiens

<400> SEQUENCE: 131

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Ala Ala Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 132
<211> LENGTH: 330
<212> TYPE: PRT
<213> ORGANISM: Homo sapiens

<400> SEQUENCE: 132

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 133
<211> LENGTH: 330
<212> TYPE: PRT
<213> ORGANISM: Homo sapiens

<400> SEQUENCE: 133

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 134
<211> LENGTH: 330
<212> TYPE: PRT
<213> ORGANISM: Homo sapiens

<400> SEQUENCE: 134

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

Ala Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 135
<211> LENGTH: 107
<212> TYPE: PRT
<213> ORGANISM: Homo sapiens

<400> SEQUENCE: 135

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 136
<211> LENGTH: 106
<212> TYPE: PRT
<213> ORGANISM: Homo sapiens

<400> SEQUENCE: 136

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 137
<211> LENGTH: 197
<212> TYPE: PRT
<213> ORGANISM: Homo sapiens

<400> SEQUENCE: 137

Gln Ala Gly Pro Leu Pro Lys Pro Thr Leu Trp Ala Glu Pro Gly Ser
1               5                   10                  15

Val Ile Ser Trp Gly Asn Ser Val Thr Ile Trp Cys Gln Gly Thr Leu
            20                  25                  30

Glu Ala Arg Glu Tyr Arg Leu Asp Lys Glu Glu Ser Pro Ala Pro Trp
        35                  40                  45

Asp Arg Gln Asn Pro Leu Glu Pro Lys Asn Lys Ala Arg Phe Ser Ile
    50                  55                  60

Pro Ser Met Thr Glu Asp Tyr Ala Gly Arg Tyr Arg Cys Tyr Tyr Arg

```
                65                  70                  75                  80
Ser Pro Val Gly Trp Ser Gln Pro Ser Asp Pro Leu Glu Leu Val Met
                85                  90                  95

Thr Gly Ala Tyr Ser Lys Pro Thr Leu Ser Ala Leu Pro Ser Pro Leu
                100                 105                 110

Val Thr Ser Gly Lys Ser Val Thr Leu Leu Cys Gln Ser Arg Ser Pro
                115                 120                 125

Met Asp Thr Phe Leu Leu Ile Lys Glu Arg Ala Ala His Pro Leu Leu
        130                 135                 140

His Leu Arg Ser Glu His Gly Ala Gln Gln His Gln Ala Glu Phe Pro
145                 150                 155                 160

Met Ser Pro Val Thr Ser Val His Gly Gly Thr Tyr Arg Cys Phe Ser
                165                 170                 175

Ser His Gly Phe Ser His Tyr Leu Leu Ser His Pro Ser Asp Pro Leu
        180                 185                 190

Glu Leu Ile Val Ser
        195

<210> SEQ ID NO 138
<211> LENGTH: 2477
<212> TYPE: PRT
<213> ORGANISM: Homo sapiens

<400> SEQUENCE: 138

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
                100                 105                 110

Glu Arg Pro Lys Asp Ser Met Ile Trp Asp Cys Thr Cys Ile Gly Ala
                115                 120                 125

Gly Arg Gly Arg Ile Ser Cys Thr Ile Ala Asn Arg Cys His Glu Gly
        130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
                180                 185                 190

Thr Ser Tyr Val Val Gly Glu Thr Trp Glu Lys Pro Tyr Gln Gly Trp
                195                 200                 205

Met Met Val Asp Cys Thr Cys Leu Gly Glu Gly Ser Gly Arg Ile Thr
        210                 215                 220

Cys Thr Ser Arg Asn Arg Cys Asn Asp Gln Asp Thr Arg Thr Ser Tyr
225                 230                 235                 240
```

```
Arg Ile Gly Asp Thr Trp Ser Lys Lys Asp Asn Arg Gly Asn Leu Leu
            245                 250                 255

Gln Cys Ile Cys Thr Gly Asn Gly Arg Gly Glu Trp Lys Cys Glu Arg
        260                 265                 270

His Thr Ser Val Gln Thr Thr Ser Ser Gly Ser Gly Pro Phe Thr Asp
    275                 280                 285

Val Arg Ala Ala Val Tyr Gln Pro Gln Pro His Pro Gln Pro Pro Pro
290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
```

```
                    660                 665                 670
Pro Gly Val Val Tyr Glu Gly Gln Leu Ile Ser Ile Gln Gln Tyr Gly
            675                 680                 685

His Gln Glu Val Thr Arg Phe Asp Phe Thr Thr Ser Thr Ser Thr
690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
                740                 745                 750

Glu Tyr Glu Leu Ser Glu Glu Gly Asp Glu Pro Gln Tyr Leu Asp Leu
                755                 760                 765

Pro Ser Thr Ala Thr Ser Val Asn Ile Pro Asp Leu Leu Pro Gly Arg
                770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Thr Thr Val Asp Gln Val Asp Asp Thr Ser Ile Val Val Arg Trp Ser
                820                 825                 830

Arg Pro Gln Ala Pro Ile Thr Gly Tyr Arg Ile Val Tyr Ser Pro Ser
                835                 840                 845

Val Glu Gly Ser Ser Thr Glu Leu Asn Leu Pro Glu Thr Ala Asn Ser
                850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
                900                 905                 910

Leu Gln Phe Val Glu Val Thr Asp Val Lys Val Thr Ile Met Trp Thr
                915                 920                 925

Pro Pro Glu Ser Ala Val Thr Gly Tyr Arg Val Asp Val Ile Pro Val
                930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
                980                 985                 990

Gln Thr Thr Lys Leu Asp Ala Pro Thr Asn Leu Gln Phe Val Asn Glu
                995                 1000                1005

Thr Asp Ser Thr Val Leu Val Arg Trp Thr Pro Pro Arg Ala Gln
            1010                1015                1020

Ile Thr Gly Tyr Arg Leu Thr Val Gly Leu Thr Arg Arg Gly Gln
            1025                1030                1035

Pro Arg Gln Tyr Asn Val Gly Pro Ser Val Ser Lys Tyr Pro Leu
            1040                1045                1050

Arg Asn Leu Gln Pro Ala Ser Glu Tyr Thr Val Ser Leu Val Ala
            1055                1060                1065

Ile Lys Gly Asn Gln Glu Ser Pro Lys Ala Thr Gly Val Phe Thr
            1070                1075                1080
```

-continued

```
Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200

Thr Gly Tyr Arg Ile Thr Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260

Ile Pro Glu Val Pro Gln Leu Thr Asp Leu Ser Phe Val Asp Ile
    1265                1270                1275

Thr Asp Ser Ser Ile Gly Leu Arg Trp Thr Pro Leu Asn Ser Ser
    1280                1285                1290

Thr Ile Ile Gly Tyr Arg Ile Thr Val Val Ala Ala Gly Glu Gly
    1295                1300                1305

Ile Pro Ile Phe Glu Asp Phe Val Asp Ser Ser Val Gly Tyr Tyr
    1310                1315                1320

Thr Val Thr Gly Leu Glu Pro Gly Ile Asp Tyr Asp Ile Ser Val
    1325                1330                1335

Ile Thr Leu Ile Asn Gly Gly Glu Ser Ala Pro Thr Thr Leu Thr
    1340                1345                1350

Gln Gln Thr Ala Val Pro Pro Pro Thr Asp Leu Arg Phe Thr Asn
    1355                1360                1365

Ile Gly Pro Asp Thr Met Arg Val Thr Trp Ala Pro Pro Pro Ser
    1370                1375                1380

Ile Asp Leu Thr Asn Phe Leu Val Arg Tyr Ser Pro Val Lys Asn
    1385                1390                1395

Glu Glu Asp Val Ala Glu Leu Ser Ile Ser Pro Ser Asp Asn Ala
    1400                1405                1410

Val Val Leu Thr Asn Leu Leu Pro Gly Thr Glu Tyr Val Val Ser
    1415                1420                1425

Val Ser Ser Val Tyr Glu Gln His Glu Ser Thr Pro Leu Arg Gly
    1430                1435                1440

Arg Gln Lys Thr Gly Leu Asp Ser Pro Thr Gly Ile Asp Phe Ser
    1445                1450                1455

Asp Ile Thr Ala Asn Ser Phe Thr Val His Trp Ile Ala Pro Arg
    1460                1465                1470
```

```
Ala Thr Ile Thr Gly Tyr Arg Ile Arg His His Pro Glu His Phe
    1475                1480                1485

Ser Gly Arg Pro Arg Glu Asp Arg Val Pro His Ser Arg Asn Ser
    1490                1495                1500

Ile Thr Leu Thr Asn Leu Thr Pro Gly Thr Glu Tyr Val Val Ser
    1505                1510                1515

Ile Val Ala Leu Asn Gly Arg Glu Ser Pro Leu Leu Ile Gly
    1520                1525                1530

Gln Gln Ser Thr Val Ser Asp Val Pro Arg Asp Leu Glu Val Val
    1535                1540                1545

Ala Ala Thr Pro Thr Ser Leu Leu Ile Ser Trp Asp Ala Pro Ala
    1550                1555                1560

Val Thr Val Arg Tyr Tyr Arg Ile Thr Tyr Gly Glu Thr Gly Gly
    1565                1570                1575

Asn Ser Pro Val Gln Glu Phe Thr Val Pro Gly Ser Lys Ser Thr
    1580                1585                1590

Ala Thr Ile Ser Gly Leu Lys Pro Gly Val Asp Tyr Thr Ile Thr
    1595                1600                1605

Val Tyr Ala Val Thr Gly Arg Gly Asp Ser Pro Ala Ser Ser Lys
    1610                1615                1620

Pro Ile Ser Ile Asn Tyr Arg Thr Glu Ile Asp Lys Pro Ser Gln
    1625                1630                1635

Met Gln Val Thr Asp Val Gln Asp Asn Ser Ile Ser Val Lys Trp
    1640                1645                1650

Leu Pro Ser Ser Ser Pro Val Thr Gly Tyr Arg Val Thr Thr Thr
    1655                1660                1665

Pro Lys Asn Gly Pro Gly Pro Thr Lys Thr Lys Thr Ala Gly Pro
    1670                1675                1680

Asp Gln Thr Glu Met Thr Ile Glu Gly Leu Gln Pro Thr Val Glu
    1685                1690                1695

Tyr Val Val Ser Val Tyr Ala Gln Asn Pro Ser Gly Glu Ser Gln
    1700                1705                1710

Pro Leu Val Gln Thr Ala Val Thr Asn Ile Asp Arg Pro Lys Gly
    1715                1720                1725

Leu Ala Phe Thr Asp Val Asp Val Asp Ser Ile Lys Ile Ala Trp
    1730                1735                1740

Glu Ser Pro Gln Gly Gln Val Ser Arg Tyr Arg Val Thr Tyr Ser
    1745                1750                1755

Ser Pro Glu Asp Gly Ile His Glu Leu Phe Pro Ala Pro Asp Gly
    1760                1765                1770

Glu Glu Asp Thr Ala Glu Leu Gln Gly Leu Arg Pro Gly Ser Glu
    1775                1780                1785

Tyr Thr Val Ser Val Val Ala Leu His Asp Asp Met Glu Ser Gln
    1790                1795                1800

Pro Leu Ile Gly Thr Gln Ser Thr Ala Ile Pro Ala Pro Thr Asp
    1805                1810                1815

Leu Lys Phe Thr Gln Val Thr Pro Thr Ser Leu Ser Ala Gln Trp
    1820                1825                1830

Thr Pro Pro Asn Val Gln Leu Thr Gly Tyr Arg Val Arg Val Thr
    1835                1840                1845

Pro Lys Glu Lys Thr Gly Pro Met Lys Glu Ile Asn Leu Ala Pro
    1850                1855                1860

Asp Ser Ser Ser Val Val Val Ser Gly Leu Met Val Ala Thr Lys
```

```
                1865                1870                1875

Tyr Glu Val Ser Val Tyr Ala Leu Lys Asp Thr Leu Thr Ser Arg
    1880                1885                1890

Pro Ala Gln Gly Val Val Thr Thr Leu Glu Asn Val Ser Pro Pro
    1895                1900                1905

Arg Arg Ala Arg Val Thr Asp Ala Thr Glu Thr Thr Ile Thr Ile
    1910                1915                1920

Ser Trp Arg Thr Lys Thr Glu Thr Ile Thr Gly Phe Gln Val Asp
    1925                1930                1935

Ala Val Pro Ala Asn Gly Gln Thr Pro Ile Gln Arg Thr Ile Lys
    1940                1945                1950

Pro Asp Val Arg Ser Tyr Thr Ile Thr Gly Leu Gln Pro Gly Thr
    1955                1960                1965

Asp Tyr Lys Ile Tyr Leu Tyr Thr Leu Asn Asp Asn Ala Arg Ser
    1970                1975                1980

Ser Pro Val Val Ile Asp Ala Ser Thr Ala Ile Asp Ala Pro Ser
    1985                1990                1995

Asn Leu Arg Phe Leu Ala Thr Thr Pro Asn Ser Leu Leu Val Ser
    2000                2005                2010

Trp Gln Pro Pro Arg Ala Arg Ile Thr Gly Tyr Ile Ile Lys Tyr
    2015                2020                2025

Glu Lys Pro Gly Ser Pro Arg Glu Val Val Pro Arg Pro Arg
    2030                2035                2040

Pro Gly Val Thr Glu Ala Thr Ile Thr Gly Leu Glu Pro Gly Thr
    2045                2050                2055

Glu Tyr Thr Ile Tyr Val Ile Ala Leu Lys Asn Asn Gln Lys Ser
    2060                2065                2070

Glu Pro Leu Ile Gly Arg Lys Lys Thr Asp Glu Leu Pro Gln Leu
    2075                2080                2085

Val Thr Leu Pro His Pro Asn Leu His Gly Pro Glu Ile Leu Asp
    2090                2095                2100

Val Pro Ser Thr Val Gln Lys Thr Pro Phe Val Thr His Pro Gly
    2105                2110                2115

Tyr Asp Thr Gly Asn Gly Ile Gln Leu Pro Gly Thr Ser Gly Gln
    2120                2125                2130

Gln Pro Ser Val Gly Gln Gln Met Ile Phe Glu Glu His Gly Phe
    2135                2140                2145

Arg Arg Thr Thr Pro Pro Thr Thr Ala Thr Pro Ile Arg His Arg
    2150                2155                2160

Pro Arg Pro Tyr Pro Pro Asn Val Gly Glu Glu Ile Gln Ile Gly
    2165                2170                2175

His Ile Pro Arg Glu Asp Val Asp Tyr His Leu Tyr Pro His Gly
    2180                2185                2190

Pro Gly Leu Asn Pro Asn Ala Ser Thr Gly Gln Glu Ala Leu Ser
    2195                2200                2205

Gln Thr Thr Ile Ser Trp Ala Pro Phe Gln Asp Thr Ser Glu Tyr
    2210                2215                2220

Ile Ile Ser Cys His Pro Val Gly Thr Asp Glu Glu Pro Leu Gln
    2225                2230                2235

Phe Arg Val Pro Gly Thr Ser Thr Ser Ala Thr Leu Thr Gly Leu
    2240                2245                2250

Thr Arg Gly Ala Thr Tyr Asn Val Ile Val Glu Ala Leu Lys Asp
    2255                2260                2265
```

Gln Gln Arg His Lys Val Arg Glu Val Val Thr Val Gly Asn
        2270                2275                2280

Ser Val Asn Glu Gly Leu Asn Gln Pro Thr Asp Asp Ser Cys Phe
    2285                2290                2295

Asp Pro Tyr Thr Val Ser His Tyr Ala Val Gly Asp Glu Trp Glu
2300                2305                2310

Arg Met Ser Glu Ser Gly Phe Lys Leu Leu Cys Gln Cys Leu Gly
    2315                2320                2325

Phe Gly Ser Gly His Phe Arg Cys Asp Ser Ser Arg Trp Cys His
    2330                2335                2340

Asp Asn Gly Val Asn Tyr Lys Ile Gly Glu Lys Trp Asp Arg Gln
    2345                2350                2355

Gly Glu Asn Gly Gln Met Met Ser Cys Thr Cys Leu Gly Asn Gly
    2360                2365                2370

Lys Gly Glu Phe Lys Cys Asp Pro His Glu Ala Thr Cys Tyr Asp
    2375                2380                2385

Asp Gly Lys Thr Tyr His Val Gly Glu Gln Trp Gln Lys Glu Tyr
    2390                2395                2400

Leu Gly Ala Ile Cys Ser Cys Thr Cys Phe Gly Gly Gln Arg Gly
    2405                2410                2415

Trp Arg Cys Asp Asn Cys Arg Arg Pro Gly Gly Glu Pro Ser Pro
    2420                2425                2430

Glu Gly Thr Thr Gly Gln Ser Tyr Asn Gln Tyr Ser Gln Arg Tyr
    2435                2440                2445

His Gln Arg Thr Asn Thr Asn Val Asn Cys Pro Ile Glu Cys Phe
    2450                2455                2460

Met Pro Leu Asp Val Gln Ala Asp Arg Glu Asp Ser Arg Glu
    2465                2470                2475

<210> SEQ ID NO 139
<211> LENGTH: 2446
<212> TYPE: PRT
<213> ORGANISM: Homo sapiens

<400> SEQUENCE: 139

Gln Ala Gln Gln Met Val Gln Pro Gln Ser Pro Val Ala Val Ser Gln
1               5                   10                  15

Ser Lys Pro Gly Cys Tyr Asp Asn Gly Lys His Tyr Gln Ile Asn Gln
                20                  25                  30

Gln Trp Glu Arg Thr Tyr Leu Gly Asn Ala Leu Val Cys Thr Cys Tyr
            35                  40                  45

Gly Gly Ser Arg Gly Phe Asn Cys Glu Ser Lys Pro Glu Ala Glu Glu
        50                  55                  60

Thr Cys Phe Asp Lys Tyr Thr Gly Asn Thr Tyr Arg Val Gly Asp Thr
65                  70                  75                  80

Tyr Glu Arg Pro Lys Asp Ser Met Ile Trp Asp Cys Thr Cys Ile Gly
                85                  90                  95

Ala Gly Arg Gly Arg Ile Ser Cys Thr Ile Ala Asn Arg Cys His Glu
            100                 105                 110

Gly Gly Gln Ser Tyr Lys Ile Gly Asp Thr Trp Arg Arg Pro His Glu
        115                 120                 125

Thr Gly Gly Tyr Met Leu Glu Cys Val Cys Leu Gly Asn Gly Lys Gly
    130                 135                 140

Glu Trp Thr Cys Lys Pro Ile Ala Glu Lys Cys Phe Asp His Ala Ala

-continued

```
            145                 150                 155                 160
Gly Thr Ser Tyr Val Val Gly Glu Thr Trp Glu Lys Pro Tyr Gln Gly
                    165                 170                 175
Trp Met Met Val Asp Cys Thr Cys Leu Gly Glu Gly Ser Gly Arg Ile
                    180                 185                 190
Thr Cys Thr Ser Arg Asn Arg Cys Asn Asp Gln Asp Thr Arg Thr Ser
                    195                 200                 205
Tyr Arg Ile Gly Asp Thr Trp Ser Lys Lys Asp Asn Arg Gly Asn Leu
        210                 215                 220
Leu Gln Cys Ile Cys Thr Gly Asn Gly Arg Gly Glu Trp Lys Cys Glu
225                 230                 235                 240
Arg His Thr Ser Val Gln Thr Thr Ser Ser Gly Ser Gly Pro Phe Thr
                    245                 250                 255
Asp Val Arg Ala Ala Val Tyr Gln Pro Gln Pro His Pro Gln Pro Pro
                    260                 265                 270
Pro Tyr Gly His Cys Val Thr Asp Ser Gly Val Val Tyr Ser Val Gly
                    275                 280                 285
Met Gln Trp Leu Lys Thr Gln Gly Asn Lys Gln Met Leu Cys Thr Cys
            290                 295                 300
Leu Gly Asn Gly Val Ser Cys Gln Glu Thr Ala Val Thr Gln Thr Tyr
305                 310                 315                 320
Gly Gly Asn Ser Asn Gly Glu Pro Cys Val Leu Pro Phe Thr Tyr Asn
                    325                 330                 335
Gly Arg Thr Phe Tyr Ser Cys Thr Thr Glu Gly Arg Gln Asp Gly His
                    340                 345                 350
Leu Trp Cys Ser Thr Thr Ser Asn Tyr Glu Gln Asp Gln Lys Tyr Ser
                    355                 360                 365
Phe Cys Thr Asp His Thr Val Leu Val Gln Thr Arg Gly Gly Asn Ser
            370                 375                 380
Asn Gly Ala Leu Cys His Phe Pro Phe Leu Tyr Asn Asn His Asn Tyr
385                 390                 395                 400
Thr Asp Cys Thr Ser Glu Gly Arg Arg Asp Asn Met Lys Trp Cys Gly
                    405                 410                 415
Thr Thr Gln Asn Tyr Asp Ala Asp Gln Lys Phe Gly Phe Cys Pro Met
                    420                 425                 430
Ala Ala His Glu Glu Ile Cys Thr Thr Asn Glu Gly Val Met Tyr Arg
                    435                 440                 445
Ile Gly Asp Gln Trp Asp Lys Gln His Asp Met Gly His Met Met Arg
        450                 455                 460
Cys Thr Cys Val Gly Asn Gly Arg Gly Glu Trp Thr Cys Ile Ala Tyr
465                 470                 475                 480
Ser Gln Leu Arg Asp Gln Cys Ile Val Asp Asp Ile Thr Tyr Asn Val
                    485                 490                 495
Asn Asp Thr Phe His Lys Arg His Glu Glu Gly His Met Leu Asn Cys
                    500                 505                 510
Thr Cys Phe Gly Gln Gly Arg Gly Arg Trp Lys Cys Asp Pro Val Asp
                    515                 520                 525
Gln Cys Gln Asp Ser Glu Thr Gly Thr Phe Tyr Gln Ile Gly Asp Ser
            530                 535                 540
Trp Glu Lys Tyr Val His Gly Val Arg Tyr Gln Cys Tyr Cys Tyr Gly
545                 550                 555                 560
Arg Gly Ile Gly Glu Trp His Cys Gln Pro Leu Gln Thr Tyr Pro Ser
                    565                 570                 575
```

```
Ser Ser Gly Pro Val Glu Val Phe Ile Thr Glu Thr Pro Ser Gln Pro
            580                 585                 590

Asn Ser His Pro Ile Gln Trp Asn Ala Pro Gln Pro Ser His Ile Ser
        595                 600                 605

Lys Tyr Ile Leu Arg Trp Arg Pro Lys Asn Ser Val Gly Arg Trp Lys
610                 615                 620

Glu Ala Thr Ile Pro Gly His Leu Asn Ser Tyr Thr Ile Lys Gly Leu
625                 630                 635                 640

Lys Pro Gly Val Val Tyr Glu Gly Gln Leu Ile Ser Ile Gln Gln Tyr
                645                 650                 655

Gly His Gln Glu Val Thr Arg Phe Asp Phe Thr Thr Ser Thr Ser
            660                 665                 670

Thr Pro Val Thr Ser Asn Thr Val Thr Gly Glu Thr Thr Pro Phe Ser
            675                 680                 685

Pro Leu Val Ala Thr Ser Glu Ser Val Thr Glu Ile Thr Ala Ser Ser
        690                 695                 700

Phe Val Val Ser Trp Val Ser Ala Ser Asp Thr Val Ser Gly Phe Arg
705                 710                 715                 720

Val Glu Tyr Glu Leu Ser Glu Glu Gly Asp Glu Pro Gln Tyr Leu Asp
                725                 730                 735

Leu Pro Ser Thr Ala Thr Ser Val Asn Ile Pro Asp Leu Leu Pro Gly
            740                 745                 750

Arg Lys Tyr Ile Val Asn Val Tyr Gln Ile Ser Glu Asp Gly Glu Gln
        755                 760                 765

Ser Leu Ile Leu Ser Thr Ser Gln Thr Thr Ala Pro Asp Ala Pro Pro
770                 775                 780

Asp Thr Thr Val Asp Gln Val Asp Asp Thr Ser Ile Val Val Arg Trp
785                 790                 795                 800

Ser Arg Pro Gln Ala Pro Ile Thr Gly Tyr Arg Ile Val Tyr Ser Pro
                805                 810                 815

Ser Val Glu Gly Ser Ser Thr Glu Leu Asn Leu Pro Glu Thr Ala Asn
            820                 825                 830

Ser Val Thr Leu Ser Asp Leu Gln Pro Gly Val Gln Tyr Asn Ile Thr
        835                 840                 845

Ile Tyr Ala Val Glu Glu Asn Gln Glu Ser Thr Pro Val Val Ile Gln
850                 855                 860

Gln Glu Thr Thr Gly Thr Pro Arg Ser Asp Thr Val Pro Ser Pro Arg
865                 870                 875                 880

Asp Leu Gln Phe Val Glu Val Thr Asp Val Lys Val Thr Ile Met Trp
                885                 890                 895

Thr Pro Pro Glu Ser Ala Val Thr Gly Tyr Arg Val Asp Val Ile Pro
            900                 905                 910

Val Asn Leu Pro Gly Glu His Gly Gln Arg Leu Pro Ile Ser Arg Asn
        915                 920                 925

Thr Phe Ala Glu Val Thr Gly Leu Ser Pro Gly Val Thr Tyr Tyr Phe
930                 935                 940

Lys Val Phe Ala Val Ser His Gly Arg Glu Ser Lys Pro Leu Thr Ala
945                 950                 955                 960

Gln Gln Thr Thr Lys Leu Asp Ala Pro Thr Asn Leu Gln Phe Val Asn
                965                 970                 975

Glu Thr Asp Ser Thr Val Leu Val Arg Trp Thr Pro Pro Arg Ala Gln
            980                 985                 990
```

-continued

```
Ile Thr Gly Tyr Arg Leu Thr Val Gly Leu Thr Arg Arg Gly Gln Pro
            995                 1000                1005

Arg Gln Tyr Asn Val Gly Pro Ser Val Ser Lys Tyr Pro Leu Arg
        1010                1015                1020

Asn Leu Gln Pro Ala Ser Glu Tyr Thr Val Ser Leu Val Ala Ile
        1025                1030                1035

Lys Gly Asn Gln Glu Ser Pro Lys Ala Thr Gly Val Phe Thr Thr
        1040                1045                1050

Leu Gln Pro Gly Ser Ser Ile Pro Pro Tyr Asn Thr Glu Val Thr
        1055                1060                1065

Glu Thr Thr Ile Val Ile Thr Trp Thr Pro Ala Pro Arg Ile Gly
        1070                1075                1080

Phe Lys Leu Gly Val Arg Pro Ser Gln Gly Gly Glu Ala Pro Arg
        1085                1090                1095

Glu Val Thr Ser Asp Ser Gly Ser Ile Val Val Ser Gly Leu Thr
        1100                1105                1110

Pro Gly Val Glu Tyr Val Tyr Thr Ile Gln Val Leu Arg Asp Gly
        1115                1120                1125

Gln Glu Arg Asp Ala Pro Ile Val Asn Lys Val Val Thr Pro Leu
        1130                1135                1140

Ser Pro Pro Thr Asn Leu His Leu Glu Ala Asn Pro Asp Thr Gly
        1145                1150                1155

Val Leu Thr Val Ser Trp Glu Arg Ser Thr Thr Pro Asp Ile Thr
        1160                1165                1170

Gly Tyr Arg Ile Thr Thr Thr Pro Thr Asn Gly Gln Gln Gly Asn
        1175                1180                1185

Ser Leu Glu Glu Val Val His Ala Asp Gln Ser Ser Cys Thr Phe
        1190                1195                1200

Asp Asn Leu Ser Pro Gly Leu Glu Tyr Asn Val Ser Val Tyr Thr
        1205                1210                1215

Val Lys Asp Asp Lys Glu Ser Val Pro Ile Ser Asp Thr Ile Ile
        1220                1225                1230

Pro Glu Val Pro Gln Leu Thr Asp Leu Ser Phe Val Asp Ile Thr
        1235                1240                1245

Asp Ser Ser Ile Gly Leu Arg Trp Thr Pro Leu Asn Ser Ser Thr
        1250                1255                1260

Ile Ile Gly Tyr Arg Ile Thr Val Val Ala Ala Gly Glu Gly Ile
        1265                1270                1275

Pro Ile Phe Glu Asp Phe Val Asp Ser Ser Val Gly Tyr Tyr Thr
        1280                1285                1290

Val Thr Gly Leu Glu Pro Gly Ile Asp Tyr Asp Ile Ser Val Ile
        1295                1300                1305

Thr Leu Ile Asn Gly Gly Glu Ser Ala Pro Thr Thr Leu Thr Gln
        1310                1315                1320

Gln Thr Ala Val Pro Pro Pro Thr Asp Leu Arg Phe Thr Asn Ile
        1325                1330                1335

Gly Pro Asp Thr Met Arg Val Thr Trp Ala Pro Pro Ser Ile
        1340                1345                1350

Asp Leu Thr Asn Phe Leu Val Arg Tyr Ser Pro Val Lys Asn Glu
        1355                1360                1365

Glu Asp Val Ala Glu Leu Ser Ile Ser Pro Ser Asp Asn Ala Val
        1370                1375                1380

Val Leu Thr Asn Leu Leu Pro Gly Thr Glu Tyr Val Val Ser Val
```

```
            1385                1390                1395

Ser Ser Val Tyr Glu Gln His Glu Ser Thr Pro Leu Arg Gly Arg
    1400                1405                1410

Gln Lys Thr Gly Leu Asp Ser Pro Thr Gly Ile Asp Phe Ser Asp
    1415                1420                1425

Ile Thr Ala Asn Ser Phe Thr Val His Trp Ile Ala Pro Arg Ala
    1430                1435                1440

Thr Ile Thr Gly Tyr Arg Ile Arg His His Pro Glu His Phe Ser
    1445                1450                1455

Gly Arg Pro Arg Glu Asp Arg Val Pro His Ser Arg Asn Ser Ile
    1460                1465                1470

Thr Leu Thr Asn Leu Thr Pro Gly Thr Glu Tyr Val Val Ser Ile
    1475                1480                1485

Val Ala Leu Asn Gly Arg Glu Glu Ser Pro Leu Leu Ile Gly Gln
    1490                1495                1500

Gln Ser Thr Val Ser Asp Val Pro Arg Asp Leu Glu Val Val Ala
    1505                1510                1515

Ala Thr Pro Thr Ser Leu Leu Ile Ser Trp Asp Ala Pro Ala Val
    1520                1525                1530

Thr Val Arg Tyr Tyr Arg Ile Thr Tyr Gly Glu Thr Gly Gly Asn
    1535                1540                1545

Ser Pro Val Gln Glu Phe Thr Val Pro Gly Ser Lys Ser Thr Ala
    1550                1555                1560

Thr Ile Ser Gly Leu Lys Pro Gly Val Asp Tyr Thr Ile Thr Val
    1565                1570                1575

Tyr Ala Val Thr Gly Arg Gly Asp Ser Pro Ala Ser Ser Lys Pro
    1580                1585                1590

Ile Ser Ile Asn Tyr Arg Thr Glu Ile Asp Lys Pro Ser Gln Met
    1595                1600                1605

Gln Val Thr Asp Val Gln Asp Asn Ser Ile Ser Val Lys Trp Leu
    1610                1615                1620

Pro Ser Ser Ser Pro Val Thr Gly Tyr Arg Val Thr Thr Thr Pro
    1625                1630                1635

Lys Asn Gly Pro Gly Pro Thr Lys Thr Lys Thr Ala Gly Pro Asp
    1640                1645                1650

Gln Thr Glu Met Thr Ile Glu Gly Leu Gln Pro Thr Val Glu Tyr
    1655                1660                1665

Val Val Ser Val Tyr Ala Gln Asn Pro Ser Gly Glu Ser Gln Pro
    1670                1675                1680

Leu Val Gln Thr Ala Val Thr Asn Ile Asp Arg Pro Lys Gly Leu
    1685                1690                1695

Ala Phe Thr Asp Val Asp Val Asp Ser Ile Lys Ile Ala Trp Glu
    1700                1705                1710

Ser Pro Gln Gly Gln Val Ser Arg Tyr Arg Val Thr Tyr Ser Ser
    1715                1720                1725

Pro Glu Asp Gly Ile His Glu Leu Phe Pro Ala Pro Asp Gly Glu
    1730                1735                1740

Glu Asp Thr Ala Glu Leu Gln Gly Leu Arg Pro Gly Ser Glu Tyr
    1745                1750                1755

Thr Val Ser Val Val Ala Leu His Asp Asp Met Glu Ser Gln Pro
    1760                1765                1770

Leu Ile Gly Thr Gln Ser Thr Ala Ile Pro Ala Pro Thr Asp Leu
    1775                1780                1785
```

```
Lys Phe Thr Gln Val Thr Pro Thr Ser Leu Ser Ala Gln Trp Thr
    1790                1795                1800

Pro Pro Asn Val Gln Leu Thr Gly Tyr Arg Val Arg Val Thr Pro
    1805                1810                1815

Lys Glu Lys Thr Gly Pro Met Lys Glu Ile Asn Leu Ala Pro Asp
    1820                1825                1830

Ser Ser Ser Val Val Val Ser Gly Leu Met Val Ala Thr Lys Tyr
    1835                1840                1845

Glu Val Ser Val Tyr Ala Leu Lys Asp Thr Leu Thr Ser Arg Pro
    1850                1855                1860

Ala Gln Gly Val Val Thr Thr Leu Glu Asn Val Ser Pro Pro Arg
    1865                1870                1875

Arg Ala Arg Val Thr Asp Ala Thr Glu Thr Thr Ile Thr Ile Ser
    1880                1885                1890

Trp Arg Thr Lys Thr Glu Thr Ile Thr Gly Phe Gln Val Asp Ala
    1895                1900                1905

Val Pro Ala Asn Gly Gln Thr Pro Ile Gln Arg Thr Ile Lys Pro
    1910                1915                1920

Asp Val Arg Ser Tyr Thr Ile Thr Gly Leu Gln Pro Gly Thr Asp
    1925                1930                1935

Tyr Lys Ile Tyr Leu Tyr Thr Leu Asn Asp Asn Ala Arg Ser Ser
    1940                1945                1950

Pro Val Val Ile Asp Ala Ser Thr Ala Ile Asp Ala Pro Ser Asn
    1955                1960                1965

Leu Arg Phe Leu Ala Thr Thr Pro Asn Ser Leu Leu Val Ser Trp
    1970                1975                1980

Gln Pro Pro Arg Ala Arg Ile Thr Gly Tyr Ile Ile Lys Tyr Glu
    1985                1990                1995

Lys Pro Gly Ser Pro Pro Arg Glu Val Val Pro Arg Pro Arg Pro
    2000                2005                2010

Gly Val Thr Glu Ala Thr Ile Thr Gly Leu Glu Pro Gly Thr Glu
    2015                2020                2025

Tyr Thr Ile Tyr Val Ile Ala Leu Lys Asn Asn Gln Lys Ser Glu
    2030                2035                2040

Pro Leu Ile Gly Arg Lys Lys Thr Asp Glu Leu Pro Gln Leu Val
    2045                2050                2055

Thr Leu Pro His Pro Asn Leu His Gly Pro Glu Ile Leu Asp Val
    2060                2065                2070

Pro Ser Thr Val Gln Lys Thr Pro Phe Val Thr His Pro Gly Tyr
    2075                2080                2085

Asp Thr Gly Asn Gly Ile Gln Leu Pro Gly Thr Ser Gly Gln Gln
    2090                2095                2100

Pro Ser Val Gly Gln Gln Met Ile Phe Glu Glu His Gly Phe Arg
    2105                2110                2115

Arg Thr Thr Pro Pro Thr Thr Ala Thr Pro Ile Arg His Arg Pro
    2120                2125                2130

Arg Pro Tyr Pro Pro Asn Val Gly Glu Glu Ile Gln Ile Gly His
    2135                2140                2145

Ile Pro Arg Glu Asp Val Asp Tyr His Leu Tyr Pro His Gly Pro
    2150                2155                2160

Gly Leu Asn Pro Asn Ala Ser Thr Gly Gln Glu Ala Leu Ser Gln
    2165                2170                2175
```

-continued

```
Thr Thr Ile Ser Trp Ala Pro Phe Gln Asp Thr Ser     Glu Tyr Ile
    2180                2185                2190

Ile Ser Cys His Pro Val Gly Thr Asp Glu Glu Pro     Leu Gln Phe
    2195                2200                2205

Arg Val Pro Gly Thr Ser Ser Ala Thr Leu Thr Gly     Leu Thr
    2210                2215                2220

Arg Gly Ala Thr Tyr Asn Val Ile Val Glu Ala Leu     Lys Asp Gln
    2225                2230                2235

Gln Arg His Lys Val Arg Glu Val Val Thr Val Gly     Asn Ser
    2240                2245                2250

Val Asn Glu Gly Leu Asn Gln Pro Thr Asp Asp Ser     Cys Phe Asp
    2255                2260                2265

Pro Tyr Thr Val Ser His Tyr Ala Val Gly Asp Glu     Trp Glu Arg
    2270                2275                2280

Met Ser Glu Ser Gly Phe Lys Leu Leu Cys Gln Cys     Leu Gly Phe
    2285                2290                2295

Gly Ser Gly His Phe Arg Cys Asp Ser Ser Arg Trp     Cys His Asp
    2300                2305                2310

Asn Gly Val Asn Tyr Lys Ile Gly Glu Lys Trp Asp     Arg Gln Gly
    2315                2320                2325

Glu Asn Gly Gln Met Met Ser Cys Thr Cys Leu Gly     Asn Gly Lys
    2330                2335                2340

Gly Glu Phe Lys Cys Asp Pro His Glu Ala Thr Cys     Tyr Asp Asp
    2345                2350                2355

Gly Lys Thr Tyr His Val Gly Glu Gln Trp Gln Lys     Glu Tyr Leu
    2360                2365                2370

Gly Ala Ile Cys Ser Cys Thr Cys Phe Gly Gly Gln     Arg Gly Trp
    2375                2380                2385

Arg Cys Asp Asn Cys Arg Arg Pro Gly Gly Glu Pro     Ser Pro Glu
    2390                2395                2400

Gly Thr Thr Gly Gln Ser Tyr Asn Gln Tyr Ser Gln     Arg Tyr His
    2405                2410                2415

Gln Arg Thr Asn Thr Asn Val Asn Cys Pro Ile Glu     Cys Phe Met
    2420                2425                2430

Pro Leu Asp Val Gln Ala Asp Arg Glu Asp Ser Arg     Glu
    2435                2440                2445

<210> SEQ ID NO 140
<211> LENGTH: 577
<212> TYPE: PRT
<213> ORGANISM: Homo sapiens

<400> SEQUENCE: 140

Gln Ala Gln Gln Met Val Gln Pro Gln Ser Pro Val Ala Val Ser Gln
1               5                   10                  15

Ser Lys Pro Gly Cys Tyr Asp Asn Gly Lys His Tyr Gln Ile Asn Gln
            20                  25                  30

Gln Trp Glu Arg Thr Tyr Leu Gly Asn Ala Leu Val Cys Thr Cys Tyr
        35                  40                  45

Gly Gly Ser Arg Gly Phe Asn Cys Glu Ser Lys Pro Glu Ala Glu Glu
    50                  55                  60

Thr Cys Phe Asp Lys Tyr Thr Gly Asn Thr Tyr Arg Val Gly Asp Thr
65                  70                  75                  80

Tyr Glu Arg Pro Lys Asp Ser Met Ile Trp Asp Cys Thr Cys Ile Gly
                85                  90                  95
```

-continued

```
Ala Gly Arg Gly Arg Ile Ser Cys Thr Ile Ala Asn Arg Cys His Glu
            100                 105                 110

Gly Gly Gln Ser Tyr Lys Ile Gly Asp Thr Trp Arg Pro His Glu
            115                 120                 125

Thr Gly Gly Tyr Met Leu Glu Cys Val Cys Leu Gly Asn Gly Lys Gly
            130                 135                 140

Glu Trp Thr Cys Lys Pro Ile Ala Glu Lys Cys Phe Asp His Ala Ala
145                 150                 155                 160

Gly Thr Ser Tyr Val Val Gly Glu Thr Trp Glu Lys Pro Tyr Gln Gly
                165                 170                 175

Trp Met Met Val Asp Cys Thr Cys Leu Gly Glu Gly Ser Gly Arg Ile
            180                 185                 190

Thr Cys Thr Ser Arg Asn Arg Cys Asn Asp Gln Asp Thr Arg Thr Ser
            195                 200                 205

Tyr Arg Ile Gly Asp Thr Trp Ser Lys Lys Asp Asn Arg Gly Asn Leu
            210                 215                 220

Leu Gln Cys Ile Cys Thr Gly Asn Gly Arg Gly Glu Trp Lys Cys Glu
225                 230                 235                 240

Arg His Thr Ser Val Gln Thr Thr Ser Ser Gly Ser Gly Pro Phe Thr
                245                 250                 255

Asp Val Arg Ala Ala Val Tyr Gln Pro Gln Pro His Pro Gln Pro Pro
            260                 265                 270

Pro Tyr Gly His Cys Val Thr Asp Ser Gly Val Val Tyr Ser Val Gly
            275                 280                 285

Met Gln Trp Leu Lys Thr Gln Gly Asn Lys Gln Met Leu Cys Thr Cys
290                 295                 300

Leu Gly Asn Gly Val Ser Cys Gln Glu Thr Ala Val Thr Gln Thr Tyr
305                 310                 315                 320

Gly Gly Asn Ser Asn Gly Glu Pro Cys Val Leu Pro Phe Thr Tyr Asn
            325                 330                 335

Gly Arg Thr Phe Tyr Ser Cys Thr Thr Glu Gly Arg Gln Asp Gly His
            340                 345                 350

Leu Trp Cys Ser Thr Thr Ser Asn Tyr Glu Gln Asp Gln Lys Tyr Ser
            355                 360                 365

Phe Cys Thr Asp His Thr Val Leu Val Gln Thr Arg Gly Gly Asn Ser
370                 375                 380

Asn Gly Ala Leu Cys His Phe Pro Phe Leu Tyr Asn Asn His Asn Tyr
385                 390                 395                 400

Thr Asp Cys Thr Ser Glu Gly Arg Arg Asp Asn Met Lys Trp Cys Gly
            405                 410                 415

Thr Thr Gln Asn Tyr Asp Ala Asp Gln Lys Phe Gly Phe Cys Pro Met
            420                 425                 430

Ala Ala His Glu Glu Ile Cys Thr Thr Asn Glu Gly Val Met Tyr Arg
            435                 440                 445

Ile Gly Asp Gln Trp Asp Lys Gln His Asp Met Gly His Met Met Arg
            450                 455                 460

Cys Thr Cys Val Gly Asn Gly Arg Gly Glu Trp Thr Cys Ile Ala Tyr
465                 470                 475                 480

Ser Gln Leu Arg Asp Gln Cys Ile Val Asp Asp Ile Thr Tyr Asn Val
                485                 490                 495

Asn Asp Thr Phe His Lys Arg His Glu Glu Gly His Met Leu Asn Cys
            500                 505                 510
```

```
Thr Cys Phe Gly Gln Gly Arg Gly Arg Trp Lys Cys Asp Pro Val Asp
            515                 520                 525

Gln Cys Gln Asp Ser Glu Thr Gly Thr Phe Tyr Gln Ile Gly Asp Ser
530                 535                 540

Trp Glu Lys Tyr Val His Gly Val Arg Tyr Gln Cys Tyr Cys Tyr Gly
545                 550                 555                 560

Arg Gly Ile Gly Glu Trp His Cys Gln Pro Leu Gln Thr Tyr Pro Ser
                565                 570                 575

Ser
```

<210> SEQ ID NO 141
<211> LENGTH: 241
<212> TYPE: PRT
<213> ORGANISM: Homo sapiens

<400> SEQUENCE: 141

```
Gln Ala Gln Gln Met Val Gln Pro Gln Ser Pro Val Ala Val Ser Gln
1               5                   10                  15

Ser Lys Pro Gly Cys Tyr Asp Asn Gly Lys His Tyr Gln Ile Asn Gln
                20                  25                  30

Gln Trp Glu Arg Thr Tyr Leu Gly Asn Ala Leu Val Cys Thr Cys Tyr
            35                  40                  45

Gly Gly Ser Arg Gly Phe Asn Cys Glu Ser Lys Pro Glu Ala Glu Glu
        50                  55                  60

Thr Cys Phe Asp Lys Tyr Thr Gly Asn Thr Tyr Arg Val Gly Asp Thr
65                  70                  75                  80

Tyr Glu Arg Pro Lys Asp Ser Met Ile Trp Asp Cys Thr Cys Ile Gly
                85                  90                  95

Ala Gly Arg Gly Arg Ile Ser Cys Thr Ile Ala Asn Arg Cys His Glu
            100                 105                 110

Gly Gly Gln Ser Tyr Lys Ile Gly Asp Thr Trp Arg Arg Pro His Glu
        115                 120                 125

Thr Gly Gly Tyr Met Leu Glu Cys Val Cys Leu Gly Asn Gly Lys Gly
130                 135                 140

Glu Trp Thr Cys Lys Pro Ile Ala Glu Lys Cys Phe Asp His Ala Ala
145                 150                 155                 160

Gly Thr Ser Tyr Val Val Gly Glu Thr Trp Glu Lys Pro Tyr Gln Gly
                165                 170                 175

Trp Met Met Val Asp Cys Thr Cys Leu Gly Glu Gly Ser Gly Arg Ile
            180                 185                 190

Thr Cys Thr Ser Arg Asn Arg Cys Asn Asp Gln Asp Thr Arg Thr Ser
        195                 200                 205

Tyr Arg Ile Gly Asp Thr Trp Ser Lys Lys Asp Asn Arg Gly Asn Leu
210                 215                 220

Leu Gln Cys Ile Cys Thr Gly Asn Gly Arg Gly Glu Trp Lys Cys Glu
225                 230                 235                 240

Arg
```

<210> SEQ ID NO 142
<211> LENGTH: 336
<212> TYPE: PRT
<213> ORGANISM: Homo sapiens

<400> SEQUENCE: 142

```
His Thr Ser Val Gln Thr Thr Ser Ser Gly Ser Gly Pro Phe Thr Asp
1               5                   10                  15
```

Val Arg Ala Ala Val Tyr Gln Pro Gln Pro His Pro Gln Pro Pro
            20                  25                  30

Tyr Gly His Cys Val Thr Asp Ser Gly Val Val Tyr Ser Val Gly Met
        35                  40                  45

Gln Trp Leu Lys Thr Gln Gly Asn Lys Gln Met Leu Cys Thr Cys Leu
 50                  55                  60

Gly Asn Gly Val Ser Cys Gln Glu Thr Ala Val Thr Gln Thr Tyr Gly
 65                  70                  75                  80

Gly Asn Ser Asn Gly Glu Pro Cys Val Leu Pro Phe Thr Tyr Asn Gly
                 85                  90                  95

Arg Thr Phe Tyr Ser Cys Thr Thr Glu Gly Arg Gln Asp Gly His Leu
                100                 105                 110

Trp Cys Ser Thr Thr Ser Asn Tyr Glu Gln Asp Gln Lys Tyr Ser Phe
            115                 120                 125

Cys Thr Asp His Thr Val Leu Val Gln Thr Arg Gly Gly Asn Ser Asn
130                 135                 140

Gly Ala Leu Cys His Phe Pro Phe Leu Tyr Asn Asn His Asn Tyr Thr
145                 150                 155                 160

Asp Cys Thr Ser Glu Gly Arg Arg Asp Asn Met Lys Trp Cys Gly Thr
                165                 170                 175

Thr Gln Asn Tyr Asp Ala Asp Gln Lys Phe Gly Phe Cys Pro Met Ala
                180                 185                 190

Ala His Glu Glu Ile Cys Thr Thr Asn Glu Gly Val Met Tyr Arg Ile
            195                 200                 205

Gly Asp Gln Trp Asp Lys Gln His Asp Met Gly His Met Met Arg Cys
210                 215                 220

Thr Cys Val Gly Asn Gly Arg Gly Glu Trp Thr Cys Ile Ala Tyr Ser
225                 230                 235                 240

Gln Leu Arg Asp Gln Cys Ile Val Asp Asp Ile Thr Tyr Asn Val Asn
                245                 250                 255

Asp Thr Phe His Lys Arg His Glu Glu Gly His Met Leu Asn Cys Thr
                260                 265                 270

Cys Phe Gly Gln Gly Arg Gly Arg Trp Lys Cys Asp Pro Val Asp Gln
            275                 280                 285

Cys Gln Asp Ser Glu Thr Gly Thr Phe Tyr Gln Ile Gly Asp Ser Trp
290                 295                 300

Glu Lys Tyr Val His Gly Val Arg Tyr Gln Cys Tyr Cys Tyr Gly Arg
305                 310                 315                 320

Gly Ile Gly Glu Trp His Cys Gln Pro Leu Gln Thr Tyr Pro Ser Ser
                325                 330                 335

<210> SEQ ID NO 143
<211> LENGTH: 44
<212> TYPE: PRT
<213> ORGANISM: Homo sapiens

<400> SEQUENCE: 143

Pro Gly Cys Tyr Asp Asn Gly Lys His Tyr Gln Ile Asn Gln Gln Trp
1               5                   10                  15

Glu Arg Thr Tyr Leu Gly Asn Ala Leu Val Cys Thr Cys Tyr Gly Gly
            20                  25                  30

Ser Arg Gly Phe Asn Cys Glu Ser Lys Pro Glu Ala
            35                  40

-continued

```
<210> SEQ ID NO 144
<211> LENGTH: 44
<212> TYPE: PRT
<213> ORGANISM: Homo sapiens

<400> SEQUENCE: 144

Glu Thr Cys Phe Asp Lys Tyr Thr Gly Asn Thr Tyr Arg Val Gly Asp
1               5                   10                  15

Thr Tyr Glu Arg Pro Lys Asp Ser Met Ile Trp Asp Cys Thr Cys Ile
            20                  25                  30

Gly Ala Gly Arg Gly Arg Ile Ser Cys Thr Ile Ala
        35                  40

<210> SEQ ID NO 145
<211> LENGTH: 44
<212> TYPE: PRT
<213> ORGANISM: Homo sapiens

<400> SEQUENCE: 145

Asn Arg Cys His Glu Gly Gly Gln Ser Tyr Lys Ile Gly Asp Thr Trp
1               5                   10                  15

Arg Arg Pro His Glu Thr Gly Gly Tyr Met Leu Glu Cys Val Cys Leu
            20                  25                  30

Gly Asn Gly Lys Gly Glu Trp Thr Cys Lys Pro Ile
        35                  40

<210> SEQ ID NO 146
<211> LENGTH: 46
<212> TYPE: PRT
<213> ORGANISM: Homo sapiens

<400> SEQUENCE: 146

Ala Glu Lys Cys Phe Asp His Ala Ala Gly Thr Ser Tyr Val Val Gly
1               5                   10                  15

Glu Thr Trp Glu Lys Pro Tyr Gln Gly Trp Met Met Val Asp Cys Thr
            20                  25                  30

Cys Leu Gly Glu Gly Ser Gly Arg Ile Thr Cys Thr Ser Arg
        35                  40                  45

<210> SEQ ID NO 147
<211> LENGTH: 45
<212> TYPE: PRT
<213> ORGANISM: Homo sapiens

<400> SEQUENCE: 147

Asn Arg Cys Asn Asp Gln Asp Thr Arg Thr Ser Tyr Arg Ile Gly Asp
1               5                   10                  15

Thr Trp Ser Lys Lys Asp Asn Arg Gly Asn Leu Leu Gln Cys Ile Cys
            20                  25                  30

Thr Gly Asn Gly Arg Gly Glu Trp Lys Cys Glu Arg His
        35                  40                  45

<210> SEQ ID NO 148
<211> LENGTH: 372
<212> TYPE: PRT
<213> ORGANISM: Homo sapiens

<400> SEQUENCE: 148

Met Ala Ala Pro Val Pro Trp Ala Cys Cys Ala Val Leu Ala Ala Ala
1               5                   10                  15

Ala Ala Val Val Tyr Ala Gln Arg His Ser Pro Gln Glu Ala Pro His
```

```
            20                  25                  30
Val Gln Tyr Glu Arg Leu Gly Ser Asp Val Thr Leu Pro Cys Gly Thr
            35                  40                  45

Ala Asn Trp Asp Ala Ala Val Thr Trp Arg Val Asn Gly Thr Asp Leu
            50                  55                  60

Ala Pro Asp Leu Leu Asn Gly Ser Gln Leu Val Leu His Gly Leu Glu
 65                  70                  75                  80

Leu Gly His Ser Gly Leu Tyr Ala Cys Phe His Arg Asp Ser Trp His
                    85                  90                  95

Leu Arg His Gln Val Leu Leu His Val Gly Leu Pro Pro Arg Glu Pro
                100                 105                 110

Val Leu Ser Cys Arg Ser Asn Thr Tyr Pro Lys Gly Phe Tyr Cys Ser
                115                 120                 125

Trp His Leu Pro Thr Pro Thr Tyr Ile Pro Asn Thr Phe Asn Val Thr
            130                 135                 140

Val Leu His Gly Ser Lys Ile Met Val Cys Glu Lys Asp Pro Ala Leu
145                 150                 155                 160

Lys Asn Arg Cys His Ile Arg Tyr Met His Leu Phe Ser Thr Ile Lys
                165                 170                 175

Tyr Lys Val Ser Ile Ser Val Ser Asn Ala Leu Gly His Asn Ala Thr
                180                 185                 190

Ala Ile Thr Phe Asp Glu Phe Thr Ile Val Lys Pro Asp Pro Pro Glu
            195                 200                 205

Asn Val Val Ala Arg Pro Val Pro Ser Asn Pro Arg Arg Leu Glu Val
            210                 215                 220

Thr Trp Gln Thr Pro Ser Thr Trp Pro Asp Pro Glu Ser Phe Pro Leu
225                 230                 235                 240

Lys Phe Phe Leu Arg Tyr Arg Pro Leu Ile Leu Asp Gln Trp Gln His
                245                 250                 255

Val Glu Leu Ser Asp Gly Thr Ala His Thr Ile Thr Asp Ala Tyr Ala
            260                 265                 270

Gly Lys Glu Tyr Ile Ile Gln Val Ala Ala Lys Asp Asn Glu Ile Gly
            275                 280                 285

Thr Trp Ser Asp Trp Ser Val Ala Ala His Ala Thr Pro Trp Thr Glu
            290                 295                 300

Glu Pro Arg His Leu Thr Thr Glu Ala Gln Ala Ala Glu Thr Thr Thr
305                 310                 315                 320

Ser Thr Thr Ser Ser Leu Ala Pro Pro Thr Thr Lys Ile Cys Asp
                325                 330                 335

Pro Gly Glu Leu Gly Ser Gly Gly Pro Ser Ala Pro Phe Leu Val
            340                 345                 350

Ser Val Pro Ile Thr Leu Ala Leu Ala Ala Ala Thr Ala Ser
            355                 360                 365

Ser Leu Leu Ile
    370

<210> SEQ ID NO 149
<211> LENGTH: 350
<212> TYPE: PRT
<213> ORGANISM: Homo sapiens

<400> SEQUENCE: 149

Gln Arg His Ser Pro Gln Glu Ala Pro His Val Gln Tyr Glu Arg Leu
 1               5                  10                  15
```

```
Gly Ser Asp Val Thr Leu Pro Cys Gly Thr Ala Asn Trp Asp Ala Ala
            20                  25                  30

Val Thr Trp Arg Val Asn Gly Thr Asp Leu Ala Pro Asp Leu Leu Asn
        35                  40                  45

Gly Ser Gln Leu Val Leu His Gly Leu Glu Leu Gly His Ser Gly Leu
    50                  55                  60

Tyr Ala Cys Phe His Arg Asp Ser Trp His Leu Arg His Gln Val Leu
65                  70                  75                  80

Leu His Val Gly Leu Pro Pro Arg Glu Pro Val Leu Ser Cys Arg Ser
                85                  90                  95

Asn Thr Tyr Pro Lys Gly Phe Tyr Cys Ser Trp His Leu Pro Thr Pro
            100                 105                 110

Thr Tyr Ile Pro Asn Thr Phe Asn Val Thr Val Leu His Gly Ser Lys
        115                 120                 125

Ile Met Val Cys Glu Lys Asp Pro Ala Leu Lys Asn Arg Cys His Ile
    130                 135                 140

Arg Tyr Met His Leu Phe Ser Thr Ile Lys Tyr Lys Val Ser Ile Ser
145                 150                 155                 160

Val Ser Asn Ala Leu Gly His Asn Ala Thr Ala Ile Thr Phe Asp Glu
                165                 170                 175

Phe Thr Ile Val Lys Pro Asp Pro Glu Asn Val Val Ala Arg Pro
            180                 185                 190

Val Pro Ser Asn Pro Arg Arg Leu Glu Val Thr Trp Gln Thr Pro Ser
        195                 200                 205

Thr Trp Pro Asp Pro Glu Ser Phe Pro Leu Lys Phe Phe Leu Arg Tyr
    210                 215                 220

Arg Pro Leu Ile Leu Asp Gln Trp Gln His Val Glu Leu Ser Asp Gly
225                 230                 235                 240

Thr Ala His Thr Ile Thr Asp Ala Tyr Ala Gly Lys Glu Tyr Ile Ile
                245                 250                 255

Gln Val Ala Ala Lys Asp Asn Glu Ile Gly Thr Trp Ser Asp Trp Ser
            260                 265                 270

Val Ala Ala His Ala Thr Pro Trp Thr Glu Glu Pro Arg His Leu Thr
        275                 280                 285

Thr Glu Ala Gln Ala Ala Glu Thr Thr Thr Ser Thr Thr Ser Ser Leu
    290                 295                 300

Ala Pro Pro Pro Thr Thr Lys Ile Cys Asp Pro Gly Glu Leu Gly Ser
305                 310                 315                 320

Gly Gly Gly Pro Ser Ala Pro Phe Leu Val Ser Val Pro Ile Thr Leu
                325                 330                 335

Ala Leu Ala Ala Ala Ala Ala Thr Ala Ser Ser Leu Leu Ile
            340                 345                 350

<210> SEQ ID NO 150
<211> LENGTH: 320
<212> TYPE: PRT
<213> ORGANISM: Homo sapiens

<400> SEQUENCE: 150

Gln Arg His Ser Pro Gln Glu Ala Pro His Val Gln Tyr Glu Arg Leu
1               5                   10                  15

Gly Ser Asp Val Thr Leu Pro Cys Gly Thr Ala Asn Trp Asp Ala Ala
            20                  25                  30

Val Thr Trp Arg Val Asn Gly Thr Asp Leu Ala Pro Asp Leu Leu Asn
        35                  40                  45
```

Gly Ser Gln Leu Val Leu His Gly Leu Glu Leu Gly His Ser Gly Leu
 50                  55                  60

Tyr Ala Cys Phe His Arg Asp Ser Trp His Leu Arg His Gln Val Leu
 65                  70                  75                  80

Leu His Val Gly Leu Pro Pro Arg Glu Pro Val Leu Ser Cys Arg Ser
                 85                  90                  95

Asn Thr Tyr Pro Lys Gly Phe Tyr Cys Ser Trp His Leu Pro Thr Pro
            100                 105                 110

Thr Tyr Ile Pro Asn Thr Phe Asn Val Thr Val Leu His Gly Ser Lys
        115                 120                 125

Ile Met Val Cys Glu Lys Asp Pro Ala Leu Lys Asn Arg Cys His Ile
130                 135                 140

Arg Tyr Met His Leu Phe Ser Thr Ile Lys Tyr Lys Val Ser Ile Ser
145                 150                 155                 160

Val Ser Asn Ala Leu Gly His Asn Ala Thr Ala Ile Thr Phe Asp Glu
                165                 170                 175

Phe Thr Ile Val Lys Pro Asp Pro Glu Asn Val Val Ala Arg Pro
            180                 185                 190

Val Pro Ser Asn Pro Arg Arg Leu Glu Val Thr Trp Gln Thr Pro Ser
        195                 200                 205

Thr Trp Pro Asp Pro Glu Ser Phe Pro Leu Lys Phe Phe Leu Arg Tyr
210                 215                 220

Arg Pro Leu Ile Leu Asp Gln Trp Gln His Val Glu Leu Ser Asp Gly
225                 230                 235                 240

Thr Ala His Thr Ile Thr Asp Ala Tyr Ala Gly Lys Glu Tyr Ile Ile
                245                 250                 255

Gln Val Ala Ala Lys Asp Asn Glu Ile Gly Thr Trp Ser Asp Trp Ser
            260                 265                 270

Val Ala Ala His Ala Thr Pro Trp Thr Glu Glu Pro Arg His Leu Thr
        275                 280                 285

Thr Glu Ala Gln Ala Ala Glu Thr Thr Thr Ser Thr Thr Ser Ser Leu
290                 295                 300

Ala Pro Pro Pro Thr Thr Lys Ile Cys Asp Pro Gly Glu Leu Gly Ser
305                 310                 315                 320

<210> SEQ ID NO 151
<211> LENGTH: 82
<212> TYPE: PRT
<213> ORGANISM: Homo sapiens

<400> SEQUENCE: 151

Gln Arg His Ser Pro Gln Glu Ala Pro His Val Gln Tyr Glu Arg Leu
1               5                   10                  15

Gly Ser Asp Val Thr Leu Pro Cys Gly Thr Ala Asn Trp Asp Ala Ala
            20                  25                  30

Val Thr Trp Arg Val Asn Gly Thr Asp Leu Ala Pro Asp Leu Leu Asn
        35                  40                  45

Gly Ser Gln Leu Val Leu His Gly Leu Glu Leu Gly His Ser Gly Leu
 50                  55                  60

Tyr Ala Cys Phe His Arg Asp Ser Trp His Leu Arg His Gln Val Leu
 65                  70                  75                  80

Leu His

<210> SEQ ID NO 152

```
<211> LENGTH: 118
<212> TYPE: PRT
<213> ORGANISM: Homo sapiens

<400> SEQUENCE: 152

Pro Pro Arg Glu Pro Val Leu Ser Cys Arg Ser Asn Thr Tyr Pro Lys
1               5                   10                  15

Gly Phe Tyr Cys Ser Trp His Leu Pro Thr Pro Thr Tyr Ile Pro Asn
            20                  25                  30

Thr Phe Asn Val Thr Val Leu His Gly Ser Lys Ile Met Val Cys Glu
        35                  40                  45

Lys Asp Pro Ala Leu Lys Asn Arg Cys His Ile Arg Tyr Met His Leu
50                  55                  60

Phe Ser Thr Ile Lys Tyr Lys Val Ser Ile Ser Val Ser Asn Ala Leu
65                  70                  75                  80

Gly His Asn Ala Thr Ala Ile Thr Phe Asp Glu Phe Thr Ile Val Lys
                85                  90                  95

Pro Asp Pro Pro Glu Asn Val Val Ala Arg Pro Val Pro Ser Asn Pro
            100                 105                 110

Arg Arg Leu Glu Val Thr
            115

<210> SEQ ID NO 153
<211> LENGTH: 81
<212> TYPE: PRT
<213> ORGANISM: Homo sapiens

<400> SEQUENCE: 153

Trp Gln Thr Pro Ser Thr Trp Pro Asp Pro Glu Ser Phe Pro Leu Lys
1               5                   10                  15

Phe Phe Leu Arg Tyr Arg Pro Leu Ile Leu Asp Gln Trp Gln His Val
            20                  25                  30

Glu Leu Ser Asp Gly Thr Ala His Thr Ile Thr Asp Ala Tyr Ala Gly
        35                  40                  45

Lys Glu Tyr Ile Ile Gln Val Ala Ala Lys Asp Asn Glu Ile Gly Thr
50                  55                  60

Trp Ser Asp Trp Ser Val Ala Ala His Ala Thr Pro Trp Thr Glu Glu
65                  70                  75                  80

Pro

<210> SEQ ID NO 154
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 154

His His His His His His
1               5

<210> SEQ ID NO 155
<211> LENGTH: 136
<212> TYPE: PRT
<213> ORGANISM: Homo sapiens

<400> SEQUENCE: 155

Pro Thr Leu Ser Ala Leu Pro Ser Pro Leu Val Thr Ser Gly Lys Ser
1               5                   10                  15
```

-continued

```
Val Thr Leu Leu Cys Gln Ser Arg Ser Pro Met Asp Thr Phe Leu Leu
             20                  25                  30

Ile Lys Glu Arg Ala Ala His Pro Leu Leu His Leu Arg Ser Glu His
         35                  40                  45

Gly Ala Gln Gln His Gln Ala Glu Phe Pro Met Ser Pro Val Thr Ser
     50                  55                  60

Val His Gly Gly Thr Tyr Arg Cys Phe Ser Ser His Gly Phe Ser His
 65                  70                  75                  80

Tyr Leu Leu Ser His Pro Ser Asp Pro Leu Glu Leu Ile Val Ser Gly
                 85                  90                  95

Ser Leu Glu Asp Pro Arg Pro Ser Pro Thr Arg Ser Val Ser Thr Ala
            100                 105                 110

Ala Gly Pro Glu Asp Gln Pro Leu Met Pro Thr Gly Ser Val Pro His
        115                 120                 125

Ser Gly Leu Arg Arg His Trp Glu
    130                 135

<210> SEQ ID NO 156
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
             20                  25                  30

Gly Met Ser Trp Val Arg Gln Ala Pro Gly Lys Gly Leu Glu Trp Val
         35                  40                  45

Ala Thr Ile Ser Ser Gly Gly Thr Tyr Thr Phe Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Trp Leu Leu His Tyr Tyr Ala Met Asp Tyr Trp Gly
            100                 105                 110

Gln Gly Thr Ser Val Thr Val Ser Ser
        115                 120

<210> SEQ ID NO 157
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Glu Val Gln Leu Val Glu Ser Gly Gly Gly Leu Met Gln Pro Gly Gly
1               5                  10                  15

Ser Leu Arg Leu Ser Cys Ala Ala Ser Gly Phe Thr Phe Ser Ser Tyr
             20                  25                  30

Gly Met Ser Trp Val Arg Gln Ala Pro Gly Lys Gly Leu Glu Trp Val
         35                  40                  45
```

Ala Thr Ile Ser Ser Gly Gly Thr Tyr Thr Phe Tyr Pro Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Trp Leu Leu His Tyr Tyr Ala Met Asp Tyr Trp Gly
            100                 105                 110

Gln Gly Thr Ser Val Thr Val Ser Ser
            115                 120

<210> SEQ ID NO 158
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Gly Thr Ile Ser Ser Gly Gly Thr Tyr Thr Phe Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Trp Leu Leu His Tyr Tyr Ala Met Asp Tyr Trp Gly
            100                 105                 110

Gln Gly Thr Leu Val Thr Val Ser Ser
            115                 120

<210> SEQ ID NO 159
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Thr Tyr Thr Phe Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Trp Leu Leu His Tyr Tyr Ala Met Asp Tyr Trp Gly
            100                 105                 110

Gln Gly Thr Leu Val Thr Val Ser Ser
        115                 120

<210> SEQ ID NO 160
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Glu Val Gln Leu Val Glu Ser Gly Gly Gly Leu Met Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Thr Tyr Thr Phe Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Trp Leu Leu His Tyr Tyr Ala Met Asp Tyr Trp Gly
            100                 105                 110

Gln Gly Thr Leu Val Thr Val Ser Ser
        115                 120

<210> SEQ ID NO 161
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asp Ile Gln Leu Thr Gln Ser Pro Ser Phe Leu Ser Ala Ser Val Gly
1               5                   10                  15

Asp Arg Val Thr Ile Thr Cys Arg Pro Ser Glu Ser Val Asp Ser Phe
            20                  25                  30

Gly Asn Ser Phe Met His Trp Phe Gln Gln Lys Pro Gly Lys Ala Pro
        35                  40                  45

Lys Leu Leu Ile Tyr Leu Ser Ser Lys Leu Glu Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Glu Asp Phe Ala Thr Tyr Tyr Cys Gln Gln His Asn
                85                  90                  95

Glu Asp Pro Phe Thr Phe Gly Gln Gly Thr Lys Val Glu Ile Lys
            100                 105                 110

<210> SEQ ID NO 162
<211> LENGTH: 118
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Phe Ser Gly Ser Ser Thr Ile Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Asp Gly Arg Gly Ala Met Asp Tyr Trp Gly Gln Gly Thr
            100                 105                 110

Thr Val Thr Val Ser Ser
        115

<210> SEQ ID NO 163
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ser Tyr Ile Phe Ser Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Asp Gly Arg Gly Ala Met Asp Tyr Trp Gly Gln Gly Thr
            100                 105                 110

Leu Val Thr Val Ser Ser
        115

<210> SEQ ID NO 164
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Asp Ile Gln Met Thr Gln Ser Pro Ser Ser Leu Ser Ala Ser Val Gly
1               5                   10                  15
```

-continued

```
Asp Arg Val Thr Ile Thr Cys Arg Ala Ser Gln Asp Ile Ser Lys Phe
            20              25              30

Leu Asn Trp Tyr Gln Gln Lys Pro Gly Lys Ala Pro Lys Leu Leu Ile
        35              40              45

Tyr Tyr Thr Ser Arg Leu His Ser Gly Val Pro Ser Arg Phe Ser Gly
    50              55              60

Ser Gly Ser Gly Thr Asp Phe Thr Phe Thr Ile Ser Ser Leu Gln Pro
65              70              75              80

Glu Asp Ile Ala Thr Tyr Phe Cys Gln Gln Gly Asn Thr Leu Pro Trp
                85              90              95

Thr Phe Gly Gly Gly Thr Lys Leu Glu Ile Lys
            100             105
```

ILT3-BINDING AGENTS AND METHODS OF USE THEREOF

CROSS-REFERENCE TO RELATED APPLICATION

This application claims the benefit of priority of U.S. Provisional Appl. No. 62/950,434, filed Dec. 19, 2019, the contents of which are incorporated by reference herein in its entirety.

SEQUENCE LISTING

The present specification is being filed with a computer readable form (CRF) copy of the Sequence Listing. The CRF entitled 47702-0093001_SL.txt, which was created on Dec. 6, 2020 and is 176,499 bytes in size, is identical to the paper copy of the Sequence Listing and is incorporated herein by reference in its entirety.

FIELD OF THE DISCLOSURE

The present disclosure generally relates to agents that bind immunoglobulin-like transcript 3 (ILT3), particularly antibodies that bind human ILT3, as well as compositions comprising the ILT3-binding agents and methods of using the agents and compositions.

BACKGROUND

The basis for immunotherapy is the manipulation and/or modulation of the immune system, including both innate immune responses and adaptive immune responses. The general aim of immunotherapy is to treat diseases by controlling the immune response to a "foreign agent", for example a pathogen or a tumor cell. However, in some instances, immunotherapy is used to treat autoimmune diseases, which may arise from an abnormal immune response against proteins, molecules, and/or tissues normally present in the body. Immunotherapy may include methods to induce or enhance specific immune responses or to inhibit or reduce specific immune responses.

The immune system is a highly complex system made up of a great number of cell types, including but not limited to, T-cells, B-cells, natural killer cells, antigen-presenting cells, dendritic cells, monocytes, and macrophages. These cells possess complex and subtle systems for controlling their interactions and responses. The cells utilize both activating and inhibitory mechanisms and feedback loops to keep responses in check and not allow negative consequences of an uncontrolled immune response (e.g., autoimmune diseases or a cytokine storm).

Some of the inhibitory mechanisms of the immune system use proteins from the leukocyte Ig-like receptor (LILR) family. The leukocyte Ig-like receptor subfamily B (LILRB) is a group of type I transmembrane glycoproteins with extracellular Ig-like domains and cytoplasmic immunoreceptor tyrosine-based inhibitory motifs (ITIMs). This group of ITIM-containing receptors includes 5 members: LILRB1 (also known as CD85J, LIR1, ILT2), LILRB2 (also known as CD85D, LIR2, ILT4), LILRB3 (also known as CD85A, LIR3, ILT5), LILRB4 (also known as CD85K, LIR5, ILT3), and LILRB5 (also known as CD85C, LIRE). The biological functions and clinical significance of many of these LILRBs (ILTs) are still being investigated.

The concept of cancer immunosurveillance is based on the theory that the immune system can recognize tumor cells, mount an immune response, and suppress the development and/or growth of a tumor. However, it is clear that many cancerous cells have developed mechanisms and/or hijacked normal inhibitory mechanisms to evade the immune system which can allow for uninhibited growth of tumors. Cancer/tumor immunotherapy (immuno-oncology) focuses on the development of new and novel agents that can activate and/or boost the immune system to achieve a more effective attack against cancer/tumor cells resulting in increased killing of cancer/tumor cells and/or inhibition of cancer/tumor growth.

BRIEF SUMMARY

The present disclosure provides agents that bind immunoglobulin-like transcript 3 (ILT3). Although the LILRB family members are referred to by many names in publications, the term "ILT3" (LILRB4) will be used herein. The agents include, but are not limited to, polypeptides such as antibodies that specifically bind ILT3. The agents may be referred to herein as "ILT3-binding agents". The disclosure provides methods of making and of using an ILT3-binding agent. In some embodiments, an ILT3-binding agent inhibits ILT3 activity. In some embodiments, an ILT3-binding agent enhances an immune response. In some embodiments, an ILT3-binding agent reverses suppression of an immune cell. In some embodiments, an ILT3-binding agent is used in a combination therapy. In some embodiments, an ILT3-binding agent is used in combination with at least one additional therapeutic agent.

The disclosure also provides compositions comprising the ILT3-binding agents described herein. In some embodiments, the disclosure provides pharmaceutical compositions comprising the ILT3-binding agents described herein. Polynucleotides and/or vectors encoding the ILT3-binding agents are provided. Cells comprising the polynucleotides and/or the vectors described herein are also provided. Cells comprising or producing the ILT3-binding agents described herein are provided. Methods of making the binding agents described herein are also provided.

In one aspect, this disclosure features an antibody that binds human ILT3 and inhibits binding of human ILT3 to fibronectin. In some instances, this antibody has one or more (e.g., 1, 2, 3, 4, 5, 6, 7, 8, 9, 10, 11, or 12) of the following properties in any combination or permutation: also binds cyno ILT3; does not bind, or only weakly binds (relative to ILT3), ILT2, ILT4, ILT5, and LILRB5; does not bind, or only weakly binds (relative to ILT3), LILRA1, LILRA2, LILRA4, LILRA5, and LILRA6; is an ILT3 antagonist; inhibits ILT3 activity; inhibits ILT3 signaling in cells that express ILT3; inhibits binding of ILT3 to APOE; inhibits binding of ILT3 to CNTFR; inhibits ILT3-induced suppression of myeloid cells; inhibits ILT3-induced suppression of myeloid cell activity; restores FcR activation in myeloid cells that express ILT3; and restores chemokine production in myeloid cells that express ILT3. In some instances, this antibody has a $K_D$ for human ILT3 of 1 µM to 1 pM, 1 nM to 1 pM, or 100 nM to 1 pM (e.g., as assessed by Biacore). In some instances, this antibody comprises a human IgG1 constant region. In some instances, this antibody comprises a human kappa light chain constant region. In some instances, this antibody comprises a human IgG1 constant region and a human kappa light chain constant region. In certain cases, the human IgG1 constant region comprises one or more mutations that reduce or eliminate Fc effector functions. In certain cases, the human IgG1 constant region comprises a N297G mutation that reduces effector function. In some instances, this antibody is an ILT3-binding antibody fragment.

In one aspect, the present disclosure provides agents that bind ILT3. In some embodiments, an agent binds human ILT3. In some embodiments, an agent binds cynomolgus monkey ("cyno") ILT3. In some embodiments, an agent binds human ILT3 and cyno ILT3. In some embodiments, an agent binds SEQ ID NO:2, SEQ ID NO:3, SEQ ID NO:4, and/or SEQ ID NO:5. In some embodiments, an agent binds SEQ ID NO:7, SEQ ID NO:8, SEQ ID NO:9, and/or SEQ ID NO:10. In some embodiments, an agent is an antibody. In some embodiments, an agent is an antibody that binds human ILT3. In some embodiments, an agent is an antibody that binds cyno ILT3. In some embodiments, an agent is an antibody that binds human ILT3 and cyno ILT3.

In some embodiments, an agent binds within the extracellular domain of ILT3. In some embodiments, an agent binds within amino acids 22-259 of SEQ ID NO:1. In some embodiments, an agent binds within amino acids 27-118 of SEQ ID NO:1. In some embodiments, an agent binds within amino acids 124-218 of SEQ ID NO:1. In some embodiments, an agent binds within amino acids 27-218 of SEQ ID NO:1 In some embodiments, an agent binds within amino acids 124-259 of SEQ ID NO:1 In some embodiments, an agent binds a conformational epitope within the extracellular domain of ILT3. In some embodiments, an agent binds a conformational epitope within one of the Ig-like C2-type domains of ILT3 (e.g., D1 or D2 domain). In some embodiments, an agent binds a conformational epitope within the two Ig-like C2-type domains of ILT3 (D1 and D2 domains). In some embodiments, an agent binds a conformational epitope within the D2-stem region of ILT3. In some embodiment, an agent binds to a conformational epitope located between D1 and D2 domain (e.g., the junction between D1 and D2 domain) of ILT3.

In one aspect, the present disclosure provides agents that bind human ILT3 and have at least one or more of the following properties: (i) binds cyno ILT3; (ii) binds human and cyno ILT3; (iii) does not bind ILT2, ILT4, ILT5, and LILRB5; (iv) does not bind LILRA1, LILRA2, LILRA4, LILRA5, and LILRA6; (v) is an ILT3 antagonist; (vi) inhibits ILT3 activity; (vii) inhibits ILT3 signaling in cells that express ILT3; (viii) inhibits binding of ILT3 to APOE; (ix) inhibits binding of ILT3 to fibronectin; (x) inhibits binding of ILT3 to CNTFR; (xi) inhibits ILT3-induced suppression of myeloid cells; (xii) inhibits ILT3-induced suppression of myeloid cell activity; (xiii) restores FcR activity in myeloid cells that express ILT3; and (xiv) restores or increases chemokine production in myeloid cells that express ILT3. In some embodiments, the myeloid cells are monocytes. In some embodiments, the myeloid cells are macrophages. In some embodiments, the myeloid cells are dendritic cells. In some embodiments, the myeloid cells are tolerogenic dendritic cells. In some embodiments, the myeloid cells are antigen-presenting cells (APCs).

In one aspect, the present disclosure provides agents that specifically bind human ILT3. In some embodiments, the present disclosure provides an ILT3-binding agent (e.g., an antibody), wherein the binding agent comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or SEQ ID NO:29 with one substitution (e.g., of methionine at position 5 to another amino acid (e.g., tyrosine)), and (b) a light chain variable region comprising a light chain variable region CDR1 comprising the amino acid sequence RAS-ESVDSYGNSFMH (SEQ ID NO:30) or SEQ ID NO:30 with one or two substitutions (e.g., of aspartic acid at position 7 to another amino acid (e.g., glutamic acid)) and/or asparagine at position 11 to another amino acid (e.g., serine), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, the ILT3-binding agent comprises heavy and light chain variable region CDRs with amino acid sequences substantially identical to SEQ ID NOs:27-32. In some embodiments, the ILT3-binding agent comprises a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRYTLYAMDY (SEQ ID NO:105), and a light chain variable region comprising a light chain variable region CDR1 comprising the amino acid sequence RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, the ILT3-binding agent comprises heavy and light chain variable region CDRs with amino acid sequences substantially identical to SEQ ID NOs:27, 28, 105, 106, 31 and 32.

In some embodiments, an ILT3-binding agent (e.g., an antibody) comprises: (a) a heavy chain variable region having at least 80% sequence identity to SEQ ID NO:111 (5A7) or SEQ ID NO:123 (Hz5A7.v5); and/or (b) a light chain variable region having at least 80% sequence identity to SEQ ID NO:112 (5A7) or SEQ ID NO:124 (Hz5A7.v5). In some embodiments, an ILT3-binding agent comprises a heavy chain variable region having least 80%, at least 85%, at least 90%, at least 95%, at least 96%, at least 97%, at least 98%, or at least 99% sequence identity to SEQ ID NO:111 and/or a light chain variable region having least 80%, at least 85%, at least 90%, at least 95%, at least 96%, at least 97%, at least 98%, or at least 99% sequence identity to SEQ ID NO:112. In some embodiments, an ILT3-binding agent comprises a heavy chain variable region having least 80%, at least 85%, at least 90%, at least 95%, at least 96%, at least 97%, at least 98%, or at least 99% sequence identity to SEQ ID NO:123 and/or a light chain variable region having least 80%, at least 85%, at least 90%, at least 95%, at least 96%, at least 97%, at least 98%, or at least 99% sequence identity to SEQ ID NO:124. In some embodiments, an ILT3-binding agent comprises a heavy chain variable region of SEQ ID NO:111 and/or a light chain variable region of SEQ ID NO:112. In some embodiments, the ILT3-binding agent comprises a heavy chain variable region of SEQ ID NO:111 and a light chain variable region of SEQ ID NO:112. In some embodiments, an ILT3-binding agent comprises a heavy chain variable region of SEQ ID NO:123 and/or a light chain variable region of SEQ ID NO:124. In some embodiments, an ILT3-binding agent comprises a heavy chain variable region of SEQ ID NO:123 and a light chain variable region of SEQ ID NO:124.

In some embodiments, an ILT3-binding agent (e.g., an antibody) comprises a heavy chain variable region CDR1, CDR2, and CDR3 from the amino acid sequence of SEQ ID NO:111 and/or a light chain variable region CDR1, CDR2, and CDR3 from the amino acid sequence of SEQ ID NO:112. In some embodiments, an ILT3-binding agent comprises a heavy chain variable region CDR1, CDR2, and CDR3 from the amino acid sequence of SEQ ID NO:123 and/or a light chain variable region CDR1, CDR2, and CDR3 from the amino acid sequence of SEQ ID NO:124. In some embodiments, an ILT3-binding agent (e.g., an antibody) comprises a heavy chain variable region CDR1, CDR2, and CDR3 with amino acid sequences substantially identical to CDR1, CDR2, and CDR3 from the amino acid sequence of SEQ ID NO:111 and/or a light chain variable region CDR1, CDR2, and CDR3 with amino acid sequences substantially identical to CDR1, CDR2, and CDR3 from the amino acid sequence of SEQ ID NO:112. In some embodiments, an ILT3-binding agent comprises a heavy chain variable region CDR1, CDR2, and CDR3 with amino acid sequences substantially identical to CDR1, CDR2, and CDR3 from the amino acid sequence of SEQ ID NO:123 and/or a light chain variable region CDR1, CDR2, and CDR3 with amino acid sequences substantially identical to CDR1, CDR2, and CDR3 from the amino acid sequence of SEQ ID NO:124.

In some embodiments, an ILT3-binding agent (e.g., an antibody) comprises a heavy chain variable region comprising a heavy chain variable region CDR1, CDR2, and CDR3 from the amino acid sequence of SEQ ID NO:111 and/or a light chain variable region comprising a light chain variable region CDR1, CDR2, and CDR3 from the amino acid sequence of SEQ ID NO:112. In some embodiments, an ILT3-binding agent comprises a heavy chain variable region comprising a heavy chain variable region CDR1, CDR2, and CDR3 from the amino acid sequence of SEQ ID NO:123 and/or a light chain variable region comprising a light chain variable region CDR1, CDR2, and CDR3 from the amino acid sequence of SEQ ID NO:124. In some embodiments, an ILT3-binding agent (e.g., an antibody) comprises a heavy chain variable region comprising a heavy chain variable region CDR1, CDR2, and CDR3 with amino acid sequences substantially identical to CDR1, CDR2, and CDR3 from the amino acid sequence of SEQ ID NO:111 and/or a light chain variable region comprising a light chain variable region CDR1, CDR2, and CDR3 with amino acid sequences substantially identical to CDR1, CDR2, and CDR3 from the amino acid sequence of SEQ ID NO:112. In some embodiments, an ILT3-binding agent comprises a heavy chain variable region comprising a heavy chain variable region CDR1, CDR2, and CDR3 with amino acid sequences substantially identical to CDR1, CDR2, and CDR3 from the amino acid sequence of SEQ ID NO:123 and/or a light chain variable region comprising a light chain variable region CDR1, CDR2, and CDR3 with amino acid sequences substantially identical to CDR1, CDR2, and CDR3 from the amino acid sequence of SEQ ID NO:124.

In some embodiments, an ILT3-binding agent is an antibody that comprises a heavy chain of SEQ ID NO:126 and/or a light chain of SEQ ID NO:128. In some embodiments, an ILT3-binding agent is an antibody that comprises a heavy chain of SEQ ID NO:126 and a light chain of SEQ ID NO:128. In some embodiments, an ILT3-binding agent is a monoclonal antibody that comprises a heavy chain comprising the amino acid sequence of SEQ ID NO:126 and a light chain comprising the amino acid sequence of SEQ ID NO:128.

In some embodiments, an ILT3-binding agent is an antibody that comprises a heavy chain with the VH CDRs of Hz5A7.v5 and an amino acid sequence at least 70% (e.g., at least 75%, at least 80%, at least 85%, at least 90%, at least 91%, at least 92%, at least 93%, at least 94%, at least 95%, at least 96%, at least 97%, at least 98%, at least 99%) identical to SEQ ID NO:126 and/or a light chain with the VL CDRs of Hz5A7.v5 and an amino acid sequence at least 70% (e.g., at least 75%, at least 80%, at least 85%, at least 90%, at least 91%, at least 92%, at least 93%, at least 94%, at least 95%, at least 96%, at least 97%, at least 98%, at least 99%) identical to SEQ ID NO:128. In some embodiments, an ILT3-binding agent is an antibody that comprises a heavy chain with an amino acid sequence at least 70% (e.g., at least 75%, at least 80%, at least 85%, at least 90%, at least 91%, at least 92%, at least 93%, at least 94%, at least 95%, at least 96%, at least 97%, at least 98%, at least 99%) identical to SEQ ID NO:126 and a light chain with an amino acid sequence at least 70% (e.g., at least 75%, at least 80%, at least 85%, at least 90%, at least 91%, at least 92%, at least 93%, at least 94%, at least 95%, at least 96%, at least 97%, at least 98%, at least 99%) identical to SEQ ID NO:128. In some embodiments, an ILT3-binding agent is a monoclonal antibody that comprises a heavy chain with an amino acid sequence at least 70% (e.g., at least 75%, at least 80%, at least 85%, at least 90%, at least 91%, at least 92%, at least 93%, at least 94%, at least 95%, at least 96%, at least 97%, at least 98%, at least 99%) identical to SEQ ID NO:126 and a light chain with an amino acid sequence at least 70% (e.g., at least 75%, at least 80%, at least 85%, at least 90%, at least 91%, at least 92%, at least 93%, at least 94%, at least 95%, at least 96%, at least 97%, at least 98%, at least 99%) identical to SEQ ID NO:128.

In some embodiments, the heavy chain variable region of Hz48A6, as set forth in any one of SEQ ID NOS:156-160 or the heavy chain variable region of Hz45G10, as set forth in any one of SEQ ID NOS:162-163 is appended to SEQ ID NO:129. In certain embodiments, the heavy chain variable region of Hz48A6, as set forth in any one of SEQ ID NOS:156-160 or the heavy chain variable region of Hz45G10, as set forth in any one of SEQ ID NOS:162-163 is appended to SEQ ID NO:129, except that N297G mutation is introduced in SEQ ID NO:129 to eliminate effector functions.

In some embodiments, the light chain variable region of Hz48A6 as set forth in SEQ ID NO:161 or the light chain variable region of Hz45G10 set forth in SEQ ID NO:164 is appended to SEQ ID NO:135. In other embodiments, the light chain variable region of Hz48A6 as set forth in SEQ ID NO: 161 or the light chain variable region of Hz45G10 set forth in SEQ ID NO: 164 is appended to SEQ ID NO:136.

In some embodiments, an ILT3-binding agent (e.g., an antibody) comprises (a) a heavy chain variable region comprising a heavy chain variable region CDR1 comprising the amino acid sequence GFSLTSYGVH (SEQ ID NO:11), a heavy chain variable region CDR2 comprising the amino acid sequence VIWPGGTINYNSALMS (SEQ ID NO:12), and a heavy chain variable region CDR3 comprising the amino acid sequence DKYDGGWFAY (SEQ ID NO:13), and/or (b) a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16). In some embodiments, the ILT3-binding agent comprises heavy and light chain variable region CDRs with amino acid sequences substantially identical to SEQ ID NOs:11-16.

In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:109 and/or a light chain variable region having at least 80% (e.g., at least 85%, at least 90%, at least 95%, at least 96%, at least 97%, at least 98%, or at least 99%) identity to SEQ ID NO:110. In some embodiments, the ILT3-binding agent comprises a heavy chain variable region of SEQ ID NO:109 and/or a light chain variable region of SEQ ID NO:110. In some embodiments, an ILT3-binding agent comprises a heavy chain variable region of SEQ ID NO:109 and a light chain variable region of SEQ ID NO:110.

In some embodiments, an ILT3-binding agent comprises a heavy chain variable region CDR1, CDR2, and CDR3 from the amino acid sequence of SEQ ID NO:109 and/or a light chain variable region CDR1, CDR2, and CDR3 from the amino acid sequence of SEQ ID NO:110. In some embodiments, an ILT3-binding agent (e.g., an antibody) comprises a heavy chain variable region CDR1, CDR2, and CDR3 with amino acid sequences substantially identical to CDR1, CDR2, and CDR3 from the amino acid sequence of SEQ ID NO:109 and/or a light chain variable region CDR1, CDR2, and CDR3 with amino acid sequences substantially identical to CDR1, CDR2, and CDR3 from the amino acid sequence of SEQ ID NO:110.

In some embodiments, an ILT3-binding agent comprises a heavy chain variable region comprising a heavy chain variable region CDR1, CDR2, and CDR3 from the amino acid sequence of SEQ ID NO:109 and/or a light chain variable region comprising a light chain variable region CDR1, CDR2, and CDR3 from the amino acid sequence of SEQ ID NO:110. In some embodiments, an ILT3-binding agent (e.g., an antibody) comprises a heavy chain variable region comprising a heavy chain variable region CDR1, CDR2, and CDR3 with amino acid sequences substantially identical to CDR1, CDR2, and CDR3 from the amino acid sequence of SEQ ID NO:109 and/or a light chain variable region comprising a light chain variable region CDR1, CDR2, and CDR3 with amino acid sequences substantially identical to CDR1, CDR2, and CDR3 from the amino acid sequence of SEQ ID NO:110.

In some embodiments, an ILT3-binding agent (e.g., an antibody) comprises (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPNNGGTGYNQKFNS (SEQ ID NO:44), and a heavy chain variable region CDR3 comprising the amino acid sequence SPYYDYVGSYAMDY (SEQ ID NO:45), and/or (b) a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48). In some embodiments, the ILT3-binding agent comprises heavy and light chain variable region CDRs with amino acid sequences substantially identical to SEQ ID NOs:43-48.

In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:113 and/or a light chain variable region having at least 80% (e.g., at least 85%, at least 90%, at least 95%, at least 96%, at least 97%, at least 98%, or at least 99%) identity to SEQ ID NO:114. In some embodiments, the ILT3-binding agent comprises a heavy chain variable region of SEQ ID NO:113 and/or a light chain variable region of SEQ ID NO:114. In some embodiments, an ILT3-binding agent comprises a heavy chain variable region of SEQ ID NO:113 and a light chain variable region of SEQ ID NO:114.

In some embodiments, an ILT3-binding agent comprises a heavy chain variable region CDR1, CDR2, and CDR3 from the amino acid sequence of SEQ ID NO:113 and/or a light chain variable region CDR1, CDR2, and CDR3 from the amino acid sequence of SEQ ID NO:114. In some embodiments, an ILT3-binding agent (e.g., an antibody) comprises a heavy chain variable region CDR1, CDR2, and CDR3 with amino acid sequences substantially identical to CDR1, CDR2, and CDR3 from the amino acid sequence of SEQ ID NO:113 and/or a light chain variable region CDR1, CDR2, and CDR3 with amino acid sequences substantially identical to CDR1, CDR2, and CDR3 from the amino acid sequence of SEQ ID NO:114.

In some embodiments, an ILT3-binding agent comprises a heavy chain variable region comprising a heavy chain variable region CDR1, CDR2, and CDR3 from the amino acid sequence of SEQ ID NO:113 and/or a light chain variable region comprising a light chain variable region CDR1, CDR2, and CDR3 from the amino acid sequence of SEQ ID NO:114. In some embodiments, an ILT3-binding agent (e.g., an antibody) comprises a heavy chain variable region comprising a heavy chain variable region CDR1, CDR2, and CDR3 with amino acid sequences substantially identical to CDR1, CDR2, and CDR3 from the amino acid sequence of SEQ ID NO:113 and/or a light chain variable region comprising a light chain variable region CDR1, CDR2, and CDR3 with amino acid sequences substantially identical to CDR1, CDR2, and CDR3 from the amino acid sequence of SEQ ID NO:114.

In some embodiments, an ILT3-binding agent (e.g., an antibody) comprises (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPSNGGTGYNQKFKS (SEQ ID NO:59), and a heavy chain variable region CDR3 comprising the amino acid sequence VPYYDYLYYYAMDY (SEQ ID NO:60), and/or (b) a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63). In some embodiments, the ILT3-binding agent comprises heavy and light chain variable region CDRs with amino acid sequences substantially identical to SEQ ID NOs:43, 59, 60, 61, 62, and 63.

In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:115 and/or a light chain variable region having at least 80% (e.g., at least 85%, at least 90%, at least 95%, at least 96%, at least 97%, at least 98%, or at least 99%) identity to SEQ ID NO:116. In some embodiments, the ILT3-binding agent comprises a heavy chain variable region of SEQ ID NO:115 and/or a light chain variable region of SEQ ID NO:116. In some embodiments, an ILT3-binding agent comprises a heavy chain variable region of SEQ ID NO:115 and a light chain variable region of SEQ ID NO:116.

In some embodiments, an ILT3-binding agent comprises a heavy chain variable region CDR1, CDR2, and CDR3 from the amino acid sequence of SEQ ID NO:115 and/or a light chain variable region CDR1, CDR2, and CDR3 from the amino acid sequence of SEQ ID NO:116. In some embodiments, an ILT3-binding agent (e.g., an antibody) comprises a heavy chain variable region CDR1, CDR2, and CDR3 with amino acid sequences substantially identical to CDR1, CDR2, and CDR3 from the amino acid sequence of SEQ ID NO:115 and/or a light chain variable region CDR1, CDR2, and CDR3 with amino acid sequences substantially identical to CDR1, CDR2, and CDR3 from the amino acid sequence of SEQ ID NO:116.

In some embodiments, an ILT3-binding agent comprises a heavy chain variable region comprising a heavy chain variable region CDR1, CDR2, and CDR3 from the amino acid sequence of SEQ ID NO:115 and/or a light chain variable region comprising a light chain variable region CDR1, CDR2, and CDR3 from the amino acid sequence of SEQ ID NO:116. In some embodiments, an ILT3-binding agent (e.g., an antibody) comprises a heavy chain variable region comprising a heavy chain variable region CDR1, CDR2, and CDR3 with amino acid sequences substantially identical to CDR1, CDR2, and CDR3 from the amino acid sequence of SEQ ID NO:115 and/or a light chain variable region comprising a light chain variable region CDR1, CDR2, and CDR3 with amino acid sequences substantially identical to CDR1, CDR2, and CDR3 from the amino acid sequence of SEQ ID NO:116.

In some embodiments, an ILT3-binding agent (e.g., an antibody) comprises (a) a heavy chain variable region comprising a heavy chain variable region comprising a heavy chain variable region CDR1 comprising the amino acid sequence GFTFSDYGMH (SEQ ID NO:71), a heavy chain variable region CDR2 comprising the amino acid sequence YIFSGSSTIYYADTVKG (SEQ ID NO:72), and a heavy chain variable region CDR3 comprising the amino acid sequence ADGRGAMDY (SEQ ID NO:73), and/or (b) a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76). In some embodiments, the ILT3-binding agent comprises heavy and light chain variable region CDRs with amino acid sequences substantially identical to SEQ ID NOs:71-76.

In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:117 and/or a light chain variable region having at least 80% (e.g., at least 85%, at least 90%, at least 95%, at least 96%, at least 97%, at least 98%, or at least 99%) identity to SEQ ID NO:118. In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:162 and/or a light chain variable region having at least 80% (e.g., at least 85%, at least 90%, at least 95%, at least 96%, at least 97%, at least 98%, or at least 99%) identity to SEQ ID NO:164. In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:163 and/or a light chain variable region having at least 80% (e.g., at least 85%, at least 90%, at least 95%, at least 96%, at least 97%, at least 98%, or at least 99%) identity to SEQ ID NO:164. In some embodiments, the ILT3-binding agent comprises a heavy chain variable region of SEQ ID NO:117 and/or a light chain variable region of SEQ ID NO:118. In some embodiments, an ILT3-binding agent comprises a heavy chain variable region of SEQ ID NO:117 and a light chain variable region of SEQ ID NO:118. In some embodiments, the ILT3-binding agent comprises a heavy chain variable region of SEQ ID NO:162 and/or a light chain variable region of SEQ ID NO:164. In some embodiments, an ILT3-binding agent comprises a heavy chain variable region of SEQ ID NO:162 and a light chain variable region of SEQ ID NO:164. In some embodiments, the ILT3-binding agent comprises a heavy chain variable region of SEQ ID NO:163 and/or a light chain variable region of SEQ ID NO:164. In some embodiments, an ILT3-binding agent comprises a heavy chain variable region of SEQ ID NO:163 and a light chain variable region of SEQ ID NO:163.

In some embodiments, an ILT3-binding agent comprises a heavy chain variable region CDR1, CDR2, and CDR3 from the amino acid sequence of SEQ ID NO:117 and/or a light chain variable region CDR1, CDR2, and CDR3 from the amino acid sequence of SEQ ID NO:118. In some embodiments, an ILT3-binding agent (e.g., an antibody) comprises a heavy chain variable region CDR1, CDR2, and CDR3 with amino acid sequences substantially identical to CDR1, CDR2, and CDR3 from the amino acid sequence of SEQ ID NO:117 and/or a light chain variable region CDR1, CDR2, and CDR3 with amino acid sequences substantially identical to CDR1, CDR2, and CDR3 from the amino acid sequence of SEQ ID NO:118.

In some embodiments, an ILT3-binding agent comprises a heavy chain variable region comprising a heavy chain variable region CDR1, CDR2, and CDR3 from the amino acid sequence of SEQ ID NO:117 and/or a light chain variable region comprising a light chain variable region CDR1, CDR2, and CDR3 from the amino acid sequence of SEQ ID NO:118. In some embodiments, an ILT3-binding agent (e.g., an antibody) comprises a heavy chain variable region comprising a heavy chain variable region CDR1, CDR2, and CDR3 with amino acid sequences substantially identical to CDR1, CDR2, and CDR3 from the amino acid sequence of SEQ ID NO:117 and/or a light chain variable region comprising a light chain variable region CDR1, CDR2, and CDR3 with amino acid sequences substantially identical to CDR1, CDR2, and CDR3 from the amino acid sequence of SEQ ID NO:118.

In some embodiments, an ILT3-binding agent (e.g., an antibody) comprises (a) a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88), and/or (b) a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91).). In some embodiments, the ILT3-binding agent comprises heavy and light chain variable region CDRs with amino acid sequences substantially identical to SEQ ID NOs:27, 87, 88, 89, 90 and 91.

In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:119 and/or a light chain variable region having at least 80% (e.g., at least 85%, at least 90%, at least 95%, at least 96%, at least 97%, at least 98%, or at least 99%) identity to SEQ ID NO:120. In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:156 and/or a light chain variable region having at least 80% (e.g., at least 85%, at least 90%, at least 95%, at least 96%, at least 97%, at least 98%, or at least 99%) identity to SEQ ID NO:161. In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:157 and/or a light chain variable region having at least 80% (e.g., at least 85%, at least 90%, at least 95%, at least 96%, at least 97%, at least 98%, or at least 99%) identity to SEQ ID NO:161. In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:158 and/or a light chain variable region having at least 80% (e.g., at least 85%, at least 90%, at least 95%, at least 96%, at least 97%, at least 98%, or at least 99%) identity to SEQ ID NO:161. In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:159 and/or a light chain variable region having at least 80% (e.g., at least 85%, at least 90%, at least 95%, at least 96%, at least 97%, at least 98%, or at least 99%) identity to SEQ ID NO:161, In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:160 and/or a light chain variable region having at least 80% (e.g., at least 85%, at least 90%, at least 95%, at least 96%, at least 97%, at least 98%, or at least 99%) identity to SEQ ID NO:161. In some embodiments, the ILT3-binding agent comprises a heavy chain variable region of SEQ ID NO:119 and/or a light chain variable region of SEQ ID NO:120. In some embodiments, an ILT3-binding agent comprises a heavy chain variable region of SEQ ID NO:119 and a light chain variable region of SEQ ID NO:120. In some embodiments, the ILT3-binding agent comprises a heavy chain variable region of SEQ ID NO:156 and/or a light chain variable region of SEQ ID NO:161. In some embodiments, an ILT3-binding agent comprises a heavy chain variable region of SEQ ID NO:156 and a light chain variable region of SEQ ID NO:161. In some embodiments, the ILT3-binding agent comprises a heavy chain variable region of SEQ ID NO:157 and/or a light chain variable region of SEQ ID NO:161. In some embodiments, an ILT3-binding agent comprises a heavy chain variable region of SEQ ID NO:157 and a light chain variable region of SEQ ID NO:161. In some embodiments, the ILT3-binding agent comprises a heavy chain variable region of SEQ ID NO:158 and/or a light chain variable region of SEQ ID NO:161. In some embodiments, an ILT3-binding agent comprises a heavy chain variable region of SEQ ID NO:158 and a light chain variable region of SEQ ID NO:161. In some embodiments, the ILT3-binding agent comprises a heavy chain variable region of SEQ ID NO:159 and/or a light chain variable region of SEQ ID NO:161. In some embodiments, an ILT3-binding agent comprises a heavy chain variable region of SEQ ID NO:159 and a light chain variable region of SEQ ID NO:161. In some embodiments, the ILT3-binding agent comprises a heavy chain variable region of SEQ ID NO:160 and/or a light chain variable region of SEQ ID NO:161. In some embodiments, an ILT3-binding agent comprises a heavy chain variable region of SEQ ID NO:160 and a light chain variable region of SEQ ID NO:161.

In some embodiments, an ILT3-binding agent comprises a heavy chain variable region CDR1, CDR2, and CDR3 from the amino acid sequence of SEQ ID NO:119 and/or a light chain variable region CDR1, CDR2, and CDR3 from the amino acid sequence of SEQ ID NO:120. In some embodiments, an ILT3-binding agent (e.g., an antibody) comprises a heavy chain variable region CDR1, CDR2, and CDR3 with amino acid sequences substantially identical to CDR1, CDR2, and CDR3 from the amino acid sequence of SEQ ID NO:119 and/or a light chain variable region CDR1, CDR2, and CDR3 with amino acid sequences substantially identical to CDR1, CDR2, and CDR3 from the amino acid sequence of SEQ ID NO:120.

In some embodiments, an ILT3-binding agent comprises a heavy chain variable region comprising a heavy chain variable region CDR1, CDR2, and CDR3 from the amino acid sequence of SEQ ID NO:119 and/or a light chain variable region comprising a light chain variable region CDR1, CDR2, and CDR3 from the amino acid sequence of SEQ ID NO:120. In some embodiments, an ILT3-binding agent (e.g., an antibody) comprises a heavy chain variable region comprising a heavy chain variable region CDR1, CDR2, and CDR3 with amino acid sequences substantially identical to CDR1, CDR2, and CDR3 from the amino acid sequence of SEQ ID NO:119 and/or a light chain variable region comprising a light chain variable region CDR1, CDR2, and CDR3 with amino acid sequences substantially identical to CDR1, CDR2, and CDR3 from the amino acid sequence of SEQ ID NO:120.

In some embodiments, an ILT3-binding agent (e.g., an antibody) comprises (a) a heavy chain variable region comprising a heavy chain variable region CDR1 comprising the amino acid sequence GFTFSDYGMH (SEQ ID NO:71), a heavy chain variable region CDR2 comprising the amino acid sequence YISTGIITVYYADTVKG (SEQ ID NO:99), and a heavy chain variable region CDR3 comprising the amino acid sequence ADGRGAMDY (SEQ ID NO:73), and/or (b) a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76). In some embodiments, the ILT3-binding agent comprises heavy and light chain variable region CDRs with amino acid sequences substantially identical to SEQ ID NOs:71, 99, 73, 100, 75, and 76.

In some embodiments, an ILT3-binding agent comprises a heavy chain variable region having at least 80% (e.g., at least 85%, at least 90%, at least 95%, at least 96%, at least 97%, at least 98%, or at least 99%) identity to SEQ ID NO:121 and/or a light chain variable region having at least 80% (e.g., at least 85%, at least 90%, at least 95%, at least 96%, at least 97%, at least 98%, or at least 99%) identity to SEQ ID NO:122. In some embodiments, the ILT3-binding agent comprises a heavy chain variable region of SEQ ID NO:121 and/or a light chain variable region of SEQ ID NO:122. In some embodiments, an ILT3-binding agent comprises a heavy chain variable region of SEQ ID NO:121 and a light chain variable region of SEQ ID NO:122.

In some embodiments, an ILT3-binding agent comprises a heavy chain variable region CDR1, CDR2, and CDR3 from the amino acid sequence of SEQ ID NO:121 and/or a light chain variable region CDR1, CDR2, and CDR3 from the amino acid sequence of SEQ ID NO:122. In some embodiments, an ILT3-binding agent (e.g., an antibody) comprises a heavy chain variable region CDR1, CDR2, and CDR3 with amino acid sequences substantially identical to CDR1, CDR2, and CDR3 from the amino acid sequence of SEQ ID NO:121 and/or a light chain variable region CDR1, CDR2, and CDR3 with amino acid sequences substantially identical to CDR1, CDR2, and CDR3 from the amino acid sequence of SEQ ID NO:122.

In some embodiments, an ILT3-binding agent comprises a heavy chain variable region comprising a heavy chain variable region CDR1, CDR2, and CDR3 from the amino acid sequence of SEQ ID NO:121 and/or a light chain variable region comprising a light chain variable region CDR1, CDR2, and CDR3 from the amino acid sequence of SEQ ID NO:122. In some embodiments, an ILT3-binding agent (e.g., an antibody) comprises a heavy chain variable region comprising a heavy chain variable region CDR1, CDR2, and CDR3 with amino acid sequences substantially identical to CDR1, CDR2, and CDR3 from the amino acid sequence of SEQ ID NO:121 and/or a light chain variable region comprising a light chain variable region CDR1, CDR2, and CDR3 with amino acid sequences substantially identical to CDR1, CDR2, and CDR3 from the amino acid sequence of SEQ ID NO:122.

In another aspect of the disclosure, provided herein is a binding agent (e.g., an antibody) that competes for binding to ILT3 with any of the ILT3-binding agents described herein. In some embodiments, provided herein is an agent that competes for binding to ILT3 with a reference antibody, wherein the reference antibody comprises (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRYTLYAMDY (SEQ ID NO:105), and (b) a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, provided herein is an agent that competes for binding to ILT3 with a reference antibody, wherein the reference antibody comprises (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRYTLYAMDY (SEQ ID NO:105), and (b) a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32) and wherein the agent that competes with the reference antibody comprises: (a) a heavy chain variable region CDR1 comprising the amino acid sequence GFTFSSYGMS (SEQ ID NO:27), a heavy chain variable region CDR2 comprising the amino acid sequence TISGGTYTFYPDSVKG (SEQ ID NO:87), and a heavy chain variable region CDR3 comprising the amino acid sequence RGWLLHYYAMDY (SEQ ID NO:88), and (b) a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91).

In some embodiments of each of the aforementioned aspects and embodiments, as well as other aspects and embodiments described herein, an ILT3-binding agent is an antibody. In some embodiments, the antibody is a monoclonal antibody. In some embodiments, the antibody is a humanized antibody. In some embodiments, the antibody is a human antibody. In some embodiments, the antibody is a chimeric antibody (i.e., the variable regions of the antibody are from one species and the constant region of the antibody is from a different species). In some embodiments, the antibody is a whole or intact antibody. In some embodiments, the antibody is a bispecific antibody or a multispecific antibody. In some embodiments, the antibody is an antibody fragment comprising at least one antigen-binding site. In some embodiments, the antibody or antibody fragment is a Fab, Fab', F(ab')$_2$, Fv, scFv, (scFv)$_2$, single chain antibody, dual variable region antibody, single variable region antibody, linear antibody, diabody, nanobody, or a V region antibody. In some embodiments, the antibody is an IgG antibody. In some embodiments, the antibody is an IgG1 antibody, an IgG2 antibody, an IgG3 antibody, or an IgG4 antibody. In some embodiments, the antibody comprises a kappa light chain. In some embodiments, the antibody comprises a lambda light chain.

In some embodiments of each of the aforementioned aspects and embodiments, as well as other aspects and embodiments described herein, an ILT3-binding agent is attached (either directly or indirectly) to a half-life extending moiety.

In some embodiments of each of the aforementioned aspects and embodiments, as well as other aspects and embodiments described herein, an ILT3-binding agent described herein is an antagonist of ILT3. In some embodiments, an ILT3-binding agent inhibits ILT3 activity. In some embodiments, the ILT3-binding agent is an antagonistic antibody. In some embodiments, the ILT3-binding agent is an antibody that inhibits ILT3-induced immune cell suppression. In some embodiments, the ILT3-binding agent is an antibody that inhibits ILT3-induced myeloid cell suppression. In some embodiments, the ILT3-binding agent is an antibody that reactivates tolerogenic dendritic cells.

In another aspect, the disclosure provides compositions comprising an ILT3-binding agent described herein. In some embodiments, a composition comprises an anti-ILT3 antibody described herein. In some embodiments, a composition comprises a monoclonal anti-ILT3 antibody described herein. In some embodiments, a composition comprises an anti-ILT3 antibody selected from the group consisting of:

3A3, 5A7, Hz5A7.v5, 12A12, 16C5, 45G10, 48A6, Hz45G10, Hz48A6, and 53F10.

In another aspect, the disclosure provides pharmaceutical compositions comprising an ILT3-binding agent described herein and a pharmaceutically acceptable carrier. In some embodiments, a pharmaceutical composition comprises an anti-ILT3 antibody described herein and a pharmaceutically acceptable carrier. In some embodiments, a pharmaceutical composition comprises a monoclonal anti-ILT3 antibody described herein and a pharmaceutically acceptable carrier. In some embodiments, a pharmaceutical composition comprises an anti-ILT3 antibody selected from the group consisting of: 3A3, 5A7, Hz5A7.v5, 12A12, 16C5, 45G10, 48A6, Hz45G10, Hz48A6, and 53F10 and a pharmaceutically acceptable carrier. In some embodiments, a pharmaceutical composition comprises an anti-ILT3 antibody comprising a heavy chain variable region comprising a VHCDR1, a VHCDR2, and a VHCDR3 of an anti-ILT3 antibody selected from the group consisting of: 3A3, 5A7, Hz5A7.v5, 12A12, 16C5, 45G10, 48A6, Hz45G10 (any of the 2 humanized Hz45G10 antibodies described in Example 15), Hz48A6 (any of the 5 humanized Hz48A6 antibodies described in Example 15), and 53F10; and a light chain variable region comprising a VLCDR1, a VLCDR2, and a VLCDR3 of an anti-ILT3 antibody selected from the group consisting of: 3A3, 5A7, Hz5A7.v5, 12A12, 16C5, 45G10, 48A6, Hz45G10 (any of the 2 humanized Hz45G10 antibodies described in Example 15), Hz48A6 (any of the 5 humanized Hz48A6 antibodies described in Example 15), and 53F10; and a pharmaceutically acceptable carrier.

In some embodiments of each of the aforementioned aspects, as well as other aspects and/or embodiments described elsewhere herein, the ILT3-binding agent is isolated. In some embodiments, the ILT3-binding agent is substantially pure.

In another aspect, the disclosure provides polynucleotides comprising one or more polynucleotides that encode an ILT3-binding agent described herein. In some embodiments, the one or more polynucleotide(s) are isolated. In some embodiments, a vector comprises one or more polynucleotides that encode an ILT3-binding agent described herein. In some embodiments, an isolated cell comprises one or more polynucleotide that encode an ILT3-binding agent described herein. In some embodiments, an isolated cell comprises a vector comprising one or more polynucleotides that encode an ILT3-binding agent described herein. In some embodiments, a cell comprises an ILT3-binding agent described herein. In some embodiments, a cell produces an ILT3-binding agent described herein. In some embodiments, the cell is a monoclonal cell line. In some embodiments, the cell is a hybridoma.

In another aspect, the disclosure provides methods of using the ILT3-binding agents described herein. In some embodiments, a method comprises using a composition comprising an ILT3-binding agent described herein. In some embodiments, a method comprises using a pharmaceutical composition comprising an ILT3-binding agent described herein.

In some embodiments, methods of disrupting, inhibiting, or blocking the binding of ILT3 to a ligand and/or binding partner are provided. In some embodiments, a method of disrupting, inhibiting, or blocking the binding of ILT3 to fibronectin in a mixture of cells comprises contacting the cells with an ILT3-binding agent described herein. In some embodiments, a method of disrupting, inhibiting, or blocking the binding of ILT3 to APOE in a mixture of cells comprises contacting the cells with an ILT3-binding agent described herein. In some embodiments, a method of disrupting, inhibiting, or blocking the binding of ILT3 to CNTFR in a mixture of cells comprises contacting the cells with an ILT3-binding agent described herein.

In some embodiments, a method of disrupting, inhibiting, or blocking the binding of ILT3 to fibronectin in a subject comprises administering to the subject an effective amount of an ILT3-binding agent described herein. In some embodiments, a method of disrupting, inhibiting, or blocking the binding of ILT3 to APOE in a subject comprises administering to the subject an effective amount of an ILT3-binding agent described herein. In some embodiments, a method of disrupting, inhibiting, or blocking the binding of ILT3 to CNTFR in a subject comprises administering to the subject an effective amount of an ILT3-binding agent described herein.

In some embodiments, methods of disrupting, inhibiting, or blocking ILT3 activity are provided. In some embodiments, a method of disrupting, inhibiting, or blocking fibronectin-induced ILT3 activity in a mixture of cells comprises contacting the cells with an ILT3-binding agent described herein. In some embodiments, a method of disrupting, inhibiting, or blocking ILT3-induced suppression of myeloid cells comprises contacting the cells with an ILT3-binding agent described herein. In some embodiments, a method of disrupting, inhibiting, or blocking ILT3-induced suppression of myeloid cell activity comprises contacting the cells with an ILT3-binding agent described herein. In some embodiments, a method of disrupting, inhibiting, or blocking ILT3-induced suppression of myeloid cell activity restores FcR activity in the myeloid cells. In some embodiments, a method of disrupting, inhibiting, or blocking ILT3-induced suppression of myeloid activity restores chemokine/cytokine production in the myeloid cells. In some embodiments, a method of disrupting, inhibiting, or blocking ILT3-induced suppression of myeloid cell activity restores the cell proliferation activity. In some embodiments, the myeloid cells are monocytes. In some embodiments, the myeloid cells are macrophages. In some embodiments, the myeloid cells are dendritic cells. In some embodiments, the myeloid cells are tolerogenic dendritic cells. In some embodiments, the myeloid cells are APCs.

In some embodiments, a method of disrupting, inhibiting, or blocking fibronectin-induced ILT3 activity in a subject comprises administering to the subject an effective amount of an ILT3-binding agent described herein. In some embodiments, a method of disrupting, inhibiting, or blocking ILT3-induced suppression of myeloid cells in a subject, comprising administering to the subject an effective amount of an ILT3-binding agent described herein. In some embodiments, a method of disrupting, inhibiting, or blocking ILT3-induced suppression of myeloid cell activity in a subject comprises administering to the subject an effective amount of an ILT3-binding agent described herein. In some embodiments, a method of disrupting, inhibiting, or blocking ILT3-induced suppression of myeloid cell activity in a subject restores FcR activity in myeloid cells, and/or restores chemokine/cytokine production in myeloid cells. In some embodiments, the myeloid cells are monocytes. In some embodiments, the myeloid cells are macrophages. In some embodiments, the myeloid cells are dendritic cells. In some embodiments, the myeloid cells are tolerogenic dendritic cells. In some embodiments, the myeloid cells are antigen-presenting cells (APCs).

In some embodiments, a method of treating cancer in a subject comprises administering to the subject a therapeutically effective amount of an ILT3-binding agent described herein. In some embodiments, administration of an ILT3-binding agent described herein stimulates/activates tumor-associated suppressive myeloid cells, for example, by blocking the interaction between ILT3 and fibronectin, APOE or CNTFR, resulting in an increase of immune responses such as anti-tumor T cell responses, and thus activates immune response against the cancer/tumor in the subject. In some embodiments, administration of an ILT3-binding agent described herein blocks the interaction between ILT3 and fibronectin in a suppressive tumor microenvironment, and reprograms/stimulates myeloid cells such as tolerogenic dendritic cells. As a result, this increases the secretion of T cell-recruiting chemokines by the myeloid cells, and the ability of myeloid cells to induce proliferation and cytokine secretion of T cells in the tumor microenvironment. In some embodiments, the cancer is breast cancer, lung cancer, head and neck cancer, colorectal cancer, prostate cancer, skin cancer, melanoma, stomach cancer, gastric cancer, intestinal cancer, cervical cancer, uterine cancer, endometrial cancer, urinary bladder cancer, brain cancer, esophageal cancer, liver cancer, kidney cancer, or testicular cancer. In some embodiments, the cancer is a pancreatic cancer. In some embodiments, the cancer is an ovarian cancer. In some embodiments, the cancer is a sarcoma. In some embodiments, the cancer is a hematologic cancer. In some embodiments, the cancer is a myelogenous leukemia. In some embodiments, the myelogenous cancer is acute myeloid leukemia (AML). In some embodiments, the myelogenous cancer is a chronic myeloid leukemia. In some embodiments, the cancer is a myelodysplastic syndrome. Myelodysplastic syndromes (MDS) are a group of cancers in which immature blood cells in the bone marrow do not mature and therefore do not become healthy blood cells. In some embodiments, myelodysplastic syndrome develops into AML. In some embodiments, the cancer or the microenvironment where the cancer resides is fibronectin rich. In some embodiments, the cancer or the microenvironment where the cancer resides has higher expression of fibronectin than its non-cancerous counterpart. In some embodiments, the tumor microenvironment of the cancer has increased expression level of fibronectin. In some embodiments, the cancer expresses ILT3. In some embodiments, the cancer is a certain type of B cell leukemia or lymphoma which expresses ILT3.

In some embodiments, a method of inhibiting tumor growth in a subject comprises administering to the subject a therapeutically effective amount of an ILT3-binding agent described herein. In some embodiments, a method of increasing or enhancing an immune response to a tumor or tumor cells in a subject comprises administering to the subject a therapeutically effective amount of an ILT3-binding agent described herein. In some embodiments, a method of activating or enhancing a persistent or long-term immune response to a tumor or tumor cells in a subject comprises administering to the subject a therapeutically effective amount of an ILT3-binding agent described herein. In some embodiments, a method of inhibiting tumor relapse or tumor regrowth in a subject comprises administering to the subject a therapeutically effective amount of an ILT3-binding agent described herein. In some embodiments a method of inducing a persistent or long-term immunity that inhibits tumor relapse or tumor regrowth in a subject comprises administering to the subject a therapeutically effective amount of an ILT3-binding agent described herein. In some embodiments, the tumor is a pancreatic tumor, a breast tumor, a lung tumor, a head and neck tumor, a colorectal tumor, a prostate tumor, a skin tumor, a melanoma tumor, a stomach tumor, a gastric tumor, an intestinal tumor, an ovarian tumor, a cervical tumor, an uterine tumor, an endometrial tumor, a bladder tumor, a brain tumor, an esophageal tumor, a liver tumor, a kidney tumor, a testicular tumor, a sarcoma, or a hematologic tumor. In some embodiments, the tumor arises from Myelodysplastic syndromes. In some embodiments, the tumor expresses ILT3. In some embodiments, the tumor is a certain type of B cell leukemia or lymphoma which expresses ILT3.

In some embodiments, a method of activating myeloid cells, for example, in the tumor microenvironment, in a subject with a tumor comprises administering to the subject a therapeutically effective amount of an ILT3-binding agent described herein. In some embodiments, the myeloid cells are primary dendritic cells or tolerogenic dendritic cells. In some embodiments, the myeloid cells are monocytes or macrophages. In some embodiments, a method of reactivating tolerogenic dendritic cells in a subject comprises administering to the subject a therapeutically effective amount of an ILT3-binding agent described herein. In some embodiments, the tolerogenic dendritic cells are found in the tumor microenvironment.

In yet another aspect, the disclosure provides a method of treating cancer in a human subject. The method comprises administering to the human subject a therapeutically effective amount of the antibody or the pharmaceutical composition described herein. In some cases, the cancer or the microenvironment where the cancer resides is fibronectin rich. In some embodiments, the cancer or the microenvironment where the cancer resides has higher expression of fibronectin than its non-cancerous counterpart. In some embodiments, the tumor microenvironment of the cancer has increased expression level of fibronectin. In some embodiments, the cancer expresses ILT3. In certain cases, the cancer is pancreatic cancer, breast cancer, lung cancer, head and neck cancer, colorectal cancer, prostate cancer, skin cancer, melanoma, stomach cancer, gastric cancer, intestinal cancer, ovarian cancer, cervical cancer, uterine cancer, endometrial cancer, urinary bladder cancer, brain cancer, esophageal cancer, liver cancer, kidney cancer, sarcoma or testicular cancer, a hematologic cancer, myelogenous leukemia, acute myeloid leukemia (AML), chronic myeloid leukemia, or myelodysplastic syndrome.

In some embodiments of any of the methods described herein, the ILT3-binding agent is administered to a subject as part of a combination therapy. In some embodiments, the combination therapy comprises at least one additional therapeutic agent.

In another aspect, the disclosure provides a combination comprising a binding agent or antibody described herein and an anti-PD-1 antibody. In another aspect, the disclosure provides a combination comprising a means for inhibiting the interaction between human ILT-3 and fibronectin and an anti-PD-1 antibody. The means for inhibiting the interaction between ILT-3 and fibronectin is an antibody described herein.

In another aspect, the disclosure features a pharmaceutical composition comprising the antibody described herein, and a pharmaceutically acceptable carrier. Also disclosed is the use of an ILT3-binding agent (e.g., an antibody) described herein in the manufacture of a medicament for the treatment of cancer. In some embodiments, use of an ILT3-binding agent described herein is for treatment of cancer. In some embodiments, use of an ILT3-binding agent described herein is for inhibition of tumor growth.

In another aspect, the disclosure features a pharmaceutical composition comprising a means for inhibiting the interaction between human ILT3 and fibronectin; and a pharmaceutically acceptable carrier. In some instances, the means for inhibiting the interaction between human ILT3 and fibronectin is an anti-human ILT3 antibody. In certain cases, the antibody comprises the VH-CDR1, VH-CDR2, and VH-CDR3 of a heavy chain variable region and the VL-CDR1, VL-CDR2, and VL-CDR3 of a light chain variable region, wherein the heavy chain variable region and the light chain variable region comprises the amino acids sequences respectively in: SEQ ID NOs.:123 and 124; SEQ ID NOs.: 156 and 161; SEQ ID NOs.:157 and 161; SEQ ID NOs.:158 and 161; SEQ ID NOs.:159 and 161; SEQ ID NOs.:160 and 161; SEQ ID NOs.:162 and 164; or SEQ ID NOs.:163 and 164. In some cases, the antibody comprises the VH-CDR1, VH-CDR2, and VH-CDR3 of a heavy chain variable region and the VL-CDR1, VL-CDR2, and VL-CDR3 of a light chain variable region, wherein the heavy chain variable region and the light chain variable region comprises the amino acids sequences respectively in: SEQ ID NOs.:123 and 124; SEQ ID NOs.:156 and 161; SEQ ID NOs.:157 and 161; SEQ ID NOs.:158 and 161; SEQ ID NOs.:159 and 161; SEQ ID NOs.:160 and 161; SEQ ID NOs.:162 and 164; or SEQ ID NOs.:163 and 164.

In some embodiments of each of the aforementioned aspects and embodiments, as well as other aspects and embodiments described herein, the subject is human.

Where aspects or embodiments of the disclosure are described in terms of a Markush group or other grouping of alternatives, the present disclosure encompasses not only the entire group listed as a whole, but also each member of the group individually and all possible subgroups of the main group, and also the main group absent one or more of the group members. The present disclosure also envisages the explicit exclusion of one or more of any of the group members in the claimed disclosure.

DETAILED DESCRIPTION

Figure 1A:
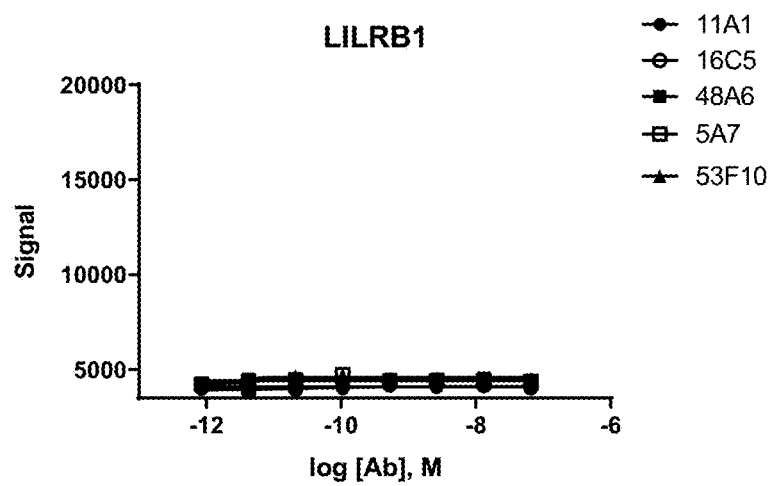
FIG. 1A-1F. Representative results of FACS screening with anti-ILT3 antibodies and LILRB-expressing cells.
Figure 1B:
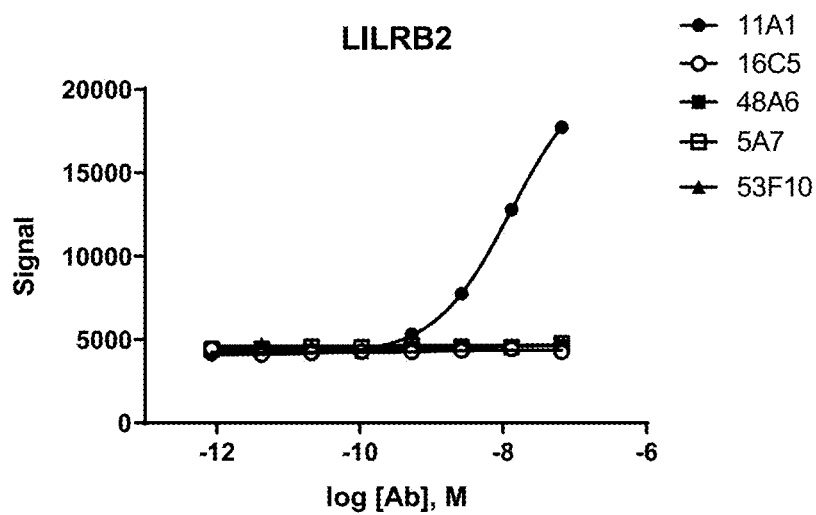
Figure 1C:
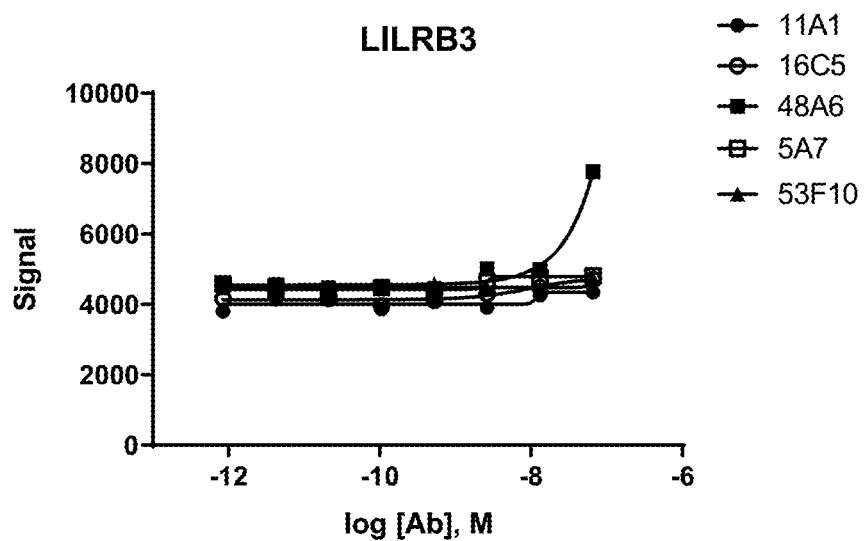
Figure 1D:
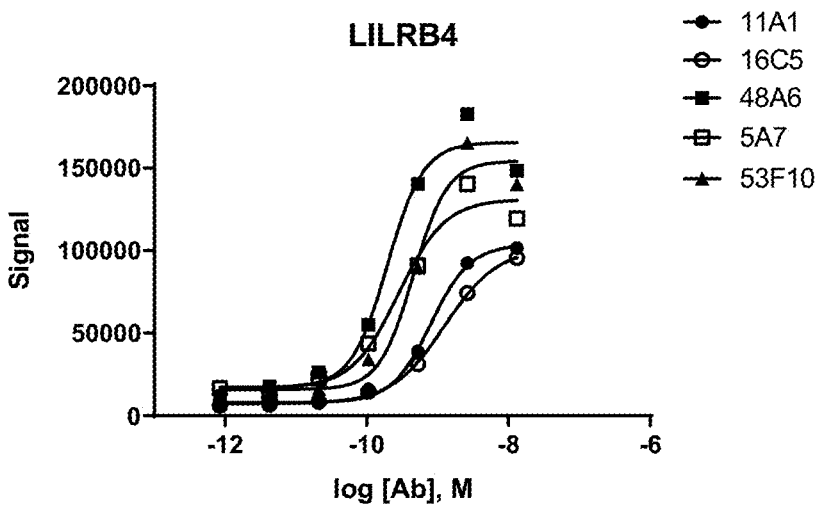
Figure 1E:
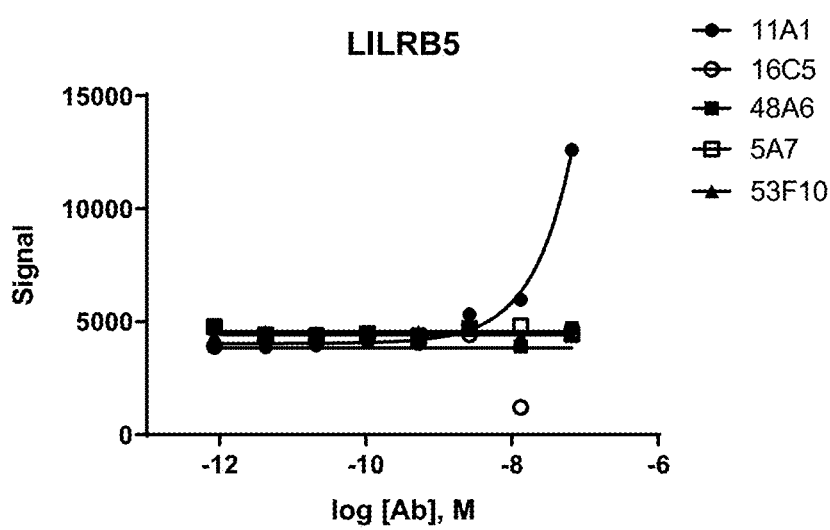
Figure 1F:
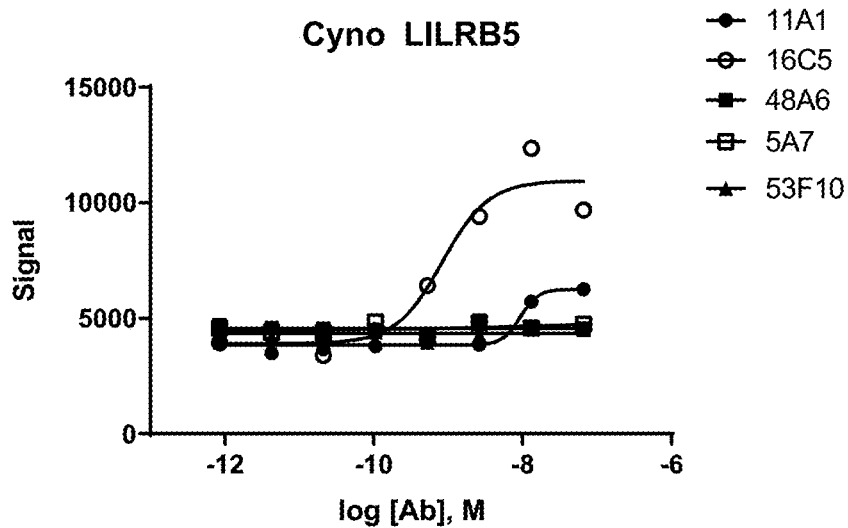
Figure 2A:
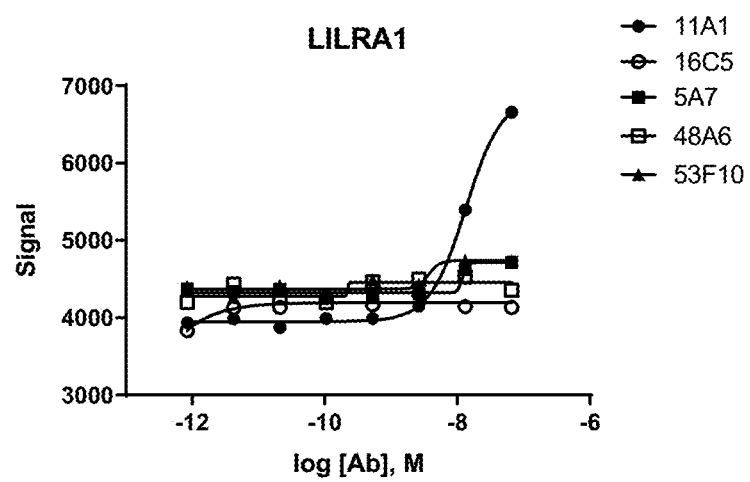
FIG. 2A-2E. Representative results of FACS screening with anti-ILT3 antibodies and LILRA-expressing cells.
Figure 2B:
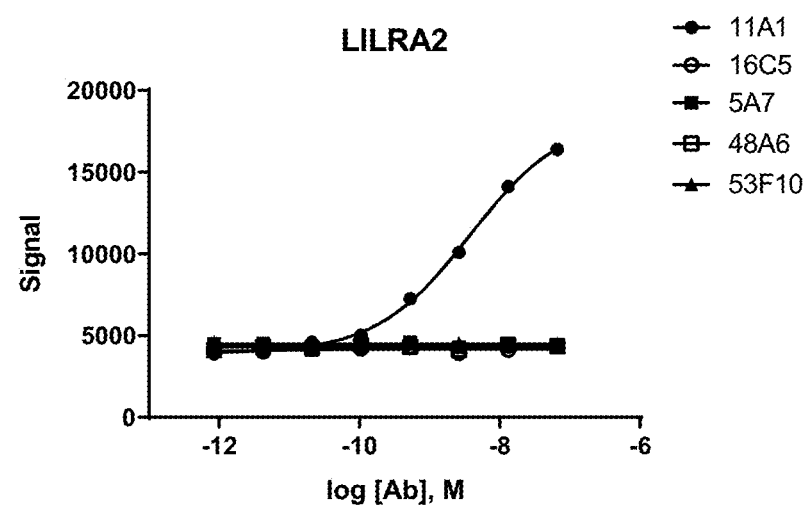
Figure 2C:
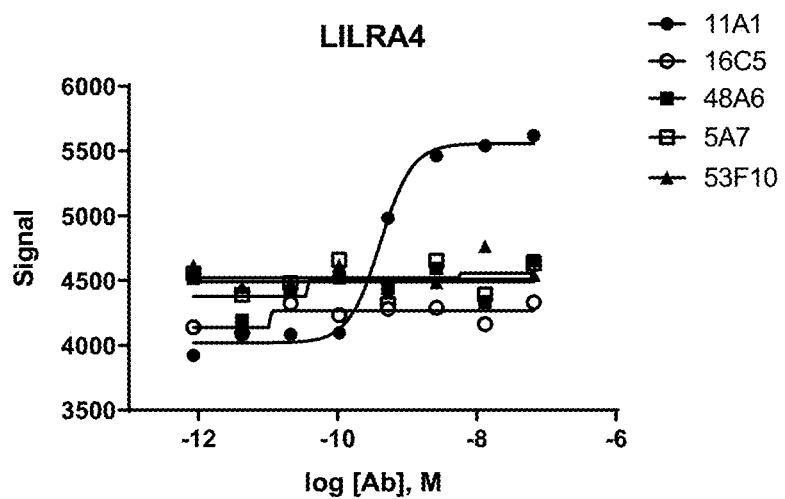
Figure 2D:
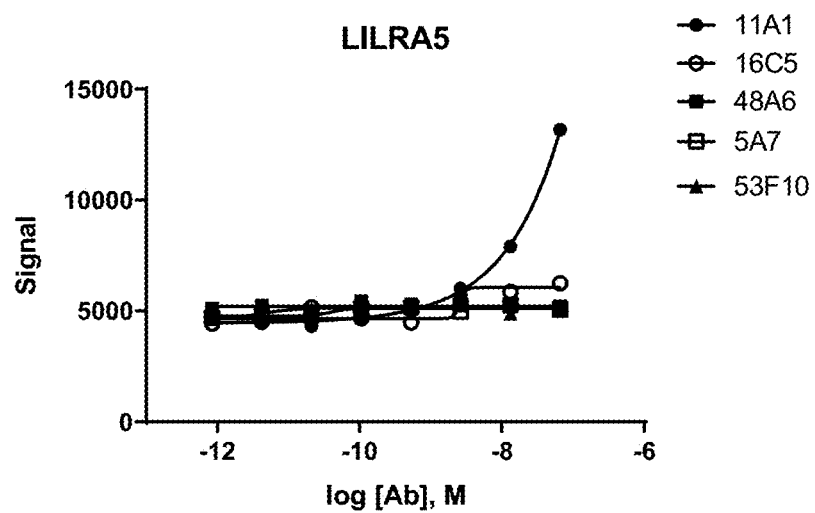
Figure 2E:
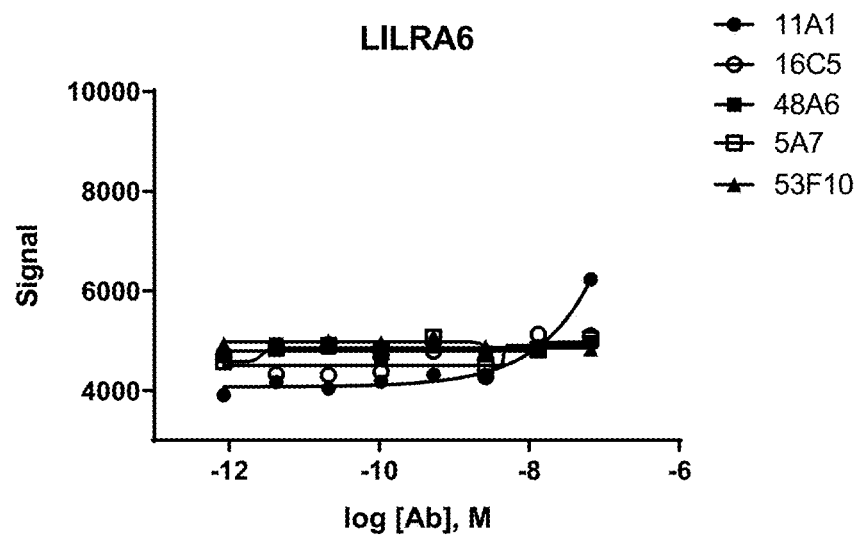

The present disclosure provides novel agents, including but not limited to polypeptides such as antibodies, that bind immunoglobulin-like transcript 3 (ILT3). The ILT3-binding agents include, but are not limited to, polypeptides, antibodies (including antigen-binding fragments thereof), scaffold proteins, and heterodimeric molecules. ILT3-binding agents include, but are not limited to, antagonists of ILT3 activity, inhibitors of ILT3 activity, and/or agents that inhibit ILT3 suppressive activity. Related polypeptides, polynucleotides, vectors, compositions comprising the agents, cells comprising the related polynucleotides or vectors, and methods of making the agents are also provided. Methods of using the novel ILT3-binding agents are also provided.

I. Definitions

In order that the application may be more completely understood, several definitions are set forth below. Such definitions are meant to encompass grammatical equivalents.

The term "antibody" is used in the broadest sense and includes, for example, an intact immunoglobulin, and an antibody fragment containing an antigen binding portion. Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to antibodies or antibody fragments (antibody monomers) that generally are based on the IgG class, which has several subclasses, including, but not limited to IgG1, IgG2, IgG3, and IgG4. In general, IgG1, IgG2 and IgG4 are used more frequently than IgG3. It should be noted that IgGs have different allotypes. All IgGs allotypes can be used for this invention. For example, IgG1 has polymorphisms at 356 (D or E) and 358 (L or M). The sequences depicted herein use the 356E/358M allotype, however, the other allotypes are included herein. As will be appreciated by those in the art, the exact numbering and placement of the Complementary Determining Regions (CDRs) can be different among different numbering systems. However, it should be understood that the disclosure of a variable heavy and/or variable light sequence includes the disclosure of the associated (inherent) CDRs. Accordingly, the disclosure of each variable heavy region (VH) is a disclosure of the VHCDRs (e.g. VHCDR1, VHCDR2 and VHCDR3) and the disclosure of each variable light region (VL) is a disclosure of the VLCDRs (e.g. VLCDR1, VLCDR2 and VLCDR3).

A useful comparison of CDR numbering is as below, see Lafranc et al., Dev. Comp. Immunol. 27(1):55-77 (2003):

|  | Kabat + Chothia | IMGT | Kabat | AbM | Chothia | Contact |
| --- | --- | --- | --- | --- | --- | --- |
| vhCDR1 | 26-35 | 27-38 | 31-35 | 26-35 | 26-32 | 30-35 |
| vhCDR2 | 50-65 | 56-65 | 50-65 | 50-58 | 52-56 | 47-58 |
| vhCDR3 | 95-102 | 105-117 | 95-102 | 95-102 | 95-102 | 93-101 |
| vlCDR1 | 24-34 | 27-38 | 24-34 | 24-34 | 24-34 | 30-36 |
| vlCDR2 | 50-56 | 56-65 | 50-56 | 50-56 | 50-56 | 46-55 |
| vlCDR3 | 89-97 | 105-117 | 89-97 | 89-97 | 89-97 | 89-96 |

"Percent (%) amino acid sequence identity", "Percent (%) sequence identity" or "Percent (%) identity" with respect to a protein sequence is defined as the percentage of amino acid residues in a candidate sequence that are identical with the amino acid residues in the specific (parental) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. One particular program is the ALIGN-2 program outlined at paragraphs [0279] to [0280] of US Pub. No. 20160244525, hereby incorporated by reference. Another approximate alignment for nucleic acid sequences is provided by the local homology algorithm of Smith and Waterman, Advances in Applied Mathematics, 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986).

By "Fc" or "Fc region" or "Fc domain" as used herein is meant the polypeptide comprising the constant region of an antibody excluding the first constant region immunoglobulin domain (e.g., CH1) and in some cases, part of the hinge. For IgG, the Fc domain comprises immunoglobulin domains CH2 and CH3 (Cγ2 and Cγ3) and the lower hinge region between CH1 (Cγ1) and CH2 (Cγ2). Although the boundaries of the Fc region may vary, the human IgG heavy chain Fc region is usually defined to include residues C226 or P230 to its carboxyl-terminus, wherein the numbering is according to the EU index as in Kabat. Accordingly, "CH" domains in the context of IgG are as follows: "CH1" refers to positions 118-215 according to the EU index as in Kabat. "Hinge" refers to positions 216-230 according to the EU index as in Kabat. "CH2" refers to positions 231-340 according to the EU index as in Kabat, and "CH3" refers to positions 341-447 according to the EU index as in Kabat. Thus, the "Fc domain" includes the —CH2-CH3 domain, and optionally a hinge domain (hinge-CH2-CH3). In some embodiments, as is more fully described below, amino acid modifications are made to the Fc region, for example to alter binding to one or more FcγR receptors or to the FcRn receptor.

By "myeloid cells" as used herein refer to any cells having myeloid origin, including but not limited to monocytes, macrophages, and dendritic cells.

By "substantially identical" as used herein with respect to a CDR amino acid sequence refers to at least 1 amino acid modification (e.g., 1, 2, 3, 4, 5, or 6 amino acid modifications) in the CDR sequence, wherein the modification of the CDR sequence in combination with the rest five CDRs (with or without further modifications in any one or more of the five CDRs) do not change the affinity ($K_D$ measured by e.g., SPR technology in a Biacore system) of the resulting antigen binding domain more than 50 folds in comparison to the antigen binding domain comprising the six original CDRs.

II. ILT3-Binding Agents

Amino acid (aa) sequences for human ILT3 (UniProtKB No. Q8NHJ6) and cynomolgus monkey ("cyno") ILT3 (NCBI Ref No. XP_015297198) are provided herein as SEQ ID NO:1 and SEQ ID NO:6, respectively. As used herein, reference to amino acid positions of ILT3 refer to the numbering of amino acid sequences including the signal sequence.

ILT3 is a single pass type I transmembrane protein with a predicted molecular weight of approximately 47 kDa. ILT3 has been observed to be predominantly expressed on myeloid antigen presenting cells, such as normal monocytes, macrophages, and dendritic cells. ILT3 is characterized by an extracellular domain comprising two Ig-like C2 type domains, a transmembrane domain, and a long cytoplasmic domain containing 3 ITIM domains (see, e.g., Cella et al., 1997, *J Exp. Med.*, 185:1743-1751). The two Ig-like C2-type domains may be referred to herein as Domain 1 (D1) and Domain 2 (D2). D1 is situated at the N-terminal portion of the protein and D2 is situated closest to the transmembrane region. As characterized within UniProtKB, human ILT3 is a protein of 448 amino acids (aa)—the signal sequence is aa 1-21, the extracellular domain is aa 22-259, the transmembrane region is aa 260-280, and the cytoplasmic domain is aa 281-448. Within the extracellular domain, D1 is aa 27-188, D2 is aa 124-218, and the "stem region" is aa 219-259. With the cytoplasmic domain, ITIMs are aa 358-363, 410-415, and 440-445.

In some embodiments, an ILT3-binding agent binds ILT3 or a fragment of ILT3. In some embodiments, a fragment of ILT3 comprises the extracellular domain. In some embodiments, a fragment of ILT3 comprises one of the Ig-like C2 type domains (e.g., D1 or D2). In some embodiments, a fragment of ILT3 comprises both of the Ig-like C2 type domains (e.g., D1-D2). In some embodiments, a fragment of ILT3 comprises both of the Ig-like C2 type domains and the stem region (e.g., D1-D2-stem). In some embodiments, a fragment of ILT3 comprises one of the Ig-like C2 type domains and the stem region (e.g., D1-stem or D2-stem). In some embodiments, the extracellular domain of human ILT3 comprises amino acids 22-259 of SEQ ID NO:1. In some embodiments, D1 of human ILT3 comprises amino acids 27-118 of SEQ ID NO:1. In some embodiments, D2 of human ILT3 comprises amino acids 124-218 of SEQ ID NO:1. In some embodiments, D1-D2 of human ILT3 comprises amino acids 27-218 of SEQ ID NO:1. In some embodiments, D1-D2-stem of human ILT3 comprises amino acids 27-259 of SEQ ID NO:1. In some embodiments, D2-stem of human ILT3 comprises amino acids 124-259 of SEQ ID NO:1. In some embodiments, a fragment of human ILT3 comprises the amino acid sequence of SEQ ID NO:3. In some embodiments, a fragment of human ILT3 comprises the amino acid sequence of SEQ ID NO:4. In some embodiments, a fragment of human ILT3 comprises the amino acid sequence of SEQ ID NO:5. In some embodiments, a fragment of human ILT3 comprises the amino acid sequence of SEQ ID NO:4 and SEQ ID NO:5. In some embodiments, the extracellular domain of cyno ILT3 comprises amino acids 22-259 of SEQ ID NO:6. In some embodiments, D1 of cyno ILT3 comprises amino acids 27-118 of SEQ ID NO:6. In some embodiments, D2 of cyno ILT3 comprises amino acids 124-218 of SEQ ID NO:6. In some embodiments, D1-D2 of cyno ILT3 comprises amino acids 27-218 of SEQ ID NO:6. In some embodiments, D1-D2-stem of cyno ILT3 comprises amino acids 27-259 of SEQ ID NO:6. In some embodiments, D2-stem of cyno ILT3 comprises amino acids 124-259 of SEQ ID NO:6. In some embodiments, a fragment of cyno ILT3 comprises the amino acid sequence of SEQ ID NO:8. In some embodiments, a fragment of cyno ILT3 comprises the amino acid sequence of SEQ ID NO:9. In some embodiments, a fragment of cyno ILT3 comprises the amino acid sequence of SEQ ID NO:10. In some embodiments, a fragment of cyno ILT3 comprises the amino acid sequence of SEQ ID NO:9 and SEQ ID NO:10. It is understood that the domains of ILT3 (e.g., human ILT3 or cyno ILT3) may be defined differently by those of skill in the art, therefore the N-terminal amino acids and the C-terminal amino acids of any ILT3 domain or region may vary by 1, 2, 3, 4, 5, or more amino acid residues.

The present disclosure provides agents (e.g., antibodies) that bind ILT3. In some embodiments, an ILT3-binding agent binds a fragment of ILT3. In some embodiments, an ILT3-binding agent binds within a specific region of ILT3. In some embodiments, an ILT3-binding agent binds within the extracellular domain of ILT3. In some embodiments, an ILT3-binding agent binds within the D1 domain of ILT3. In some embodiments, an ILT3-binding agent binds within the D2 domain of ILT3. In some embodiments, an ILT3-binding agent binds within the D2-stem region of ILT3. In some embodiments, an ILT3-binding agent binds within the junction between D1 and D2 domains of ILT3. In some embodiments, an ILT3-binding agent binds an epitope on ILT3. In some embodiments, an ILT3-binding agent binds a conformational epitope on ILT3. In some embodiments, an ILT3-binding agent does not bind other human LILRB proteins (e.g., ILT2, ILT4, ILT5, or LILRB5). In some embodiments, an ILT3-binding agent does not bind human LILRA proteins (e.g., LILRA1, LILRA2, LILRA4, LILRA5, or LILRA6).

In some embodiments, an ILT3-binding agent binds human ILT3. In some embodiments, an ILT3-binding agent binds cyno ILT3. In some embodiments, an ILT3-binding agent binds human ILT3 and cyno ILT3. In some embodiments, an ILT3-binding agent binds SEQ ID NO:1. In some embodiments, an ILT3-binding agent binds SEQ ID NO:2. In some embodiments, an ILT3-binding agent binds within amino acids 22-259 of SEQ ID NO:1. In some embodiments, an ILT3-binding agent binds within amino acids 27-118 of SEQ ID NO:1. In some embodiments, an ILT3-binding agent binds within amino acids 124-218 of SEQ ID NO:1. In some embodiments, an ILT3-binding agent binds within amino acids 124-259 of SEQ ID NO:1. In some embodiments, an ILT3-binding agent binds within amino acids 27-218 of SEQ ID NO:1. In some embodiments, an ILT3-binding agent binds SEQ ID NO:3. In some embodiments, an ILT3-binding agent binds SEQ ID NO:4. In some embodiments, an ILT3-binding agent binds SEQ ID NO:5. In some embodiments, an ILT3-binding agent binds a fragment of ILT3 that comprises SEQ ID NO:4 and SEQ ID NO:5. In some embodiments, an ILT3-binding agent binds SEQ ID NO:6. In some embodiments, an ILT3-binding agent binds SEQ ID NO:7. In some embodiments, an ILT3-binding agent binds within amino acids 22-259 of SEQ ID NO:6. In some embodiments, an ILT3-binding agent binds within amino acids 27-118 of SEQ ID NO:6. In some embodiments, an ILT3-binding agent binds within amino acids 124-218 of SEQ ID NO:6. In some embodiments, an ILT3-binding agent binds within amino acids 27-218 of SEQ ID NO:6. In some embodiments, an ILT3-binding agent binds SEQ ID NO:8. In some embodiments, an ILT3-binding agent binds SEQ ID NO:9. In some embodiments, an ILT3-binding agent binds SEQ ID NO:10. In some embodiments, an ILT3-binding agent binds a fragment of ILT3 that comprises SEQ ID NO:9 and SEQ ID NO:10.

In some embodiments, an ILT3-binding agent binds a polypeptide comprising the amino acid sequence of SEQ ID NO:2. In some embodiments, an ILT3-binding agent binds a polypeptide comprising the amino acid sequence of SEQ ID NO:3. In some embodiments, an ILT3-binding agent binds a polypeptide comprising the amino acid sequence of SEQ ID NO:4. In some embodiments, an ILT3-binding agent binds a polypeptide comprising the amino acid sequence of SEQ ID NO:5. In some embodiments, an ILT3-binding agent binds a polypeptide comprising the amino acid sequence of SEQ ID NO:4 and the amino acid sequence of SEQ ID NO:5. In some embodiments, an ILT3-binding agent binds a polypeptide comprising the amino acid sequence of SEQ ID NO:7. In some embodiments, an ILT3-binding agent binds a polypeptide comprising the amino acid sequence of SEQ ID NO:8. In some embodiments, an ILT3-binding agent binds a polypeptide comprising the amino acid sequence of SEQ ID NO:9. In some embodiments, an ILT3-binding agent binds a polypeptide comprising the amino acid sequence of SEQ ID NO:10.

In some embodiments, an ILT3-binding agent binds a polypeptide comprising the amino acid sequence of SEQ ID NO:9 and the amino acid sequence of SEQ ID NO:10.

In some embodiments, an ILT3-binding agent binds an epitope comprising amino acids within SEQ ID NO:2. In some embodiments, an ILT3-binding agent binds an epitope comprising amino acids within SEQ ID NO:3. In some embodiments, an ILT3-binding agent binds an epitope comprising amino acids within SEQ ID NO:4. In some embodiments, an ILT3-binding agent binds an epitope comprising amino acids within SEQ ID NO:5. In some embodiments, an ILT3-binding agent binds an epitope comprising amino acids within SEQ ID NO:4 and SEQ ID NO:5. In some embodiments, an ILT3-binding agent binds an epitope comprising amino acids within SEQ ID NO:7. In some embodiments, an ILT3-binding agent binds an epitope comprising amino acids within SEQ ID NO:8. In some embodiments, an ILT3-binding agent binds an epitope comprising amino acids within SEQ ID NO:9. In some embodiments, an ILT3-binding agent binds an epitope comprising amino acids within SEQ ID NO:10. In some embodiments, an ILT3-binding agent binds an epitope comprising amino acids within SEQ ID NO:9 and SEQ ID NO:10.

In some embodiments, an ILT3-binding agent binds human ILT3 and has at least one or more of the following properties: (i) binds cyno ILT3; (ii) binds human and cyno ILT3; (iii) does not bind ILT2, ILT4, ILT5, and LILRB5; (iv) does not bind LILRA1, LILRA2, LILRA4, LILRA5, and LILRA6; (v) is an ILT3 antagonist; (vi) inhibits ILT3 activity; (vii) inhibits ILT3 signaling in cells that express ILT3; (viii) inhibits binding of ILT3 to APOE; (ix) inhibits binding of ILT3 to fibronectin; (x) inhibits binding of ILT3 to CNTFR; (xi) inhibits ILT3-induced suppression of myeloid cells; (xii) inhibits ILT3-induced suppression of myeloid cell activity; (xiii) restores FcR activity in myeloid cells that express ILT3; and (xiv) restores the ability of myeloid cells that express ILT3 to respond to chemokines.

In some embodiments, an ILT3-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgG antibody. In some embodiments, the antibody is an IgG1 antibody. In some embodiments, the antibody is an IgG2 antibody. In some embodiments, the antibody is an IgG3 antibody. In some embodiments, the antibody is an IgG4 antibody. In some embodiments, the antibody comprises an IgG heavy chain. In some embodiments, the antibody comprises an IgG1 heavy chain. In some embodiments, the antibody comprises an IgG2 heavy chain. In some embodiments, the antibody comprises an IgG4 heavy chain. In some embodiments, the antibody comprises a kappa light chain. In some embodiments, the antibody comprises a kappa light chain constant region. In some embodiments, the antibody comprises a lambda light chain. In some embodiments, the antibody comprises a lambda light chain constant region. In some embodiments, the antibody is an antibody fragment comprising an antigen-binding site. In some embodiments, the antibody is an scFv. In some embodiments, the antibody is a disulfide-linked scFv. In some embodiments, the antibody is a disulfide-linked sc(Fv)$_2$. In some embodiments, the antibody is a Fab, Fab', or a F(ab)$_2$ antibody. In some embodiments, the antibody is a diabody. In some embodiments, the antibody is a nanobody. In some embodiments, the antibody is a monospecific antibody. In some embodiments, the antibody is a bispecific antibody. In some embodiments, the antibody is a multispecific antibody. In some embodiments, the antibody is a monovalent antibody. In some embodiments, the antibody is a multivalent antibody. In some embodiments, the antibody is a bivalent antibody. In some embodiments, the antibody is a tetravalent antibody.

In some embodiments, the antibody is isolated. In some embodiments, the antibody is substantially pure.

In some embodiments, an ILT3-binding agent is a polyclonal antibody. Polyclonal antibodies can be prepared by any method known to those of skill in the art. In some embodiments, polyclonal antibodies are produced by immunizing an animal (e.g., a rabbit, rat, mouse, goat, donkey) with an antigen of interest (e.g., a purified peptide fragment, a recombinant protein, or a fusion protein) using multiple subcutaneous or intraperitoneal injections. In some embodiments, the antigen is conjugated to a carrier such as keyhole limpet hemocyanin (KLH), serum albumin, bovine thyroglobulin, or soybean trypsin inhibitor. The antigen (with or without a carrier protein) is diluted in sterile saline and usually combined with an adjuvant (e.g., Complete or Incomplete Freund's Adjuvant) to form a stable emulsion. After a period of time, polyclonal antibodies are recovered from the immunized animal (e.g., from blood or ascites). In some embodiments, the polyclonal antibodies are purified from serum or ascites according to standard methods in the art including, but not limited to, affinity chromatography, ion-exchange chromatography, gel electrophoresis, and/or dialysis.

In some embodiments, an ILT3-binding agent is a monoclonal antibody. Monoclonal antibodies can be prepared by any method known to those of skill in the art. In some embodiments, monoclonal antibodies are prepared using hybridoma methods known to one of skill in the art. For example, using a hybridoma method, a mouse, rat, rabbit, hamster, or other appropriate host animal, is immunized as described above. In some embodiments, lymphocytes are immunized in vitro. In some embodiments, the immunizing antigen is a human protein or a fragment thereof. In some embodiments, the immunizing antigen is a mouse protein or a fragment thereof. In some embodiments, the immunizing antigen is a cyno protein or a fragment thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed specifically against a chosen antigen can be identified by a variety of methods including, but not limited to, immunoprecipitation, immunoblotting, and in vitro binding assays (e.g., flow cytometry, FACS, ELISA, SPR (e.g., Biacore), and radioimmunoassay). Once hybridoma cells that produce antibodies of the desired specificity, affinity, and/or activity are identified, the clones may be subcloned by limiting dilution techniques. In some embodiments, high-throughput methods are used to distribute single cell hybridoma cells into plates. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In some embodiments, monoclonal antibodies are made using recombinant DNA techniques as known to one skilled in the art. For example, the polynucleotides encoding an antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as E. coli, simian COS cells, Chinese hamster ovary (CHO) cells, or myeloma cells that do not otherwise produce immunoglobulin proteins.

In some embodiments, recombinant monoclonal antibodies are isolated from phage display libraries expressing variable domains or CDRs of a desired species. Screening of phage libraries can be accomplished by various techniques known in the art.

In some embodiments, a monoclonal antibody is modified by using recombinant DNA technology to generate alternative antibodies. In some embodiments, the constant domains of the light chain and heavy chain of a mouse monoclonal antibody are substituted for constant regions of a human antibody to generate a chimeric antibody. In some embodiments, the constant regions are truncated or removed to generate a desired antibody fragment of a monoclonal antibody. In some embodiments, site-directed or high-density mutagenesis of the variable region(s) is used to optimize specificity and affinity of a monoclonal antibody.

In some embodiments, an ILT3-binding agent is a humanized antibody. Various methods for generating humanized antibodies are known in the art. In some embodiments, a humanized antibody comprises one or more amino acid residues that have been introduced into it from a source that is non-human. In some embodiments, humanization is performed by substituting one or more non-human CDR sequences for the corresponding CDR sequences of a human antibody. In some embodiments, the humanized antibodies are constructed by substituting all six CDRs of a non-human antibody (e.g., a mouse antibody) for the corresponding CDRs of a human antibody.

The choice of which human heavy chain variable region and/or light chain variable region to use for generating humanized antibodies can be made based on a variety of factors and by a variety of methods known in the art. In some embodiments, the "best-fit" method is used where the sequence of the variable region of a non-human (e.g., rodent) antibody is screened against the entire library of known human variable region sequences. The human sequence that is most similar to that of the non-human (e.g., rodent) sequence is selected as the human variable region framework for the humanized antibody. In some embodiments, a particular variable region framework derived from a consensus sequence of all human antibodies of a particular subgroup of light or heavy chains is selected as the variable region framework. In some embodiments, the variable region framework sequence is derived from the consensus sequences of the most abundant human subclasses. In some embodiments, human germline genes are used as the source of the variable region framework sequences.

Other methods for humanization include, but are not limited to, a method called "superhumanization" which is described as the direct transfer of CDRs to a human germline framework, a method termed Human String Content (HSC) which is based on a metric of "antibody humanness", methods based on generation of large libraries of humanized variants (including phage, ribosomal, and yeast display libraries), and methods based on framework region shuffling.

In some embodiments, an ILT3-binding agent is a human antibody. Human antibodies can be prepared using various techniques known in the art. In some embodiments, human antibodies are generated from immortalized human B lymphocytes immunized in vitro. In some embodiments, human antibodies are generated from lymphocytes isolated from an immunized individual. In any case, cells that produce an antibody directed against a target antigen can be generated and isolated. In some embodiments, a human antibody is selected from a phage library, where that phage library expresses human antibodies. Alternatively, phage display technology may be used to produce human antibodies and antibody fragments in vitro, from immunoglobulin variable region gene repertoires from unimmunized human donors. Techniques for the generation and use of antibody phage libraries are well known in the art. Once antibodies are identified, affinity maturation strategies known in the art, including but not limited to, chain shuffling and site-directed mutagenesis, may be employed to generate higher affinity human antibodies. In some embodiments, human antibodies are produced in transgenic mice that contain human immunoglobulin loci. Upon immunization these mice are capable of producing the full repertoire of human antibodies in the absence of endogenous immunoglobulin production.

In some embodiments, an ILT3-binding agent is an antibody fragment. As used herein, the term "antibody fragment" refers to a molecule other than an intact antibody that comprises a portion of an antibody and generally an antigen-binding site. Examples of antibody fragments include, but are not limited to, Fab, Fab', F(ab')2, Fv, single chain antibody molecules (e.g., scFv), disulfide-linked scFv (dsscFv), nanobodies, diabodies, tribodies, tetrabodies, minibodies, dual variable domain antibodies (DVD), single variable domain antibodies (e.g., camelid antibodies), and multispecific antibodies formed from antibody fragments In some embodiments, an ILT3-binding agent is an scFv antibody. In some embodiments, the scFv is a disulfide-linked scFv (dsscFv), which is an scFv comprising an engineered disulfide bond between the light chain variable region and heavy chain variable region of the scFv. In some embodiments, the disulfide bond increases stability of the scFv molecule. In some embodiments, the disulfide bond increases thermostability of the scFv molecule.

In some embodiments, an ILT3-binding agent is an Fv. In some embodiments, an ILT3-binding agent is an Fab. In some embodiments, an ILT3-binding agent is a F(ab')2. In some embodiments, an ILT3-binding agent is a F(ab').

Antibody fragments can be made by various techniques, including but not limited to proteolytic digestion of an intact antibody. The antibody fragments described herein can be produced using recombinant technologies known in the art (e.g., E. coli or phage expression).

In some embodiments, an ILT3-binding agent is a bispecific antibody. Bispecific antibodies are capable of recognizing and binding at least two different antigens or epitopes. In some embodiments, an ILT3-binding agent is a multispecific antibody. Multispecific antibodies are capable of recognizing and binding at least three different antigens or epitopes. The different epitopes can either be within the same molecule (e.g., two or more epitopes on ILT3) or on different molecules (e.g., one epitope on ILT3 and the rest of the epitope(s) on one or more target(s) other than ILT3). In some embodiments, a bispecific or multispecific antibody has enhanced potency as compared to an individual antibody or to a combination of more than one antibody. In some embodiments, a bispecific or multispecific antibody has reduced toxicity as compared to an individual antibody or to a combination of more than one antibody. It is known to those of skill in the art that any therapeutic agent may have unique pharmacokinetics (PK) (e.g., circulating half-life). In some embodiments, a bispecific or multispecific antibody has the ability to synchronize the PK of two or more active binding agents wherein the two or more individual binding agents have different PK profiles. In some embodiments, a bispecific or multispecific antibody has the ability to concentrate the actions of two or more agents in a common area (e.g., tissue) in a subject (e.g., a human). In some embodiments, a bispecific or multispecific antibody has the ability to concentrate the actions of two or more agents to a common target (e.g., a specific cell type). In some embodiments, a bispecific or multispecific antibody has the ability to target the actions of two or more agents to more than one biological pathway or function. In some embodiments, a bispecific or multispecific antibody has the ability to target two or more different cells and bring them closer together.

In some embodiments, a bispecific or multispecific antibody has decreased toxicity and/or side effects. In some embodiments, a bispecific or multispecific antibody has decreased toxicity and/or side effects as compared to a mixture of the two or more individual antibodies or the antibodies as single agents. In some embodiments, a bispecific or multispecific antibody has an increased therapeutic index. In some embodiments, a bispecific or multispecific antibody has an increased therapeutic index as compared to a mixture of the two or more individual antibodies or the antibodies as single agents.

Many techniques for making bispecific or multispecific antibodies are known to those skilled in the art. In some embodiments, a bispecific or multispecific antibody comprises heavy chain constant regions with modifications in the amino acids that are part of the interface between the two heavy chains. These modifications are made to enhance heterodimer formation and generally reduce or eliminate homodimer formation. In some embodiments, the bispecific or multispecific antibody is generated using a knobs-into-holes (KIH) strategy. In some embodiments, the bispecific or multispecific antibody comprises variant hinge regions incapable of forming disulfide linkages between identical heavy chains (e.g., reduce homodimer formation). In some embodiments, the bispecific or multispecific antibody comprises heavy chains with changes in amino acids that result in altered electrostatic interactions. In some embodiments, the bispecific or multispecific antibodies comprise heavy chains with changes in amino acids that result in altered hydrophobic/hydrophilic interactions.

In some embodiments, the Bispecific or multispecific antibodies can be intact antibodies or antibody fragments comprising antigen-binding sites.

In some embodiments, an ILT3-binding agent is an antibody that binds ILT3. In some embodiments, an anti-ILT3 antibody binds human ILT3. In some embodiments, an anti-ILT3 antibody binds cyno ILT3. In some embodiments, an anti-ILT3 antibody binds human ILT3 and cyno ILT3. In some embodiments, an anti-ILT3 antibody binds an ILT3 epitope. In some embodiments, an anti-ILT3 antibody binds an ILT3 epitope within the extracellular domain of human ILT3. In some embodiments, an anti-ILT3 antibody binds an ILT3 epitope within the extracellular domain of cyno ILT3. In some embodiments, an anti-ILT3 antibody binds an epitope comprising at least one amino acid within amino acids 22-259 of SEQ ID NO:1. In some embodiments, an anti-ILT3 antibody binds an epitope comprising at least one amino acid within amino acids 22-120 of SEQ ID NO:1. In some embodiments, an anti-ILT3 antibody binds an epitope comprising at least one amino acid within amino acids 27-118 of SEQ ID NO:1. In some embodiments, an anti-ILT3 antibody binds an epitope comprising at least one amino acid within amino acids 121-259 of SEQ ID NO:1. In some embodiments, an anti-ILT3 antibody binds an epitope comprising at least one amino acid within amino acids 124-218 of SEQ ID NO:1. In some embodiments, an anti-ILT3 antibody binds an epitope comprising at least one amino acid within amino acids 124-259 of SEQ ID NO:1. In some embodiments, an anti-ILT3 antibody binds an epitope comprising amino acids within SEQ ID NO:3. In some embodiments, an anti-ILT3 antibody binds an epitope comprising amino acids within SEQ ID NO:4. In some embodiments, an anti-ILT3 antibody binds an epitope comprising amino acids within SEQ ID NO:5. In some embodiments, an anti-ILT3 antibody binds an epitope comprising amino acids within SEQ ID NO:4 and SEQ ID NO:5. In some embodiments, the epitope is a conformational epitope. In some embodiments, the epitope is a linear epitope.

In some embodiments, an anti-ILT3 antibody competes with a second agent for binding within the extracellular domain of human ILT3. In some embodiments, an anti-ILT3 antibody competes with a second agent for binding within the extracellular domain of cyno ILT3. In some embodiments, an anti-ILT3 antibody competes with a second agent for binding within amino acids 22-259 of SEQ ID NO:1. In some embodiments, an anti-ILT3 antibody competes with a second agent for binding within amino acids 22-120 of SEQ ID NO:1. In some embodiments, an anti-ILT3 antibody competes with a second agent for binding within amino acids 27-118 of SEQ ID NO:1. In some embodiments, an anti-ILT3 antibody competes with a second agent for binding within amino acids 121-259 of SEQ ID NO:1. In some embodiments, an anti-ILT3 antibody competes with a second agent for binding within amino acids 124-218 of SEQ ID NO:1. In some embodiments, an anti-ILT3 antibody competes with a second agent for binding within amino acids 124-259 of SEQ ID NO:1. In some embodiments, an anti-ILT3 antibody competes with a second agent for binding within amino acid sequence SEQ ID NO:3. In some embodiments, an anti-ILT3 antibody competes with a second agent for binding within amino acid sequence SEQ ID NO:4. In some embodiments, an anti-ILT3 antibody competes with a second agent for binding within amino acid sequence SEQ ID NO:5. In some embodiments, an anti-ILT3 antibody competes with a second agent for binding within amino acid sequences SEQ ID NO:4 and SEQ ID NO:5.

In some embodiments, an ILT3-binding agent is an anti-ILT3 antibody described herein. In some embodiments, the ILT3-binding agent is a variant of an anti-ILT3 antibody described herein. In some embodiments, the variant of an ILT3 antibody retain one or more binding characteristics of the ILT3-binding agent described herein. In some embodiments, a variant of an anti-ILT3 antibody comprises one to thirty amino acid substitutions. In some embodiments, a variant of the anti-ILT3 antibody comprises one to twenty-five amino acid substitutions. In some embodiments, a variant of the anti-ILT3 antibody comprises one to twenty amino acid substitutions. In some embodiments, a variant of the anti-ILT3 antibody comprises one to fifteen amino acid substitutions. In some embodiments, a variant of the anti-ILT3 antibody comprises one to ten amino acid substitutions. In some embodiments, a variant of the anti-ILT3 antibody comprises one to five amino acid substitutions. In some embodiments, the variant of the anti-ILT3 antibody comprises one to three amino acid substitutions. In some embodiments, the amino acid substitution(s) is in a CDR of the antibody. In some embodiments, the amino acid substitution(s) is not in a CDR of the antibody. In some embodiments, the amino acid substitution(s) is in a framework region of the antibody. In some embodiments, the amino acid substitution(s) is a conservative amino acid substitution.

In some embodiments, an ILT3-binding agent comprises one or more (e.g., 1, 2, 3, 4, 5, or 6 etc.) amino acid substitutions in a CDR of an antibody described herein while retaining one or more binding characteristics of the ILT3-binding agent described herein. In some embodiments, the amino acid substitutions are conservative substitutions. In some embodiments, a CDR comprises one amino acid substitution. In some embodiments, a CDR comprises two amino acid substitutions. In some embodiments, a CDR comprises three amino acid substitutions. In some embodiments, a CDR comprises four amino acid substitutions. In some embodiments, the CDR is a heavy chain variable region CDR1. In some embodiments, the CDR is a heavy chain variable region CDR2. In some embodiment, the CDR is a heavy chain variable region CDR3. In some embodiments, the CDR is a light chain variable region CDR1. In some embodiments, the CDR is a light chain variable region CDR2. In some embodiments, the CDR is a light chain variable region CDR3. In some embodiments, one or more of such six CDRs have no more than six amino acids substitutions. In some embodiments, the substitutions are made as part of a humanization process. In some embodiments, the substitutions are made as part of a germline humanization process. In some embodiments, the substitutions are made as part of an affinity maturation process. In some embodiments, the substitutions are made as part of an optimization process.

CDRs of an antibody are defined using a variety of methods/systems by those skilled in the art. These systems and/or definitions have been developed and refined over a number of years and include Kabat, Chothia, IMGT, AbM, and Contact. The Kabat definition is based on sequence variability and is commonly used. The Chothia definition is based on the location of the structural loop regions. The IMGT system is based on sequence variability and location within the structure of the variable domain. The AbM definition is a compromise between Kabat and Chothia. The Contact definition is based on analyses of the available antibody crystal structures. An Exemplary system is a combination of Kabat and Chothia. Software programs (e.g., abYsis) are available and known to those of skill in the art for analysis of antibody sequence and determination of CDRs.

The specific CDR sequences defined herein are generally based on a combination of Kabat and Chothia definitions (Exemplary definition). However, it will be understood that reference to a heavy chain variable region CDR or CDRs and/or a light chain variable region CDR or CDRs of a specific antibody will encompass all CDR definitions as known to those of skill in the art.

In some embodiments, an anti-ILT3 antibody described herein comprises the six CDRs of antibody 3A3, 5A7, Hz5A7, 12A12, 16C5, 45G10, 48A6, or 53F10 based on the Kabat definition. In some embodiments, an anti-ILT3 antibody described herein comprises the six CDRs of antibody 3A3, 5A7, Hz5A7, 12A12, 16C5, 45G10, 48A6, or 53F10 based on the Chothia definition. In some embodiments, an anti-ILT3 antibody described herein comprises the six CDRs of antibody 3A3, 5A7, Hz5A7, 12A12, 16C5, 45G10, 48A6, or 53F10 based on the AbM definition. In some embodiments, an anti-ILT3 antibody described herein comprises the six CDRs of antibody 3A3, 5A7, Hz5A7, 12A12, 16C5, 45G10, 48A6, or 53F10 based on the IMGT definition. In some embodiments, an anti-ILT3 antibody described herein comprises the six CDRs of antibody 3A3, 5A7, Hz5A7, 12A12, 16C5, 45G10, 48A6, or 53F10 based on the Contact definition. In some embodiments, an anti-ILT3 antibody described herein comprises the six CDRs of antibody 3A3, 5A7, Hz5A7, 12A12, 16C5, 45G10, 48A6, or 53F10 based on the Exemplary definition.

In some embodiments, an ILT3-binding agent is an anti-ILT3 antibody that comprises one, two, three, four, five, and/or six CDRs of any one of the antibodies described herein. In some embodiments, an anti-ILT3 antibody comprises (i) a heavy chain variable region comprising one, two, and/or three heavy chain variable region CDRs from Table 1, and/or (ii) a light chain variable region comprising one, two, and/or three light chain variable region CDRs from Table 1. In some embodiments, an anti-ILT3 antibody comprises (i) a heavy chain variable region comprising one, two, and/or three heavy chain variable region CDRs from Table 2, and/or (ii) a light chain variable region comprising one, two, and/or three light chain variable region CDRs from Table 2. In some embodiments, an anti-ILT3 antibody comprises (i) a heavy chain variable region comprising one, two, and/or three heavy chain variable region CDRs from Table 3, and/or (ii) a light chain variable region comprising one, two, and/or three light chain variable region CDRs from Table 3. In some embodiments, an anti-ILT3 antibody comprises (i) a heavy chain variable region comprising one, two, and/or three heavy chain variable region CDRs from Table 4, and/or (ii) a light chain variable region comprising one, two, and/or three light chain variable region CDRs from Table 4. In some embodiments, an anti-ILT3 antibody comprises (i) a heavy chain variable region comprising one, two, and/or three heavy chain variable region CDRs from Table 5, and/or (ii) a light chain variable region comprising one, two, and/or three light chain variable region CDRs from Table 5. In some embodiments, an anti-ILT3 antibody comprises (i) a heavy chain variable region comprising one, two, and/or three heavy chain variable region CDRs from Table 6, and/or (ii) a light chain variable region comprising one, two, and/or three light chain variable region CDRs from Table 6. In some embodiments, an anti-ILT3 antibody comprises (i) a heavy chain variable region comprising one, two, and/or three heavy chain variable region CDRs from Table 7, and/or (ii) a light chain variable region comprising one, two, and/or three light chain variable region CDRs from Table 7. In some embodiments, an anti-ILT3 antibody comprises (i) a heavy chain variable region comprising one, two, and/or three heavy chain variable region CDRs from Table 8, and/or (ii) a light chain variable region comprising one, two, and/or three light chain variable region CDRs from Table 8.

In some embodiments, an anti-ILT3 antibody comprises (i) a heavy chain variable region comprising three heavy chain variable region CDRs from Table 1, and (ii) a light chain variable region comprising three light chain variable region CDRs from Table 1. In some embodiments, an anti-ILT3 antibody comprises (i) a heavy chain variable region comprising three heavy chain variable region CDRs from Table 2, and (ii) a light chain variable region comprising three light chain variable region CDRs from Table 2. In some embodiments, an anti-ILT3 antibody comprises (i) a heavy chain variable region comprising three heavy chain variable region CDRs from Table 3, and (ii) a light chain variable region comprising three light chain variable region CDRs from Table 3. In some embodiments, an anti-ILT3 antibody comprises (i) a heavy chain variable region comprising three heavy chain variable region CDRs from Table 4, and (ii) a light chain variable region comprising three light chain variable region CDRs from Table 4. In some embodiments, an anti-ILT3 antibody comprises (i) a heavy chain variable region comprising three heavy chain variable region CDRs from Table 5, and (ii) a light chain variable region comprising three light chain variable region CDRs from Table 5. In some embodiments, an anti-ILT3 antibody comprises (i) a heavy chain variable region comprising three heavy chain variable region CDRs from Table 6, and (ii) a light chain variable region comprising three light chain variable region CDRs from Table 6. In some embodiments, an anti-ILT3 antibody comprises (i) a heavy chain variable region comprising three heavy chain variable region CDRs from Table 7, and (ii) a light chain variable region comprising three light chain variable region CDRs from Table 7. In some embodiments, an anti-ILT3 antibody comprises (i) a heavy chain variable region comprising three heavy chain variable region CDRs from Table 8, and (ii) a light chain variable region comprising three light chain variable region CDRs from Table 8.

TABLE 1

Antibody 3A3 Sequences

| | Exemplary | Chothia | AbM | Kabat | Contact |
|---|---|---|---|---|---|
| Heavy Chain variable region CDR1 | GFSLTSYGVH (SEQ ID NO: 11) | GFSLTSY (SEQ ID NO: 17) | GFSLTSYGVH (SEQ ID NO: 11) | SYGVH (SEQ ID NO: 20) | TSYGVH (SEQ ID NO: 21) |
| Heavy Chain variable region CDR2 | VIWPGGTINYNSALMS (SEQ ID NO: 12) | WPGGT (SEQ ID NO: 18) | VIWPGGTIN (SEQ ID NO: 19) | VIWPGGTINYNSALMS (SEQ ID NO: 12) | WLGVIWPGGTIN (SEQ ID NO: 22) |
| Heavy Chain variable region CDR3 | DKYDGGWFAY (SEQ ID NO: 13) | DKYDGGWFAY (SEQ ID NO: 13) | DKYDGGWFAY (SEQ ID NO: 13) | DKYDGGWFAY (SEQ ID NO: 13) | ASDKYDGGWFA (SEQ ID NO: 23) |
| Light Chain variable region CDR1 | KASQNVRTAVA (SEQ ID NO: 14) | KASQNVRTAVA (SEQ ID NO: 14) | KASQNVRTAVA (SEQ ID NO: 14) | KASQNVRTAVA (SEQ ID NO: 14) | RTAVAWY (SEQ ID NO: 24) |
| Light Chain variable region CDR2 | LASNRHT (SEQ ID NO: 15) | LASNRHT (SEQ ID NO: 15) | LASNRHT (SEQ ID NO: 15) | LASNRHT (SEQ ID NO: 15) | ALIYLASNRH (SEQ ID NO: 25) |
| Light Chain variable region CDR3 | LQHLNYPLT (SEQ ID NO: 16) | LQHLNYPLT (SEQ ID NO: 16) | LQHLNYPLT (SEQ ID NO: 16) | LQHLNYPLT (SEQ ID NO: 16) | LQHLNYPL (SEQ ID NO: 26) |

3A3 Heavy chain variable region (SEQ ID NO: 109)

QVQLKESGPGLVAPSQSLSITCTVSGFSLTSYGVHWVRQPPGKGLEWLGVIWPGGTINYN
SALMSRLSISKDNSKSQVFLKLNSLQTDDTAMYYCASDKYDGGWFAYWGQGTLVTVSA

3A3 Light chain variable region (SEQ ID NO: 110)

DIVMTQSQKFMSTSVGDRVSITCKASQNVRTAVAWYQQKPGQSPEALIYLASNRHTGVPD
RFTGSGSGTDFSLSISNVQSEDLADYFCLQHLNYPLTFGSGTKLEIK

TABLE 2

Antibody 5A7 Sequences

| | Exemplary | Chothia | AbM | Kabat | Contact |
|---|---|---|---|---|---|
| Heavy Chain variable region CDR1 | GFTFSSYGMS (SEQ ID NO: 27) | GFTFSSY (SEQ ID NO: 33) | GFTFSSYGMS (SEQ ID NO: 27) | SYGMS (SEQ ID NO: 36) | SSYGMS (SEQ ID NO: 37) |
| Heavy Chain variable region CDR2 | TISGGGSYTNYPDSVKG (SEQ ID NO: 28) | SGGGSY (SEQ ID NO: 34) | TISGGGSYTN (SEQ ID NO: 35) | TISGGGSYTNYPDSVKG (SEQ ID NO: 28) | WVATISGGGSYTN (SEQ ID NO: 38) |
| Heavy Chain variable region CDR3 | REWRMTLYAMDY (SEQ ID NO: 29) | REWRMTLYAMDY (SEQ ID NO: 29) | REWRMTLYAMDY (SEQ ID NO: 29) | REWRMTLYAMDY (SEQ ID NO: 29) | ARREWRMTLYAMD (SEQ ID NO: 39) |
| Light Chain variable region CDR1 | RASESVDSYGNSFMH (SEQ ID NO: 30) | RASESVDSYGNSFMH (SEQ ID NO: 30) | RASESVDSYGNSFMH (SEQ ID NO: 30) | RASESVDSYGNSFMH (SEQ ID NO: 30) | DSYGNSFMHWY (SEQ ID NO: 40) |

TABLE 2-continued

Antibody 5A7 Sequences

| | Exemplary | Chothia | AbM | Kabat | Contact |
|---|---|---|---|---|---|
| Light Chain variable region CDR2 | LTSNLES (SEQ ID NO: 31) | LTSNLES (SEQ ID NO: 31) | LTSNLES (SEQ ID NO: 31) | LTSNLES (SEQ ID NO: 31) | LLIYLTSNLE (SEQ ID NO: 41) |
| Light Chain variable region CDR3 | QQNNEDPFT (SEQ ID NO: 32) | QQNNEDPFT (SEQ ID NO: 32) | QQNNEDPFT (SEQ ID NO: 32) | QQNNEDPFT (SEQ ID NO: 32) | QQNNEDPF (SEQ ID NO: 42) |

5A7 Heavy chain variable region (SEQ ID NO: 111)

EVKLVESGGGLVKPGGSLKLSCAASGFTFSSYGMSWVRQTPEKRLEWVATISGGGSYTNY
PDSVKGRLTISRDNAKKNLYLEMSSLRSEDTALYYCARREWRMTLYAMDYWGQGTSVTVSS

5A7 Light chain variable region (SEQ ID NO: 112)

NIVLTQSPASLAVSLGQRATISCRASESVDSYGNSFMHWYQQKPGQAPKLLIYLTSNLES
GVPARFSGSGSRTDFTLTIDPVEADDAATYYCQQNNEDPFTFGSGTKLEIK

TABLE 3

Antibody 12A12 Sequences

| | Exemplary | Chothia | AbM | Kabat | Contact |
|---|---|---|---|---|---|
| Heavy Chain variable region CDR1 | GYTFTDYNMD (SEQ ID NO: 43) | GYTFTDY (SEQ ID NO: 49) | GYTFTDYNMD (SEQ ID NO: 43) | DYNMD (SEQ ID NO: 52) | TDYNMD (SEQ ID NO: 53) |
| Heavy Chain variable region CDR2 | YIYPNNGGTGYNQKFNS (SEQ ID NO: 44) | YPNNGG (SEQ ID NO: 50) | YIYPNNGGTG (SEQ ID NO: 51) | YIYPNNGGTGYNQKFNS (SEQ ID NO: 44) | WIGYIYPNNGGTG (SEQ ID NO: 54) |
| Heavy Chain variable region CDR3 | SPYYDYVGSYAMDY (SEQ ID NO: 45) | SPYYDYVGSYAMDY (SEQ ID NO: 45) | SPYYDYVGSYAMDY (SEQ ID NO: 45) | SPYYDYVGSYAMDY (SEQ ID NO: 45) | ASSPYYDYVGSYAMD (SEQ ID NO: 55) |
| Light Chain variable region CDR1 | TASSSVSSSYLH (SEQ ID NO: 46) | TASSSVSSSYLH (SEQ ID NO: 46) | TASSSVSSSYLH (SEQ ID NO: 46) | TASSSVSSSYLH (SEQ ID NO: 46) | SSSYLHWY (SEQ ID NO: 56) |
| Light Chain variable region CDR2 | STSNLAS (SEQ ID NO: 47) | STSNLAS (SEQ ID NO: 47) | STSNLAS (SEQ ID NO: 47) | STSNLAS (SEQ ID NO: 47) | LWIYSTSNLA (SEQ ID NO: 57) |
| Light Chain variable region CDR3 | HQYHRSPRT (SEQ ID NO: 48) | HQYHRSPRT (SEQ ID NO: 48) | HQYHRSPRT (SEQ ID NO: 48) | HQYHRSPRT (SEQ ID NO: 48) | HQYHRSPR (SEQ ID NO: 58) |

12A12 Heavy chain variable region (SEQ ID NO: 113)

EVQLQQSGPELVKPGASVKISCKASGYTFTDYNMDWVKQSHGKSLEWIGYIYPNNGGTGY
NQKFNSKATLTVDKSSSTAYMELHSLTSEDSAVYYCASSPYYDYVGSYAMDYWGQGTSVTVSS

12A12 Light chain variable region (SEQ ID NO: 114)

QIVLTQSPAIMSASLGERVTMTCTASSSVSSSYLHWYQQKPGSSPKLWIYSTSNLASGVP
ARFSGSGSGTSYSLTISSMEAEDAATYYCHQYHRSPRTFGGGTKLEIK

TABLE 4

Antibody 16C5 Sequences

| | Exemplary | Chothia | AbM | Kabat | Contact |
|---|---|---|---|---|---|
| Heavy Chain variable region CDR1 | GYTFTDYNMD (SEQ ID NO: 43) | GYTFTDY (SEQ ID NO: 49) | GYTFTDYNMD (SEQ ID NO: 43) | DYNMD (SEQ ID NO: 52) | TDYNMD (SEQ ID NO: 53) |

TABLE 4-continued

Antibody 16C5 Sequences

| | Exemplary | Chothia | AbM | Kabat | Contact |
|---|---|---|---|---|---|
| Heavy Chain variable region CDR2 | YIYPSNGGTGYNQKFKS (SEQ ID NO: 59) | YPSNGG (SEQ ID NO: 64) | YIYPSNGGTG (SEQ ID NO: 65) | YIYPSNGGTGYNQKFKS (SEQ ID NO: 59) | WIGYIYPSNGGTG (SEQ ID NO: 66) |
| Heavy Chain variable region CDR3 | VPYYDYLYYYAMDY (SEQ ID NO: 60) | VPYYDYLYYYAMDY (SEQ ID NO: 60) | VPYYDYLYYYAMDY (SEQ ID NO: 60) | VPYYDYLYYYAMDY (SEQ ID NO: 60) | ARVPYYDYLYYYAMD (SEQ ID NO: 67) |
| Light Chain variable region CDR1 | RASSSVSFMH (SEQ ID NO: 61) | RASSSVSFMH (SEQ ID NO: 61) | RASSSVSFMH (SEQ ID NO: 61) | RASSSVSFMH (SEQ ID NO: 61) | SFMHWY (SEQ ID NO: 68) |
| Light Chain variable region CDR2 | ATSNLAS (SEQ ID NO: 62) | ATSNLAS (SEQ ID NO: 62) | ATSNLAS (SEQ ID NO: 62) | ATSNLAS (SEQ ID NO: 62) | PWIYATSNLA (SEQ ID NO: 69) |
| Light Chain variable region CDR3 | QQWSTNPYMYT (SEQ ID NO: 63) | QQWSTNPYMYT (SEQ ID NO: 63) | QQWSTNPYMYT (SEQ ID NO: 63) | QQWSTNPYMYT (SEQ ID NO: 63) | QQWSTNPYMY (SEQ ID NO: 70) |

16C5 Heavy chain variable region
(SEQ ID NO: 115)

EVQLQQSGPELVKPGASVKISCKASGYTFTDYNMDWVKQSHGKSLEWIGYIYPSNGGTGY
NQKFKSKATLTVDKSSNTAYMELHSLTSEDSAVYYCARVPYYDYLYYYAMDYWGQGTSVTVSS

16C5 Light chain variable region
(SEQ ID NO: 116)

QIVLSQSPAILSASPGEKVTMACRASSSVSFMHWYQQKPGSSPQPWIYATSNLASGVPAR
FSGSGSGTSYSLTISRVEAEDAATYYCQQWSTNPYMYTFGGGTKLEIK

TABLE 5

Antibody 45G10 Sequences

| | Exemplary | Chothia | AbM | Kabat | Contact |
|---|---|---|---|---|---|
| Heavy Chain variable region CDR1 | GFTFSDYGMH (SEQ ID NO:71) | GFTFSDY (SEQ ID NO: 77) | GFTFSDYGMH (SEQ ID NO: 71) | DYGMH (SEQ ID NO: 80) | SDYGMH (SEQ ID NO: 81) |
| Heavy Chain variable region CDR2 | YIFSGSSTIYYADTVKG (SEQ ID NO: 72) | FSGSST (SEQ ID NO: 78) | YIFSGSSTIY (SEQ ID NO: 79) | YIFSGSSTIYYADTVKG (SEQ ID NO: 72) | WVAYIFSGSSTIY (SEQ ID NO: 82) |
| Heavy Chain variable region CDR3 | ADGRGAMDY (SEQ ID NO: 73) | ADGRGAMDY (SEQ ID NO: 73) | ADGRGAMDY (SEQ ID NO: 73) | ADGRGAMDY (SEQ ID NO: 73) | ARADGRGAMD (SEQ ID NO: 83) |
| Light Chain variable region CDR1 | RASQDISKFLN (SEQ ID NO: 74) | RASQDISKFLN (SEQ ID NO: 74) | RASQDISKFLN (SEQ ID NO: 74) | RASQDISKFLN (SEQ ID NO: 74) | SKFLNWY (SEQ ID NO: 84) |
| Light Chain variable region CDR2 | YTSRLHS (SEQ ID NO: 75) | YTSRLHS (SEQ ID NO: 75) | YTSRLHS (SEQ ID NO: 75) | YTSRLHS (SEQ ID NO: 75) | LLIYYTSRLH (SEQ ID NO: 85) |
| Light Chain variable region CDR3 | QQGNTLPWT (SEQ ID NO: 76) | QQGNTLPWT (SEQ ID NO: 76) | QQGNTLPWT (SEQ ID NO: 76) | QQGNTLPWT (SEQ ID NO: 76) | QQGNTLPW (SEQ ID NO: 86) |

45G10 Heavy chain variable region
(SEQ ID NO: 117)

EVQLVESGGGLVKPGGSLKLSCAASGFTFSDYGMHWVRQAPEKGLEWVAYIFSGSSTIYY
ADTVKGRFTISRDNAKNTLFLQMTSLRSEDTAMYYCARADGRGAMDYWGQGTSVTVSS

45G10 Light chain variable region
(SEQ ID NO: 118)

DVQMTQTTSSLSASLGDRVTISCRASQDISKFLNWYQQKPDGTVTLLIYYTSRLHSGVPS
RFSGSGSGTDYSLTISNLDQEDIATYFCQQGNTLPWTFGGGTKLEIK

TABLE 6

| Antibody 48A6 Sequences | | | | | |
|---|---|---|---|---|---|
| | Exemplary | Chothia | AbM | Kabat | Contact |
| Heavy Chain variable region CDR1 | GFTFSSYGMS (SEQ ID NO: 27) | GFTFSSY (SEQ ID NO: 33) | GFTFSSYGMS (SEQ ID NO: 27) | SYGMS (SEQ ID NO: 36) | SSYGMS (SEQ ID NO: 37) |
| Heavy Chain variable region CDR2 | TISSGGTYTFYPDSVKG (SEQ ID NO: 87) | SSGGTY (SEQ ID NO: 92) | TISSGGTYTF (SEQ ID NO: 93) | TISSGGTYTFYPDSVKG (SEQ ID NO: 87) | WVATISSGGTYTF (SEQ ID NO: 94) |
| Heavy Chain variable region CDR3 | RGWLLHYYAMDY (SEQ ID NO: 88) | RGWLLHYYAMDY (SEQ ID NO: 88) | RGWLLHYYAMDY (SEQ ID NO: 88) | RGWLLHYYAMDY (SEQ ID NO: 88) | ARRGWLLHYYAMD (SEQ ID NO: 95) |
| Light Chain variable region CDR1 | RPSESVDSFGNSFMH (SEQ ID NO: 89) | RPSESVDSFGNSFMH (SEQ ID NO: 89) | RPSESVDSFGNSFMH (SEQ ID NO: 89) | RPSESVDSFGNSFMH (SEQ ID NO: 89) | DSFGNSFMHWF (SEQ ID NO: 96) |
| Light Chain variable region CDR2 | LSSKLES (SEQ ID NO: 90) | LSSKLES (SEQ ID NO: 90) | LSSKLES (SEQ ID NO: 90) | LSSKLES (SEQ ID NO: 90) | LLIYLSSKLE (SEQ ID NO: 97) |
| Light Chain variable region CDR3 | QQHNEDPFT (SEQ ID NO: 91) | QQHNEDPFT (SEQ ID NO: 91) | QQHNEDPFT (SEQ ID NO: 91) | QQHNEDPFT (SEQ ID NO: 91) | QQHNEDPF (SEQ ID NO: 98) |

48A6 Heavy chain variable region (SEQ ID NO: 119)

EVQLVESGGDLMKPGGSLKLSCAASGFTFSSYGMSWVRQTPDKRLEWVATISSGGTYTFY
PDSVKGRFTISRDNAKNTLYLQMSSLKSEDTAMYYCARRGWLLHYYAMDYWGQGTSVTVSS

48A6 Light chain variable region (SEQ ID NO: 120)

NIVLTQSPASLAVSLGQRATISCRPSESVDSFGNSFMHWFQQKPGQPPKLLIYLSSKLES
GVPARFSGSGSRTDFTLTIDPVEADDAATYYCQQHNEDPFTFGSGTKLEI

TABLE 7

| Antibody 53F10 Sequences | | | | | |
|---|---|---|---|---|---|
| | Exemplary | Chothia | AbM | Kabat | Contact |
| Heavy Chain variable region CDR1 | GFTFSDYGMH (SEQ ID NO: 71) | GFTFSDY (SEQ ID NO: 77) | GFTFSDYGMH (SEQ ID NO: 71) | DYGMH (SEQ ID NO: 80) | SDYGMH (SEQ ID NO: 81) |
| Heavy Chain variable region CDR2 | YISTGIITVYYADTVKG (SEQ ID NO: 99) | STGIIT (SEQ ID NO: 101) | YISTGIITVY (SEQ ID NO: 102) | YISTGIITVYYADTVKG (SEQ ID NO: 99) | WVAYISTGIITVY (SEQ ID NO: 103) |
| Heavy Chain variable region CDR3 | ADGRGAMDY (SEQ ID NO: 73) | ADGRGAMDY (SEQ ID NO: 73) | ADGRGAMDY (SEQ ID NO: 73) | ADGRGAMDY (SEQ ID NO: 73) | ARADGRGAMD (SEQ ID NO: 83) |
| Light Chain variable region CDR1 | RASQDISNFLN (SEQ ID NO: 100) | RASQDISNFLN (SEQ ID NO: 100) | RASQDISNFLN (SEQ ID NO: 100) | RASQDISNFLN (SEQ ID NO: 100) | SNFLNWY (SEQ ID NO: 104) |
| Light Chain variable region CDR2 | YTSRLHS (SEQ ID NO: 75) | YTSRLHS (SEQ ID NO: 75) | YTSRLHS (SEQ ID NO: 75) | YTSRLHS (SEQ ID NO: 75) | LLIYYTSRLH (SEQ ID NO: 85) |
| Light Chain variable region CDR3 | QQGNTLPWT (SEQ ID NO: 76) | QQGNTLPWT (SEQ ID NO: 76) | QQGNTLPWT (SEQ ID NO: 76) | QQGNTLPWT (SEQ ID NO: 76) | QQGNTLPW (SEQ ID NO: 86) |

53F10 Heavy chain variable region (SEQ ID NO: 121)

EVQVVESGGGLVKPGGSLKLSCAASGFTFSDYGMHWVRQAPEKGLEWVAYISTGIITVYY
ADTVKGRFTMSRDNAKNTLFLQMTSLRSEDTAIYYCARADGRGAMDYWGQGTSVIVSS

TABLE 7-continued

Antibody 53F10 Sequences

| | Exemplary | Chothia | AbM | Kabat | Contact |
|---|---|---|---|---|---|

53F10 Light chain variable region (SEQ ID NO: 122)

```
DIQMTQTTSSLSASLGDRVTISCRASQDISNFLNWYQQKPDGTVTLLIYYTSRLHSGVPS
RFSGSGSGTDYSLTISNLEQEDFATYFCQQGNTLPWTFGGGTKLEIK
```

TABLE 8

Antibody Hz5A7.v5 Sequences

| | Exemplary | Chothia | AbM | Kabat | Contact |
|---|---|---|---|---|---|
| Heavy Chain variable region CDR1 | GFTFSSYGMS (SEQ ID NO: 27) | GFTFSSY (SEQ ID NO: 33) | GFTFSSYGMS (SEQ ID NO: 27) | SYGMS (SEQ ID NO: 36) | SSYGMS (SEQ ID NO: 37) |
| Heavy Chain variable region CDR2 | TISGGGSYTNYPDSVKG (SEQ ID NO: 28) | SGGGSY (SEQ ID NO: 34) | TISGGGSYTN (SEQ ID NO: 35) | TISGGGSYTNYPDSVKG (SEQ ID NO: 28) | WVATISGGGSYTN (SEQ ID NO: 38) |
| Heavy Chain variable region CDR3 | REWRYTLYAMDY (SEQ ID NO: 105) | REWRYTLYAMDY (SEQ ID NO: 105) | REWRYTLYAMDY (SEQ ID NO: 105) | REWRYTLYAMDY (SEQ ID NO: 105) | ARREWRYTLYAMD (SEQ ID NO: 107) |
| Light Chain variable region CDR1 | RASESVESYGSSFMH (SEQ ID NO: 106) | RASESVESYGSSFMH (SEQ ID NO: 106) | RASESVESYGSSFMH (SEQ ID NO: 106) | RASESVESYGSSFMH (SEQ ID NO: 106) | ESYGSSFMHWY (SEQ ID NO: 108) |
| Light Chain variable region CDR2 | LTSNLES (SEQ ID NO: 31) | LTSNLES (SEQ ID NO: 31) | LTSNLES (SEQ ID NO: 31) | LTSNLES (SEQ ID NO: 31) | LLIYLTSNLE (SEQ ID NO: 41) |
| Light Chain variable region CDR3 | QQNNEDPFT (SEQ ID NO: 32) | QQNNEDPFT (SEQ ID NO: 32) | QQNNEDPFT (SEQ ID NO: 32) | QQNNEDPFT (SEQ ID NO: 32) | QQNNEDPF (SEQ ID NO: 42) |

Hz5A7.v5 Heavy chain variable region (SEQ ID NO: 123)

```
EVQLVESGGGLVQPGGSLRLSCAASGFTFSSYGMSWVRQAPGKGLEWVATISGGGSYTNY
PDSVKGRFTISRDNAKNSLYLQMNSLRAEDTAVYYCARREWRYTLYAMDYWGQGTTVTVSS
```

Hz5A7.v5 Light chain variable region (SEQ ID NO: 124)

```
DIQLTQSPSFLSASVGDRVTITCRASESVESYGSSFMHWYQQKPGKAPKLLIYLTSNLES
GVPSRFSGSGSGTEFTLTISSLQPEDFATYYCQQNNEDPFTFGQGTKLEIK
```

In some embodiments, an ILT3-binding agent comprises a heavy chain variable region CDR1, CDR2, and CDR3 and/or a light chain variable region CDR1, CDR2, and CDR3 from an antibody described herein. In some embodiments, an ILT3-binding agent comprises a heavy chain variable region CDR1, CDR2, and CDR3 and a light chain variable region CDR1, CDR2, and CDR3 from an antibody described herein. In some embodiments, an ILT3-binding agent comprises: (a) a heavy chain variable region comprising a heavy chain variable region CDR1, CDR2, and CDR3; and (b) a light chain variable region comprising a light chain variable region CDR1, CDR2, and CDR3 from an antibody described herein.

In some embodiments, an ILT3-binding agent comprises a heavy chain variable region CDR1, CDR2, and CDR3 and/or a light chain variable region CDR1, CDR2, and CDR3 from antibody 5A7, a humanized version thereof, or variants thereof. In some embodiments, an ILT3-binding agent comprises a heavy chain variable region comprising a heavy chain variable region CDR1, a heavy chain variable region CDR2, and a heavy chain variable region CDR3 from antibody 5A7. In other embodiments, an ILT3-binding agent comprises a light chain variable region comprising a light chain variable region CDR1, a light chain variable region CDR2, and a light chain variable region CDR3 from antibody 5A7. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 5A7. In some embodiments, an ILT3-binding agent is a humanized version of antibody 5A7 (e.g., Hz5A7). In some embodiments, an ILT3-binding agent is a variant of antibody 5A7 or humanized 5A7 (e.g., Hz5A7.v5). In some embodiments, an ILT3-binding agent comprises a heavy chain variable region comprising a heavy chain variable region CDR1, a heavy chain variable region CDR2, and a heavy chain variable region CDR3 from antibody Hz5A7.v5. In other embodiments, an ILT3-binding agent comprises a light chain variable region comprising a light chain variable region CDR1, a light chain variable region CDR2, and a light chain variable region CDR3 from antibody Hz5A7.v5. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody Hz5A7.v5.

In some embodiments, an ILT3-binding agent comprises a heavy chain variable region CDR1, CDR2, and CDR3 and/or a light chain variable region CDR1, CDR2, and CDR3 from antibody 3A3, a humanized version thereof, or variants thereof. In some embodiments, an ILT3-binding agent comprises a heavy chain variable region comprising a heavy chain variable region CDR1, a heavy chain variable region CDR2, and a heavy chain variable region CDR3 from antibody 3A3. In other embodiments, an ILT3-binding agent comprises a light chain variable region comprising a light chain variable region CDR1, a light chain variable region CDR2, and a light chain variable region CDR3 from antibody 3A3. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 3A3. In some embodiments, an ILT3-binding agent is a humanized version of antibody 3A3. In some embodiments, an ILT3-binding agent is a variant of antibody 3A3.

In some embodiments, an ILT3-binding agent comprises a heavy chain variable region CDR1, CDR2, and CDR3 and/or a light chain variable region CDR1, CDR2, and CDR3 from antibody 12A12, a humanized version thereof, or variants thereof. In some embodiments, an ILT3-binding agent comprises a heavy chain variable region comprising a heavy chain variable region CDR1, a heavy chain variable region CDR2, and a heavy chain variable region CDR3 from antibody 12A12. In other embodiments, an ILT3-binding agent comprises a light chain variable region comprising a light chain variable region CDR1, a light chain variable region CDR2, and a light chain variable region CDR3 from antibody 12A12. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 12A12. In some embodiments, an ILT3-binding agent is a humanized version of antibody 12A12. In some embodiments, an ILT3-binding agent is a variant of antibody 12A12.

In some embodiments, an ILT3-binding agent comprises a heavy chain variable region CDR1, CDR2, and CDR3 and/or a light chain variable region CDR1, CDR2, and CDR3 from antibody 16C5, a humanized version thereof, or variants thereof. In some embodiments, an ILT3-binding agent comprises a heavy chain variable region comprising a heavy chain variable region CDR1, a heavy chain variable region CDR2, and a heavy chain variable region CDR3 from antibody 16C5. In other embodiments, an ILT3-binding agent comprises a light chain variable region comprising a light chain variable region CDR1, a light chain variable region CDR2, and a light chain variable region CDR3 from antibody 16C5. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 16C5. In some embodiments, an ILT3-binding agent is a humanized version of antibody 16C5. In some embodiments, an ILT3-binding agent is a variant of antibody 16C5.

In some embodiments, an ILT3-binding agent comprises a heavy chain variable region CDR1, CDR2, and CDR3 and/or a light chain variable region CDR1, CDR2, and CDR3 from antibody 45G10, a humanized version thereof, or variants thereof. In some embodiments, an ILT3-binding agent comprises a heavy chain variable region comprising a heavy chain variable region CDR1, a heavy chain variable region CDR2, and a heavy chain variable region CDR3 from antibody 45G10. In other embodiments, an ILT3-binding agent comprises a light chain variable region comprising a light chain variable region CDR1, a light chain variable region CDR2, and a light chain variable region CDR3 from antibody 45G10. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 45G10. In some embodiments, an ILT3-binding agent is a humanized version of antibody 45G10. In some embodiments, an ILT3-binding agent is a variant of antibody 45G10.

In some embodiments, an ILT3-binding agent comprises a heavy chain variable region CDR1, CDR2, and CDR3 and/or a light chain variable region CDR1, CDR2, and CDR3 from antibody 48A6, a humanized version thereof, or variants thereof. In some embodiments, an ILT3-binding agent comprises a heavy chain variable region comprising a heavy chain variable region CDR1, a heavy chain variable region CDR2, and a heavy chain variable region CDR3 from antibody 48A6. In other embodiments, an ILT3-binding agent comprises a light chain variable region comprising a light chain variable region CDR1, a light chain variable region CDR2, and a light chain variable region CDR3 from antibody 48A6. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 48A6. In some embodiments, an ILT3-binding agent is a humanized version of antibody 48A6. In some embodiments, an ILT3-binding agent is a variant of antibody 48A6.

In some embodiments, an ILT3-binding agent comprises a heavy chain variable region CDR1, CDR2, and CDR3 and/or a light chain variable region CDR1, CDR2, and CDR3 from antibody 53F10, a humanized version thereof, or variants thereof. In some embodiments, an ILT3-binding agent comprises a heavy chain variable region comprising a heavy chain variable region CDR1, a heavy chain variable region CDR2, and a heavy chain variable region CDR3 from antibody 53F10. In other embodiments, an ILT3-binding agent comprises a light chain variable region comprising a light chain variable region CDR1, a light chain variable region CDR2, and a light chain variable region CDR3 from antibody 53F10. In certain embodiments, an ILT3-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 53F10. In some embodiments, an ILT3-binding agent is a humanized version of antibody 53F10. In some embodiments, an ILT3-binding agent is a variant of antibody 53F10.

In some embodiments, an ILT3-binding agent (e.g., an antibody) comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRYTLYAMDY (SEQ ID NO:105), and a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32); (b) a heavy chain variable region comprising a heavy chain variable region CDR1 comprising the amino acid sequence GFTFSSY (SEQ ID NO:33), a heavy chain variable region CDR2 comprising the amino acid sequence SGGGSY (SEQ ID NO:34), and a heavy chain variable region CDR3 comprising the amino acid sequence REWRMTLYAMDY (SEQ ID NO:29) or REWRYTLYAMDY (SEQ ID NO:105), and a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32); (c) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTN (SEQ ID NO:35), and a heavy chain variable region CDR3 comprising the amino acid sequence REWRMTLYAMDY (SEQ ID NO:29) or REWRYTLYAMDY (SEQ ID NO:105), and a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32); (d) a heavy chain variable region comprising a heavy chain variable region CDR1 comprising the amino acid sequence SYGMS (SEQ ID NO:36), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRYTLYAMDY (SEQ ID NO:105), and a light chain variable region comprising a light chain variable region CDR1 comprising the amino acid sequence RASESVDSYGNSFMH (SEQ ID NO:30) or RASESVE-SYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32); or (e) a heavy chain variable region comprising a heavy chain variable region CDR1 comprising the amino acid sequence SSYGMS (SEQ ID NO:37), a heavy chain variable region CDR2 comprising the amino acid sequence WVATISGGGSYTN (SEQ ID NO:38), and a heavy chain variable region CDR3 comprising the amino acid sequence ARREWRMTLYAMD (SEQ ID NO:39) or ARREWRYTLYAMD (SEQ ID NO:107), and a light chain variable region comprising a light chain variable region CDR1 comprising the amino acid sequence DSYGNSFMHWY (SEQ ID NO:40) or ESYGSSFMHWY (SEQ ID NO:108), a light chain variable region CDR2 comprising the amino acid sequence LLIYLTSNLE (SEQ ID NO:41), and a light chain variable region CDR3 comprising the amino acid sequence QQNNEDPF (SEQ ID NO:42).

In some embodiments, an ILT3-binding agent (e.g., an antibody) comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRYTLYAMDY (SEQ ID NO:105), and/or (b) a light chain variable region comprising a light chain variable region CDR1 comprising the amino acid sequence RASESVDSYGNSFMH (SEQ ID NO:30) or RASESVE-SYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, the ILT3-binding agent comprises a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29). In some embodiments, the ILT3-binding agent comprises a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRYTLYAMDY (SEQ ID NO:105). In some embodiments, the ILT3-binding agent comprises a light chain variable region comprising a light chain variable region CDR1 comprising the amino acid sequence RASESVDSYGNSFMH (SEQ ID NO:30), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, the ILT3-binding agent comprises a light chain variable region comprising a light chain variable region CDR1 comprising the amino acid sequence RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, the ILT3-binding agent comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29), and (b) a light chain variable region comprising a light chain variable region CDR1 comprising the amino acid sequence RASESVDSYGNSFMH (SEQ ID NO:30), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, the ILT3-binding agent comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRYTLYAMDY (SEQ ID NO:105), and (b) a light chain variable region comprising a light chain variable region CDR1 comprising the amino acid sequence RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32).

In certain embodiments, an ILT3-binding agent (e.g., an antibody) comprises: (a) a heavy chain variable region comprising a heavy chain variable region CDR1 comprising the amino acid sequence GFTFSSYGMS (SEQ ID NO:27), or a variant thereof comprising 1, 2, 3, 4, 5 or 6 amino acid substitutions; a heavy chain variable region CDR2 comprising the amino acid sequence TISGGGSYTNYPDSVKG (SEQ ID NO:28), or a variant thereof comprising 1, 2, 3, 4, 5 or 6 amino acid substitutions; and a heavy chain variable region CDR3 comprising the amino acid sequence REWRMTLYAMDY (SEQ ID NO:29), REWRYTLYAMDY (SEQ ID NO:105), or a variant thereof comprising 1, 2, 3, 4, 5 or 6 amino acid substitutions; and (b) a light chain variable region comprising a light chain variable region CDR1 comprising the amino acid sequence RASESVDSYGNSFMH (SEQ ID NO:30), RASESVESYGSSFMH (SEQ ID NO:106), or a variant thereof comprising 1, 2, 3, 4, 5 or 6 amino acid substitutions; a light chain variable region CDR2 comprising the amino acid sequence LTSNLES (SEQ ID NO:31), or a variant thereof comprising 1, 2, 3, 4, 5 or 6 amino acid substitutions; and a light chain variable region CDR3 comprising the amino acid sequence QQNNEDPFT (SEQ ID NO:32), or a variant thereof comprising 1, 2, 3, 4, 5 or 6 amino acid substitutions.

In some embodiments, an ILT3-binding agent (e.g., an antibody) comprises one or more heavy chain variable region CDRs or light chain variable region CDRs that have been modified to reduce deamidation within the CDR sequence. Deamidation is a chemical reaction in which an amide functional group in the side chain of the amino acids asparagine (Asn or N) or glutamine (Gln or Q) is removed or converted to another functional group. Generally, asparagine is converted to aspartic acid or isoaspartic acid and glutamine is converted to glutamic acid or polyglutamic acid. In some situations, deamidation may change the structure, function, and/or stability of a polypeptide, potentially resulting in decreased biological activity. In some embodiments, the light chain variable region CDR1, CDR2, and/or CDR3 of an antibody described herein is modified to reduce deamidation. In some embodiments, the light chain variable region CDR1, CDR2, and/or CDR3 of an antibody described herein is modified to reduce deamidation. Any one of the heavy chain variable region CDRs and light chain variable region CDRs of antibody 5A7, 3A3, Hz5A7, 12A12, 16C5, 45G10, 48A6, or 53F10 can be modified to reduce deamidation.

In some embodiments, an ILT3-binding agent (e.g., an antibody) comprises one or more heavy chain variable region CDRs or light chain variable region CDRs that have been modified to reduce isomerization. Isomerization is a chemical process by which a compound is transformed into any of its isomeric forms, i.e., forms with the same chemical composition but with different structure or configuration and, potentially with different physical and chemical properties. Studies have shown that aspartate (Asp or D) isomerization within a CDR can impact antibody binding and/or stability. In some embodiments, the heavy chain variable region CDR1, CDR2, and/or CDR3 of an antibody described herein is modified to reduce isomerization. In some embodiments, the light chain variable region CDR1, CDR2, and/or CDR3 is modified to reduce isomerization. Any one of the heavy chain variable region CDRs and light chain variable region CDRs of antibody 5A7, 3A3, Hz5A7, 12A12, 16C5, 45G10, 48A6, or 53F10 can be modified to reduce isomerization.

In some embodiments, an ILT3-binding agent (e.g., an antibody) comprises one or more heavy chain variable region CDRs or light chain variable region CDRs that have been modified to reduce oxidation. Oxidation is a chemical process by which an oxygen is added to an atom, for example, methionine is converted to methionine sulfoxide by addition of an oxygen to the sulfur atom. Oxidation of one or more amino acids can potentially affect the physical and chemical properties of a protein. Studies have shown that oxidation of methionine (Met or M) within a CDR has the potential to impact antibody binding and/or stability. In some embodiments, the heavy chain variable region CDR1, CDR2, and/or CDR3 of an antibody described herein is modified to reduce oxidation (e.g., methionine oxidation). In some embodiments, the light chain variable region CDR1, CDR2, and/or CDR3 of an antibody described herein is modified to reduce oxidation (e.g., methionine oxidation). Any one of the heavy chain variable region CDRs and light chain variable region CDRs of antibody 5A7, 3A3, Hz5A7, 12A12, 16C5, 45G10, 48A6, or 53F10 can be modified to reduce methionine oxidation.

In some embodiments, an anti-ILT3 binding agent (e.g., antibody) comprises a heavy chain variable region comprising the amino acid sequence of heavy chain variable region CDR1, CDR2, and CDR3 of antibody 5A7 and which has at least 75%, at least 80%, at least 85%, at least 90%, at least 95%, at least 96%, at least 97%, at least 98%, at least 99%, or 100% identity to the sequence of SEQ ID NO:111 and a light chain variable region comprising the amino acid sequence of light chain variable region CDR1, CDR2, and CDR3 of antibody 5A7 and which has at least 75%, at least 80%, at least 85%, at least 90%, at least 95%, at least 96%, at least 97%, at least 98%, at least 99%, or 100% identity to the sequence of SEQ ID NO:112. In some embodiments, an anti-ILT3 binding agent comprises a heavy chain variable region comprising the amino acid sequence of heavy chain variable region CDR1, CDR2, and CDR3 of antibody Hz5A7.v5 and which has at least 75%, at least 80%, at least 85%, at least 90%, at least 95%, at least 96%, at least 97%, at least 98%, at least 99%, or 100% identity to the sequence of SEQ ID NO:123 and a light chain variable region comprising the amino acid sequence of light chain variable region CDR1, CDR2, and CDR3s of antibody Hz5A7.v5 and which has at least 75%, at least 80%, at least 85%, at least 90%, at least 95%, at least 96%, at least 97%, at least 98%, at least 99%, or 100% identity to the sequence of SEQ ID NO:124.

In some embodiments, an ILT3-binding agent (e.g., an antibody) comprises a heavy chain variable region having at least 80%, at least 85%, at least 90%, at least 95%, at least 97%, or at least 99% identity to the sequence of SEQ ID NO:111. In some embodiments, an ILT3-binding agent comprises a light chain variable region having at least 80%, at least 85%, at least 90%, at least 95%, at least 97%, or at least 99% identity to the sequence of SEQ ID NO:112. In some embodiments, an ILT3-binding agent comprises a heavy chain variable region having at least 80%, at least 85%, at least 90%, at least 95%, at least 97%, or at least 99% identity to the sequence of SEQ ID NO:123. In some embodiments, an ILT3-binding agent comprises a light chain variable region having at least 80%, at least 85%, at least 90%, at least 95%, at least 97%, or at least 99% identity to the sequence of SEQ ID NO:124.

In some embodiments, an ILT3-binding agent (e.g., an antibody) comprises a heavy chain variable region comprising an amino acid sequence of SEQ ID NO:111. In some embodiments, an ILT3-binding agent comprises a light chain variable region comprising an amino acid sequence of SEQ ID NO:112. In some embodiments, an ILT3-binding agent comprises a heavy chain variable region comprising an amino acid sequence of SEQ ID NO:123. In some embodiments, an ILT3-binding agent comprises a light chain variable region comprising an amino acid sequence of SEQ ID NO:124.

In some embodiments, an ILT3-binding agent (e.g., an antibody) comprises a heavy chain variable region having at least 80% sequence identity to SEQ ID NO:111 and a light chain variable region having at least 80% sequence identity to SEQ ID NO:112. In some embodiments, an ILT3-binding agent comprises a heavy chain variable region having at least 90% sequence identity to SEQ ID NO:111 and a light chain variable region having at least 90% sequence identity to SEQ ID NO:112. In some embodiments, an ILT3-binding agent comprises a heavy chain variable region having at least 95% sequence identity to SEQ ID NO:111 and a light chain variable region having at least 95% sequence identity to SEQ ID NO:112. In some embodiments, an ILT3-binding agent comprises a heavy chain variable region comprising an amino acid sequence of SEQ ID NO:111 and a light chain variable region comprising an amino acid sequence of SEQ ID NO:112.

In some embodiments, an ILT3-binding agent (e.g., an antibody) comprises a heavy chain variable region having at least 80% sequence identity to SEQ ID NO:123 and a light chain variable region having at least 80% sequence identity to SEQ ID NO:124. In some embodiments, an ILT3-binding agent comprises a heavy chain variable region having at least 90% sequence identity to SEQ ID NO:123 and a light chain variable region having at least 90% sequence identity to SEQ ID NO:124. In some embodiments, an ILT3-binding agent comprises a heavy chain variable region having at least 95% sequence identity to SEQ ID NO:123 and a light chain variable region having at least 95% sequence identity to SEQ ID NO:124. In some embodiments, an ILT3-binding agent comprises a heavy chain variable region comprising an amino acid sequence of SEQ ID NO:123 and a light chain variable region comprising an amino acid sequence of SEQ ID NO:124.

In certain embodiments, an ILT3-binding agent (e.g., an antibody) comprises a heavy chain variable region comprising a heavy chain variable region CDR1 comprising GFTFSSYGMS (SEQ ID NO:27), a heavy chain variable region CDR2 comprising TISGGGSYTNYPDSVKG (SEQ ID NO:28), a heavy chain variable region CDR3 comprising REWRYTLYAMDY (SEQ ID NO:105), and a light chain variable region comprising a light chain variable region CDR1 comprising RASESVESYGSSFMH (SEQ ID NO:106), a light chain variable region CDR2 comprising LTSNLES (SEQ ID NO:31), and a light chain variable region CDR3 comprising QQNNEDPFT (SEQ ID NO:32), wherein the heavy chain variable region comprises at least 80%, at least 85%, at least 90%, at least 95%, at least 97% identity to the sequence of SEQ ID NO:123, and wherein the light chain variable region comprises at least 80%, at least 85%, at least 90%, at least 95%, at least 97% identity to the sequence of SEQ ID NO:124.

In certain embodiments, an ILT3-binding agent (e.g., an antibody) comprises a heavy chain comprising a heavy chain variable region CDR1 comprising GFTFSSYGMS (SEQ ID NO:27), a heavy chain variable region CDR2 comprising TISGGGSYTNYPDSVKG (SEQ ID NO:28), a heavy chain variable region CDR3 comprising REWRYTLYAMDY (SEQ ID NO:105), and a light chain comprising a light chain variable region CDR1 comprising RASESVESYGSSFMH (SEQ ID NO:106), a light chain variable region CDR2 comprising LTSNLES (SEQ ID NO:31), and a light chain variable region CDR3 comprising QQNNEDPFT (SEQ ID NO:32), wherein the heavy chain comprises at least 80%, at least 85%, at least 90%, at least 95%, at least 97%, or 100% identity to the sequence of SEQ ID NO:126, and wherein the light chain comprises at least 80%, at least 85%, at least 90%, at least 95%, at least 97%, or 100% identity to the sequence of SEQ ID NO:128. In certain embodiments, an ILT3-binding agent comprises a heavy chain comprising a heavy chain variable region CDR1 comprising GFTFSSYGMS (SEQ ID NO:27), a heavy chain variable region CDR2 comprising TISGGGSYTNYPDSVKG (SEQ ID NO:28), a heavy chain variable region CDR3 comprising REWRYTLYAMDY (SEQ ID NO:105), and a light chain comprising a light chain variable region CDR1 comprising RASESVESYGSSFMH (SEQ ID NO:106), a light chain variable region CDR2 comprising LTSNLES (SEQ ID NO:31), and a light chain variable region CDR3 comprising QQNNEDPFT (SEQ ID NO:32), wherein the heavy chain comprises at least 95% identity to the sequence of SEQ ID NO:126, and wherein the light chain comprises at least 95% identity to the sequence of SEQ ID NO:128. In certain embodiments, an ILT3-binding agent comprises (a) a heavy chain comprising the amino acids of SEQ ID NO:126 and (b) a light chain comprising a light chain variable region CDR1 comprising RASESVESYGSSFMH (SEQ ID NO:106), a light chain variable region CDR2 comprising LTSNLES (SEQ ID NO:31), and a light chain variable region CDR3 comprising QQNNEDPFT (SEQ ID NO:32), wherein the light chain comprises at least 80%, at least 85%, at least 90%, at least 95%, at least 97%, or 100% identity to the sequence of SEQ ID NO:128. In certain embodiments, an ILT3-binding agent comprises (a) a heavy chain comprising a heavy chain variable region CDR1 comprising GFTFSSYGMS (SEQ ID NO:27), a heavy chain variable region CDR2 comprising TISGGGSYTNYPDSVKG (SEQ ID NO:28), a heavy chain variable region CDR3 comprising REWRYTLYAMDY (SEQ ID NO:105), wherein the heavy chain comprises at least 80%, at least 85%, at least 90%, at least 95%, at least 97%, or 100% identity to the sequence of SEQ ID NO:126, and (b) a light chain comprising the amino acid sequence of SEQ ID NO:128. In some embodiments, an ILT3-binding agent is an antibody comprising a heavy chain comprising the amino acid sequence of SEQ ID NO:126 and a light chain comprising the amino acid sequence of SEQ ID NO:128.

In some embodiments, the ILT3-binding agent is antibody 5A7. In some embodiments, the ILT3-binding agent is antibody Hz5A7.v5.

In some embodiments, an ILT3-binding agent (e.g., an antibody) comprises: (a) a heavy chain variable region comprising a heavy chain variable region CDR1 comprising the amino acid sequence GFSLTSYGVH (SEQ ID NO:11), a heavy chain variable region CDR2 comprising the amino acid sequence VIWPGGTINYNSALMS (SEQ ID NO:12), and a heavy chain variable region CDR3 comprising the amino acid sequence DKYDGGWFAY (SEQ ID NO:13), and a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16); (b) a heavy chain variable region comprising a heavy chain variable region CDR1 comprising the amino acid sequence GFSLTSY (SEQ ID NO:17), a heavy chain variable region CDR2 comprising the amino acid sequence WPGGT (SEQ ID NO:18), and a heavy chain variable region CDR3 comprising the amino acid sequence DKYDGGWFAY (SEQ ID NO:13), and a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16); (c) a heavy chain variable region comprising a heavy chain variable region CDR1 comprising the amino acid sequence GFSLTSYGVH (SEQ ID NO:11), a heavy chain variable region CDR2 comprising the amino acid sequence VIWPGGTIN (SEQ ID NO:19), and a heavy chain variable region CDR3 comprising the amino acid sequence DKYDGGWFAY (SEQ ID NO:13), and a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16); (d) a heavy chain variable region comprising a heavy chain variable region CDR1 comprising the amino acid sequence SYGVH (SEQ ID NO:20), a heavy chain variable region CDR2 comprising the amino acid sequence VIWPGGTINYNSALMS (SEQ ID NO:12), and a heavy chain variable region CDR3 comprising the amino acid sequence DKYDGGWFAY (SEQ ID NO:13), and a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16); or (e) a heavy chain variable region comprising a heavy chain variable region CDR1 comprising the amino acid sequence TSYGVH (SEQ ID NO:21), a heavy chain variable region CDR2 comprising the amino acid sequence WLGVIWPGGTIN (SEQ ID NO:22), and a heavy chain variable region CDR3 comprising the amino acid sequence ASDKYDGGWFA (SEQ ID NO:23), and a light chain variable region comprising a light chain variable region CDR1 comprising the amino acid sequence RTAVAWY (SEQ ID NO:24), a light chain variable region CDR2 comprising the amino acid sequence ALIYLASNRH (SEQ ID NO:25), and a light chain variable region CDR3 comprising the amino acid sequence LQHLNYPL (SEQ ID NO:26).

In some embodiments, an ILT3-binding agent comprises a heavy chain variable region comprising a heavy chain variable region CDR1 comprising the amino acid sequence GFSLTSYGVH (SEQ ID NO:11), a heavy chain variable region CDR2 comprising the amino acid sequence VIWPGGTINYNSALMS (SEQ ID NO:12), and a heavy chain variable region CDR3 comprising the amino acid sequence DKYDGGWFAY (SEQ ID NO:13). In some embodiments, an ILT3-binding agent comprises a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16). In some embodiments, an ILT3-binding agent comprises (a) a heavy chain variable region comprising a heavy chain variable region CDR1 comprising the amino acid sequence GFSLTSYGVH (SEQ ID NO:11), a heavy chain variable region CDR2 comprising the amino acid sequence VIWPGGTINYNSALMS (SEQ ID NO:12), and a heavy chain variable region CDR3 comprising the amino acid sequence DKYDGGWFAY (SEQ ID NO:13), and (b) a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16).

In some embodiments, an ILT3-binding agent comprises a heavy chain variable region having at least 80%, at least 85%, at least 90%, at least 95%, at least 97%, or at least 99% identity to the sequence of SEQ ID NO:109. In some embodiments, an ILT3-binding agent comprises a light chain variable region having at least 80%, at least 85%, at least 90%, at least 95%, at least 97%, or at least 99% identity to the sequence of SEQ ID NO:110. In some embodiments, an ILT3-binding agent comprises a heavy chain variable region comprising an amino acid sequence of SEQ ID NO:109. In some embodiments, an ILT3-binding agent comprises a light chain variable region comprising an amino acid sequence of SEQ ID NO:110.

In some embodiments, an ILT3-binding agent comprises a heavy chain variable region having at least 80% sequence identity to SEQ ID NO:109 and a light chain variable region having at least 80% sequence identity to SEQ ID NO:110. In some embodiments, an ILT3-binding agent comprises a heavy chain variable region having at least 90% sequence identity to SEQ ID NO:109 and a light chain variable region having at least 90% sequence identity to SEQ ID NO:110. In some embodiments, an ILT3-binding agent comprises a heavy chain variable region having at least 95% sequence identity to SEQ ID NO:109 and a light chain variable region having at least 95% sequence identity to SEQ ID NO:110. In some embodiments, an ILT3-binding agent comprises a heavy chain variable region comprising an amino acid sequence of SEQ ID NO:109 and a light chain variable region comprising an amino acid sequence of SEQ ID NO:110.

In some embodiments, the ILT3-binding agent is antibody 3A3. In some embodiments, the ILT3-binding agent is a humanized version of antibody 3A3. In some embodiments, the ILT3-binding agent is a variant of antibody 3A3 or humanized antibody 3A3.

In certain embodiments, an ILT3-binding agent (e.g., an antibody) comprises: (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPNNGGTGYNQKFNS (SEQ ID NO:44), and a heavy chain variable region CDR3 comprising the amino acid sequence SPYYDYVGSYAMDY (SEQ ID NO:45), and a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48); (b) a heavy chain variable region comprising a heavy chain variable region CDR1 comprising the amino acid sequence GYTFTDY (SEQ ID NO:49), a heavy chain variable region CDR2 comprising the amino acid sequence YPNNGG (SEQ ID NO:50), and a heavy chain variable region CDR3 comprising the amino acid sequence SPYYDYVGSYAMDY (SEQ ID NO:45), and a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48); (c) a heavy chain variable region comprising a heavy chain variable region CDR1 comprising the amino acid sequence GYTFTDYNMD (SEQ ID NO:43), a heavy chain variable region CDR2 comprising the amino acid sequence YIYPNNGGTG (SEQ ID NO:51), and a heavy chain variable region CDR3 comprising the amino acid sequence SPYYDYVGSYAMDY (SEQ ID NO:45), and a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48); (d) a heavy chain variable region comprising a heavy chain variable region CDR1 comprising the amino acid sequence DYNMD (SEQ ID NO:52), a heavy chain variable region CDR2 comprising the amino acid sequence YIYPNNGGTGYNQKFNS (SEQ ID NO:44), and a heavy chain variable region CDR3 comprising the amino acid sequence SPYYDYVGSYAMDY (SEQ ID NO:45), and a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48); or (e) a heavy chain variable region comprising a heavy chain variable region CDR1 comprising the amino acid sequence TDYNMD (SEQ ID NO:53), a heavy chain variable region CDR2 comprising the amino acid sequence WIGYIYPNNGGTG (SEQ ID NO:54), and a heavy chain variable region CDR3 comprising the amino acid sequence ASSPYYDYVGSYAMD (SEQ ID NO:55), and a light chain variable region comprising a light chain variable region CDR1 comprising the amino acid sequence SSSYLHWY (SEQ ID NO:56), a light chain variable region CDR2 comprising the amino acid sequence LWIYSTSNLA (SEQ ID NO:57), and a light chain variable region CDR3 comprising the amino acid sequence HQYHRSPR (SEQ ID NO:58).

In some embodiments, an ILT3-binding agent comprises a heavy chain variable region comprising a heavy chain variable region CDR1 comprising the amino acid sequence GYTFTDYNMD (SEQ ID NO:43), a heavy chain variable region CDR2 comprising the amino acid sequence YIYPNNGGTGYNQKFNS (SEQ ID NO:44), and a heavy chain variable region CDR3 comprising the amino acid sequence SPYYDYVGSYAMDY (SEQ ID NO:45). In some embodiments, an ILT3-binding agent comprises a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48). In some embodiments, an ILT3-binding agent comprises (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPNNGGTGYNQKFNS (SEQ ID NO:44), and a heavy chain variable region CDR3 comprising the amino acid sequence SPYYDYVGSYAMDY (SEQ ID NO:45), and (b) a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48).

In some embodiments, an ILT3-binding agent comprises a heavy chain variable region having at least 80%, at least 85%, at least 90%, at least 95%, at least 97%, or at least 99% identity to the sequence of SEQ ID NO:113. In some embodiments, an ILT3-binding agent comprises a light chain variable region having at least 80%, at least 85%, at least 90%, at least 95%, at least 97%, or at least 99% identity to the sequence of SEQ ID NO:114. In some embodiments, an ILT3-binding agent comprises a heavy chain variable region comprising an amino acid sequence of SEQ ID NO:113. In some embodiments, an ILT3-binding agent comprises a light chain variable region comprising an amino acid sequence of SEQ ID NO:114.

In some embodiments, an ILT3-binding agent comprises a heavy chain variable region having at least 80% sequence identity to SEQ ID NO:113 and a light chain variable region having at least 80% sequence identity to SEQ ID NO:114. In some embodiments, an ILT3-binding agent comprises a heavy chain variable region having at least 90% sequence identity to SEQ ID NO:113 and a light chain variable region having at least 90% sequence identity to SEQ ID NO:114. In some embodiments, an ILT3-binding agent comprises a heavy chain variable region having at least 95% sequence identity to SEQ ID NO:113 and a light chain variable region having at least 95% sequence identity to SEQ ID NO:114. In some embodiments, an ILT3-binding agent comprises a heavy chain variable region comprising an amino sequence of SEQ ID NO:113 and a light chain variable region comprising an amino acid sequence of SEQ ID NO:114.

In some embodiments, the ILT3-binding agent is antibody 12A12. In some embodiments, the ILT3-binding agent is a humanized version of antibody 12A12. In some embodiments, the ILT3-binding agent is a variant of antibody 12A12 or humanized antibody 12A12.

In certain embodiments, an ILT3-binding agent (e.g., an antibody) comprises: (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPSNGGTGYNQKFKS (SEQ ID NO:59), and a heavy chain variable region CDR3 comprising the amino acid sequence VPYYDYLYYYAMDY (SEQ ID NO:60), and a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63); (b) a heavy chain variable region comprising a heavy chain variable region CDR1 comprising the amino acid sequence GYTFTDY (SEQ ID NO:49), a heavy chain variable region CDR2 comprising the amino acid sequence YPSNGG (SEQ ID NO:64), and a heavy chain variable region CDR3 comprising the amino acid sequence VPYYDYLYYYAMDY (SEQ ID NO:60), and a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63); (c) a heavy chain variable region comprising a heavy chain variable region CDR1 comprising the amino acid sequence GYTFTDYNMD (SEQ ID NO:43), a heavy chain variable region CDR2 comprising the amino acid sequence YIYPSNGGTG (SEQ ID NO:65), and a heavy chain variable region CDR3 comprising the amino acid sequence VPYYDYLYYYAMDY (SEQ ID NO:60), and a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63); (d) a heavy chain variable region comprising a heavy chain variable region CDR1 comprising the amino acid sequence DYNMD (SEQ ID NO:52), a heavy chain variable region CDR2 comprising the amino acid sequence YIYPSNGGTGYNQKFKS (SEQ ID NO:59), and a heavy chain variable region CDR3 comprising the amino acid sequence VPYYDYLYYYAMDY (SEQ ID NO:60), and a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63); or (e) a heavy chain variable region comprising a heavy chain variable region CDR1 comprising the amino acid sequence TDYNMD (SEQ ID NO:53), a heavy chain variable region CDR2 comprising the amino acid sequence WIGYIYPSNGGTG (SEQ ID NO:66), and a heavy chain variable region CDR3 comprising the amino acid sequence ARVPYYDYLYYYAMD (SEQ ID NO:67), and a light chain variable region comprising a light chain variable region CDR1 comprising the amino acid sequence SFMHWY (SEQ ID NO:68), a light chain variable region CDR2 comprising the amino acid sequence PWIYATSNLA (SEQ ID NO:69), and a light chain variable region CDR3 comprising the amino acid sequence QQWSTNPYMY (SEQ ID NO:70).

In some embodiments, an ILT3-binding agent comprises a heavy chain variable region comprising a heavy chain variable region CDR1 comprising the amino acid sequence GYTFTDYNMD (SEQ ID NO:43), a heavy chain variable region CDR2 comprising the amino acid sequence YIYPSNGGTGYNQKFKS (SEQ ID NO:59), and a heavy chain variable region CDR3 comprising the amino acid sequence VPYYDYLYYYAMDY (SEQ ID NO:60). In some embodiments, an ILT3-binding agent comprises a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63). In some embodiments, an ILT3-binding agent comprises (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPSNGGTGYNQKFKS (SEQ ID NO:59), and a heavy chain variable region CDR3 comprising the amino acid sequence VPYYDYLYYYAMDY (SEQ ID NO:60), and (b) a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63).

In some embodiments, an ILT3-binding agent comprises a heavy chain variable region having at least 80%, at least 85%, at least 90%, at least 95%, at least 97%, or at least 99% identity to the sequence of SEQ ID NO:115. In some embodiments, an ILT3-binding agent comprises a light chain variable region having at least 80%, at least 85%, at least 90%, at least 95%, at least 97%, or at least 99% identity to the sequence of SEQ ID NO:116. In some embodiments, an ILT3-binding agent comprises a heavy chain variable region comprising an amino acid sequence of SEQ ID NO:115. In some embodiments, an ILT3-binding agent comprises a light chain variable region comprising an amino acid sequence of SEQ ID NO:116.

In some embodiments, an ILT3-binding agent comprises a heavy chain variable region having at least 80% sequence identity to SEQ ID NO:115 and a light chain variable region having at least 80% sequence identity to SEQ ID NO:116. In some embodiments, an ILT3-binding agent comprises a heavy chain variable region having at least 90% sequence identity to SEQ ID NO:115 and a light chain variable region having at least 90% sequence identity to SEQ ID NO:116. In some embodiments, an ILT3-binding agent comprises a heavy chain variable region having at least 95% sequence identity to SEQ ID NO:115 and a light chain variable region having at least 95% sequence identity to SEQ ID NO:116. In some embodiments, an ILT3-binding agent comprises a heavy chain variable region comprising an amino acid sequence of SEQ ID NO:115 and a light chain variable region comprising an amino acid sequence of SEQ ID NO:116.

In some embodiments, the ILT3-binding agent is antibody 16C5. In some embodiments, the ILT3-binding agent is a humanized version of antibody 16C5. In some embodiments, the ILT3-binding agent is a variant of antibody 16C5 or humanized antibody 16C5.

In certain embodiments, an ILT3-binding agent (e.g., an antibody) comprises: (a) a heavy chain variable region comprising a heavy chain variable region CDR1 comprising the amino acid sequence GFTFSDYGMH (SEQ ID NO:71), a heavy chain variable region CDR2 comprising the amino acid sequence YIFSGSSTIYYADTVKG (SEQ ID NO:72), and a heavy chain variable region CDR3 comprising the amino acid sequence ADGRGAMDY (SEQ ID NO:73), and a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76); (b) a heavy chain variable region comprising a heavy chain variable region CDR1 comprising the amino acid sequence GFTFSDY (SEQ ID NO:77), a heavy chain variable region CDR2 comprising the amino acid sequence FSGSST (SEQ ID NO:78), and a heavy chain variable region CDR3 comprising the amino acid sequence ADGRGAMDY (SEQ ID NO:73), and a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76); (c) a heavy chain variable region comprising a heavy chain variable region CDR1 comprising the amino acid sequence GFTFSDYGMH (SEQ ID NO:71), a heavy chain variable region CDR2 comprising the amino acid sequence YIFSGSSTIY (SEQ ID NO:79), and a heavy chain variable region CDR3 comprising the amino acid sequence ADGRGAMDY (SEQ ID NO:73), and a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76); (d) a heavy chain variable region comprising a heavy chain variable region CDR1 comprising the amino acid sequence DYGMH (SEQ ID NO:80), a heavy chain variable region CDR2 comprising the amino acid sequence YIFSGSSTIYYADTVKG (SEQ ID NO:72), and a heavy chain variable region CDR3 comprising the amino acid sequence ADGRGAMDY (SEQ ID NO:73), and a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76); or (e) a heavy chain variable region comprising a heavy chain variable region CDR1 comprising the amino acid sequence SDYGMH (SEQ ID NO:81), a heavy chain variable region CDR2 comprising the amino acid sequence WVAYIFSGSSTIY (SEQ ID NO:82), and a heavy chain variable region CDR3 comprising the amino acid sequence ARADGRGAMD (SEQ ID NO:83), and a light chain variable region comprising a light chain variable region CDR1 comprising the amino acid sequence SKFLNWY (SEQ ID NO:84), a light chain variable region CDR2 comprising the amino acid sequence LLIYYTSRLH (SEQ ID NO:85), and a light chain variable region CDR3 comprising the amino acid sequence QQGNTLPW (SEQ ID NO:86).

In some embodiments, an ILT3-binding agent comprises a heavy chain variable region comprising a heavy chain variable region CDR1 comprising the amino acid sequence GFTFSDYGMH (SEQ ID NO:71), a heavy chain variable region CDR2 comprising the amino acid sequence YIFSGSSTIYYADTVKG (SEQ ID NO:72), and a heavy chain variable region CDR3 comprising the amino acid sequence ADGRGAMDY (SEQ ID NO:73). In some embodiments, an ILT3-binding agent comprises a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76). In some embodiments, an ILT3-binding agent comprises (a) a heavy chain variable region comprising a heavy chain variable region CDR1 comprising the amino acid sequence GFTFSDYGMH (SEQ ID NO:71), a heavy chain variable region CDR2 comprising the amino acid sequence YIFSGSSTIYYADTVKG (SEQ ID NO:72), and a heavy chain variable region CDR3 comprising the amino acid sequence ADGRGAMDY (SEQ ID NO:73), and (b) a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76).

In some embodiments, an ILT3-binding agent comprises a heavy chain variable region having at least 80%, at least 85%, at least 90%, at least 95%, at least 97%, or at least 99% identity to the sequence of SEQ ID NO:117. In some embodiments, an ILT3-binding agent comprises a light chain variable region having at least 80%, at least 85%, at least 90%, at least 95%, at least 97%, or at least 99% identity to the sequence of SEQ ID NO:118. In some embodiments, an ILT3-binding agent comprises a heavy chain variable region comprising an amino acid sequence of SEQ ID NO:117. In some embodiments, an ILT3-binding agent comprises a light chain variable region comprising an amino acid sequence of SEQ ID NO:118.

In some embodiments, an ILT3-binding agent comprises a heavy chain variable region having at least 80% sequence identity to SEQ ID NO:117 and a light chain variable region having at least 80% sequence identity to SEQ ID NO:118. In some embodiments, an ILT3-binding agent comprises a heavy chain variable region having at least 90% sequence identity to SEQ ID NO:117 and a light chain variable region having at least 90% sequence identity to SEQ ID NO:118. In some embodiments, an ILT3-binding agent comprises a heavy chain variable region having at least 95% sequence identity to SEQ ID NO:117 and a light chain variable region having at least 95% sequence identity to SEQ ID NO:118. In some embodiments, an ILT3-binding agent comprises a heavy chain variable region comprising an amino acid sequence of SEQ ID NO:117 and a light chain variable region comprising an amino acid sequence of SEQ ID NO:118.

In some embodiments, an ILT3-binding agent comprises a heavy chain variable region having at least 80%, at least 85%, at least 90%, at least 95%, at least 97%, or at least 99% identity to the sequence selected from SEQ ID NOs:162-163. In some embodiments, an ILT3-binding agent comprises a light chain variable region having at least 80%, at least 85%, at least 90%, at least 95%, at least 97%, or at least 99% identity to the sequence of SEQ ID NO:164. In some embodiments, an ILT3-binding agent comprises a heavy chain variable region comprising an amino acid sequence selected from SEQ ID NOs:162-163. In some embodiments, an ILT3-binding agent comprises a light chain variable region comprising an amino acid sequence of SEQ ID NO:164.

In some embodiments, an ILT3-binding agent comprises a heavy chain variable region having at least 80% (e.g., at least 85%, at least 90%, at least 95%, at least 97%, or at least 99%) sequence identity to an amino acid sequence selected from SEQ ID Nos:162-163, and a light chain variable region having at least 80% (e.g., at least 85%, at least 90%, at least 95%, at least 97%, or at least 99%) sequence identity to SEQ ID NO:164. In some embodiments, an ILT3-binding agent comprises a heavy chain variable region comprising an amino acid sequence of SEQ ID NO:162 and a light chain variable region comprising an amino acid sequence of SEQ ID NO:164. In some embodiments, an ILT3-binding agent comprises a heavy chain variable region comprising an amino acid sequence of SEQ ID NO:163 and a light chain variable region comprising an amino acid sequence of SEQ ID NO:164.

In some embodiments, the ILT3-binding agent is antibody 45G10. In some embodiments, the ILT3-binding agent is a humanized version of antibody 45G10. In some embodiments, the ILT3-binding agent is a variant of antibody 45G10 or humanized antibody 45G10.

In certain embodiments, an ILT3-binding agent (e.g., an antibody) comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88), and a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91); (b) a heavy chain variable region comprising a heavy chain variable region CDR1 comprising the amino acid sequence GFTFSSY (SEQ ID NO:33), a heavy chain variable region CDR2 comprising the amino acid sequence SSGGTY (SEQ ID NO:92), and a heavy chain variable region CDR3 comprising the amino acid sequence RGWLLHYYAMDY (SEQ ID NO:88), and a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91); (c) a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTF (SEQ ID NO:93), and a heavy chain variable region CDR3 comprising the amino acid sequence RGWLLHYYAMDY (SEQ ID NO:88), and a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91); (d) a heavy chain variable region comprising a heavy chain variable region CDR1 comprising the amino acid sequence SYGMS (SEQ ID NO:36), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88), and a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91); or (e) a heavy chain variable region comprising a heavy chain variable region CDR1 comprising the amino acid sequence SSYGMS (SEQ ID NO:37), a heavy chain variable region CDR2 comprising the amino acid sequence WVATISSGGTYTF (SEQ ID NO:94), and a heavy chain variable region CDR3 comprising the amino acid sequence ARRGWLLHYYAMD (SEQ ID NO:95), and a light chain variable region comprising a light chain variable region CDR1 comprising the amino acid sequence DSFGNSFMHWF (SEQ ID NO:96), a light chain variable region CDR2 comprising the amino acid sequence LLIYLSSKLE (SEQ ID NO:97), and a light chain variable region CDR3 comprising the amino acid sequence QQHNEDPF (SEQ ID NO:98).

In some embodiments, an ILT3-binding agent comprises a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88). In some embodiments, an ILT3-binding agent comprises a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91). In some embodiments, an ILT3-binding agent comprises (a) a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88), and (b) a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91).

In some embodiments, an ILT3-binding agent comprises a heavy chain variable region having at least 80%, at least 85%, at least 90%, at least 95%, at least 97%, or at least 99% identity to the sequence of SEQ ID NO:119. In some embodiments, an ILT3-binding agent comprises a light chain variable region having at least 80%, at least 85%, at least 90%, at least 95%, at least 97%, or at least 99% identity to the sequence of SEQ ID NO:120. In some embodiments, an ILT3-binding agent comprises a heavy chain variable region comprising an amino acid sequence of SEQ ID NO:119. In some embodiments, an ILT3-binding agent comprises a light chain variable region comprising an amino acid sequence of SEQ ID NO:120.

In some embodiments, an ILT3-binding agent comprises a heavy chain variable region having at least 80% sequence identity to SEQ ID NO:119 and a light chain variable region having at least 80% sequence identity to SEQ ID NO:120. In some embodiments, an ILT3-binding agent comprises a heavy chain variable region having at least 90% sequence identity to SEQ ID NO:119 and a light chain variable region having at least 90% sequence identity to SEQ ID NO:120. In some embodiments, an ILT3-binding agent comprises a heavy chain variable region having at least 95% sequence identity to SEQ ID NO:119 and a light chain variable region having at least 95% sequence identity to SEQ ID NO:120. In some embodiments, an ILT3-binding agent comprises a heavy chain variable region comprising an amino acid sequence of SEQ ID NO:119 and a light chain variable region comprising an amino acid sequence of SEQ ID NO:120.

In some embodiments, an ILT3-binding agent comprises a heavy chain variable region having at least 80%, at least 85%, at least 90%, at least 95%, at least 97%, or at least 99% identity to the sequence selected from SEQ ID NOs:156-160. In some embodiments, an ILT3-binding agent comprises a light chain variable region having at least 80%, at least 85%, at least 90%, at least 95%, at least 97%, or at least 99% identity to the sequence of SEQ ID NO:161. In some embodiments, an ILT3-binding agent comprises a heavy chain variable region comprising an amino acid sequence selected from SEQ ID NOs:156-160. In some embodiments, an ILT3-binding agent comprises a light chain variable region comprising an amino acid sequence of SEQ ID NO:161.

In some embodiments, an ILT3-binding agent comprises a heavy chain variable region having at least 80% (e.g., at least 85%, at least 90%, at least 95%, at least 97%, or at least 99%) sequence identity to an amino acid sequence selected from SEQ ID Nos:156-160, and a light chain variable region having at least 80% (e.g., at least 85%, at least 90%, at least 95%, at least 97%, or at least 99%) sequence identity to SEQ ID NO:161. In some embodiments, an ILT3-binding agent comprises a heavy chain variable region comprising an amino acid sequence of SEQ ID NO:156 and a light chain variable region comprising an amino acid sequence of SEQ ID NO:161. In some embodiments, an ILT3-binding agent comprises a heavy chain variable region comprising an amino acid sequence of SEQ ID NO:157 and a light chain variable region comprising an amino acid sequence of SEQ ID NO:161. In some embodiments, an ILT3-binding agent comprises a heavy chain variable region comprising an amino acid sequence of SEQ ID NO:158 and a light chain variable region comprising an amino acid sequence of SEQ ID NO:161. In some embodiments, an ILT3-binding agent comprises a heavy chain variable region comprising an amino acid sequence of SEQ ID NO:159 and a light chain variable region comprising an amino acid sequence of SEQ ID NO:161. In some embodiments, an ILT3-binding agent comprises a heavy chain variable region comprising an amino acid sequence of SEQ ID NO:160 and a light chain variable region comprising an amino acid sequence of SEQ ID NO:161.

In some embodiments, the ILT3-binding agent is antibody 48A6. In some embodiments, the ILT3-binding agent is a humanized version of antibody 48A6. In some embodiments, the ILT3-binding agent is a variant of antibody 48A6 or humanized antibody 48A6.

In certain embodiments, an ILT3-binding agent (e.g., an antibody) comprises: (a) a heavy chain variable region comprising a heavy chain variable region CDR1 comprising the amino acid sequence GFTFSDYGMH (SEQ ID NO:71), a heavy chain variable region CDR2 comprising the amino acid sequence YISTGIITVYYADTVKG (SEQ ID NO:99), and a heavy chain variable region CDR3 comprising the amino acid sequence ADGRGAMDY (SEQ ID NO:73), and a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76); (b) a heavy chain variable region comprising a heavy chain variable region CDR1 comprising the amino acid sequence GFTFSDY (SEQ ID NO:77), a heavy chain variable region CDR2 comprising the amino acid sequence STGIIT (SEQ ID NO:101), and a heavy chain variable region CDR3 comprising the amino acid sequence ADGRGAMDY (SEQ ID NO:73), and a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76); (c) a heavy chain variable region comprising a heavy chain variable region CDR1 comprising the amino acid sequence GFTFSDYGMH (SEQ ID NO:71), a heavy chain variable region CDR2 comprising the amino acid sequence YISTGIITVY (SEQ ID NO:102), and a heavy chain variable region CDR3 comprising the amino acid sequence ADGRGAMDY (SEQ ID NO:73), and a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76); (d) a heavy chain variable region comprising a heavy chain variable region CDR1 comprising the amino acid sequence DYGMH (SEQ ID NO:80), a heavy chain variable region CDR2 comprising the amino acid sequence YISTGIITVYYADTVKG (SEQ ID NO:99), and a heavy chain variable region CDR3 comprising the amino acid sequence ADGRGAMDY (SEQ ID NO:73), and a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76); or (e) a heavy chain variable region comprising a heavy chain variable region CDR1 comprising the amino acid sequence SDYGMH (SEQ ID NO:81), a heavy chain variable region CDR2 comprising the amino acid sequence WVAYISTGIITVY (SEQ ID NO:103), and a heavy chain variable region CDR3 comprising the amino acid sequence ARADGRGAMD (SEQ ID NO:83), and a light chain variable region comprising a light chain variable region CDR1 comprising the amino acid sequence SNFLNWY (SEQ ID NO:104), a light chain variable region CDR2 comprising the amino acid sequence LLIYYTSRLH (SEQ ID NO:85), and a light chain variable region CDR3 comprising the amino acid sequence QQGNTLPW (SEQ ID NO:86).

In some embodiments, an ILT3-binding agent comprises a heavy chain variable region comprising a heavy chain variable region comprising a heavy chain variable region CDR1 comprising the amino acid sequence GFTFSDYGMH (SEQ ID NO:71), a heavy chain variable region CDR2 comprising the amino acid sequence YISTGIITVYYADTVKG (SEQ ID NO:99), and a heavy chain variable region CDR3 comprising the amino acid sequence ADGRGAMDY (SEQ ID NO:73). In some embodiments, an ILT3-binding agent comprises a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76). In some embodiments, an ILT3-binding agent comprises (a) a heavy chain variable region comprising a heavy chain variable region CDR1 comprising the amino acid sequence GFTFSDYGMH (SEQ ID NO:71), a heavy chain variable region CDR2 comprising the amino acid sequence YISTGIITVYYADTVKG (SEQ ID NO:99), and a heavy chain variable region CDR3 comprising the amino acid sequence ADGRGAMDY (SEQ ID NO:73), and (b) a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76).

In some embodiments, an ILT3-binding agent comprises a heavy chain variable region having at least 80%, at least 85%, at least 90%, at least 95%, at least 97%, or at least 99% identity to the sequence of SEQ ID NO:121. In some embodiments, an ILT3-binding agent comprises a light chain variable region having at least 80%, at least 85%, at least 90%, at least 95%, at least 97%, or at least 99% identity to the sequence of SEQ ID NO:122. In some embodiments, an ILT3-binding agent comprises a heavy chain variable region comprising an amino acid sequence of SEQ ID NO:121. In some embodiments, an ILT3-binding agent comprises a light chain variable region comprising an amino acid sequence of SEQ ID NO:122.

In some embodiments, an ILT3-binding agent comprises a heavy chain variable region having at least 80% sequence identity to SEQ ID NO:121 and a light chain variable region having at least 80% sequence identity to SEQ ID NO:122. In some embodiments, an ILT3-binding agent comprises a heavy chain variable region having at least 90% sequence identity to SEQ ID NO:121 and a light chain variable region having at least 90% sequence identity to SEQ ID NO:122. In some embodiments, an ILT3-binding agent comprises a heavy chain variable region having at least 95% sequence identity to SEQ ID NO:121 and a light chain variable region having at least 95% sequence identity to SEQ ID NO:122. In some embodiments, an ILT3-binding agent comprises a heavy chain variable region comprising an amino acid sequence of SEQ ID NO:121 and a light chain variable region comprising an amino acid sequence of SEQ ID NO:122.

In some embodiments, the ILT3-binding agent is antibody 53F10. In some embodiments, the ILT3-binding agent is a humanized version of antibody 53F10. In some embodiments, the ILT3-binding agent is a variant of antibody 53F10 or humanized antibody 53F10.

Provided herein are agents that compete with one or more of the binding agents (e.g., antibodies) described herein for binding to ILT3. In some embodiments, an agent competes with one of more of the antibodies described herein for binding to ILT3. In some embodiments, an agent that competes with one of more of the antibodies described herein is an antibody. In some embodiments, an agent binds the same epitope as one of the antibodies described herein. In some embodiments, an agent binds an epitope overlapping with an epitope bound by one of the antibodies described herein. Antibodies and antigen-binding fragments that compete with or bind the same epitope as the antibodies described herein are expected to show similar functional properties.

In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRYTLYAMDY (SEQ ID NO:105), and (b) a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRYTLYAMDY (SEQ ID NO:105), and (b) a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32); and wherein the competing agent comprises a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88), and a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91).

In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GFSLTSYGVH (SEQ ID NO:11), a heavy chain variable region CDR2 comprising the amino acid sequence VIWPGGTINYNSALMS (SEQ ID NO:12), and a heavy chain variable region CDR3 comprising the amino acid sequence DKYDGGWFAY (SEQ ID NO:13), and (b) a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16). In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPNNGGTGYNQKFNS (SEQ ID NO:44), and a heavy chain variable region CDR3 comprising the amino acid sequence SPYYDYVGSYAMDY (SEQ ID NO:45), and (b) a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48). In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPSNGGTGYNQKFKS (SEQ ID NO:59), and a heavy chain variable region CDR3 comprising the amino acid sequence VPYYDYLYYYAMDY (SEQ ID NO:60), and (b) a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63). In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GFTFSDYGMH (SEQ ID NO:71), a heavy chain variable region CDR2 comprising the amino acid sequence YIFSGSSTIYYADTVKG (SEQ ID NO:72), and a heavy chain variable region CDR3 comprising the amino acid sequence ADGRGAMDY (SEQ ID NO:73), and (b) a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76). In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88), and (b) a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91). In some embodiments, an agent (e.g., an antibody) competes for binding to human ILT3 with a reference antibody, wherein the reference antibody comprises: (a) a heavy chain variable region comprising a heavy chain variable region CDR1 comprising the amino acid sequence GFTFSDYGMH (SEQ ID NO:71), a heavy chain variable region CDR2 comprising the amino acid sequence YISTGIITVYYADTVKG (SEQ ID NO:99), and a heavy chain variable region CDR3 comprising the amino acid sequence ADGRGAMDY (SEQ ID NO:73), and (b) a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76).

In some embodiments, an ILT3-binding agent described herein comprises an antibody in which at least one or more of the constant regions of the antibody has been modified or deleted. In some embodiments, an antibody comprises one or more modifications to one or more of the three heavy chain constant regions (CH1, CH2 or CH3) and/or to the light chain constant region (CL). In some embodiments, an antibody comprises one or more modifications to the hinge region. In some embodiments, the heavy chain constant region of the modified antibody comprises at least one human constant region. In some embodiments, the heavy chain constant region of the modified antibody comprises more than one human constant region. In some embodiments, modifications to the constant region comprise additions, deletions, or substitutions of one or more amino acids in one or more regions. In some embodiments, one or more regions are partially or entirely deleted from the constant regions of a modified antibody. In some embodiments, the entire CH2 domain has been removed from an antibody (ΔCH2 constructs). In some embodiments, one or more regions are partially or entirely deleted from the hinge region of a modified antibody. In some embodiments, a deleted constant region is replaced by a short amino acid spacer that provides some of the molecular flexibility typically imparted by the absent constant region. In some embodiments, a deleted hinge region is replaced by a short amino acid spacer that provides some of the molecular flexibility typically imparted by the absent hinge region. In some embodiments, a modified antibody comprises a CH3 domain directly fused to the hinge region of the antibody. In some embodiments, a modified antibody comprises a peptide spacer inserted between the hinge region and modified CH2 and/or CH3 domains.

It is known in the art that the constant region(s) of an antibody mediates several effector functions and these effector functions can vary depending on the isotype of the antibody. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can be involved in autoimmune hypersensitivity. In addition, the Fc region of an antibody can bind a cell expressing a Fc receptor (FcR). There are a number of Fc receptors that are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In some embodiments, an ILT3-binding agent (e.g., an antibody) comprises a variant Fc region. The amino acid sequences of the Fc region of human IgG1, IgG2, IgG3, and IgG4 are known to those of ordinary skill in the art (e.g., a representative human IgG1 region is SEQ ID NO:129). In some cases, Fc regions with amino acid variations have been identified in native antibodies. In some embodiments, a variant Fc region is engineered with substitutions at specific amino acid positions as compared to a native Fc region. Variant Fc regions are well-known in the art and include, but are not limited to, SEQ ID NO:130, SEQ ID NO:131, SEQ ID NO:132, SEQ ID NO:133, and SEQ ID NO:134.

In some embodiments, a modified antibody (e.g., comprising a modified Fc region) provides for altered effector functions that, in turn, affect the biological profile of the antibody. For example, in some embodiments, the deletion or inactivation (through point mutations or other means) of a constant region reduces Fc receptor binding of a modified antibody as it circulates. In some embodiments, constant region modifications increase the serum half-life of an antibody. In some embodiments, constant region modifications reduce the serum half-life of an antibody. In some embodiments, constant region modifications decrease or remove ADCC and/or complement-dependent cytotoxicity (CDC) of an antibody. In some embodiments, specific amino acid substitutions in a human IgG1 Fc region with corresponding IgG2 or IgG4 residues reduce effector functions (e.g., ADCC and CDC) in a modified antibody. In some embodiments, a modified antibody does not have one or more effector functions. In some embodiments, a modified antibody does not have any detectable effector functions (e.g., "effectorless" antibodies). In some embodiments, a modified antibody has no ADCC activity and/or no CDC activity. In some embodiments, a modified antibody does not bind an Fc receptor and/or complement factors. In some embodiments, a modified antibody has no effector function(s). In some embodiments, constant region modifications increase or enhance ADCC and/or CDC of an antibody. In some embodiments, the constant region is modified to eliminate disulfide linkages or oligosaccharide moieties. In some embodiments, the constant region is modified to add/substitute one or more amino acids to provide one or more cytotoxin, oligosaccharide, or carbohydrate attachment sites.

In some embodiments, an ILT3-binding agent (e.g., an antibody) comprises a heavy chain having at least 80%, at least 85%, at least 90%, or at least 95% identity to the amino acid sequence of SEQ ID NO:126. In some embodiments, an ILT3-binding agent (e.g., an antibody) comprises a light chain having at least 80%, at least 85%, at least 90%, or at least 95% identity to the amino acid sequence of SEQ ID NO:128. In some embodiments, an ILT3-binding agent comprises a heavy chain having at least 80%, at least 85%, at least 90%, or at least 95% identity to the amino acid sequence of SEQ ID NO:126 and a light chain having at least 80%, at least 85%, at least 90%, or at least 95% identity to the amino acid sequence of SEQ ID NO:128. In some embodiments, an ILT3-binding agent comprises a heavy chain having at least 90% identity to the amino acid sequence of SEQ ID NO:126. In some embodiments, an ILT3-binding agent comprises a light chain having at least 90% identity to the amino acid sequence of SEQ ID NO:128. In some embodiments, an ILT3-binding agent comprises a heavy chain having at least 90% identity to the amino acid sequence of SEQ ID NO:126 and a light chain having at least 90% identity to the amino acid sequence of SEQ ID NO:128. In some embodiments, an ILT3-binding agent comprises a heavy chain comprising the amino acid sequence of SEQ ID NO:126. In some embodiments, an ILT3-binding agent comprises a light chain comprising the amino acid sequence of SEQ ID NO:128. In some embodiments, an ILT3-binding agent comprises a heavy chain comprising the amino acid sequence of SEQ ID NO:126 and a light chain comprising the amino acid sequence of SEQ ID NO:128. In some embodiments, an ILT3-binding agent is an antibody that comprises a heavy chain of SEQ ID NO:126 and/or a light chain of SEQ ID NO:128. In some embodiments, an ILT3-binding agent is an antibody that comprises a heavy chain of SEQ ID NO:126. In some embodiments, an ILT3-binding agent is an antibody that comprises a light chain of SEQ ID NO:128. In some embodiments, an ILT3-binding agent is an antibody that comprises a heavy chain of SEQ ID NO:126 and a light chain of SEQ ID NO:128.

Modifications to the constant region of antibodies described herein may be made using well-known biochemical or molecular engineering techniques. In some embodiments, antibody variants are prepared by introducing appropriate nucleotide changes into the encoding DNA, and/or by synthesis of the desired antibody or polypeptide. Using these engineering techniques to modify an antibody it may be possible to disrupt the activity or effector function provided by a specific sequence or region while substantially maintaining the structure, binding activity, and other desired characteristics of the modified antibody.

The present disclosure further embraces additional variants and equivalents that are substantially homologous to the recombinant, monoclonal, chimeric, humanized, and human antibodies, or antibody fragments thereof, described herein. In some embodiments, it is desirable to improve the binding affinity of the antibody. In some embodiments, it is desirable to modulate biological properties of the antibody, including but not limited to, specificity, thermostability, expression level, effector function(s), glycosylation, immunogenicity, and/or solubility. Those skilled in the art will appreciate that amino acid changes may alter post-translational processes of an antibody, such as changing the number or position of glycosylation sites or altering membrane anchoring characteristics.

Variations may be a substitution, deletion, or insertion of one or more nucleotides encoding the antibody or polypeptide that results in a change in the amino acid sequence as compared with the native antibody or polypeptide sequence. In some embodiments, amino acid substitutions are the result of replacing one amino acid with another amino acid having similar structural and/or chemical properties, such as the replacement of a leucine with a serine (i.e., conservative amino acid replacements). In some embodiments, the substitution, deletion, or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the parent molecule. In some embodiments, variations in the amino acid sequence that are biologically useful and/or relevant are determined by systematically making insertions, deletions, or substitutions in the sequence and testing the resulting variant proteins for activity as compared to the parental antibody.

In some embodiments, variants may include addition of amino acid residues at the amino- and/or carboxyl-terminal end of the antibody or polypeptide. The length of additional amino acids residues may range from one residue to a hundred or more residues. In some embodiments, a variant comprises an N-terminal methionyl residue. In some embodiments, the variant comprises an additional polypeptide/protein to create a fusion protein. In some embodiments, a variant is engineered to be detectable and may comprise a detectable label and/or protein (e.g., a fluorescent tag, a fluorescent protein, or an enzyme).

In some embodiments, a cysteine residue not involved in maintaining the proper conformation of an antibody is substituted or deleted to modulate the antibody's characteristics, for example, to improve oxidative stability and/or prevent aberrant disulfide crosslinking. Conversely, in some embodiments, one or more cysteine residues are added to create disulfide bond(s) to improve stability.

In some embodiments, an antibody of the present disclosure is "deimmunized". The deimmunization of antibodies generally consists of introducing specific amino acid mutations (e.g., substitutions, deletions, additions) that result in removal of T-cell epitopes (known or predicted) without significantly reducing the binding affinity or other desired activities of the antibody.

The variant antibodies or polypeptides described herein may be generated using methods known in the art, including but not limited to, site-directed mutagenesis, alanine scanning mutagenesis, and PCR mutagenesis.

In some embodiments, an ILT3-binding agent described herein is chemically modified. In some embodiments, an ILT3-binding agent is an anti-ILT3 antibody that is chemically modified by glycosylation, acetylation, pegylation, phosphorylation, amidation, derivatization by known protecting/blocking groups, proteolytic cleavage, and/or linkage to a cellular ligand or other protein. Any of numerous chemical modifications may be carried out by known techniques. In some embodiments, an ILT3-binding agent is an antibody fragment (e.g., scFv, Fv, Fab, F(ab')$_2$, or F(ab')), wherein the antibody fragment is attached (either directly or indirectly) to a half-life extending moiety including, but not limited to, a Fc region or its variants, a human serum albumin, a CH3 domain of an immunoglobulin, polyethylene glycol (PEG), a PEG mimetic, XTEN®, serum albumin, polysialic acid, N-(2-hydroxypropyl)methacrylamide, or dextran.

The present disclosure encompasses ILT3-binding agents built upon non-immunoglobulin backbones, wherein the agents bind the same epitope or essentially the same epitope as an anti-ILT3 antibody disclosed herein. In some embodiments, a non-immunoglobulin-based binding agent is an agent that competes with an anti-ILT3 antibody described herein in a competitive binding assay. In some embodiments, alternative ILT3-binding agents comprise a scaffold protein. Generally, scaffold proteins can be assigned to one of three groups based on the architecture of their backbone (1) scaffolds consisting of α-helices; (2) small scaffolds with few secondary structures or an irregular architecture of α-helices and β-sheets; and (3) scaffolds consisting of predominantly β-sheets. Scaffold proteins include, but are not limited to, anticalins, which are based upon the lipocalin scaffold; adnectins, which are based on the $10^{th}$ domain of human fibronectin type 3; affibodies, which are based on the B-domain in the Ig-binding region of *Staphylococcus aureus* protein A; darpins, which are based on ankyrin repeat domain proteins; fynomers, which are based on the SH3 domain of the human Fyn protein kinase; affitins, which are based on Sac7d from *Sulfolobus acidocaldarius*; affilins, which are based on human γ-B-crystallin or human ubiquitin; avimers, which are based on the A-domains of membrane receptor proteins; knottins (cysteine knot miniproteins), which are based upon a stable 30-amino acid antiparallel β-strand protein fold; and Kunitz domain inhibitor scaffolds, which are based upon a structure that contains three disulfide bonds and three loops.

In some embodiments, an ILT3-binding agent comprises an engineered scaffold protein comprising a heavy chain variable region CDR1, CDR2, and CDR3 and a light chain variable region CDR1, CDR2, and CDR3 shown in Table 1. In some embodiments, an ILT3-binding agent comprises an engineered scaffold protein comprising a heavy chain variable region CDR1 comprising the amino acid sequence GFSLTSYGVH (SEQ ID NO:11), a heavy chain variable region CDR2 comprising the amino acid sequence VIWPGGTINYNSALMS (SEQ ID NO:12), a heavy chain variable region CDR3 comprising the amino acid sequence DKYDGGWFAY (SEQ ID NO:13), a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16). In some embodiments, an ILT3-binding agent comprises an engineered scaffold protein comprising a heavy chain variable region CDR1, CDR2, and CDR3 and a light chain variable region CDR1, CDR2, and CDR3 from antibody 3A3.

In some embodiments, an ILT3-binding agent comprises an engineered scaffold protein comprising a heavy chain variable region CDR1, CDR2, and CDR3 and a light chain variable region CDR1, CDR2, and CDR3 shown in Table 2. In some embodiments, an ILT3-binding agent comprises an engineered scaffold protein comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), a heavy chain variable region CDR3 comprising the amino acid sequence REWRMTLYAMDY (SEQ ID NO:29), a light chain variable region CDR1 comprising the amino acid sequence RASESVDSYGNSFMH (SEQ ID NO:30), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, an ILT3-binding agent comprises an engineered scaffold protein comprising a heavy chain variable region CDR1, CDR2, and CDR3 and a light chain variable region CDR1, CDR2, and CDR3 from antibody 5A7. In some embodiments, an ILT3-binding agent comprises an engineered scaffold protein comprising a heavy chain variable region CDR1, CDR2, and CDR3 and a light chain variable region CDR1, CDR2, and CDR3 shown in Table 8. In some embodiments, an ILT3-binding agent comprises an engineered scaffold protein comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), a heavy chain variable region CDR3 comprising the amino acid sequence REWRYTLYAMDY (SEQ ID NO:105), a light chain variable region CDR1 comprising the amino acid sequence RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments, an ILT3-binding agent comprises an engineered scaffold protein comprising a heavy chain variable region CDR1, CDR2, and CDR3 and a light chain variable region CDR1, CDR2, and CDR3 from antibody Hz5A7.v5.

In some embodiments, an ILT3-binding agent comprises an engineered scaffold protein comprising a heavy chain variable region CDR1, CDR2, and CDR3 and a light chain variable region CDR1, CDR2, and CDR3 shown in Table 3. In some embodiments, an ILT3-binding agent comprises an engineered scaffold protein comprising a heavy chain variable region CDR1 comprising the amino acid sequence GYTFTDYNMD (SEQ ID NO:43), a heavy chain variable region CDR2 comprising the amino acid sequence YIYPNNGGTGYNQKFNS (SEQ ID NO:44), a heavy chain variable region CDR3 comprising the amino acid sequence SPYYDYVGSYAMDY (SEQ ID NO:45), a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48). In some embodiments, an ILT3-binding agent comprises an engineered scaffold protein comprising a heavy chain variable region CDR1, CDR2, and CDR3 and a light chain variable region CDR1, CDR2, and CDR3 from antibody 12A12.

In some embodiments, an ILT3-binding agent comprises an engineered scaffold protein comprising a heavy chain variable region CDR1, CDR2, and CDR3 and a light chain variable region CDR1, CDR2, and CDR3 shown in Table 4. In some embodiments, an ILT3-binding agent comprises an engineered scaffold protein comprising a heavy chain variable region CDR1 comprising the amino acid sequence GYTFTDYNMD (SEQ ID NO:43), a heavy chain variable region CDR2 comprising the amino acid sequence YIYPSNGGTGYNQKFKS (SEQ ID NO:59), a heavy chain variable region CDR3 comprising the amino acid sequence VPYYDYLYYYAMDY (SEQ ID NO:60), a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63). In some embodiments, an ILT3-binding agent comprises an engineered scaffold protein comprising a heavy chain variable region CDR1, CDR2, and CDR3 and a light chain variable region CDR1, CDR2, and CDR3 from antibody 16C5.

In some embodiments, an ILT3-binding agent comprises an engineered scaffold protein comprising a heavy chain variable region CDR1, CDR2, and CDR3 and a light chain variable region CDR1, CDR2, and CDR3 shown in Table 5. In some embodiments, an ILT3-binding agent comprises an engineered scaffold protein comprising a heavy chain variable region CDR1 comprising the amino acid sequence GFTFSDYGMH (SEQ ID NO:71), a heavy chain variable region CDR2 comprising the amino acid sequence YIFSGSSTIYYADTVKG (SEQ ID NO:72), a heavy chain variable region CDR3 comprising the amino acid sequence ADGRGAMDY (SEQ ID NO:73), a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76). In some embodiments, an ILT3-binding agent comprises an engineered scaffold protein comprising a heavy chain variable region CDR1, CDR2, and CDR3 and a light chain variable region CDR1, CDR2, and CDR3 from antibody 45G10.

In some embodiments, an ILT3-binding agent comprises an engineered scaffold protein comprising a heavy chain variable region CDR1, CDR2, and CDR3 and a light chain variable region CDR1, CDR2, and CDR3 shown in Table 6. In some embodiments, an ILT3-binding agent comprises an engineered scaffold protein comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), a heavy chain variable region CDR3 comprising the amino acid sequence RGWLLHYYAMDY (SEQ ID NO:88), a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91). In some embodiments, an ILT3-binding agent comprises an engineered scaffold protein comprising a heavy chain variable region CDR1, CDR2, and CDR3 and a light chain variable region CDR1, CDR2, and CDR3 from antibody 48A6.

In some embodiments, an ILT3-binding agent comprises an engineered scaffold protein comprising a heavy chain variable region CDR1, CDR2, and CDR3 and a light chain variable region CDR1, CDR2, and CDR3 shown in Table 7. In some embodiments, an ILT3-binding agent comprises an engineered scaffold protein comprising a heavy chain variable region CDR1 comprising the amino acid sequence GFTFSDYGMH (SEQ ID NO:71), a heavy chain variable region CDR2 comprising the amino acid sequence YISTGIITVYYADTVKG (SEQ ID NO:99), a heavy chain variable region CDR3 comprising the amino acid sequence ADGRGAMDY (SEQ ID NO:73), a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76). In some embodiments, an ILT3-binding agent comprises an engineered scaffold protein comprising a heavy chain variable region CDR1, CDR2, and CDR3 and a light chain variable region CDR1, CDR2, and CDR3 from antibody 53F10.

In some embodiments, a composition comprises an ILT3-binding agent described herein. In some embodiments, a composition comprises an anti-ILT3 antibody described herein. In some embodiments, a composition comprises a monoclonal anti-ILT3 antibody described herein.

In some embodiments, a pharmaceutical composition comprises an ILT3-binding agent described herein and a pharmaceutically acceptable carrier. In some embodiments, a pharmaceutical composition comprises an anti-ILT3 antibody described herein and a pharmaceutically acceptable carrier. In some embodiments, a composition comprises a monoclonal anti-ILT3 antibody described herein and a pharmaceutically acceptable carrier.

In some embodiments, an ILT3-binding agent is isolated. In some embodiments, an ILT3-binding agent is substantially pure.

Generally speaking, antigen-antibody interactions are non-covalent and reversible, formed by a combination of hydrogen bonds, hydrophobic interactions, electrostatic and van der Waals forces. When describing the strength of an antigen-antibody complex, the terms affinity and/or avidity are commonly used. The binding of an antibody to its antigen is a reversible process, and the affinity of the binding is typically reported as an equilibrium dissociation constant ($K_D$). $K_D$ is the ratio of an antibody dissociation rate ($k_{off}$) (how quickly it dissociates from its antigen) to the antibody association rate ($k_{on}$) (how quickly it binds to its antigen). In some embodiments, $K_D$ values are determined by measuring the $k_{on}$ and $k_{off}$ rates of a specific antibody/antigen interaction and then using a ratio of these values to calculate the $K_D$ value. $K_D$ values may be used to evaluate and rank order the strength of individual antibody/antigen interactions. The lower the $K_D$ of an antibody, the higher the affinity of the antibody for its target. In some embodiments, affinity is measured using SPR technology in a Biacore system. Avidity gives a measure of the overall strength of an antibody-antigen complex. It is dependent on three major parameters: (i) affinity of the antibody for the target, (ii) valency of both the antibody and antigen, and (iii) structural arrangement of the parts that interact.

In some embodiments, an ILT3-binding agent (e.g., an antibody) binds ILT3 with a dissociation constant ($K_D$) of 1 µM or less, 100 nM or less, 40 nM or less, 20 nM or less, 10 nM or less, 1 nM or less, 0.1 nM or less, 50 pM or less, 10 pM or less, or 1 pM or less. In some embodiments, an ILT3-binding agent binds ILT3 with a $K_D$ of about 20 nM or less. In some embodiments, an ILT3-binding agent binds ILT3 with a $K_D$ of 10 nM or less. In some embodiments, an ILT3-binding agent binds ILT3 with a $K_D$ of 5 nM or less. In some embodiments, an ILT3-binding agent binds ILT3 with a $K_D$ of 3 nM or less. In some embodiments, an ILT3-binding agent binds ILT3 with a $K_D$ of 2 nM or less. In some embodiments, an ILT3-binding agent binds ILT3 with a $K_D$ of 1 nM or less. In some embodiments, an ILT3-binding agent binds ILT3 with a $K_D$ of 0.5 nM or less. In some embodiments, an ILT3-binding agent binds ILT3 with a $K_D$ of 0.1 nM or less. In some embodiments, an ILT3-binding agent binds ILT3 with a $K_D$ of 50 pM or less. In some embodiments, an ILT3-binding agent binds ILT3 with a $K_D$ of 25 pM or less. In some embodiments, an ILT3-binding agent binds ILT3 with a $K_D$ of 10 pM or less. In some embodiments, an ILT3-binding agent binds ILT3 with a $K_D$ of 1 pM or less. In some embodiments, an ILT3-binding agent binds ILT3 with a $K_D$ of 0.01 nM to 2.5 nM. In some embodiments, an ILT3-binding agent binds ILT3 with a $K_D$ of 0.1 nM to 5 nM. In some embodiments, an ILT3-binding agent binds ILT3 with a $K_D$ of 1 nM to 5 nM. In some embodiments, the dissociation constant of the binding agent for ILT3 is the dissociation constant determined using an ILT3 protein immobilized on a Biacore chip and the binding agent flowed over the chip. In some embodiments, the dissociation constant of the binding agent for ILT3 is the dissociation constant determined using the binding agent captured by an anti-human IgG antibody on a Biacore chip and soluble ILT3 flowed over the chip.

In some embodiments, an ILT3-binding agent (e.g., an antibody) binds ILT3 with a half maximal effective concentration (EC50) of 1 µM or less, 100 nM or less, 40 nM or less, 20 nM or less, 10 nM or less, 1 nM or less, or 0.1 nM or less. In some embodiments, an ILT3-binding agent binds human ILT3 with an EC50 of 1 µM or less, 100 nM or less, 40 nM or less, 20 nM or less, 10 nM or less, 1 nM or less, or 0.1 nM or less. In some embodiments, an ILT3-binding agent binds cyno ILT3 and/or human ILT3 with an EC50 of 40 nM or less, 20 nM or less, 10 nM or less, 1 nM or less or 0.1 nM or less. In some embodiments, an ILT3-binding agent binds ILT3 with an EC50 of 0.1 nM to about 3 nM, 0.1 nM to 2 nM, 0.1 nM to 1 nM, 0.5 nM to 3 nM, 0.5 nM to 2 nM, or 0.5 nM to 1 nM.

In some embodiments, an ILT3-binding agent binds human ILT3 and has at least one or more of the following properties: (i) binds cyno ILT3; (ii) binds human and cyno ILT3; (iii) does not bind ILT2, ILT4, ILT5, and LILRB5; (iv) does not bind LILRA1, LILRA2, LILRA4, LILRA5, and LILRA6; (v) is an ILT3 antagonist; (vi) inhibits ILT3 activity; (vii) inhibits ILT3 signaling in cells that express ILT3; (viii) inhibits binding of ILT3 to APOE; (ix) inhibits binding of ILT3 to fibronectin; (x) inhibits binding of ILT3 to CNTFR; (xi inhibits ILT3-induced suppression of myeloid cells; (xii) inhibits ILT3-induced suppression of myeloid cell activity; (xiii) restores FcR activity in myeloid cells that express ILT3; and (xiv) restores the ability of myeloid cells that express ILT3 to respond to chemokines and/or produce chemokines.

The ILT3-binding agents (e.g., antibodies) described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof. In some embodiments, a DNA sequence encoding a polypeptide of interest is constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host.

In some embodiments, recombinant expression vectors are used to amplify and express DNA encoding the ILT3-binding agents described herein. For example, recombinant expression vectors can be replicable DNA constructs which have synthetic or cDNA-derived DNA fragments encoding one or more polypeptide chain(s) of an ILT3-binding agent, such as an anti-ILT3 antibody, or antigen-binding fragment thereof, operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence that is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor that participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In some embodiments, in situations where recombinant protein is expressed without a leader or transport sequence, a polypeptide may include an N-terminal methionine residue. This residue can optionally be subsequently cleaved from the expressed recombinant protein to provide a final product.

The choice of an expression control sequence and an expression vector generally depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

In some embodiments, an ILT3-binding agent (e.g., an antibody) of the present disclosure is expressed from one or more vectors. In some embodiments, a heavy chain variable region is expressed by one vector and a light chain variable region is expressed by a second vector. In some embodiments, a heavy chain variable region and a light chain variable region are expressed by one vector. In some embodiments, a vector encodes a heavy chain variable region of an ILT3-binding agent described herein. In some embodiments, a vector encodes a light chain variable region of an ILT3-binding agent described herein. In some embodiments, a vector encodes a heavy chain variable region and a light chain variable region of an ILT3-binding agent described herein. In some embodiments, a heavy chain polypeptide is expressed by one vector and a light chain polypeptide is expressed by a second vector. In some embodiments, a heavy chain polypeptide and a light chain polypeptide are expressed by one vector. In some embodiments, a vector encodes a heavy chain polypeptide of an ILT3-binding agent described herein. In some embodiments, a vector encodes a light chain polypeptide of an ILT3-binding agent described herein. In some embodiments, a vector encodes a heavy chain polypeptide and a light chain polypeptide of an ILT3-binding agent described herein.

Suitable host cells for expression of an ILT3-binding agent (e.g., an antibody) or a ILT3 protein or fragment thereof to use as an antigen or immunogen include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described herein. Cell-free translation systems may also be employed. Appropriate cloning vectors and expression vectors for use with bacterial, fungal, yeast, and mammalian cellular hosts, as well as methods of protein production, including antibody production are well known in the art.

Various mammalian culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

Thus, the present disclosure provides cells comprising the ILT3-binding agents described herein. In some embodiments, the cells produce the ILT3-binding agents described herein. In some embodiments, the cells produce an antibody. In some embodiments, the cells produce an antibody that binds human ILT3. In some embodiments, the cells produce an antibody that binds cyno ILT3. In some embodiments, the cells produce an antibody that binds human ILT3 and cyno ILT3. In some embodiments, the cells produce an antibody designated 5A7. In some embodiments, the cells produce a humanized version of antibody 5A7, referred to as Hz5A7. In some embodiments, the cells produce a variant of Hz5A7, for example, Hz5A7.v5. In some embodiments, the cells produce an antibody designated 3A3. In some embodiments, the cells produce an antibody designated 12A12. In some embodiments, the cells produce an antibody designated 16C5. In some embodiments, the cells produce an antibody designated 45G10. In some embodiments, the cells produce a humanized version of antibody 45G10, referred to as Hz45G10. In some embodiments, the cells produce an antibody designated 48A6. In some embodiments, the cells produce a humanized version of antibody 48A6, referred to as Hz48A6. In some embodiments, the cells produce an antibody designated 53F10. In some embodiments, the cell is a prokaryotic cell (e.g., E. coli). In some embodiments, the cell is an eukaryotic cell. In some embodiments, the cell is a mammalian cell. In some embodiments, the cell is a hybridoma cell.

Proteins produced by a host cell can be purified according to any suitable method. Standard methods include chromatography (e.g., ion exchange, affinity, and sizing column chromatography), centrifugation, differential solubility, or by any other standard technique for protein purification. Affinity tags such as hexahistidine (His6; SEQ ID NO:154), maltose binding domain, influenza coat sequence, and glutathione-S-transferase can be attached to the protein to allow easy purification by passage over an appropriate affinity column. Affinity chromatography methods used for purifying immunoglobulins can include, but are not limited to, Protein A, Protein G, and Protein L chromatography. Isolated proteins can be physically characterized using techniques that include, but are not limited to, proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems that secrete recombinant protein into culture media are first concentrated using a commercially available protein concentration filter, for example, an Amicon® or Millipore Pellicon® ultrafiltration unit. Following the concentration step, the concentrate can be applied to a suitable purification matrix. In some embodiments, an anion exchange resin is employed, for example, a matrix or substrate having pendant diethylaminoethyl (DEAE) groups. The matrices can be acrylamide, agarose, dextran, cellulose, or other types commonly employed in protein purification. In some embodiments, a cation exchange step is employed. Suitable cation exchangers include various insoluble matrices comprising sulfopropyl or carboxymethyl groups. In some embodiments, a hydroxyapatite media is employed, including but not limited to, ceramic hydroxyapatite (CHT). In some embodiments, one or more reverse-phase HPLC steps employing hydrophobic RP-HPLC media, e.g., silica gel having pendant methyl or other aliphatic groups, are employed to further purify a recombinant protein. In some embodiments, hydrophobic interaction chromatography (HIC) is used to separate recombinant proteins based on their hydrophobicity. HIC is a useful separation technique for purifying proteins while maintaining biological activity due to the use of conditions and matrices that operate under less denaturing conditions than some other techniques. Some or all of the foregoing purification steps, in various combinations, can be employed to provide a homogeneous recombinant protein.

ILT3-binding agents (e.g., antibodies) of the present disclosure may be analyzed for their physical/chemical properties and/or biological activities by various assays known in the art. In some embodiments, an anti-ILT3 antibody is tested for its ability to bind ILT3 (e.g., human ILT3 and/or cyno ILT3). Binding assays include, but are not limited to, SPR (e.g., Biacore), ELISA, and FACS. In some embodiments, an anti-ILT3 antibody is tested for its ability to inhibit, reduce, or block binding to fibronectin, APOE, and/or CNTFR. In addition, antibodies may be evaluated for solubility, stability, thermostability, viscosity, expression levels, expression quality, and/or purification efficiency.

In some embodiments, monoclonal antibodies generated against ILT3 are grouped based upon the epitope each individual antibody recognizes, a process known as "epitope binning". Generally, antibodies are tested in a pairwise combinatorial manner and antibodies that compete with each other are grouped together into bins. For example, in a premix binning assay, a first antibody is immobilized on a surface and a premixed solution of a second antibody and antigen is flowed over the immobilized first antibody. In tandem, the antigen is immobilized on a surface and the two antibodies are flowed over the immobilized antigen and compete to bind. Using these techniques, antibodies that block one another can be identified. A competitive blocking profile is created for each antibody relative to the other antibodies. The blocking results determine which bin each antibody is placed in. High-throughput methods of epitope binning are known in the art and allow for screening and characterization of large numbers of antibodies within a short period of time. Antibodies that bind similar epitopes often share similar functions and/or capabilities. Conversely, antibodies that bind different epitopes may have different functional activities.

In some embodiments, an epitope bin comprises at least one antibody from the group consisting of: 3A3, 5A7, 12A12, 16C5, 45G10, 48A6, and 53F10. In some embodiments, an epitope bin comprises at least antibodies 5A7 and 48A6. In some embodiments, an epitope bin comprises at least antibodies 12A12 and 16C5. In some embodiments, an epitope bin comprises at least antibodies 45G10 and 53F10. In some embodiments, an epitope bin comprises at least antibodies 12A12 and 16C5.

Epitope mapping is the process of identifying the binding site, or epitope on a target protein/antigen where an antibody (or other binding agent) binds. A variety of methods are known in the art for mapping epitopes on target proteins. These methods include (i) mutagenesis, including but not limited to, shotgun mutagenesis, site-directed mutagenesis, and alanine scanning; (ii) domain or fragment scanning; (iii) peptide scanning (e.g., Pepscan technology); (iv) display methods, including but not limited to, phage display, microbial display, and ribosome/mRNA display; (v) methods involving proteolysis and mass spectroscopy; (vi) methods involving amide hydrogen/deuterium exchange; and (vii) structural determination, including but not limited to, x-ray crystallography and NMR.

In some embodiments, purified anti-ILT3 antibodies are characterized by assays including, but not limited to, N-terminal sequencing, amino acid analysis, HPLC, mass spectrometry, differential scanning fluorimetry (DSF), nanoDSF, capillary isoelectric focusing (cIEF), ion exchange chromatography, and papain digestion.

In vitro assays that characterize immune cells function include, but are not limited to, cell activation assays (e.g., cell proliferation assays), cytotoxic T-cell (CTL) assays, mixed lymphocyte reaction (MLR) assays, cytokine/chemokine production assays, FcR binding assays, and cell migration assays. In some embodiments, assays are provided for identifying anti-ILT3 antibodies that affect ILT3 activity. "Affect or affecting ILT3 activity" may include, for example, inhibiting, reducing, blocking, antagonizing, suppressing, and/or interfering with ILT3 activity. As ILT3 generally acts a negative regulator/inhibitory molecule, in some embodiments, inhibiting, reducing, blocking, antagonizing, suppressing, and/or interfering with ILT3 activity results in a release of ILT3-induced suppression of a biological function (e.g., an activation signal). As described herein, ILT3 is expressed on myeloid cells, such as monocytes, macrophages, dendritic cells (DCs), and myeloid APCs. ILT3 is highly expressed on suppressive myeloid cells such as tolerogenic dendritic cells (tolDCs) and myeloid-derived suppressor cells (MDSCs). ILT3 activity or ILT3 signaling activity includes, but is not limited to, suppression of myeloid cells, suppression of myeloid cell activity, and suppression of tumor-associated myeloid cells. In some embodiments, inhibiting, reducing, blocking, antagonizing, suppressing, and/or interfering with ILT3 activity results in a release of ILT3-induced suppression of an activation signal. In some embodiments, an anti-ILT3 antibody inhibits ILT3 signaling. In some embodiments, an anti-ILT3 antibody inhibits ILT3 signaling thereby reversing an ILT3-induced suppressive effect. In some embodiments, an anti-ILT3 antibody inhibits an ILT3-induced extinction signal.

In some embodiments, an anti-ILT3 antibody disrupts the ILT3 signaling pathway. In some embodiments, an anti-ILT3 antibody disrupts the ILT3 signaling pathway and activates myeloid cells. In some embodiments, an anti-ILT3 antibody disrupts the ILT3 signaling pathway and activates myeloid APCs. In some embodiments, an anti-ILT3 antibody disrupts the ILT3 signaling pathway and activates dendritic cells. In some embodiments, an anti-ILT3 antibody disrupts the ILT3 signaling pathway and activates or reactivates tolDCs. In some embodiments, an anti-ILT3 antibody disrupts the ILT3 signaling pathway and restores the ability of tolDCs to respond to stimuli (e.g., LPS). In some embodiments, an anti-ILT3 antibody disrupts the ILT3 signaling pathway and activates primary dendritic cells.

In some embodiments, the terms "inhibiting", "reducing", "blocking", "antagonizing", "suppressing", and "interfering" are relative to levels and/or activity in the absence of treatment with the ILT3-binding agent. In some embodiments, the terms "inhibiting", "reducing", "blocking", "antagonizing", "suppressing", and "interfering" are relative to levels and/or activity prior to treatment with the ILT3-binding agent.

In some embodiments, an anti-ILT3 antibody that inhibits ILT3 activity is antibody 3A3. In some embodiments, an anti-ILT3 antibody that inhibits ILT3 activity is antibody 5A7. In some embodiments, an anti-ILT3 antibody that inhibits ILT3 activity is antibody Hz5A7.v5. In some embodiments, an anti-ILT3 antibody that inhibits ILT3 activity is antibody 12A12. In some embodiments, an anti-ILT3 antibody that inhibits ILT3 activity is antibody 16C5. In some embodiments, an anti-ILT3 antibody that inhibits ILT3 activity is antibody 45G10. In some embodiments, an anti-ILT3 antibody that inhibits ILT3 activity is antibody 48A6. In some embodiments, an anti-ILT3 antibody that inhibits ILT3 activity is antibody 53F10. In some embodiments, an anti-ILT3 antibody that inhibits ILT3 activity is antibody Hz45G10. In some embodiments, an anti-ILT3 antibody that inhibits ILT3 activity is antibody Hz48A6.

The present disclosure also provides conjugates comprising an anti-ILT3 antibody described herein. In some embodiments, the antibody is attached to a second molecule. In some embodiments, the antibody is conjugated to a cytotoxic agent or moiety. In some embodiments, the antibody is conjugated to a cytotoxic agent to form an ADC (antibody-drug conjugate). In some embodiments, the cytotoxic agent is a chemotherapeutic agent including, but not limited to, methotrexate, adriamycin/doxorubicin, melphalan, mitomycin C, chlorambucil, duocarmycin, daunorubicin, pyrrolobenzodiazepines (PBDs), or other intercalating agents. In some embodiments, the cytotoxic agent is a microtubule inhibitor including, but not limited to, auristatins, maytansinoids (e.g., DM1 and DM4), and tubulysins. In some embodiments, the cytotoxic agent is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, an antibody is conjugated to one or more small molecule toxins, such as calicheamicins, maytansinoids, trichothenes, and CC1065. A derivative of any one of these toxins may be used as long as the derivative retains the cytotoxic activity of the parent molecule.

Conjugates comprising an anti-ILT3 antibody described herein may be made using any suitable method known in the art. In some embodiments, conjugates are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, an anti-ILT3 antibody described herein is conjugated to a detectable substance or molecule that allows the antibody to be used for diagnosis and/or detection. In some embodiments, a labeled anti-ILT3 antibody is used to monitor immune cells in a tumor or in the microenvironment of a tumor. In some embodiments, a labeled anti-ILT3 antibody is used to monitor immune cells in a tumor or in the microenvironment of a tumor after treatment. A detectable substance can include but is not limited to, enzymes, such as horseradish peroxidase, alkaline phosphatase, beta-galactosidase, and acetylcholinesterase; prosthetic groups, such as biotin and flavine(s); fluorescent materials, such as, umbelliferone, fluorescein, fluorescein isothiocyanate (FITC), rhodamine, tetramethylrhodamine isothiocyanate (TRITC), dichlorotriazinylamine fluorescein, dansyl chloride, cyanine (Cy3), and phycoerythrin; bioluminescent materials, such as luciferase; radioactive materials, such as $^{212}$Bi, $^{14}$C, $^{57}$Co, $^{51}$Cr, $^{67}$Cu, $^{18}$F, $^{68}$Ga, $^{67}$Ga, $^{153}$Gd, $^{159}$Gd, $^{68}$Ge, $^{3}$H, $^{166}$Ho, $^{131}$I, $^{125}$I, $^{123}$I, $^{121}$I, $^{115}$In, $^{113}$In, $^{112}$In, $^{140}$La, $^{177}$Lu, $^{54}$Mn, $^{99}$Mo, $^{32}$P, $^{103}$Pd, $^{149}$Pm, $^{142}$Pr, $^{186}$Re, $^{188}$Re, $^{105}$Rh, $^{97}$Ru, $^{35}$S, $^{47}$Sc, $^{75}$Se, $^{153}$Sm, $^{113}$Sn, $^{117}$Sn, $^{85}$Sr, $^{99m}$Tc, $^{201}$Ti, $^{133}$Xe, $^{90}$Y, $^{69}$Yb, $^{175}$Yb, $^{65}$Zn; positron emitting metals; and magnetic metal ions.

In some embodiments, an anti-ILT3 antibody described herein is used in an immunoassay. Immunoassays are known to those of skill in the art and include, but are not limited to, ELISA, SPR (e.g., Biacore), FACS, and immunohistochemistry (IHC). In some embodiments, an anti-ILT3 antibody described herein is used on a tissue sample or a tumor sample.

An anti-ILT3 antibody described herein can also be conjugated to a second antibody to form an antibody heteroconjugate.

An anti-ILT3 antibody as described herein may be attached to a solid support. Such solid supports include, but are not limited to, glass, cellulose, polyacrylamide, nylon, polystyrene, polyvinyl chloride, or polypropylene. In some embodiments, immobilized anti-ILT3 antibodies are used in immunoassays. In some embodiments, immobilized anti-ILT3 antibodies are used in purification of the target antigen.

III. Polynucleotides

In some embodiments, the disclosure encompasses polynucleotides comprising polynucleotides that encode a polypeptide (e.g., an ILT3-binding agent) described herein. The term "polynucleotides that encode a polypeptide" encompasses a polynucleotide that includes only coding sequences for the polypeptide as well as a polynucleotide that includes additional coding and/or non-coding sequences. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In some embodiments, a polynucleotide comprises a polynucleotide encoding a heavy chain variable region and/or a light chain variable region of an ILT3-binding agent (e.g., antibody) described herein. In some embodiments, a polynucleotide comprises a polynucleotide encoding a heavy chain variable region of an ILT3-binding agent described herein. In some embodiments, a polynucleotide comprises a polynucleotide encoding a light chain variable region of an ILT3-binding agent described herein. In some embodiments, a polynucleotide comprises a polynucleotide encoding a heavy chain variable region of an ILT3-binding agent described herein and a polynucleotide encoding a light chain variable region of the ILT3-binding agent.

In some embodiments, a polynucleotide comprises a polynucleotide encoding a heavy chain and/or a light chain of an ILT3-binding agent (e.g., antibody) described herein. In some embodiments, a polynucleotide comprises a polynucleotide encoding a heavy chain of an ILT3-binding agent described herein. In some embodiments, a polynucleotide comprises a polynucleotide encoding a light chain of an ILT3-binding agent described herein. In some embodiments, a polynucleotide comprises a polynucleotide encoding a heavy chain of an ILT3-binding agent described herein and a polynucleotide encoding a light chain of the ILT3-binding agent.

In some embodiments, the polynucleotide comprises a polynucleotide encoding a polypeptide comprising an amino acid sequence selected from the group consisting of: SEQ ID NOs:109-128. In some embodiments, the polynucleotide comprises a polynucleotide encoding a polypeptide comprising an amino acid sequence of SEQ ID NO:109. In some embodiments, the polynucleotide comprises a polynucleotide encoding a polypeptide comprising an amino acid sequence of SEQ ID NO:110. In some embodiments, the polynucleotide comprises a polynucleotide encoding a polypeptide comprising an amino acid sequence of SEQ ID NO:111. In some embodiments, the polynucleotide comprises a polynucleotide encoding a polypeptide comprising an amino acid sequence of SEQ ID NO:112. In some embodiments, the polynucleotide comprises a polynucleotide encoding a polypeptide comprising an amino acid sequence of SEQ ID NO:113. In some embodiments, the polynucleotide comprises a polynucleotide encoding a polypeptide comprising an amino acid sequence of SEQ ID NO:114. In some embodiments, the polynucleotide comprises a polynucleotide encoding a polypeptide comprising an amino acid sequence of SEQ ID NO:115. In some embodiments, the polynucleotide comprises a polynucleotide encoding a polypeptide comprising an amino acid sequence of SEQ ID NO:116. In some embodiments, the polynucleotide comprises a polynucleotide encoding a polypeptide comprising an amino acid sequence of SEQ ID NO:117. In some embodiments, the polynucleotide comprises a polynucleotide encoding a polypeptide comprising an amino acid sequence of SEQ ID NO:118. In some embodiments, the polynucleotide comprises a polynucleotide encoding a polypeptide comprising an amino acid sequence of SEQ ID NO:119. In some embodiments, the polynucleotide comprises a polynucleotide encoding a polypeptide comprising an amino acid sequence of SEQ ID NO:120. In some embodiments, the polynucleotide comprises a polynucleotide encoding a polypeptide comprising an amino acid sequence of SEQ ID NO:121. In some embodiments, the polynucleotide comprises a polynucleotide encoding a polypeptide comprising an amino acid sequence of SEQ ID NO:122. In some embodiments, the polynucleotide comprises a polynucleotide encoding a polypeptide comprising an amino acid sequence of SEQ ID NO:123. In some embodiments, the polynucleotide comprises a polynucleotide encoding a polypeptide comprising an amino acid sequence of SEQ ID NO:124. In some embodiments, the polynucleotide comprises a polynucleotide encoding a polypeptide comprising an amino acid sequence of SEQ ID NO:125. In some embodiments, the polynucleotide comprises a polynucleotide encoding a polypeptide comprising an amino acid sequence of SEQ ID NO:126. In some embodiments, the polynucleotide comprises a polynucleotide encoding a polypeptide comprising an amino acid sequence of SEQ ID NO:127. In some embodiments, the polynucleotide comprises a polynucleotide encoding a polypeptide comprising an amino acid sequence of SEQ ID NO:128.

In some embodiments, the polynucleotide comprises a polynucleotide encoding a polypeptide comprising more than one amino acid sequence selected from the group consisting of: SEQ ID NOs:109-128. In some embodiments, the polynucleotide comprises a polynucleotide encoding (i) a polypeptide comprising an amino acid sequence of SEQ ID NO:109 and (ii) a polypeptide comprising an amino acid sequence of SEQ ID NO:110. In some embodiments, the polynucleotide comprises a polynucleotide encoding (i) a polypeptide comprising an amino acid sequence of SEQ ID NO:111 and (ii) a polypeptide comprising an amino acid sequence of SEQ ID NO:112. In some embodiments, the polynucleotide comprises a polynucleotide encoding (i) a polypeptide comprising an amino acid sequence of SEQ ID NO:113 and (ii) a polypeptide comprising an amino acid sequence of SEQ ID NO:114. In some embodiments, the polynucleotide comprises a polynucleotide encoding (i) a polypeptide comprising an amino acid sequence of SEQ ID NO:115 and (ii) a polypeptide comprising an amino acid sequence of SEQ ID NO:116. In some embodiments, the polynucleotide comprises a polynucleotide encoding (i) a polypeptide comprising an amino acid sequence of SEQ ID NO:117 and (ii) a polypeptide comprising an amino acid sequence of SEQ ID NO:118. In some embodiments, the polynucleotide comprises a polynucleotide encoding (i) a polypeptide comprising an amino acid sequence of SEQ ID NO:119 and (ii) a polypeptide comprising an amino acid sequence of SEQ ID NO:120. In some embodiments, the polynucleotide comprises a polynucleotide encoding (i) a polypeptide comprising an amino acid sequence of SEQ ID NO:121 and (ii) a polypeptide comprising an amino acid sequence of SEQ ID NO:122. In some embodiments, the polynucleotide comprises a polynucleotide encoding (i) a polypeptide comprising an amino acid sequence of SEQ ID NO:123 and (ii) a polypeptide comprising an amino acid sequence of SEQ ID NO:124. In some embodiments, the polynucleotide comprises a polynucleotide encoding (i) a polypeptide comprising an amino acid sequence of SEQ ID NO:125 and (ii) a polypeptide comprising an amino acid sequence of SEQ ID NO:127. In some embodiments, the polynucleotide comprises a polynucleotide encoding (i) a polypeptide comprising an amino acid sequence of SEQ ID NO:126 and (ii) a polypeptide comprising an amino acid sequence of SEQ ID NO:128.

The present disclosure also provides variants of the polynucleotides described herein, wherein the variant encodes, for example, fragments, analogs, and/or derivatives of a polypeptide. In some embodiments, the present disclosure provides a polynucleotide comprising a polynucleotide having a nucleotide sequence at least 80% identical, at least 85% identical, at least 90% identical, at least 95% identical, and in some embodiments, at least 96%, at least 97%, at least 98%, or at least 99% identical to a polynucleotide encoding a polypeptide described herein.

In some embodiments, a polynucleotide comprises a polynucleotide having a nucleotide sequence at least 80% identical, at least 85% identical, at least 90% identical, at least 95% identical, and in some embodiments, at least 96%, at least 97%, at least 98%, or at least 99% identical to a polynucleotide encoding an amino acid sequence selected from the group consisting of: SEQ ID NOs:109-128. Also provided is a polynucleotide that comprises a polynucleotide that hybridizes to a polynucleotide encoding an amino acid sequence selected from the group consisting of: SEQ ID NOs:109-128. In some embodiments, the hybridization is under conditions of high stringency as is known to those skilled in the art.

As used herein, the phrase "a polynucleotide having a nucleotide sequence at least 95% identical to a polynucleotide sequence" is intended to mean that the nucleotide sequence of the polynucleotide is identical to a reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. It is understood by those of skill in the art that an appropriate calculation would be made for other "% identical" statements, for example, 90% identical or 85% identical. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations that produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). In some embodiments, a polynucleotide variant comprises one or more mutated codons comprising one or more (e.g., 1, 2, or 3) substitutions to the codon that change the amino acid encoded by that codon. Methods for introducing one or more substitutions into a codon are known in the art, including by not limited to, PCR mutagenesis and site-directed mutagenesis. Polynucleotide variants can be produced for a variety of reasons, for example, to optimize codon expression for a particular host (e.g., change codons in the human mRNA to those preferred by a bacterial host such as *E. coli*). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, a polynucleotide comprises the coding sequence for a polypeptide (e.g., an antibody) fused in the same reading frame to a polynucleotide that aids in expression and secretion of a polypeptide from a host cell. In some embodiments, the polynucleotide that aids in expression and secretion is a leader sequence that functions as a secretory sequence for controlling transport of a polypeptide. In some embodiments, the polypeptide has a leader sequence cleaved by the host cell to form a "mature" form of the polypeptide.

In some embodiments, a polynucleotide comprises the coding sequence for a polypeptide (e.g., an antibody) fused in the same reading frame to a marker or tag sequence. For example, in some embodiments, a marker sequence is a hexa-histidine tag (HIS-tag; SEQ ID NO:154) that allows for efficient purification of the polypeptide fused to the marker. In some embodiments, a marker sequence is a hemagglutinin (HA) tag derived from the influenza hemagglutinin protein when a mammalian host is used. In some embodiments, the marker sequence is a FLAG™ tag. In some embodiments, a marker may be used in conjunction with other markers or tags.

In some embodiments, a polynucleotide is isolated. In some embodiments, a polynucleotide is substantially pure.

Vectors and cells comprising each and every one of the polynucleotides described herein are also provided. In some embodiments, a vector (e.g., an expression vector) comprises a polynucleotide molecule encoding an ILT3-binding agent (e.g., an antibody) described herein. In some embodiments, a vector comprises a polynucleotide molecule encoding a polypeptide that is part of an ILT3-binding agent described herein. In some embodiments, a cell comprises a vector comprising a polynucleotide molecule encoding an ILT3-binding agent described herein. In some embodiments, a cell comprises a vector comprising a polynucleotide molecule encoding a polypeptide that is part of an ILT3-binding agent described herein. In some embodiments, a cell comprises a polynucleotide molecule encoding an ILT3-binding agent described herein. In some embodiments, a cell comprises one or more polynucleotides encoding an ILT3-binding agent described herein. In some embodiments, a cell comprises a single polynucleotide encoding an ILT3-binding agent described herein. In some embodiments, a cell comprises a first polynucleotide encoding a heavy chain variable region of an ILT3-binding agent described herein and a second polynucleotide encoding a light chain variable region of an ILT3-binding agent described herein. In some embodiments, a cell comprises a polynucleotide encoding a heavy chain variable region and a light chain variable region of an ILT3-binding agent described herein. In some embodiments, a cell comprises a first polynucleotide encoding a heavy chain of an ILT3-binding agent described herein and a second polynucleotide encoding a light chain of an ILT3-binding agent described herein. In some embodiments, a cell comprises a polynucleotide encoding a heavy chain and a light chain of an ILT3-binding agent described herein. In some embodiments, a cell comprises one or more vectors encoding an ILT3-binding agent described herein. In some embodiments, a cell comprises a vector encoding an ILT3-binding agent described herein. In some embodiments, a cell comprises a first vector encoding a heavy chain variable region of an ILT3-binding agent described herein and a second vector encoding a light chain variable region of an ILT3-binding agent described herein. In some embodiments, a cell comprises a single vector encoding a heavy chain variable region and a light chain variable region of an ILT3-binding agent described herein. In some embodiments, a cell comprises a first vector encoding a heavy chain of an ILT3-binding agent described herein and a second vector encoding a light chain of an ILT3-binding agent described herein. In some embodiments, a cell comprises a single vector encoding a heavy chain and a light chain of an ILT3-binding agent described herein.

IV. Methods of Making Binding Agents

The disclosure provides methods for making the ILT3-binding agents (e.g., antibodies) described herein. In some embodiments, a method comprises providing a cell comprising a heavy chain and/or light chain of an ILT3-binding agent, culturing the cell under conditions that permit the expression of the binding agent, and isolating the binding agent. In some embodiments, a method further comprises purifying the binding agent. In some embodiments, a method further comprises formulating the binding gent as a pharmaceutical composition. In some embodiments, a cell comprises one or more vectors encoding the heavy chain variable region and the light chain variable region of an ILT3-binding agent described herein. In some embodiments, a cell comprises a first vector encoding the heavy chain variable region of an ILT3-binding agent and a second vector encoding the light chain variable region of an ILT3-binding agent. In other embodiments, a cell comprises a vector encoding the heavy chain variable region and the light chain variable region of an ILT3-binding agent. In some embodiments, a cell comprises one or more vectors encoding the heavy chain and the light chain of an ILT3-binding agent described herein. In some embodiments, a cell comprises a first vector encoding the heavy chain of an ILT3-binding agent and a second vector encoding the light chain of an ILT3-binding agent. In other embodiments, a cell comprises a vector encoding the heavy chain and the light chain of an ILT3-binding agent. In some embodiments, a cell comprises one or more polynucleotides encoding the heavy chain and the light chain of an ILT3-binding agent. In some embodiments, a cell comprises a first polynucleotide encoding the heavy chain of an ILT3-binding agent and a second polynucleotide encoding the light chain of an ILT3-binding agent. In other embodiments, a cell comprises a polynucleotide encoding the heavy chain and the light chain of an ILT3-binding agent. In some embodiments, a polynucleotide encoding an ILT3-binding agent described herein is transiently transfected into a cell. In some embodiments, a polynucleotide encoding an ILT3-binding agent described herein is stably transfected into a cell.

In some embodiments, the ILT3-binding agent is an antibody fragment comprising at least one antigen-binding site and the method involves providing a cell comprising the fragment of an anti-ILT3 antibody, incubating the cell under conditions that permit the expression of the antibody fragment, and isolating the antibody fragment. In certain embodiments, the cell comprises a vector encoding an antibody fragment described herein. In certain embodiments, the cell comprises a polynucleotide encoding an antibody fragment described herein. In some embodiments, the method comprises purifying the antibody fragment. In certain embodiments, the antibody fragment is a Fab, Fab', F(ab')2, Fv, scFv, (scFv)$_2$, single chain antibody, dual variable region antibody, diabody, or nanobody.

In some embodiments, the ILT3-binding agent is a scFv and the method involves providing a cell comprising the scFv, incubating the cell under conditions that permit the expression of the scFv, and isolating the scFv. In certain embodiments, the cell comprises a vector described herein encoding the scFv. In certain embodiments, the cell comprises a polynucleotide described herein encoding the scFv. In some embodiments, the method comprises purifying the scFv.

In some embodiments, the cell used to make an ILT3-binding agent is a bacterial cell (e.g., *E. coli*). In some embodiments, the cell used to make an ILT3-binding agent is a yeast cell (e.g., *Pichia pastoris*). In some embodiments, the cell used to make an ILT3-binding agent is a mammalian cells, such as a CHO cell or a HEK-293 cell.

In some embodiments, a signal sequence is used (e.g., by fusing a signal sequence to the peptide to be expressed) for expression of an ILT3-binding agent described herein from a cell. Any suitable signal sequence can be used for this purpose. For example, for expressing an antibody heavy and light chain, an IgG kappa light chain signal peptide sequence or a native antibody signal peptide can be fused to the heavy chain and light chain sequence.

V. ILT3 Ligands

The present disclosure provides fibronectin as a newly identified ligand for human ILT3. Ciliary neurotrophic factor receptor (CNTFR) was also found to be a binding partner of ILT3. Recently, several ligands for ILT3 have been identified and include CD166 (also known as activated leukocyte cell adhesion molecule; ALCAM), apolipoprotein E (APOE), and peptidase inhibitor 16 (PI16) (Xu et al., 2018, *J. Immunol.*, 200:1207-1219; Deng et al., 2018, Nature, 562:605-609; Intl. Pub. No. WO 2018/089300). Currently, there appears to be no agreement on whether all of these proteins are biologically functional as ILT3 ligands and research is ongoing to further understand the relevance of each of these different interactions.

Amino acid (aa) sequences for human fibronectin (UniProtKB No. P02751) and human CNTFR-alpha (UniProKB No. P26992) are provided herein as SEQ ID NO:138 and SEQ ID NO:148, respectively. There are at least 17 different isoforms of human fibronectin, UniProtKB lists SEQ ID NO:138 as its canonical sequence. As used herein, reference to amino acid positions of these proteins refer to the numbering of amino acid sequences including the signal sequence.

Fibronectin (FN) usually exists as a dimer composed of two nearly identical approximately 250 kDa subunits linked covalently near their C-termini by a pair of disulfide bonds. Each monomer comprises three types of repeating units (termed FN repeats): type I, type II and type III. FN contains 12 type I repeats, two type II repeats, and 15-17 type III repeats, which together account for approximately 90% of the fibronectin sequence. See FIG. 8 for a representation of the fibronectin structure. The type I and type II repeats are stabilized by the presence of intra-domain disulfide bonds, while the type III domains are structurally more labile and subject to mechanical unfolding. Fibronectin can exist in multiple forms that arise from alternative splicing of a single pre-mRNA that can generate as many as 20 variants.

Fibronectin is a plasma protein synthesized by the liver which undergoes a cell-dependent polymerization into a fibrillar extracellular matrix in most tissues. Both plasma-derived and local synthesis by resident stromal cells contribute to the fibronectin which makes up the tissue matrix.

Fibronectin is a ligand for at least a dozen members of the integrin receptor family. Fibronectin has a wide variety of functional activities in addition to binding to cell surfaces through integrins. It binds a number of other proteins, including heparin, collagen/gelatin, and fibrin. These interactions are mediated by several distinct structural and functional domains within fibronectin and groups of the fibronectin repeats. The biological role of many of the other fibronectin domains is not characterized and/or well understood.

As disclosed herein, fibronectin was identified as a ligand for ILT3. In some embodiments, an ILT3-binding agent (e.g., an antibody) described herein inhibits, disrupts, or blocks binding of ILT3 to fibronectin. In some embodiments, an ILT3-binding agent described herein blocks the interaction of ILT3 with fibronectin. In some embodiments, an ILT3-binding agent described herein inhibits binding of ILT3 to fibronectin. In some embodiments, an ILT3-binding agent described herein blocks or inhibits a functional interaction between ILT3 and fibronectin.

In some embodiments, an ILT3 binding agent (e.g., an antibody) described herein inhibits, disrupts, or blocks binding of ILT3 to SEQ ID NO:138 or 139. In some embodiments, an ILT3 binding agent (e.g., an antibody) described herein inhibits, disrupts, or blocks binding of ILT3 to the N-terminal region of fibronectin (without the signal sequence/peptide). In some embodiments, an ILT3 binding agent (e.g., an antibody) described herein inhibits, disrupts, or blocks binding of ILT3 to the heparin-binding and collagen-binding domains of fibronectin. In some embodiments, an ILT3 binding agent (e.g., an antibody) described herein inhibits, disrupts, or blocks binding of ILT3 to the heparin-binding domain of fibronectin. In some embodiments, an ILT3 binding agent (e.g., an antibody) described herein inhibits, disrupts, or blocks binding of ILT3 to type I repeats 1-5 of fibronectin. In some embodiments, an ILT3 binding agent (e.g., an antibody) described herein inhibits, disrupts, or blocks binding of ILT3 to type I repeats 1-4 of fibronectin. In some embodiments, an ILT3 binding agent (e.g., an antibody) described herein inhibits, disrupts, or blocks binding of ILT3 to type I repeats 1-3 of fibronectin. In some embodiments, an ILT3 binding agent (e.g., an antibody) described herein inhibits, disrupts, or blocks binding of ILT3 to type I repeats 1-2 of fibronectin. The boundaries of any domain are not exactly known and the amino acids used herein to define domains and/or the repeats of FN are based on information from UniProtKB. Therefore, the boundaries of any domain and/or repeat may vary from those recited herein.

In some embodiments, an ILT3 binding agent (e.g., an antibody) described herein inhibits, disrupts, or blocks binding of ILT3 to amino acids 32-608 of SEQ ID NO:138. In some embodiments, an ILT3 binding agent (e.g., an antibody) described herein inhibits, disrupts, or blocks binding of ILT3 to amino acids 32-280 of SEQ ID NO:138. In some embodiments, an ILT3 binding agent (e.g., an antibody) described herein inhibits, disrupts, or blocks binding of ILT3 to amino acids 32-300 of SEQ ID NO:138. In some embodiments, an ILT3 binding agent (e.g., an antibody) described herein inhibits, disrupts, or blocks binding of ILT3 to amino acids 32-228 of SEQ ID NO:138. In some embodiments, an ILT3 binding agent (e.g., an antibody) described herein inhibits, disrupts, or blocks binding of ILT3 to amino acids 32-182 of SEQ ID NO:138. In some embodiments, an ILT3 binding agent (e.g., an antibody) described herein inhibits, disrupts, or blocks binding of ILT3 to amino acids 32-138 of SEQ ID NO:138. In some embodiments, an ILT3 binding agent (e.g., an antibody) described herein inhibits, disrupts, or blocks binding of ILT3 to amino acids 32-290 of SEQ ID NO:138.

In some embodiments, an ILT3-binding agent (e.g., an antibody) described herein inhibits fibronectin-induced ILT3 activity. In some embodiments, an ILT3-binding agent described herein inhibits fibronectin-induced ILT3 suppressive activity. In some embodiments, an ILT3-binding agent described herein inhibits fibronectin-induced ILT3 suppression of myeloid cells. In some embodiments, an ILT3-binding agent described herein inhibits fibronectin-induced ILT3 suppression of myeloid cell activity. In some embodiments, an ILT3-binding agent described herein inhibits fibronectin-induced ILT3 suppression of APCs. In some embodiments, an ILT3-binding agent described herein inhibits fibronectin-induced ILT3 suppression of APC activity. In some embodiments, an ILT3-binding agent described herein inhibits fibronectin-induced ILT3 suppression of dendritic cells. In some embodiments, an ILT3-binding agent described herein inhibits fibronectin-induced ILT3 suppression of dendritic cell activity. In some embodiments, an ILT3-binding agent described herein inhibits fibronectin-induced ILT3 suppression of macrophages. In some embodiments, an ILT3-binding agent described herein inhibits fibronectin-induced ILT3 suppression of macrophage activity. In some embodiments, the myeloid cells, including but not limited to dendritic cells, APCs, monocytes, and macrophages are tumor-associated cells. In some embodiments, the myeloid cells, including but not limited to dendritic cells, APCs, monocytes and macrophages are residing in the tumor microenvironment. In some embodiments, the myeloid cells, including but not limited to dendritic cells, APCs, monocytes and macrophages are residing within a tumor.

As disclosed herein, CNTFR-alpha was identified as a ligand for ILT3. CNTFR-alpha is part of a tripartite CNTFR complex that is known to bind ciliary neurotrophic factor. CNTFR-alpha subunit is a membrane bound protein and is anchored to the cell membrane by a glycosyl-phosphatidylinositol (GPI) linkage. This receptor has no signal transducing capabilities without the co-receptor components of the complex. The two other components are gp130 and leukemia inhibitory factor receptor (LIFR) beta, that provide the signal transducing capabilities of the complex (Stahl et al., 1994, *J. Neurobiol.*, 25:1454-1466). The biological relevance of ILT3 binding to CNTFR is still being investigated.

In some embodiments, an ILT3-binding agent described herein inhibits, disrupts, or blocks binding of ILT3 to CNTFR-alpha. In some embodiments, an ILT3-binding agent described herein blocks the interaction of ILT3 with CNTFR-alpha. In some embodiments, an ILT3-binding agent described herein inhibits binding of ILT3 to CNTFR-alpha. In some embodiments, an ILT3-binding agent described herein inhibits, disrupts, or blocks binding of ILT3 to CNTFR-alpha and modulates the CNTFR complex signaling.

In some embodiments, an ILT3-binding agent described herein inhibits, disrupts, or blocks binding of ILT3 to the mature form of CNTFR-alpha. In some embodiments, an ILT3-binding agent described herein inhibits, disrupts, or blocks binding of ILT3 to the Ig-like C2 type domain of CNTFR-alpha. In some embodiments, an ILT3-binding agent described herein inhibits, disrupts, or blocks binding of ILT3 to one or both of the FN type III domains (i.e., FN type III domain 1, FN type III domain 2, or FN type III domains 1 and 2) of CNTFR-alpha.

In some embodiments, an ILT3-binding agent described herein inhibits, disrupts, or blocks binding of ILT3 to SEQ ID NO:149 or SEQ ID NO:150. In some embodiments, an ILT3-binding agent described herein inhibits, disrupts, or blocks binding of ILT3 to amino acids 23-342 of SEQ ID NO:148. In some embodiments, an ILT3-binding agent described herein inhibits, disrupts, or blocks binding of ILT3 to amino acids 23-104 of SEQ ID NO:148. In some embodiments, an ILT3-binding agent described herein inhibits, disrupts, or blocks binding of ILT3 to amino acids 105-205 of SEQ ID NO:148. In some embodiments, an ILT3-binding agent described herein inhibits, disrupts, or blocks binding of ILT3 to amino acids 206-306 of SEQ ID NO:148. In some embodiments, an ILT3-binding agent described herein inhibits, disrupts, or blocks binding of ILT3 to amino acids 23-306 of SEQ ID NO:148.

VI. Methods of Use and Pharmaceutical Compositions

The ILT3-binding agents (e.g., antibodies) of the disclosure are useful in a variety of applications including, but not limited to, therapeutic treatment methods, such as treatment of cancer. In some embodiments, the therapeutic treatment methods comprise immunotherapy for cancer. In some embodiments, an ILT3-binding agent is useful for activating, promoting, increasing, and/or enhancing an immune response to cancer or cancer cells. In some embodiments, an ILT3-binding agent is useful for activating, promoting, increasing, and/or enhancing an immune response to a tumor or tumor cells. The methods of use may be in vitro, ex vivo, or in vivo methods.

The present disclosure provides methods of disrupting, inhibiting, or blocking the binding of ILT3 to fibronectin. In some embodiments, a method of disrupting, inhibiting, or blocking the binding of ILT3 to fibronectin comprises contacting cells with an ILT3-binding agent described herein. In some embodiments, a method of disrupting, inhibiting, or blocking the binding of ILT3 to fibronectin comprises contacting cells with an ILT3-binding agent described herein, wherein the method results in disrupting, inhibiting, or blocking fibronectin-induced ILT3 activity. In some embodiments, a method of disrupting, inhibiting, or blocking the binding of ILT3 to fibronectin comprises contacting cells with an ILT3-binding agent described herein, wherein the method results in disrupting, inhibiting, or blocking ILT3-induced suppression of myeloid cells. In some embodiments, a method of disrupting, inhibiting, or blocking the binding of ILT3 to fibronectin comprises contacting cells with an ILT3-binding agent described herein, wherein the method results in disrupting, inhibiting, or blocking of ILT3-induced suppression of myeloid cell activity. In some embodiments, a method of disrupting, inhibiting, or blocking the binding of ILT3 to fibronectin: (i) restores FcR signaling activity in myeloid cells; (ii) restores chemokine production by myeloid cells; and/or (iii) restores immune cell (e.g., T-cell) proliferation and/or activity. In some embodiments, the myeloid cell is a monocyte. In some embodiments, the myeloid cell is a macrophage. In some embodiments, the myeloid cell is a dendritic cell. In some embodiments, the myeloid cell is a tolDC. In some embodiments, the myeloid cell is an APC.

The present disclosure provides methods of disrupting, inhibiting, or blocking the binding of ILT3 to fibronectin in a subject. In some embodiments, a method of disrupting, inhibiting, or blocking the binding of ILT3 to fibronectin in a subject, comprises administering to the subject an effective amount of an ILT3-binding agent (e.g., an antibody) described herein. In some embodiments, a method of disrupting, inhibiting, or blocking fibronectin-induced ILT3 activity in a subject comprises administering to the subject an effective amount of an ILT3-binding agent described herein. In some embodiments, a method of disrupting, inhibiting, or blocking ILT3-induced suppression of myeloid cells in a subject comprises administering to the subject an effective amount of an ILT3-binding agent described herein. In some embodiments, a method of disrupting, inhibiting, or blocking ILT3-induced suppression of myeloid cell activity in a subject comprises administering to the subject an effective amount of an ILT3-binding agent described herein. In some embodiments, a method of disrupting, inhibiting, or blocking ILT3-induced suppression of antigen-presenting cell activity in a subject (i) restores FcR activity in myeloid cells; (ii) restores chemokine production by myeloid cells; and/or (iii) restores immune cell (e.g., T-cell) proliferation and/or activity. In some embodiments, the myeloid cell is a monocyte. In some embodiments, the myeloid cell is a macrophage. In some embodiments, the myeloid cell is a dendritic cell. In some embodiments, the myeloid cell is a tolDC. In some embodiments, the myeloid cell is an APC.

The present disclosure provides methods for activating an immune response in a subject using an ILT3-binding agent (e.g., an antibody) described herein. In some embodiments, the disclosure provides methods for promoting an immune response in a subject using an ILT3-binding agent described herein. In some embodiments, the disclosure provides methods for increasing an immune response in a subject using an ILT3-binding agent described herein. In some embodiments, the disclosure provides methods for enhancing an immune response in a subject using an ILT3-binding agent described herein. In some embodiments, the activating, promoting, increasing, and/or enhancing of an immune response comprises stimulating myeloid cells. In some embodiments, the activating, promoting, increasing, and/or enhancing of an immune response comprises stimulating monocytes. In some embodiments, the activating, promoting, increasing, and/or enhancing of an immune response comprises stimulating macrophages. In some embodiments, the activating, promoting, increasing, and/or enhancing of an immune response comprises stimulating dendritic cells. In some embodiments, the activating, promoting, increasing, and/or enhancing of an immune response comprises stimulating APCs. In some embodiments, the activating, promoting, increasing, and/or enhancing of an immune response comprises stimulating tolDCs. In some embodiments, the activating, promoting, increasing, and/or enhancing of an immune response comprises reactivating tolDCs. In some embodiments, the activating, promoting, increasing, and/or enhancing of an immune response comprises increasing cell-mediated immunity. In some embodiments, the activating, promoting, increasing, and/or enhancing of an immune response comprises increasing effector T-cell activity. In some embodiments, the activating, promoting, increasing, and/or enhancing of an immune response comprises increasing CTL activity. In some embodiments, the activating, promoting, increasing, and/or enhancing of an immune response comprises inhibiting or decreasing the suppressive activity of Tregs. In some embodiments, the activating, promoting, increasing, and/or enhancing of an immune response comprises inhibiting or decreasing the suppressive activity of MDSCs. In some embodiments, the immune response is a result of antigenic stimulation. In some embodiments, the antigenic stimulation is a tumor cell. In some embodiments, the antigenic stimulation is cancer.

The disclosure also provides methods of disrupting and/or inhibiting ILT3 signaling in a cell comprising contacting the cell with an effective amount of an ILT3-binding agent described herein. In some embodiments, the method of disrupting and/or inhibiting ILT3 signaling in a cell comprises contacting the cell with an effective amount of antibody 3A3, antibody 5A7, antibody 12A12, antibody 16C5, antibody 45G10, antibody 48A6, or antibody 53F10, or humanized versions thereof. In some embodiments, the method of disrupting and/or inhibiting ILT3 signaling in a cell comprises contacting the cell with an effective amount of antibody Hz5A7.v5. In some embodiments, the method of disrupting and/or inhibiting ILT3 signaling in a cell comprises contacting the cell with an effective amount of antibody Hz45G10. In some embodiments, the method of disrupting and/or inhibiting ILT3 signaling in a cell comprises contacting the cell with an effective amount of antibody Hz48A6. In some embodiments, the disclosure provides use of an ILT3-binding agent described herein in the manufacture or preparation of a medicament for disrupting and/or inhibiting ILT3 signaling in a cell. In certain embodiments, the cell is a myeloid cell. In some embodiments, the myeloid cell is a monocyte. In some embodiments, the myeloid cell is a macrophage. In some embodiments, the myeloid cell is a dendritic cell. In some embodiments, the myeloid cell is a tolDC. In some embodiments, the myeloid cell is an antigen-presenting cell. In certain embodiments, the method is an in vivo method wherein the step of contacting the cell with the agent comprises administering a therapeutically effective amount of an ILT3-binding agent to a subject. In some embodiments, the method is an in vitro or ex vivo method.

The present disclosure also provides methods for inhibiting growth of a tumor using an ILT3-binding agent described herein. In some embodiments, the method of inhibiting growth of a tumor comprises using antibody 3A3, antibody 5A7, antibody 12A12, antibody 16C5, antibody 45G10, antibody 48A6, or antibody 53F10, or humanized versions thereof. In some embodiments, the method of inhibiting growth of a tumor comprises using antibody Hz5A7.v5. In some embodiments, the method of inhibiting growth of a tumor comprises using antibody Hz45G10. In some embodiments, the method of inhibiting growth of a tumor comprises using antibody Hz48A6. In certain embodiments, the method of inhibiting growth of a tumor comprises contacting a cell mixture with an ILT3-binding agent in vitro. For example, an immortalized cell line or a cancer cell line mixed with immune cells (e.g., tolerogenic dendritic cells) is cultured in medium to which is added a test agent that binds ILT3. In some embodiments, tumor cells are isolated from a patient sample such as, for example, a tissue biopsy, pleural effusion, or blood sample, mixed with immune cells (e.g., tolDCs), and cultured in medium to which is added a test agent that binds ILT3. In some embodiments, the disclosure provides use of an ILT3-binding agent described herein in the manufacture or preparation of a medicament for inhibiting growth of a tumor or a tumor cell. In some embodiments, an ILT3-binding agent increases, promotes, and/or enhances the activity of effector immune cells. In some embodiments, an ILT3-binding agent inhibits tumor cell growth.

In some embodiments, a method of inhibiting tumor growth comprises contacting the tumor and/or tumor microenvironment with an ILT3-binding agent described herein in vivo. In certain embodiments, contacting a tumor and/or tumor microenvironment with an ILT3-binding agent is undertaken in an animal model. For example, a test agent may be administered to mice that have tumors. In some embodiments, an ILT3-binding agent increases, promotes, and/or enhances the activity of immune cells in the mice. In some embodiments, an ILT3-binding agent inhibits tumor growth. In some embodiments, an ILT3-binding agent causes a tumor to regress. In some embodiments, an ILT3-binding agent is administered at the same time or shortly after introduction of tumor cells into the animal to prevent tumor growth ("preventative model"). In some embodiments, an ILT3-binding agent is administered after tumors have grown to a specified size or have become "established" for treatment ("therapeutic model"). In some embodiments, an ILT3-binding agent is administered to a transgenic animal (e.g., a transgenic mouse) that expresses human ILT3, wherein the transgenic animal has a tumor derived from human cells.

In certain embodiments, a method of inhibiting tumor growth comprises administering to a subject a therapeutically effective amount of an ILT3-binding agent (e.g., an antibody) described herein. In certain embodiments, the subject is a human. In some embodiments, a method of increasing or enhancing an immune response to a tumor or tumor cells in a subject comprises administering to the subject a therapeutically effective amount of an ILT3-binding agent described herein. In some embodiments, a method of activating or enhancing a persistent or long-term immune response to a tumor or tumor cells in a subject comprises administering to the subject a therapeutically effective amount of an ILT3-binding agent described herein. In some embodiments, a method of inhibiting tumor relapse or tumor regrowth in a subject comprises administering to the subject a therapeutically effective amount of an ILT3-binding agent described herein. In some embodiments, a method of inducing a persistent or long-term immunity that inhibits tumor relapse or tumor regrowth in a subject comprises administering to the subject a therapeutically effective amount of an ILT3-binding agent described herein. In some embodiments of the methods described herein, the tumor is a solid tumor. In some embodiments, the tumor is a pancreatic tumor, a breast tumor, a lung tumor, a head and neck tumor, a colorectal tumor, a prostate tumor, a skin tumor, a melanoma tumor, a stomach tumor, a gastric tumor, an intestinal tumor, an ovarian tumor, a cervical tumor, an uterine tumor, an endometrial tumor, a bladder tumor, a brain tumor, an esophageal tumor, a liver tumor, a kidney tumor, or a testicular tumor. In some embodiments, the tumor is a pancreatic tumor. In some embodiments, the tumor is an ovarian tumor. In some embodiments, the tumor is a breast tumor. In some embodiments, the tumor is an uterine tumor. In certain embodiments, the subject has a tumor or the subject had a tumor that was at least partially removed.

In some embodiments, the disclosure provides use of an ILT3-binding agent described herein in the manufacture or preparation of a medicament for inhibiting growth of a tumor or tumor cell. In some embodiments, the method of inhibiting growth of a tumor comprises administering to a subject a therapeutically effective amount of antibody 3A3, antibody 5A7, antibody 12A12, antibody 16C5, antibody 45G10, antibody 48A6, or antibody 53F10, or humanized versions thereof. In some embodiments, the method of inhibiting growth of a tumor comprises administering to a subject a therapeutically effective amount of antibody Hz5A7.v5. In some embodiments, the method of inhibiting growth of a tumor comprises administering to a subject a therapeutically effective amount of antibody Hz48A6. In some embodiments, the method of inhibiting growth of a tumor comprises administering to a subject a therapeutically effective amount of antibody Hz45G10.

The present disclosure provides methods of treating cancer. In some embodiments, a method of treating cancer comprises administering to a subject a therapeutically effective amount of an ILT3-binding agent described herein. In some embodiments, an ILT3-binding agent binds ILT3 and inhibits or reduces growth of the cancer. In some embodiments, an ILT3-binding agent binds human ILT3-expressing cells, enhances an immune response to a cancer, and inhibits or reduces growth of the cancer. In some embodiments, an ILT3-binding agent binds human ILT3-expressing cells, reactivates tolDCs, enhances an immune response to a cancer, and inhibits or reduces growth of the cancer. In certain embodiments, the subject is a human. In certain embodiments, the subject has a cancerous tumor. In certain embodiments, the subject has had a tumor at least partially removed.

In some embodiments, the disclosure provides use of an ILT3-binding agent described herein in the manufacture or preparation of a medicament for the treatment of cancer.

In some embodiments of the methods described herein, the cancer is pancreatic cancer, breast cancer, lung cancer, head and neck cancer, colorectal cancer, prostate cancer, skin cancer, melanoma, stomach cancer, gastric cancer, intestinal cancer, ovarian cancer, cervical cancer, uterine cancer, endometrial cancer, bladder cancer, brain cancer, esophageal cancer, liver cancer, kidney cancer, or testicular cancer. In some embodiments, the cancer is a sarcoma. In some embodiments, the cancer expresses ILT3.

In some embodiments, the cancer is a hematologic cancer. In some embodiments, the cancer is a myelogenous leukemia. In some embodiments, the myelogenous cancer is acute myeloid leukemia (AML). In some embodiments, the myelogenous cancer is a chronic myeloid leukemia. In some embodiments, the cancer is a certain type of B cell leukemia or lymphoma which expresses ILT3. In some embodiments, the cancer is a myelodysplastic syndrome. Myelodysplastic syndromes (MDS) are a group of cancers in which immature blood cells in the bone marrow do not mature and therefore do not become healthy blood cells. In some embodiments, myelodysplastic syndrome develops into AML.

In some embodiments, a method for treating cancer in a subject comprises administering to the subject a therapeutically effective amount of antibody 3A3, antibody 5A7, antibody 12A12, antibody 16C5, antibody 45G10, antibody 48A6, or antibody 53F10, or humanized versions thereof. In some embodiments, a method for treating cancer in a subject comprises administering to the subject a therapeutically effective amount of antibody Hz5A7.v5. In some embodiments, a method for treating cancer in a subject comprises administering to the subject a therapeutically effective amount of antibody Hz48A6. In some embodiments, a method for treating cancer in a subject comprises administering to the subject a therapeutically effective amount of antibody Hz45G10.

In some embodiments, the disclosure provides methods of activating myeloid cells in the tumor microenvironment. In some embodiments, a method of activating myeloid cells in the tumor microenvironment in a subject with a tumor comprises administering to the subject a therapeutically effective amount of an ILT3-binding agent described herein. In some embodiments, the myeloid cells are primary dendritic cells or tolDCs. In some embodiments, the myeloid cells are monocytes. In some embodiments, the myeloid cells are macrophages. In some embodiments, the myeloid cells are APCs. In some embodiments, the disclosure provides a method of reactivating tolDCs in a subject, the method comprising administering to the subject a therapeutically effective amount of an ILT3-binding agent described herein. In some embodiments, the tolDCs are found in the tumor microenvironment.

In some embodiments of the methods described herein, the ILT3-binding agent (e.g., an antibody) comprises a heavy chain variable region CDR1, CDR2, and CDR3 and a light chain variable region CDR1, CDR2, and CDR3 of antibody 5A7. In some embodiments of the methods described herein, the ILT3-binding agent comprises a heavy chain variable region CDR1, CDR2, and CDR3 and a light chain variable region CDR1, CDR2, and CDR3 of antibody Hz5A7.v5.

In some embodiments of the methods described herein, the anti-ILT3 antibody comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29) or REWRYTLYAMDY (SEQ ID NO:105), and (b) a light chain variable region comprising a light chain variable region CDR1 comprising the amino acid sequence RASESVDSYGNSFMH (SEQ ID NO:30) or RASESVESYGSSFMH (SEQ ID NO:106), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments of the methods described herein, the anti-ILT3 antibody comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISGGGSYTNYPDSVKG (SEQ ID NO:28), and a heavy chain variable region CDR3 comprising the amino acid sequence REWRMTLYAMDY (SEQ ID NO:29), and (b) a light chain variable region comprising a light chain variable region CDR1 comprising the amino acid sequence RASESVDSYGNSFMH (SEQ ID NO:30), a light chain variable region CDR2 comprising the amino acid sequence LTSNLES (SEQ ID NO:31), and a light chain variable region CDR3 comprising the amino acid sequence QQNNEDPFT (SEQ ID NO:32). In some embodiments of the methods described herein, the anti-ILT3 antibody comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TIS-GGGSYTNYPDSVKG (SEQ ID NO:28), and a heavy chain variable region CDR3 comprising the amino acid sequence REWRYTLYAMDY (SEQ ID NO:105), and (b) a light chain variable region comprising a light chain variable region CDR1 comprising the amino acid sequence RASES-VESYGSSFMH (SEQ ID NO:106), a light chain variable region CDR2 comprising the amino acid sequence LTSN-LES (SEQ ID NO:31), and a light chain variable region CDR3 comprising the amino acid sequence QQNNEDPFT (SEQ ID NO:32).

In some embodiments of the methods described herein, the anti-ILT3 antibody comprises: (a) a heavy chain variable region of SEQ ID NO:111 and (b) a light chain variable region of SEQ ID NO:112. In some embodiments of the methods described herein, the anti-ILT3 antibody comprises: (a) a heavy chain variable region of SEQ ID NO:123 and (b) a light chain variable region of SEQ ID NO:124.

In some embodiments of the methods described herein, the anti-ILT3 antibody comprises a heavy chain of SEQ ID NO:126. In some embodiments of the methods described herein, the anti-ILT3 antibody comprises a light chain of SEQ ID NO:128. In some embodiments of the methods described herein, the anti-ILT3 antibody comprises a heavy chain of SEQ ID NO:126 and a light chain of SEQ ID NO:128. In some embodiments of the methods described herein, the anti-ILT3 antibody is a humanized version of 5A7. In some embodiments of the methods described herein, the anti-ILT3 antibody is Hz5A7.v5.

In some embodiments of the methods described herein, the ILT3-binding agent (e.g. an antibody) comprises a heavy chain variable region CDR1, CDR2, and CDR3 and a light chain variable region CDR1, CDR2, and CDR3 of antibody 3A3 or a humanized version of 3A3.

In some embodiments of the methods described herein, the anti-ILT3 antibody comprises: (a) a heavy chain variable region comprising a heavy chain variable region CDR1 comprising the amino acid sequence GFSLTSYGVH (SEQ ID NO:11), a heavy chain variable region CDR2 comprising the amino acid sequence VIWPGGTINYNSALMS (SEQ ID NO:12), and a heavy chain variable region CDR3 comprising the amino acid sequence DKYDGGWFAY (SEQ ID NO:13), and (b) a light chain variable region comprising a light chain variable region CDR1 comprising the amino acid sequence KASQNVRTAVA (SEQ ID NO:14), a light chain variable region CDR2 comprising the amino acid sequence LASNRHT (SEQ ID NO:15), and a light chain variable region CDR3 comprising the amino acid sequence LQHLNYPLT (SEQ ID NO:16).

In some embodiments of the methods described herein, the anti-ILT3 antibody comprises a heavy chain variable region of SEQ ID NO:109 and a light chain variable region of SEQ ID NO:110. In some embodiments of the methods described herein, the anti-ILT3 antibody comprises a polypeptide of SEQ ID NO:109. In some embodiments of the methods described herein, the anti-ILT3 antibody comprises a polypeptide of SEQ ID NO:110. In some embodiments of the methods described herein, the anti-ILT3 antibody comprises a polypeptide of SEQ ID NO:109 and a polypeptide of SEQ ID NO:110.

In some embodiments of the methods described herein, the anti-ILT3 antibody is antibody 3A3. In some embodiments of the methods described herein, the anti-ILT3 antibody is a humanized version of antibody 3A3. In some embodiments of the methods described herein, the anti-ILT3 antibody is a variant of antibody 3A3 or a variant of humanized 3A3.

In some embodiments of the methods described herein, the ILT3-binding agent (e.g. an antibody) comprises a heavy chain variable region CDR1, CDR2, and CDR3 and a light chain variable region CDR1, CDR2, and CDR3 of antibody 12A12 or a humanized version of 12A12.

In some embodiments of the methods described herein, the anti-ILT3 antibody comprises: (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPNNGGTGYNQKFNS (SEQ ID NO:44), and a heavy chain variable region CDR3 comprising the amino acid sequence SPYYDYVGSYAMDY (SEQ ID NO:45), and (b) a light chain variable region comprising a light chain variable region CDR1 comprising the amino acid sequence TASSSVSSSYLH (SEQ ID NO:46), a light chain variable region CDR2 comprising the amino acid sequence STSNLAS (SEQ ID NO:47), and a light chain variable region CDR3 comprising the amino acid sequence HQYHRSPRT (SEQ ID NO:48);

In some embodiments of the methods described herein, the anti-ILT3 antibody comprises a heavy chain variable region of SEQ ID NO:113 and a light chain variable region of SEQ ID NO:114. In some embodiments of the methods described herein, the anti-ILT3 antibody comprises a polypeptide of SEQ ID NO:113. In some embodiments of the methods described herein, the anti-ILT3 antibody comprises a polypeptide of SEQ ID NO:114. In some embodiments of the methods described herein, the anti-ILT3 antibody comprises a polypeptide of SEQ ID NO:113 and a polypeptide of SEQ ID NO:114.

In some embodiments of the methods described herein, the anti-ILT3 antibody is antibody 12A12. In some embodiments of the methods described herein, the anti-ILT3 antibody is a humanized version of antibody 12A12. In some embodiments of the methods described herein, the anti-ILT3 antibody is a variant of antibody 12A12 or variant of humanized 12A12.

In some embodiments of the methods described herein, the ILT3-binding agent (e.g. an antibody) comprises a heavy chain variable region CDR1, CDR2, and CDR3 and a light chain variable region CDR1, CDR2, and CDR3 of antibody 16C5 or a humanized version of 16C5.

In some embodiments of the methods described herein, the anti-ILT3 antibody comprises: (a) a heavy chain variable region comprising a heavy chain variable region CDR1 comprising the amino acid sequence GYTFTDYNMD (SEQ ID NO:43), a heavy chain variable region CDR2 comprising the amino acid sequence YIYPSNGGTGYNQKFKS (SEQ ID NO:59), and a heavy chain variable region CDR3 comprising the amino acid sequence VPYYDYLYYYAMDY (SEQ ID NO:60), and (b) a light chain variable region comprising a light chain variable region CDR1 comprising the amino acid sequence RASSSVSFMH (SEQ ID NO:61), a light chain variable region CDR2 comprising the amino acid sequence ATSNLAS (SEQ ID NO:62), and a light chain variable region CDR3 comprising the amino acid sequence QQWSTNPYMYT (SEQ ID NO:63).

In some embodiments of the methods described herein, the anti-ILT3 antibody comprises a heavy chain variable region of SEQ ID NO:115 and a light chain variable region of SEQ ID NO:116. In some embodiments of the methods described herein, the anti-ILT3 antibody comprises a polypeptide of SEQ ID NO:115. In some embodiments of the methods described herein, the anti-ILT3 antibody comprises a polypeptide of SEQ ID NO:116. In some embodiments of the methods described herein, the anti-ILT3 antibody comprises a polypeptide of SEQ ID NO:115 and a polypeptide of SEQ ID NO:116.

In some embodiments of the methods described herein, the anti-ILT3 antibody is antibody 16C5. In some embodiments of the methods described herein, the anti-ILT3 antibody is a humanized version of antibody 16C5. In some embodiments of the methods described herein, the anti-ILT3 antibody is a variant of antibody 16C5 or a variant of a humanized 16C5.

In some embodiments of the methods described herein, the ILT3-binding agent (e.g. an antibody) comprises a heavy chain variable region CDR1, CDR2, and CDR3 and a light chain variable region CDR1, CDR2, and CDR3 of antibody 45G10 or a humanized version of 45G10.

In some embodiments of the methods described herein, the anti-ILT3 antibody comprises: (a) a heavy chain variable region comprising a heavy chain variable region CDR1 comprising the amino acid sequence GFTFSDYGMH (SEQ ID NO:71), a heavy chain variable region CDR2 comprising the amino acid sequence YIFSGSSTIYYADTVKG (SEQ ID NO:72), and a heavy chain variable region CDR3 comprising the amino acid sequence ADGRGAMDY (SEQ ID NO:73), and (b) a light chain variable region comprising a light chain variable region CDR1 comprising the amino acid sequence RASQDISKFLN (SEQ ID NO:74), a light chain variable region CDR2 comprising the amino acid sequence YTSRLHS (SEQ ID NO:75), and a light chain variable region CDR3 comprising the amino acid sequence QQGNTLPWT (SEQ ID NO:76).

In some embodiments of the methods described herein, the anti-ILT3 antibody comprises a heavy chain variable region of SEQ ID NO:117 and a light chain variable region of SEQ ID NO:118. In some embodiments of the methods described herein, the anti-ILT3 antibody comprises a polypeptide of SEQ ID NO:117. In some embodiments of the methods described herein, the anti-ILT3 antibody comprises a polypeptide of SEQ ID NO:118. In some embodiments of the methods described herein, the anti-ILT3 antibody comprises a polypeptide of SEQ ID NO:117 and a polypeptide of SEQ ID NO:118.

In some embodiments of the methods described herein, the anti-ILT3 antibody is antibody 45G10. In some embodiments of the methods described herein, the anti-ILT3 antibody is a humanized version of antibody 45G10. In some embodiments of the methods described herein, the anti-ILT3 antibody is a variant of antibody 45G10 or a variant of a humanized 45G10.

In some embodiments of the methods described herein, the ILT3-binding agent (e.g. an antibody) comprises a heavy chain variable region CDR1, CDR2, and CDR3 and a light chain variable region CDR1, CDR2, and CDR3 of antibody 48A6 or a humanized version of 48A6.

In some embodiments of the methods described herein, the anti-ILT3 antibody comprises: (a) a heavy chain variable region comprising a heavy chain variable region CDR1 comprising the amino acid sequence GFTFSSYGMS (SEQ ID NO:27), a heavy chain variable region CDR2 comprising the amino acid sequence TISSGGTYTFYPDSVKG (SEQ ID NO:87), and a heavy chain variable region CDR3 comprising the amino acid sequence RGWLLHYYAMDY (SEQ ID NO:88), and (b) a light chain variable region comprising a light chain variable region CDR1 comprising the amino acid sequence RPSESVDSFGNSFMH (SEQ ID NO:89), a light chain variable region CDR2 comprising the amino acid sequence LSSKLES (SEQ ID NO:90), and a light chain variable region CDR3 comprising the amino acid sequence QQHNEDPFT (SEQ ID NO:91).

In some embodiments of the methods described herein, the anti-ILT3 antibody comprises a heavy chain variable region of SEQ ID NO:119 and a light chain variable region of SEQ ID NO:120. In some embodiments of the methods described herein, the anti-ILT3 antibody comprises a polypeptide of SEQ ID NO:119. In some embodiments of the methods described herein, the anti-ILT3 antibody comprises a polypeptide of SEQ ID NO:120. In some embodiments of the methods described herein, the anti-ILT3 antibody comprises a polypeptide of SEQ ID NO:119 and a polypeptide of SEQ ID NO:120.

In some embodiments of the methods described herein, the anti-ILT3 antibody is antibody 48A6. In some embodiments of the methods described herein, the anti-ILT3 antibody is a humanized version of antibody 48A6. In some embodiments of the methods described herein, the anti-ILT3 antibody is a variant of antibody 48A6 or a variant of a humanized 48A6.

In some embodiments of the methods described herein, the ILT3-binding agent (e.g. an antibody) comprises a heavy chain variable region CDR1, CDR2, and CDR3 and a light chain variable region CDR1, CDR2, and CDR3 of antibody 53F10 or a humanized version of 53F10.

In some embodiments of the methods described herein, the anti-ILT3 antibody comprises: (a) a heavy chain variable region comprising a heavy chain variable region CDR1 comprising the amino acid sequence GFTFSDYGMH (SEQ ID NO:71), a heavy chain variable region CDR2 comprising the amino acid sequence YISTGIITVYYADTVKG (SEQ ID NO:99), and a heavy chain variable region CDR3 comprising the amino acid sequence ADGRGAMDY (SEQ ID NO:73), and (b) a light chain variable region comprising a light chain variable region CDR1 comprising the amino acid sequence RASQDISNFLN (SEQ ID NO:100), a light chain variable region CDR2 comprising the amino acid sequence YTSRLHS (SEQ ID NO:75), and a light chain variable region CDR3 comprising the amino acid sequence QQGNTLPWT (SEQ ID NO:76).

In some embodiments of the methods described herein, the anti-ILT3 antibody comprises a heavy chain variable region of SEQ ID NO:121 and a light chain variable region of SEQ ID NO:122. In some embodiments of the methods described herein, the anti-ILT3 antibody comprises a polypeptide of SEQ ID NO:121. In some embodiments of the methods described herein, the anti-ILT3 antibody comprises a polypeptide of SEQ ID NO:122. In some embodiments of the methods described herein, the anti-ILT3 antibody comprises a polypeptide of SEQ ID NO:121 and a polypeptide of SEQ ID NO:122.

In some embodiments of the methods described herein, the anti-ILT3 antibody is antibody 53F10. In some embodiments of the methods described herein, the anti-ILT3 antibody is a humanized version of antibody 53F10. In some embodiments of the methods described herein, the anti-ILT3 antibody is a variant of antibody 53F10 or a variant of a humanized 53F10.

In some embodiments of the methods described herein, a method comprises administering an ILT3-binding agent (e.g., an antibody) described herein in combination with at least one additional therapeutic agent or therapeutic therapy. Treatment with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistance to an agent will develop.

In some embodiments of the methods described, the combination of an ILT3-binding agent (e.g., an antibody) described herein and at least one additional therapeutic agent results in additive or synergistic results. In some embodiments, the combination therapy results in an increase in the therapeutic index of the ILT3-binding agent. In some embodiments, the combination therapy results in an increase in the therapeutic index of the additional therapeutic agent(s). In some embodiments, the combination therapy results in a decrease in the toxicity and/or side effects of the ILT3-binding agent. In some embodiments, the combination therapy results in a decrease in the toxicity and/or side effects of the additional therapeutic agent(s). In some embodiments, combination therapy comprises a therapeutic agent that affects the immune response (e.g., enhances or activates the response) and a therapeutic agent that affects (e.g., inhibits or kills) the tumor/cancer cells.

In some embodiments of the methods described herein, a combination treatment comprises one additional therapeutic agent or two or more additional therapeutic agents.

Useful classes of therapeutic agents include, but are not limited to, anti-tubulin agents, auristatins, DNA minor groove binders, DNA replication inhibitors, alkylating agents (e.g., platinum complexes such as cisplatin, mono (platinum), bis(platinum) and tri-nuclear platinum complexes and carboplatin), anthracyclines, antibiotics, antifolates, anti-metabolites, chemotherapy sensitizers, duocarmycins, etoposides, fhiorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In some embodiments, the second therapeutic agent is an alkylating agent, an antimetabolite, an antimitotic, a topoisomerase inhibitor, or an angiogenesis inhibitor.

Therapeutic agents that may be administered in combination with the ILT3-binding agents described herein include chemotherapeutic agents. Thus, in some embodiments, the method or treatment involves the administration of an ILT3-binding agent of the present disclosure in combination with a chemotherapeutic agent or in combination with a cocktail of chemotherapeutic agents.

Chemotherapeutic agents useful in the present disclosure include, but are not limited to, alkylating agents such as thiotepa and cyclophosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunomycin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT 11; topoisomerase inhibitor RFS 2000; difluoromethylornithine (DMFO); retinoic acid; esperamicins; capecitabine (XELODA); and pharmaceutically acceptable salts, acids or derivatives of any of the above.

Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above.

In certain embodiments of the methods described herein, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In some embodiments, the additional therapeutic agent is irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the additional therapeutic agent is gemcitabine.

In certain embodiments of the methods described herein, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (nab-paclitaxel; ABRAXANE), DHA-paclitaxel, or PG-paclitaxel. In certain alternative embodiments, the antimitotic agent comprises a vinca alkaloid, such as vincristine, vinblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In certain embodiments, the additional therapeutic agent is paclitaxel. In certain embodiments, the additional therapeutic agent is nab-paclitaxel.

In some embodiments of the methods described herein, an additional therapeutic agent comprises an agent such as a small molecule. For example, treatment can involve the combined administration of an ILT3-binding agent of the present disclosure with a small molecule that acts as an inhibitor against tumor-associated antigens including, but not limited to, EGFR, HER2 (ErbB2), and/or VEGF. In some embodiments, an ILT3-binding agent of the present disclosure is administered in combination with a protein kinase inhibitor selected from the group consisting of: gefitinib (IRESSA), erlotinib (TARCEVA), sunitinib (SUTENT), lapatinib, vandetanib (ZACTIMA), AEE788, CH033, cediranib (RECENTIN), sorafenib (NEXAVAR), and pazopanib (GW786034B). In some embodiments, an additional therapeutic agent comprises an mTOR inhibitor.

In some embodiments of the methods described herein, an additional therapeutic agent comprises a biological molecule, such as an antibody. For example, treatment can involve the combined administration of an ILT3-binding agent of the present disclosure with antibodies against tumor-associated antigens including, but not limited to, antibodies that bind EGFR, HER2/ErbB2, and/or VEGF.

In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX).

In some embodiments of the methods described herein, the additional therapeutic agent is an antibody that modulates the immune response. In some embodiments, the additional therapeutic agent is an anti-PD-1 antibody, an anti-PD-L1 antibody, an anti-PD-L2 antibody, an anti-CTLA-4 antibody, or an anti-TIGIT antibody.

Furthermore, treatment with an ILT3-binding agent described herein can include combination treatment with other biologic molecules, such as one or more cytokines (e.g., lymphokines, interleukins, tumor necrosis factors, and/or growth factors) or can be accompanied by surgical removal of tumors, removal of cancer cells, or any other therapy deemed necessary by a treating physician. In some embodiments, the additional therapeutic agent is an immunotherapeutic agent.

In some embodiments of the methods described herein, an ILT3-binding agent is combined with a growth factor selected from the group consisting of: adrenomedullin (AM), angiopoietin (Ang), BMPs, BDNF, EGF, erythropoietin (EPO), FGF, GDNF, G-CSF, GM-CSF, GDF9, HGF, HDGF, IGF, migration-stimulating factor, myostatin (GDF-8), NGF, neurotrophins, PDGF, thrombopoietin, TGF-a, TGF-β, TNF-α, VEGF, PIGF, IL-1, IL-2, IL-3, IL-4, IL-5, IL-6, IL-7, IL-12, IL-15, and IL-18.

In some embodiments of the methods described herein, the additional therapeutic agent is an immunotherapeutic agent. In some embodiments, the immunotherapeutic agent is selected from the group consisting of granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), interleukin 1 (IL-1), interleukin 2 (IL-2), B7-1 (CD80), B7-2 (CD86), 4-1BB ligand, anti-CD3 antibody, anti-CTLA-4 antibody, anti-TIGIT antibody, anti-PD-1 antibody, anti-PD-L1 antibody, anti-LAG-3 antibody, and anti-TIM-3 antibody.

In some embodiments of the methods described herein, an immunotherapeutic agent is selected from the group consisting of: a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a cytokine, a chemokine, an interferon, an interleukin, a lymphokine, a member of the tumor necrosis factor (TNF) family, and an immunostimulatory oligonucleotide.

In some embodiments of the methods described herein, an immunotherapeutic agent is selected from the group consisting of: a PD-1 antagonist, a PD-L1 antagonist, a PD-L2 antagonist, a CTLA-4 antagonist, a CD80 antagonist, a CD86 antagonist, a KIR antagonist, a Tim-3 antagonist, a LAG3 antagonist, a TIGIT antagonist, a CD20 antagonist, a CD96 antagonist, and/or an IDO1 antagonist.

In some embodiments of the methods described herein, the PD-1 antagonist is an antibody that specifically binds PD-1. In some embodiments, the antibody that binds PD-1 is pembrolizumab (KEYTRUDA, MK-3475), pidilizumab (CT-011), nivolumab (OPDIVO, BMS-936558, MDX-1106), MEDI0680 (AMP-514), REGN2810, BGB-A317, PDR-001, or STI-A1110. In some embodiments, the antibody that binds PD-1 is described in PCT Publication WO 2014/179664, for example, an antibody identified as APE2058, APE1922, APE1923, APE1924, APE 1950, or APE1963, or an antibody containing the CDR regions of any of these antibodies. In other embodiments, the PD-1 antagonist is a fusion protein that includes PD-L2, for example, AMP-224. In other embodiments, the PD-1 antagonist is a peptide inhibitor, for example, AU P-12.

In some embodiments, the PD-L1 antagonist is an antibody that specifically binds PD-L1. In some embodiments, the antibody that binds PD-L1 is atezolizumab (TECENTRIQ, RG7446, MPDL3280A), MEDI4736, BMS-936559 (MDX-1105), avelumab (BAVENCIO, MSB0010718C), durvalumab (IMFINZI), KD033, the antibody portion of KD033, or STI-A1014. In some embodiments, the antibody that binds PD-L1 is described in PCT Publication WO 2014/055897, for example, Ab-14, Ab-16, Ab-30, Ab-31, Ab-42, Ab-50, Ab-52, or Ab-55, or an antibody that contains the CDR regions of any of these antibodies.

In some embodiments, the CTLA-4 antagonist is an antibody that specifically binds CTLA-4. In some embodiments, the antibody that binds CTLA-4 is ipilimumab (YERVOY) or tremelimumab (CP-675,206). In some embodiments, the CTLA-4 antagonist a CTLA-4 fusion protein, for example, KAHR-102.

In some embodiments, the LAG3 antagonist is an antibody that specifically binds LAG3. In some embodiments, the antibody that binds LAG3 is IMP701, IMP731, BMS-986016, LAG525, and GSK2831781. In some embodiments, the LAG3 antagonist includes a soluble LAG3 receptor, for example, IMP321.

In some embodiments, the KIR antagonist is an antibody that specifically binds KIR. In some embodiments, the antibody that binds KIR is lirilumab.

In some embodiments, an immunotherapeutic agent is selected from the group consisting of: a CD28 agonist, a 4-1BB agonist, an OX40 agonist, a CD27 agonist, a CD80 agonist, a CD86 agonist, a CD40 agonist, and a GITR agonist.

In some embodiments, the OX40 agonist includes OX40 ligand, or an OX40-binding portion thereof. For example, the OX40 agonist may be MEDI6383. In some embodiments, the OX40 agonist is an antibody that specifically binds OX40. In some embodiments, the antibody that binds OX40 is MEDI6469, MEDI0562, or MOXR0916 (RG7888). In some embodiments, the OX40 agonist is a vector (e.g., an expression vector or virus, such as an adenovirus) capable of expressing OX40 ligand. In some embodiments the OX40-expressing vector is Delta-24-RGDOX or DNX2401.

In some embodiments, the 4-1BB (CD137) agonist is a binding molecule, such as an anticalin. In some embodiments, the anticalin is PRS-343. In some embodiments, the 4-1BB agonist is an antibody that specifically binds 4-1BB. In some embodiments, antibody that binds 4-1BB is PF-2566 (PF-05082566) or urelumab (BMS-663513).

In some embodiments, the CD27 agonist is an antibody that specifically binds CD27. In some embodiments, the antibody that binds CD27 is varlilumab (CDX-1127).

In some embodiments, the GITR agonist comprises a GITR ligand or a GITR-binding portion thereof. In some embodiments, the GITR agonist is an antibody that specifically binds GITR. In some embodiments, the antibody that binds GITR is TRX518, MK-4166, or INBRX-110.

In some embodiments, immunotherapeutic agents include, but are not limited to, cytokines such as chemokines, interferons, interleukins, lymphokines, and members of the tumor necrosis factor (TNF) family. In some embodiments, immunotherapeutic agents include immunostimulatory oligonucleotides, such as CpG dinucleotides.

In some embodiments, an immunotherapeutic agent includes, but is not limited to, anti-PD-1 antibodies, anti-PD-L1 antibodies, anti-PD-L2 antibodies, anti-CTLA-4 antibodies, anti-CD28 antibodies, anti-CD80 antibodies, anti-CD86 antibodies, anti-4-1BB antibodies, anti-OX40 antibodies, anti-KIR antibodies, anti-Tim-3 antibodies, anti-LAG3 antibodies, anti-CD27 antibodies, anti-CD40 antibodies, anti-GITR antibodies, anti-TIGIT antibodies, anti-CD20 antibodies, anti-CD96 antibodies, or anti-IDO1 antibodies.

In some embodiments, treatment with an ILT3-binding agent can occur prior to, concurrently with, or subsequent to administration of the additional therapeutic agents. In some embodiments, combined administration includes co-administration, either in a single pharmaceutical formulation or using separate formulations, or consecutive administration in either order but generally within a time period such that all active agents can exert their biological activities. In some embodiments, preparation of agents and/or dosing schedules for additional therapeutic agents are according to manufacturers' instructions or as determined empirically by the skilled practitioner.

In some embodiments of the methods described herein, an ILT3-binding agent (e.g., an antibody) is administered to a subject (e.g., a human) as part of a combination therapy.

It will be appreciated that the combination of an ILT3-binding agent (e.g., an antibody) described herein and at least one additional therapeutic agent may be administered in any order or concurrently. In some embodiments, an ILT3-binding agent is administered to subjects that have previously undergone treatment with a therapeutic agent. In some embodiments, an ILT3-binding agent and a second therapeutic agent are administered substantially simultaneously or concurrently. For example, a subject may be given an ILT3-binding agent while undergoing a course of treatment with a second therapeutic agent (e.g., a chemotherapeutic agent). In some embodiments, an ILT3-binding agent is administered within 1 year of the treatment with a second therapeutic agent. In some embodiments, an ILT3-binding agent is administered within 10, 8, 6, 4, or 2 months of any treatment with a second therapeutic agent. In some embodiments, an ILT3-binding agent is administered within 4, 3, 2, or 1 weeks of any treatment with a second therapeutic agent. In some embodiments, an ILT3-binding agent is administered within 5, 4, 3, 2, or 1 days of any treatment with a second therapeutic agent. It will further be appreciated that the two (or more) agents or treatments can be administered to the subject within a matter of hours or minutes (i.e., substantially simultaneously).

For the treatment of a disease, the appropriate dosage of an ILT3-binding agent (e.g., an antibody) of the present disclosure depends on the disorder or disease to be treated, the severity and course of the disorder or disease, the responsiveness of the disorder or disease, whether the agent is administered for therapeutic or preventative purposes, previous therapy, the patient's clinical history, and so on. An ILT3-binding agent can be administered one time or over a series of treatments lasting from several days to several months, or until a cure is effected or a diminution of the disease state is achieved.

The present disclosure provides compositions comprising an ILT3-binding agent described herein. The present disclosure also provides pharmaceutical compositions comprising an ILT3-binding agent described herein and a pharmaceutically acceptable vehicle.

Formulations are prepared for storage and use by combining a purified antibody or agent of the present disclosure with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol. (*Remington: The Science and Practice of Pharmacy, 22$^{nd}$ Edition,* 2012, Pharmaceutical Press, London.). In some embodiments, the formulation is in the form of an aqueous solution. In some embodiments, the formulation is stored in a lyophilized or in an alternative dried form.

The binding agents of the present disclosure can be formulated in any suitable form for delivery to a target cell/tissue. In some embodiments, an ILT3-binding agent (e.g., an antibody) can be formulated as a liposome, microparticle, microcapsule, albumin microsphere, microemulsion, nanoparticle, nanocapsule, or macroemulsion.

In some embodiments, an ILT3-binding agent (e.g., an antibody) is formulated with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE).

In some embodiments, an ILT3-binding agent (e.g., an antibody) is formulated as a sustained-release preparation. Suitable examples of sustained-release preparations include semi-permeable matrices of solid hydrophobic polymers containing an agent, where the matrices are in the form of shaped articles (e.g., films or microcapsules). Sustained-release matrices include but are not limited to polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The pharmaceutical compositions or formulations of the present disclosure can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

EXAMPLES

Example 1

Generation of Antibodies

Anti-ILT3 antibodies were generated using the extracellular domain of human ILT3 (huILT3-ECD) and/or cyno ILT3 (cynoILT3-ECD) as the immunogen. Recombinant constructs comprising the extracellular region of human ILT3 (aa 22-259 of SEQ ID NO:1) or the extracellular region of cyno ILT3 (aa 22-259 of SEQ ID NO:6) were generated and expressed in mammalian cells. Mice were immunized with the huILT3-ECD and/or cynoILT3-ECD protein and were boosted several times to induce high titers. Blood was drawn from the immunized mice and antibody titers were determined by ELISA and FACS. Single cell suspensions of lymphocytes were obtained from the spleens and lymph nodes of immunized mice that had been determined to have suitably high antibody titers. Lymphocytes were fused with murine myeloma cells by standard methods (e.g., electrofusion). Cells were dispersed into 96-well plates in HAT-containing selection media.

Example 2

Screening of Antibodies

ELISA assays were used to screen antibodies against human ILT3 and human LILRA1,2,4-6. The antibodies that bound to human ILT3 but did not bind to human LILRA1, 2,4-6proteins were selected. These antibodies were rescreened by FACS for binding to human ILT3 and cyno ILT3 expressed on HEK-293T cells. The antibodies that bound to both human and cyno ILT3 were selected. This subset of antibodies were screened by FACS against human LILRB1-5 (ILT2, ILT4, ILT5, ILT3, and LILRB5, respectively), cyno LILRB5, and human LILRA1,2,4-6. For FACS screening, each antibody was incubated with cells expressing human ILT3, cyno ILT3, one of the LILRA proteins, or one of the LILRB proteins for 30 minutes at 4° C. After washing, the cells were incubated with labeled anti-mouse Fc antibody for 30 minutes at 4° C. After washing, cells were analyzed on a flow cytometer. Results from representative antibodies are shown in FIGS. 1A-1F and 2A-2E. Antibodies were selected on the criteria of binding to human ILT3, cyno ILT3, no or limited binding to other LILRB proteins, and no or limited binding to LILRA proteins. For example, antibody 11A1 was observed to bind human LILRB2, LILRA1, LILRA2, LILRA4 and LILRA5 and therefore was not selected for additional studies.

Example 3

Binding Characteristics of Anti-Human ILT3 Antibodies

The binding affinities of anti-ILT3 antibodies to human ILT3 and cyno ILT3 were measured using a Biacore system (GE Healthcare LifeSciences). Briefly, anti-Fc antibody (Sigma-Aldrich) was immobilized on all four flow cells of a CM5 chip using amine coupling reagents (GE Healthcare LifeSciences). Antibodies were captured on flow cells 2, 3, and 4 using flow cell 1 as a reference. Concentrations ranging from 3.3-10 nM of human or cyno ILT3-ECD were injected at a flow rate of 50 μL/min at 37° C. Kinetic data were collected over time and fit using the simultaneous global fit equation to yield affinity constants ($K_D$ values) for each antibody.

Binding data is shown in Table 9.

TABLE 9

| | Human ILT3 | | | Cyno ILT3 | | |
|---|---|---|---|---|---|---|
| Antibody | $K_{on}$ [1/Ms] | $K_{off}$ [$s^{-1}$] | $K_D$ M | $K_{on}$ [1/Ms] | $K_{off}$ [$s^{-1}$] | $K_D$ M |
| 3A3 | $3.3 \times 10^5$ | $6.5 \times 10^{-4}$ | $2.0 \times 10^{-9}$ | $3.4 \times 10^6$ | $2.1 \times 10^{-2}$ | $6.3 \times 10^{-9}$ |
| 5A7 | $3.8 \times 10^6$ | $1.1 \times 10^{-4}$ | $2.8 \times 10^{-11}$ | $3.3 \times 10^6$ | $2.2 \times 10^{-3}$ | $6.6 \times 10^{-10}$ |
| 12A12 | $1.1 \times 10^5$ | $9.4 \times 10^{-4}$ | $8.5 \times 10^{-9}$ | $1.5 \times 10^5$ | $2.8 \times 10^{-4}$ | $1.9 \times 10^{-9}$ |
| 16C5 | $1.1 \times 10^5$ | $2.0 \times 10^{-4}$ | $1.8 \times 10^{-9}$ | $2.9 \times 10^5$ | $9.0 \times 10^{-5}$ | $3.1 \times 10^{-10}$ |
| 45G10 | $3.9 \times 10^5$ | $5.1 \times 10^{-5}$ | $1.3 \times 10^{-10}$ | $1.5 \times 10^5$ | $7.6 \times 10^{-4}$ | $5.0 \times 10^{-9}$ |
| 48A6 | $7.0 \times 10^6$ | $1.8 \times 10^{-7}$ | <100 pM | $1.4 \times 10^7$ | $2.4 \times 10^{-2}$ | $1.7 \times 10^{-9}$ |
| 53F10 | $3.3 \times 10^5$ | $8.0 \times 10^{-5}$ | $2.4 \times 10^{-10}$ | $5.9 \times 10^5$ | $5.5 \times 10^{-3}$ | $9.4 \times 10^{-9}$ |

The binding sites of the anti-ILT3 antibodies on the extracellular domain of human ILT3 were also assessed (data not shown). 3A3 binds to a conformational epitope within the D2 domain or within the junction between the D1 and D2 domains of ILT3. 16C5 binds to a conformational epitope within the D1 domain of ILT3. 12A12 binds to a conformational epitope within the D2 domain or within the junction between the D1 and D2 domains of ILT3. 5A7 binds to a conformational epitope within the D2 domain or within the junction between the D1 and D2 domains of ILT3. 48A6 binds to a conformational epitope within the D2 domain or within the junction between the D1 and D2 domains of ILT3. 45G10 binds to a conformational epitope within the D2 domain or within the junction between the D1 and D2 domains of ILT3. 53F10 binds to a conformational epitope within the D2 domain or within the junction between the D1 and D2 domains of ILT3.

Competitive binding among the anti-ILT3 antibodies on the extracellular domain of human ILT3 were also carried out. Table 10 shows that some anti-ILT3 antibodies bind to overlapping or partially overlapping epitopes on ILT3, and some anti-ILT3 antibodies bind to different epitopes on ILT3. "Yes" indicates competitive binding to the extracellular domain of ILT3 between two antibodies. "Partial" indicates partially competitive binding to the extracellular domain of ILT3 between two antibodies. "No" indicates no competitive binding to the extracellular domain of ILT3 between two antibodies. "ND" indicates no data available.

TABLE 10

| | 5A7 | 3A3 | 12A12 | 16C5 | 45G10 | 48A6 | 53F10 |
|---|---|---|---|---|---|---|---|
| 5A7 | yes | | | | | | |
| 3A3 | No | yes | | | | | |
| 12A12 | No | No | yes | | | | |
| 16C5 | No | No | partial | yes | | | |
| 45G10 | No | ND | ND | No | yes | | |
| 48A6 | Yes | ND | ND | No | No | yes | |
| 53F10 | No | ND | ND | No | yes | No | yes |

Example 4

Sequence Analyses of Anti-ILT3 Antibodies

Representative antibodies 3A3, 5A7, 12A12, 16C5, 45G10, 48A6, and 53F10 were sequenced and the heavy chain variable region and light chain variable region amino acid sequences are disclosed herein and summarized in Table 11.

TABLE 11

| Antibody | Heavy Chain Variable Region | Light Chain Variable Region |
|---|---|---|
| 3A3 | SEQ ID NO: 109 | SEQ ID NO: 110 |
| 5A7 | SEQ ID NO: 111 | SEQ ID NO: 112 |
| 12A12 | SEQ ID NO: 113 | SEQ ID NO: 114 |
| 16C5 | SEQ ID NO: 115 | SEQ ID NO: 116 |
| 45G10 | SEQ ID NO: 117 | SEQ ID NO: 118 |
| 48A6 | SEQ ID NO: 119 | SEQ ID NO: 120 |

The heavy chain and light chain variable region CDRs for the individual antibodies are disclosed in Tables 1-7 and as SEQ ID NOs:11-104.

Example 5

Screening for ILT3 Ligand

Approximately 100 cell lines were screened in the process of identifying a ligand or ligands for ILT3. A construct comprising ILT3 extracellular domain (amino acids 22-259 of SEQ ID NO:1) fused to an immunoglobulin Fc region was generated (ILT3ECD-Fc). The ILT3ECD-Fc construct was used to evaluate binding to the cell lines. Previous in-house studies had suggested that CNTFR was a binding partner for ILT3 and LX-2 was included in the cell line panel to follow up on this earlier observation. LX-2 is an adherent human hepatic stellate cell line that retains key biological features. Following is a brief description of the screening assay using LX-2 as an exemplary cell line. LX-2 cells were seeded into 384-well poly-D-lysine-coated plates (Grenier) in DMEM containing 10% FBS and 1% penicillin/streptomycin. TGF-β (Peprotech) was added at 10 ng/mL to a portion of the wells to activate the LX-2 cells. After two days, the cells were washed three times with Hank's buffered saline solution (HBSS) containing $Mg^{2+}$ and $Ca^{2+}$, leaving approximately 10 μL of buffer per well. Next, cells (untreated and TGF-β-treated) were incubated with ILT3ECD-Fc (10 μL per well at a concentration of 10 μg/mL) in DMEM for 30 minutes at room temperature. An AlexaFluor 647-conjugated goat anti-human Fc antibody (1:500 dilution; Jackson ImmunoResearch Laboratories) and Hoechst stain (2.5 μM; ThermoFisher Scientific) were added to the wells. After a 30 minute incubation, cells were washed and fixed with 3.7% formalin, then washed again, and imaged at 10× on a Celllnsight instrument (ThermoFisher Scientific).

The results showed that ILT3ECD-Fc bound to activated LX-2 cells and did not bind to basal/untreated LX-2 cells. Viability of the cells was equivalent in the basal and activated cells. These results suggested that activated LX-2 cells expressed a ligand for ILT3.

Example 6

Activation of Reporter Cells by Interaction with LX-2 Cells

To investigate whether binding of ILT3 to LX-2 cells was a functional interaction, LX-2 cells were co-cultured with cells expressing a stable reporter system and a cell surface receptor of interest ("reporter cells"). In this chimeric receptor system, the extracellular domain of the receptor of interest, e.g., ILT3, is fused with the transmembrane/intracellular domain of PILRβ that associates with the adaptor protein DAP12. When the chimeric receptor is activated by binding to a ligand, DAP12 becomes phosphorylated and activates an NFAT-responsive promoter which drives GFP expression (see, e.g., Deng et al., 2014, *Blood*, 124:924-935). Bulk cultures of LX-2 cells were cultured in basal media (DMEM as described above) or in activation media (DMEM plus TGF-β as described above) for three days. Treated and untreated LX-2 cells were harvested and washed. $2 \times 10^5$ of LX-2 cells were co-cultured with $4 \times 10^5$ reporter cells containing (i) no receptor; (ii) B7-H4 extracellular domain; or (iii) ILT3 extracellular domain. Cells were incubated overnight at 37° C. in RPMI 1640 containing 10% FBS. The reporter cells were pre-stained with Cell-Tracker Deep Red (ThermoFisher) to distinguish them from LX-2 cells upon analysis. The next day, reporter cells were assayed for GFP expression by FACS.

Figure 3:
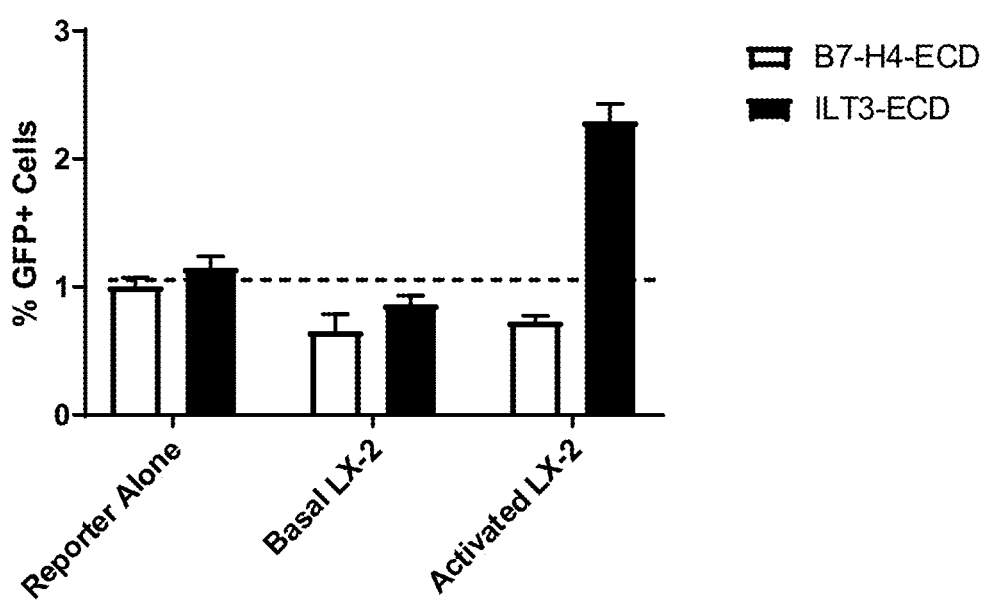
FIG. 3. Reporter cell assay—ILT3 and LX-2 cell interaction. Bulk cultures of LX-2 cells were cultured in basal media or in activation media for three days. Treated and untreated LX-2 cells were harvested and washed. 2×10$^5$ of LX-2 cells were co-cultured with 4×10$^5$ reporter cells containing (i) reporter cells with no receptor; (ii) reporter cells with B7-H4 extracellular domain; or (iii) reporter cells with ILT3 extracellular domain. Cells were incubated overnight at 37° C. in RPMI 1640 containing 10% FBS. The reporter cells were pre-stained with CellTracker Deep Red to distinguish them from LX-2 cells upon analysis. The next day, reporter cells were assayed for GFP expression by FACS.

As shown in FIG. 3, expression of GFP was induced only when ILT3 was expressed on the surface of the reporter cells and only in the presence of activated LX-2 cells. These results suggest that not only did ILT3 bind to a potential ligand on the cell surface of activated LX-2 cells but that the interaction was biologically functional.

Example 7

Identification of Fibronectin as ILT3 Ligand

Immunoprecipitation and mass spectrometry methods were used to identify the binding partner of ILT3. Briefly, LX-2 cells were seeded in basal media or activation media with $2.5 \times 10^6$ cells in a 150 mm³ tissue culture dish and incubated for 3 days. Media was removed and the cells were lysed in 100 µl of cell lysis buffer (Cell Signaling Technologies) supplemented with HALT™ protease and inhibitor cocktail (ThermoFisher). Lysates were cleared by centrifugation at >16,000 RCF at 4° C. for 10 minutes, and supernatants were transferred to new microfuge tubes. Protein concentrations of the cleared lysates were quantified using a bicinchoninic acid (BCA) assay (Pierce Biotechnology).

Immunoprecipitation was performed using Protein G dynabeads (Invitrogen/ThermoFisher Scientific) according to the manufacturer's instructions. Briefly, 10 of ILT3ECD-Fc or control human Fc was bound to 50 µl of magnetic Dynabeads for 30 minutes at 4° C. Supernatant was removed and protein lysate from the untreated or activated LX-2 cells was added. For each treatment condition, lysate containing approximately 615 µg of protein was added to the Dynabead complexes (either ILT3ECD-Fc Dynabeads or Fc Dynabeads) and incubated overnight at 4° C. with gentle rotation. Protein lysates were removed and Dynabeads were washed three times with 200 µl of lysis buffer for 5 minutes per wash. 50 µl of elution buffer comprised of protein loading buffer, reducing agent, and lysis buffer in a ratio of 15:4:1 was added to Dynabeads. Proteins were eluted at 95° C. for 5 minutes and samples (10 µl of each protein elute) were run on polyacrylamide electrophoresis gels. To identify bands of interest, silver stain analysis was performed using a PlusOne Silver Staining kit (GE Healthcare) according to the manufacturer's instructions. Gels were imaged using a Gel Doc™ EZ system (Bio-Rad).

Figure 4:
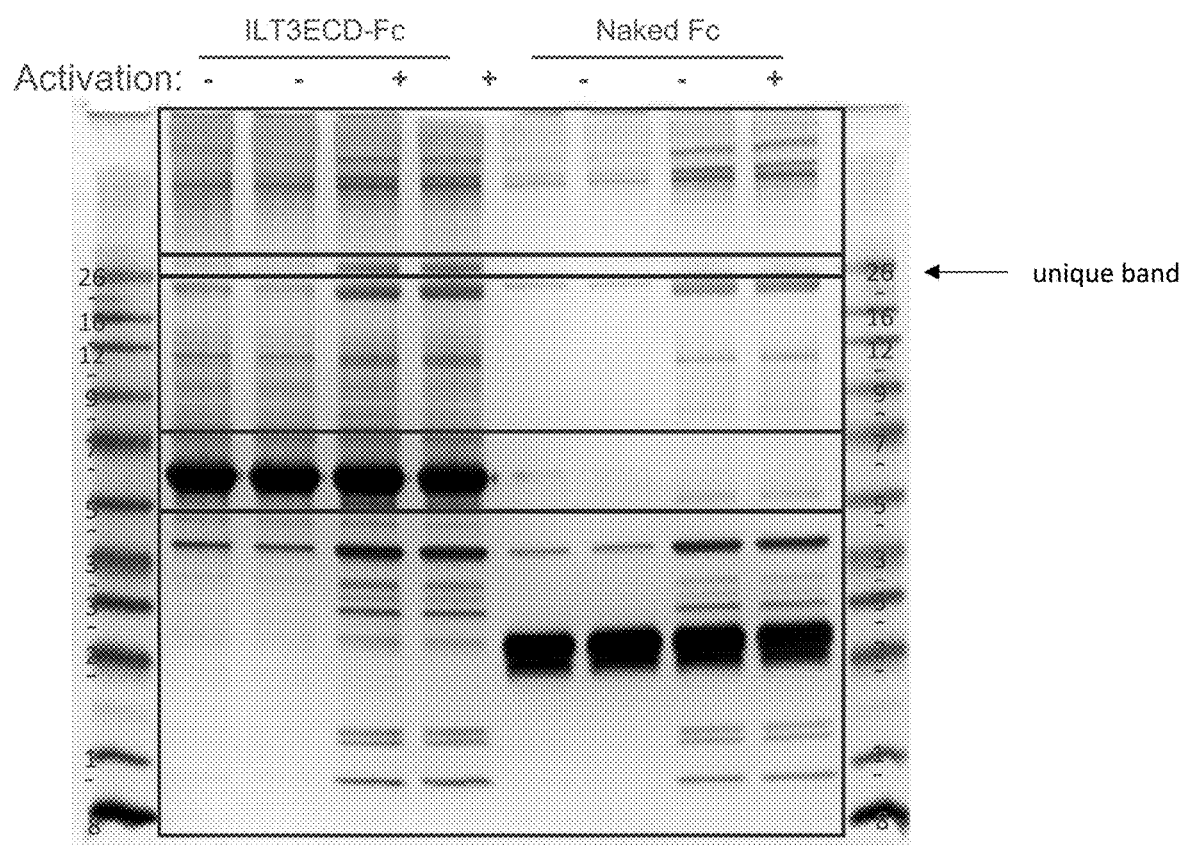
FIG. 4. Identification of ILT3 ligand using immunoprecipitation and gel electrophoresis. Immunoprecipitation was performed using Protein G dynabeads according to the manufacturer's instructions. 10 μg of ILT3ECD-Fc or control human Fc was bound to 50 μl of magnetic Dynabeads for 30 minutes at 4° C. Supernatant was removed and protein lysate from the untreated or activated LX-2 cells was added. For each treatment condition, lysate containing approximately 615 μg of protein was added to the Dynabead complexes and incubated overnight at 4° C. with gentle rotation. Protein lysates were removed and Dynabeads were washed three times with 200 μl of lysis buffer for 5 minutes per wash. 50 μl of elution buffer comprised of protein loading buffer, reducing agent, and lysis buffer in a ratio of 15:4:1 was added to Dynabeads. Proteins were eluted at 95° C. for 5 minutes and samples (10 μl of each protein elute) were run on polyacrylamide electrophoresis gels. To identify bands of interest, silver stain analysis was performed using a PlusOne Silver Staining kit (GE Healthcare) according to the manufacturer's instructions. Gels were imaged using a Gel Doc™ EZ system (Bio-Rad).

As shown in FIG. 4, a unique band was observed in the protein sample eluted from the Dynabead complex of ILT3ECD-Fc and activated LX-2 cell lysate (within box near 260 MW marker).

Gel electrophoresis was performed on the remaining 40 µl of eluate and the gel was stained with Bio-Safe Coomassie Stain (Bio-Rad). Gel bands corresponding to the unique band and control bands from other samples at the same size were excised in a biological safety cabinet and gel pieces were sliced into small fragments. Gel pieces were washed in 50% acetonitrile and 200 mM ammonium bicarbonate, incubated in 100% acetonitrile for 10 minutes, and dried in a SpeedVac vacuum concentrator. Proteins in the gel pieces were reduced and alkylated by sequential incubation with 25 mM tris(2-carboxyethyl)phosphine (TCEP) and 50 mM iodoacetamide. Gel pieces were washed and incubated with acetonitrile again and digested with trypsin (20 µg/ml in 50 mM ammonium bicarbonate, pH 8.0) overnight at 37° C.

The digested samples were analyzed by mass spectrometry. Briefly, peptides were separated over an EASY-Spray™ PepMap C18 column connected to an UltiMate™ RSLCnano LC system (ThermoFisher Scientific). Peptides were eluted from the column with a gradient of 2% to 32% acetonitrile over 135 minutes and injected into an Orbitrap Velos Pro™ mass spectrometer. Liquid chromatography with tandem mass spectrometry (LC-MS/MS) data was collected using a top10 method, with MS data collected at 60,000 resolution from 200-2000 m/z. MS/MS data was collected with dynamic exclusion, monoisotopic precursor selection, and charge state screening enabled on the ion trap. Singly charged peptides were excluded. Raw files were analyzed with PEAKS X proteomics software (Bioinformatics Solutions) searching against a database of human proteins. In the PEAKS program, proteins were identified with a −10 log p setting of 20 and a false discovery rate (FDR) of no higher than 1.5%. Hits were ranked by total peptide count and screened for hits that were found in experimental samples but not controls. Hits were additionally screened for extracellular and transmembrane proteins. Surprisingly, the unique band was identified as fibronectin. The number of identified peptides for fibronectin in the sample from ILT3ECD-Fc and activated LX-2 cells was 306, as compared to peptides for fibronectin in the sample from (1) ILT3ECD-Fc and basal LX-2 cells which was 111; (2) control-Fc and activated LX-2 cells which was 15; and (3) control-Fc and basal LX-2 cells which was 1. This clearly demonstrated the enrichment of fibronectin peptides in the ILT3ECD-Fc plus activated LX-2 cells sample.

Additional studies showed that ILT3ECD-Fc binding was undetectable in a fibronectin knock-out LX-2 cell line, whether the cells were activated or not. These results further supported the conclusion that fibronectin is a ligand for ILT3.

The binding of ILT3 to fibronectin was evaluated by Biacore. Human plasma fibronectin was immobilized onto a CM5 sensor chip surface (flow cell 2) using standard amine coupling chemistry. Collagen type IV was immobilized onto flow cell 3 and used as a control. Human ILT3ECD-Fc or human LAIR1ECD-Fc were injected over both surfaces at different concentrations (125-4000 nM) at a flow rate of 50 µL/min at 37° C. Kinetic data were collected over time and fit using the simultaneous global fit equation to yield affinity constants ($K_D$ values) for each antibody.

ILT3 bound to fibronectin with a $K_D$ of at least 5 µM and did not bind collagen IV at a detectable level. In contrast, LAIR1 bound to collagen IV with a $K_D$ of at least 5 µM and did not bind fibronectin.

Example 8

Activation of Reporter Cells by Interaction of ILT3 and Fibronectin

To investigate whether binding of ILT3 to fibronectin was a functional interaction, reporter cells expressing ILT3 ECD were incubated with fibronectin. 96-well Maxisorp (Nunc) plates were coated with 5 µg/mL of human Fc protein (R&D Systems), plasma-derived fibronectin (Millipore), or recombinant fibronectin (R&D Systems) in PBS at room temperature for 2 hrs. Plates were washed twice with PBS and then blocked with RPMI 1640 containing 10% FBS. NFAT-GFP reporter cells (as described herein in Example 5) expressing B7-H4 extracellular domain, LAIR1 extracellular domain, or ILT3 extracellular domain ($1\times10^5$ cells/well) were added to the coated wells and the plates were incubated overnight at 37° C. Cells were assayed for GFP expression by FACS and compared with non-activated reporter cells.

Figure 5:
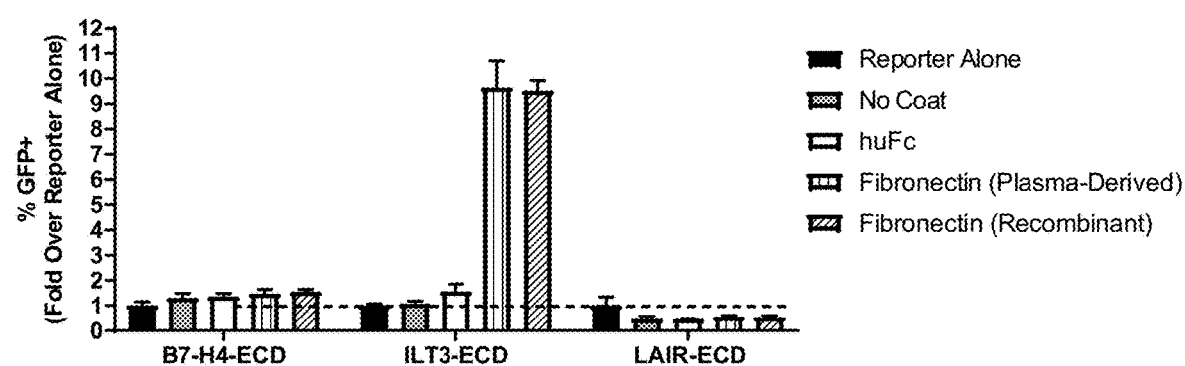
FIG. 5. Reporter cell assay—ILT3 and fibronectin interaction. 96-well Maxisorp (Nunc) plates were coated with 5 μg/mL of human Fc protein (R&D Systems), plasma-derived fibronectin (Millipore), or recombinant fibronectin (R&D Systems) in PBS at room temperature for 2 hrs. Plates were washed twice with PBS and then blocked with RPMI 1640 containing 10% FBS. NFAT-GFP reporter cells (as described herein in Example 5) expressing B7-H4 extracellular domain, LAIR1 extracellular domain, or ILT3 extracellular domain (1×10$^5$ cells/well) were added to the coated wells and the plates were incubated overnight at 37° C. Cells were assayed for GFP expression by FACS and compared with non-activated reporter cells.

As shown in FIG. 5, only cells expressing ILT3 cultured with fibronectin (either plasma-derived or recombinant) were able to activate the reporter system as demonstrated by GFP expression. These results showed that the interaction with fibronectin was specific for ILT3 as there was no GFP expression in response to B7-H4 or LAIR1-expressing cells cultured with fibronectin.

In follow-up studies, 96-well Maxisorp (Nunc) plates were coated with 5 µg/mL plasma-derived fibronectin (Millipore) in PBS at room temperature for 1 hr. After coating, an isotype control antibody, anti-ILT3 antibody 16C5, anti-fibronectin antibody F14 (rabbit monoclonal antibody from Abcam), or anti-fibronectin antibody PA5 (rabbit polyclonal antibody from ThermoFisher Scientific) were added to the wells at a final concentration of 5 or 20 µg/mL. Next, NFAT-GFP reporter cells expressing ILT3 extracellular domain ($1\times10^5$ cells/well) were added to the wells and the plates were incubated overnight at 37° C. Cells were assayed for GFP expression by FACS and compared with non-activated reporter cells.

Figure 6:
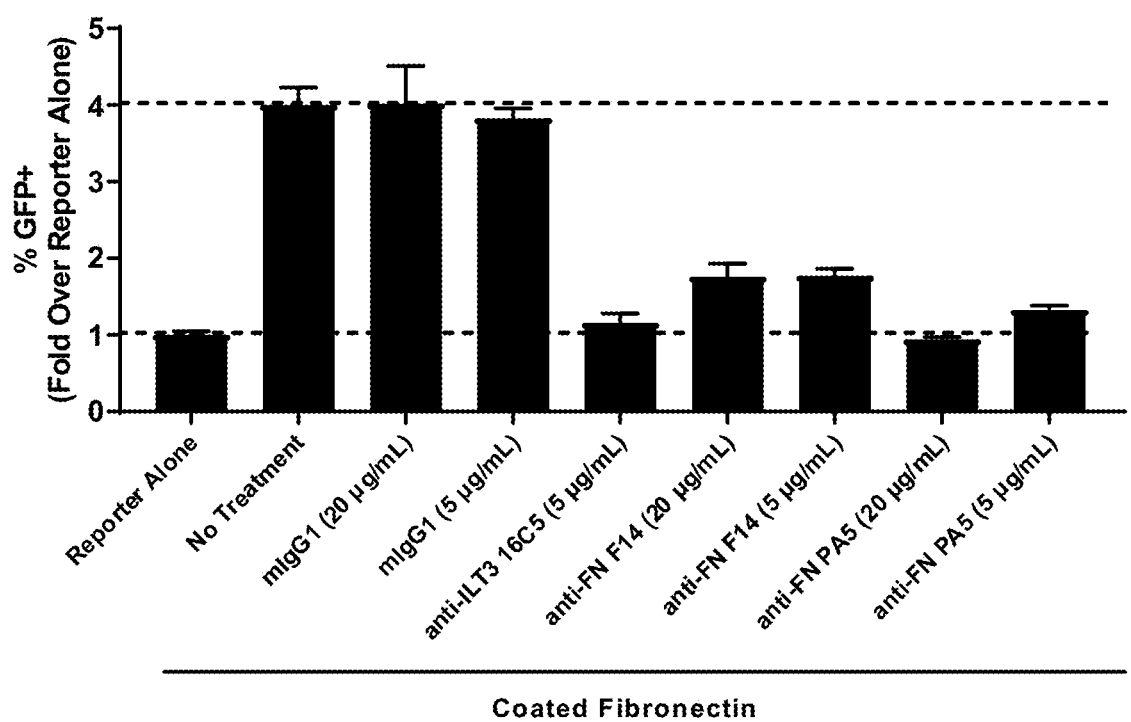
FIG. 6. Antibody inhibition of ILT3 and fibronectin interaction. 96-well Maxisorp plates were coated with 5 μg/mL plasma-derived fibronectin in PBS at room temperature for 1 hr. After coating, an isotype control antibody, anti-ILT3 antibody 16C5, anti-fibronectin antibody F14 (a rabbit monoclonal antibody), or anti-fibronectin antibody PA5 (a rabbit polyclonal antibody) were added to the wells at a final concentration of 5 or 20 μg/mL. NFAT-GFP reporter cells expressing ILT3 extracellular domain (1×10$^5$ cells/well) were added to the wells and the plates were incubated overnight at 37° C. Cells were assayed for GFP expression by FACS and compared with non-activated reporter cells.

As shown in FIG. 6, anti-ILT3 antibody 16C5 as well as anti-fibronectin antibodies F14 and PA5, reduced the expression of GFP in the reporter cells. A control antibody at two different concentrations did not inhibit the expression of GFP resulting from the interaction between ILT3 and fibronectin.

Another study was performed using anti-ILT3 antibodies 16C5 and ch5A7 (chimeric 5A7 comprising mouse heavy chain variable region and light chain variable region, and human Fc domain). As described above, 96-well Maxisorp plates were coated with 5 µg/mL plasma-derived fibronectin at room temperature for 1 hour. After coating, an isotype control antibody, anti-ILT3 antibody 16C5, or anti-ILT3 antibody ch5A7 were added to the wells in 6-fold dilutions ranging from 66 nM to 0.0002 nM. Next, NFAT-GFP reporter cells expressing ILT3 extracellular domain ($1\times10^5$ cells/well) were added to the wells and the plates were incubated overnight at 37° C. Cells were assayed for GFP expression by FACS and compared with non-activated reporter cells.

Figure 7:
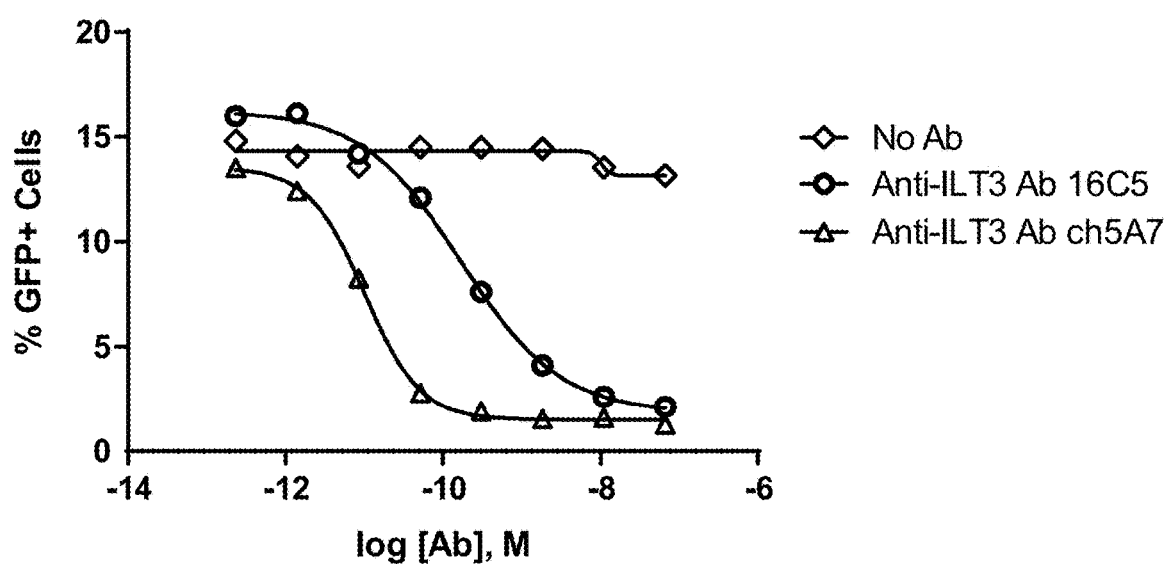
FIG. 7. Antibody inhibition of ILT3 and fibronectin interaction. 96-well Maxisorp plates were coated with 5 μg/mL plasma-derived fibronectin at room temperature for 1 hour. After coating, an isotype control antibody, anti-ILT3 antibody 16C5, or anti-ILT3 antibody ch5A7 were added to the wells in 6-fold dilutions ranging from 66 nM to 0.0002 nM. Next, NFAT-GFP reporter cells expressing ILT3 extracellular domain (1×10$^5$ cells/well) were added to the wells and the plates were incubated overnight at 37° C. Cells were assayed for GFP expression by FACS and compared with non-activated reporter cells.

As shown in FIG. 7, anti-ILT3 antibodies 16C5 and ch5A7 inhibited the interaction of ILT3 and fibronectin as assessed by the reduction of GFP expression. In contrast, the control antibody had no effect on GFP expression.

These results demonstrate that an anti-ILT3 antibody can block the interaction between ILT3 and fibronectin and importantly, block biological activities resulting from that interaction.

Example 9

Identification of ILT3 Binding Site on Fibronectin

Figure 8:
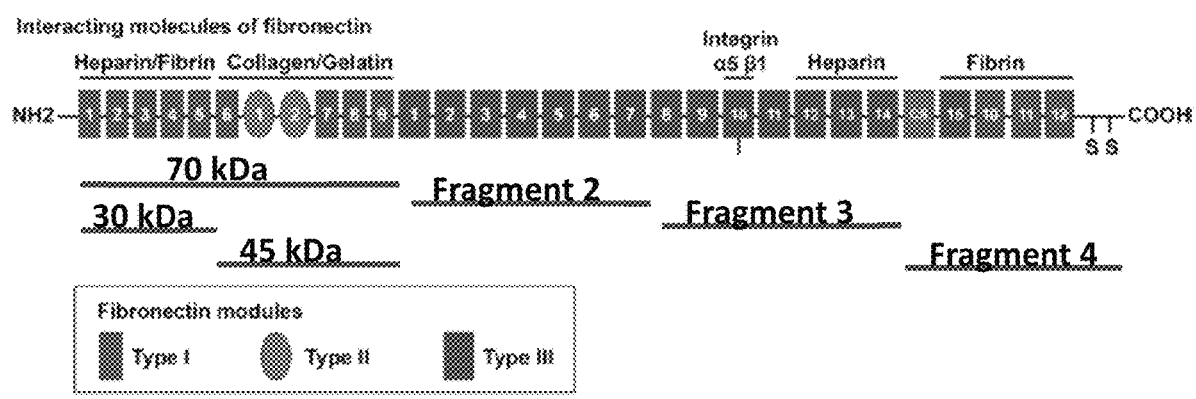
FIG. 8. Representative diagram of fibronectin structure.

A representative diagram of human fibronectin is shown in FIG. 8. Studies were performed to identify where ILT3 bound to fibronectin. 96-well Maxisorp (Nunc) plates were coated with 5 µg/mL of human Fc protein (R&D Systems), plasma-derived fibronectin (Millipore), recombinant fibronectin (R&D Systems), or the following fibronectin fragments: 70 kDa fibronectin fragment (Sigma-Aldrich), 30 kDa fibronectin fragment (Sigma-Aldrich), 45 kDa fibronectin fragment (Sigma-Aldrich), Fragment 2 (aa 607-1265 of SEQ ID NO:138; R&D Systems), Fragment 3 (aa 1266-1908 of SEQ ID NO:138; R&D Systems), or Fragment 4 (aa 1913-2477 of SEQ ID NO:138; R&D Systems). The plates were incubated at room temperature for 2 hours. Plates were washed twice with PBS and then blocked with RPMI 1640 containing 10% FBS. NFAT-GFP reporter cells expressing ILT3 extracellular domain ($1\times10^5$ cells/well) were added to the wells and the plates were incubated overnight at 37° C. Cells were assayed for GFP expression by FACS and compared with non-activated reporter cells.

Figure 9:
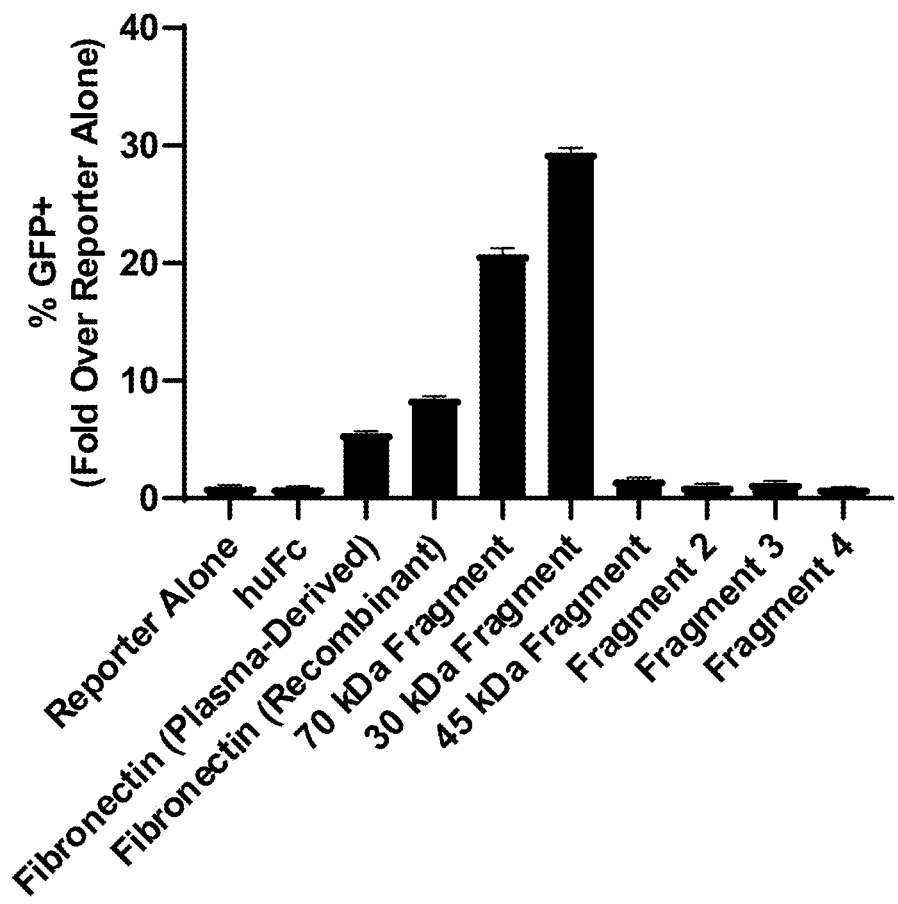
FIG. 9. Reporter cell assay to identify ILT3 binding site on fibronectin. 96-well Maxisorp plates were coated with full-length fibronectin or fibronectin fragments. The plates were incubated at room temperature for 2 hours. Plates were washed twice with PBS and then blocked with RPMI 1640 containing 10% FBS. NFAT-GFP reporter cells expressing ILT3 extracellular domain (1×10$^5$ cells/well) were added to the wells and the plates were incubated overnight at 37° C. Cells were assayed for GFP expression by FACS and compared with non-activated reporter cells.

As shown in FIG. 9, only 70 kDa and 30 kDa fibronectin fragments (as well as full-length fibronectin) were able to activate the reporter system in ILT3-expressing cells as demonstrated by GFP expression. The level of activation was higher with the fragments than with full length fibronectin at equimolar concentrations. The N-terminal region (30 kDa fragment; Type I FN modules 1-5) which encompasses the heparin/fibrin binding domain elicited the highest level of GFP activity.

Additional studies were undertaken to see if the ILT3 binding site on fibronectin could be defined in greater detail. Fibronectin fragments were prepared that consisted of (i) Type I FN modules 1-4 (aa 32-228 of SEQ ID NO:138), (ii) Type I FN modules 2-5 (aa 93-290 of SEQ ID NO:138), (iii) Type I FN modules 1-3 (aa 32-182 of SEQ ID NO:138), (iv) Type I FN modules 2-4 (aa 93-228 of SEQ ID NO:138), (v) Type IFN modules 3-5 (aa 139-290 of SEQ ID NO:138), (vi) Type I FN modules 1-2 (aa 32-138 of SEQ ID NO:138), (vii) Type I FN modules 2-3 (aa 93-182 of SEQ ID NO:138), (viii) Type IFN modules 3-4 (aa 139-228 of SEQ ID NO:138), (ix) Type I FN modules 4-5 (aa 183-290 of SEQ ID NO:138), 70 kDa fragment (aa 32-608 of SEQ ID NO:138), 30 kDa fragment (aa 32-290 of SEQ ID NO:138), and 45 kDa fragment (aa 291-608 of SEQ ID NO:138). As described above, 96-well Maxisorp (Nunc) plates were coated with 40 nM of the fibronectin fragments, as well as full-length fibronectin. The plates were incubated at room temperature for 2 hours. Plates were washed twice with PBS and then blocked with RPMI 1640 containing 10% FBS. NFAT-GFP reporter cells expressing ILT3 extracellular domain ($1\times10^5$ cells/well) were added to the wells and the plates were incubated overnight at 37° C. Cells were assayed for GFP expression by FACS and compared with non-activated reporter cells.

Figure 10:
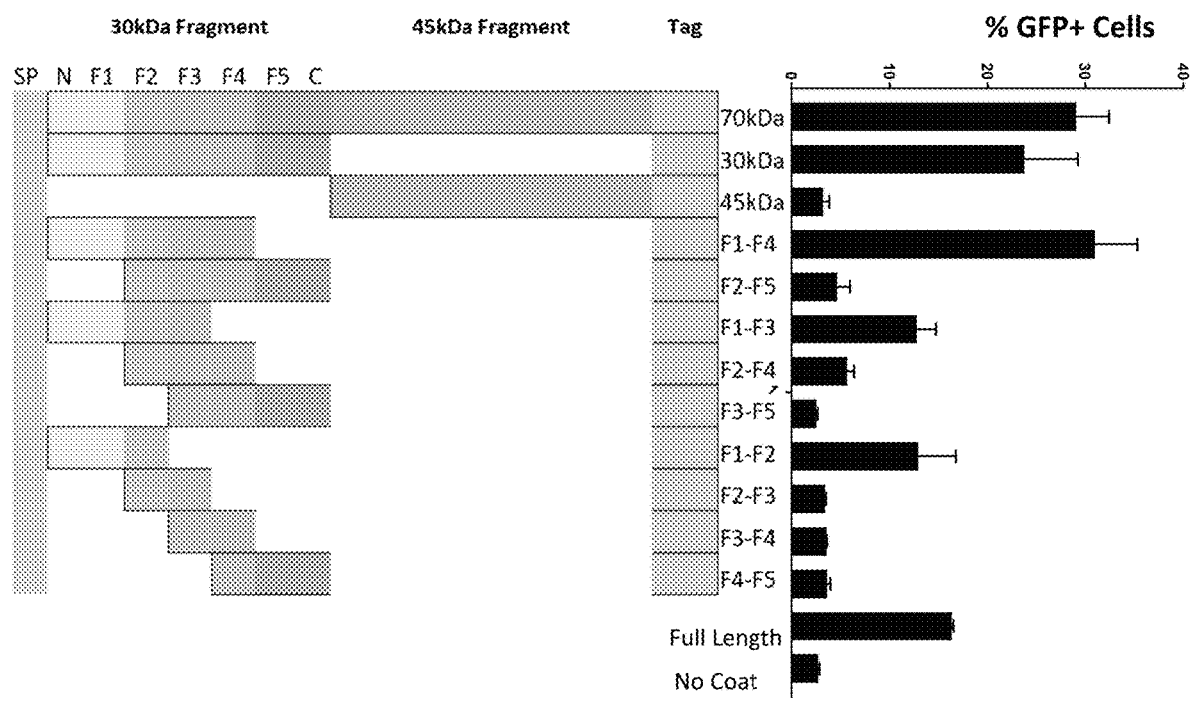
FIG. 10. Reporter cell assay to identify ILT3 binding site on fibronectin. Fibronectin fragments were prepared and coated onto 96-well Maxisorp plates, as well as full-length fibronectin. The plates were incubated at room temperature for 2 hours. Plates were washed twice with PBS and then blocked with RPMI 1640 containing 10% FBS. NFAT-GFP reporter cells expressing ILT3 extracellular domain (1×10$^5$ cells/well) were added to the wells and the plates were incubated overnight at 37° C. Cells were assayed for GFP expression by FACS and compared with non-activated reporter cells.

These studies showed that Type I FN module 1 was necessary for activity in this reporter assay (FIG. 10). We believe that Type I FN module 1 is required for binding of ILT3 to fibronectin and resulting activity, but that other modules also play a part in the ILT3/fibronectin interaction.

Example 10

In Vitro Assays of ILT3 and Fibronectin Interaction

THP-1 is a human monocytic cell line established from acute monocytic leukemia cells and was obtained from ATCC. These cells have been used to study signaling pathways modulated by ILT3 in monocytes activated through Fc receptors (Lu et al., 2009, *JBC*, 284:34839-34848). Activation of monocytes can be achieved by cross-linking of FcR on the cell surface and the crosslinking results in cytokine production, for example, TNF-α and/or IL-8. Studies have shown that ILT3 is a potent inhibitor of FcR-mediated cytokine production in monocytes. THP-1 cells were used as part of an assay to study the interaction of ILT3 and fibronectin in a myeloid cell. In addition to the wild-type THP-1 cells (THP-1), an ILT3 knock-out THP-1 cell line was generated (THP-1 ILT3-KO).

96-well Maxisorp (Nunc) plates were co-coated with fibronectin at 5 µg/mL (Millipore) and an effectorless anti-KLH antibody at 0, 1, 5, and 10 µg/mL. Plates were incubated at room temperature for 2 hours, washed twice with PBS, and blocked with RPMI 1640 containing 10% FBS. THP-1 or THP-1 ILT3-KO cells ($2 \times 10^5$ cells/well) were added to the wells and the plates were incubated overnight at 37° C. The anti-KLH antibody will bind to the FcR and activate the THP-1 and THP-1 ILT3-KO cells to produce cytokines. The presence or absence of fibronectin and its interaction with ILT3 is able to be evaluated in this assay. Cell-free culture supernatants were collected and IL-8 was measured by Luminex assay (ProcartaPlex system; ThermoFisher Scientific). In some instances, IL-8 was normalized to that of THP-1 cells without FcR stimulation.

Figure 11:
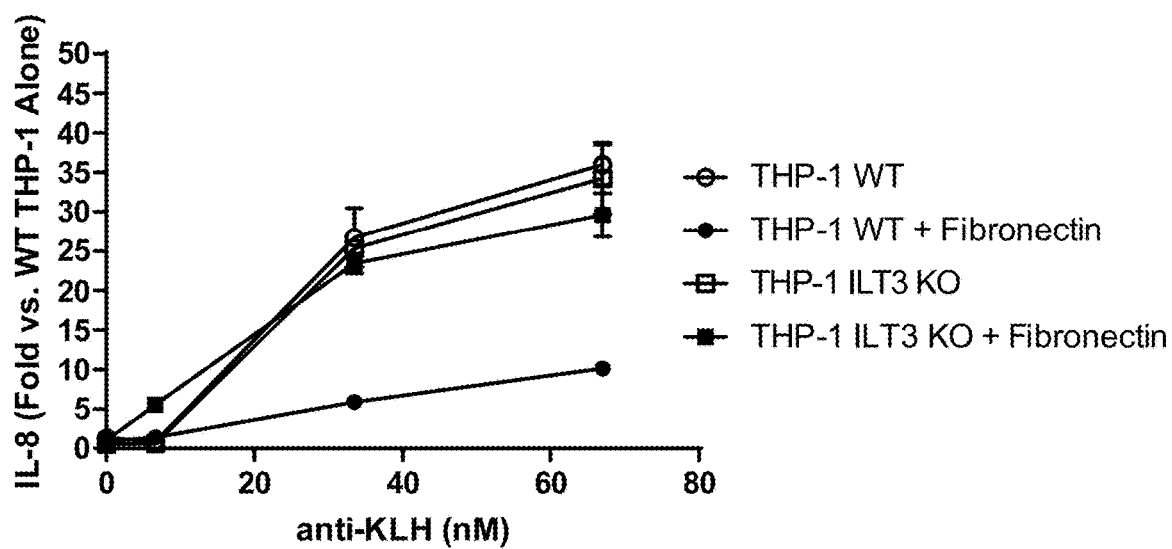
FIG. 11. FcR-induced activation in THP-1 cells. 96-well Maxisorp plates were co-coated with fibronectin at 5 μg/mL and an anti-KLH antibody at 0, 1, 5, and 10 μg/mL. Plates were incubated at room temperature for 2 hours, washed twice with PBS, and blocked with RPMI 1640 containing 10% FBS. THP-1 or THP-1 ILT3-KO cells ($2 \times 10^5$ cells/well) were added to the wells and the plates were incubated overnight at 37° C. Cell-free culture supernatants were collected and IL-8 was measured by Luminex assay. IL-8 was normalized to that of THP-1 cells without FcR stimulation.

As shown in FIG. 11, in both THP-1 cells and THP-1 cells lacking ILT3 (THP-1 ILT3-KO cells), anti-KLH antibody is able to activate the monocytes in a dose-dependent manner. In contrast, activation of THP-1 cells by anti-KLH antibody as assessed by IL-8 production is inhibited by the interaction of fibronectin and ILT3 on the cell surface. Activation of THP-1 cells by anti-KLH antibody as assessed by IL-8 production is inhibited only when fibronectin and ILT3 are both present and able to interact (i.e., no inhibition with THP-1 ILT3-KO cells and fibronectin).

These results demonstrate that ILT3 in the presence of fibronectin induces inhibition of FcR activation in myeloid cells.

A follow-up study was performed in the presence of an anti-ILT3 antibody. 96-well Maxisorp (Nunc) plates were co-coated with fibronectin at 5 µg/mL (Millipore) and an effectorless anti-KLH antibody at 5 µg/mL. Plates were incubated at room temperature for 2 hours, washed twice with PBS, and blocked with RPMI 1640 containing 10% FBS. THP-1 or THP-1 ILT3KO cells ($2 \times 10^5$ cells/well) were added to the wells in the presence of anti-ILT3 antibody 16C5 (effectorless; 5 µg/mL) or an anti-KLH antibody (effectorless; 5 µg/mL). The plates were incubated overnight at 37° C. and cell-free culture supernatants were collected and IL-8 was measured by Luminex assay.

Figure 12A:
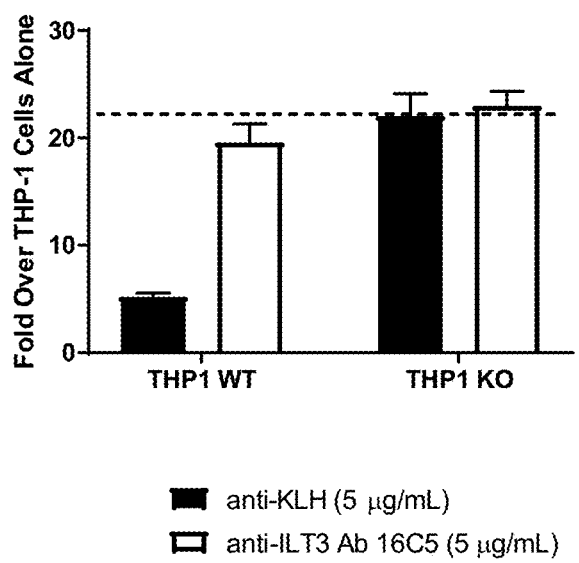
FIG. 12A-12C. FcR-induced activation in THP-1 cells. 12A. 96-well Maxisorp plates were co-coated with fibronectin and an anti-KLH antibody. Plates were incubated at room temperature for 2 hours, washed, and blocked with RPMI 1640 containing 10% FBS. THP-1 or THP-1 ILT3-KO cells ($2 \times 10^5$ cells/well) were added to the wells in the presence of anti-ILT3 antibody 16C5 (5 μg/mL) or an anti-KLH antibody. The plates were incubated overnight at 37° C., cell-free culture supernatants were collected, and IL-8 was measured by Luminex assay. 12B. Human monocytes were isolated from cryopreserved peripheral blood mononuclear cells. To generate dendritic cells, monocytes were plated at $2 \times 10^6$ cells/mL in X-VIVO™ 15 media containing human GM-CSF and human IL-4 and cultured for 5-7 days. 96-well Maxisorp plates were co-coated with fibronectin and an anti-KLH antibody. Plates were incubated at room temperature for 2 hours, washed, and blocked with RPMI 1640 containing 10% FBS. Dendritic cells ($2 \times 10^5$ cells/well) were added to the wells in the presence of anti-ILT3 antibody 16C5 or an anti-KLH antibody. The plates were incubated overnight at 37° C. and cell-free culture supernatants were collected and TNF-α was measured by Luminex assay. 12C. 96-well Maxisorp plates were coated with fibronectin and an anti-KLH antibody. Plates were incubated at room temperature for 1 hour, washed with PBS, and blocked with X-VIVO™ 15 media for 30 minutes. Dendritic cells were washed, resuspended in X-VIVO™ 15 media, and incubated with anti-ILT3 antibody 16C5, anti-ILT3 antibody ch5A7, or control anti-KLH antibody at room temperature for 20 minutes. Cells were plated into coated wells ($7 \times 10^4$ cells/well) and incubated overnight. Media was harvested for determination of TNFα production by Luminex assay after 24 hours.

As shown in FIG. 12A, the ILT3/fibronectin-induced inhibition of FcR activation of THP-1 cells is suppressed or blocked by anti-ILT3 antibody 16C5. In other words, an anti-ILT3 antibody was able to reverse the inhibition of the ILT3 and fibronectin interaction.

A similar experiment was set up with primary human dendritic cells. Human monocytes were isolated from cryo-preserved peripheral blood mononuclear cells by negative selection using a Miltenyi Monocyte Isolation Kit, according to the manufacturer's instructions. To generate dendritic cells, monocytes were plated at $2 \times 10^6$ cells/mL in X-VIVO™ 15 media (Lonza) containing 50 ng/mL recombinant human GM-CSF and 50 ng/mL recombinant human IL-4 (both from Peprotech) and cultured for 5-7 days. As described above, 96-well Maxisorp (Nunc) plates were co-coated with fibronectin at 5 µg/mL (Millipore) and an effectorless anti-KLH antibody at 5 µg/mL. Plates were incubated at room temperature for 2 hours, washed twice with PBS, and blocked with RPMI 1640 containing 10% FBS. Dendritic cells ($2 \times 10^5$ cells/well) were added to the wells in the presence of anti-ILT3 antibody 16C5 (effectorless; 5 µg/mL) or an anti-KLH antibody (effectorless; 5 µg/mL). The plates were incubated overnight at 37° C. and cell-free culture supernatants were collected and TNF-α was measured by Luminex assay.

Figure 12B:
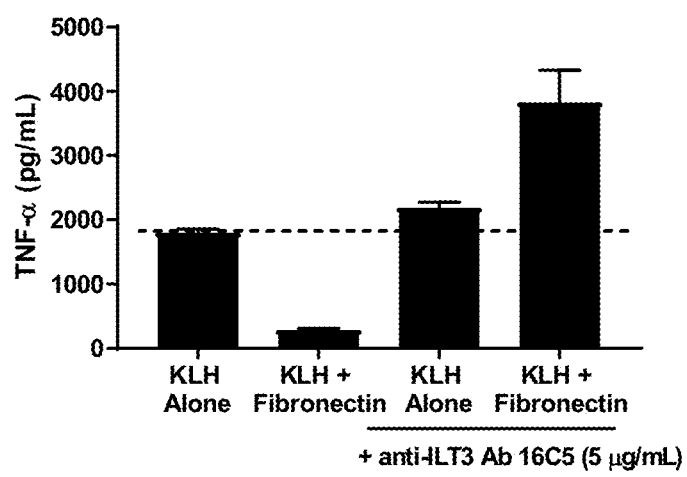

FIG. 12B shows that ILT3/fibronectin-induced suppression of FcR activation is observed in primary dendritic cells. Importantly, these results show that an exemplary anti-ILT3 antibody (e.g., antibody 16C5) is capable of inhibiting the suppression.

Figure 12C:
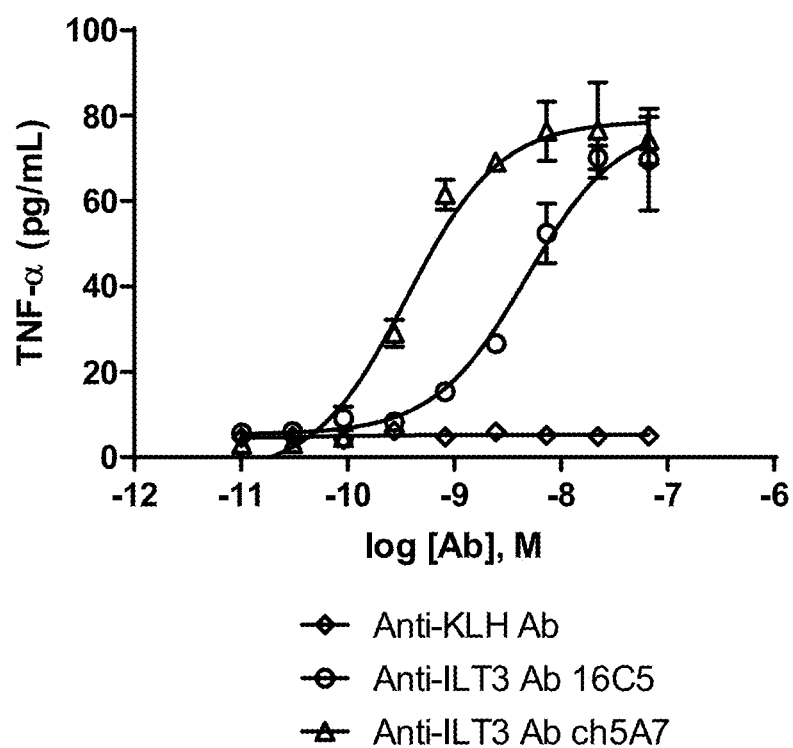

An additional study was done with anti-ILT3 antibodies 16C5 and ch5A7. As observed with previous assay, anti-ILT3 antibodies 16C5 and ch5A7 reversed the fibronectin-mediated suppression of TNF-α production by dendritic cells activated by FcR signaling (FIG. 12C).

Similar studies were undertaken in THP-1 Dual™ KI-mSTING cells that contain a NFκB-SEAP reporter (InvivoGen). Nunc Maxisorp plates were co-coated with human fibronectin and an effectorless anti-KLH antibody (each at 5 µg/mL) for 2 hr at room temperature. Plates were blocked with X-VIVO™ 15 media (Lonza) for 30 minutes prior to the addition of cells and test antibodies. THP-1 reporter cells in X-VIVO™ 15 media ($2 \times 10^6$ cells/mL) were mixed at a 1:1 ratio with a control antibody, anti-ILT3 antibody 16C5, or anti-ILT3 antibody ch5A7. The mixtures were incubated for 30 minutes, seeded onto plates at 100 µL/well, and the plates were incubated overnight. Reporter activity was measured by combining 25 µL of culture supernatant with 100 µL of Quanti-Blue SEAP substrate (InvivoGen), incubating the samples at 37° C. for 2 hours, and reading the absorbance at 620 nm.

Figure 13:
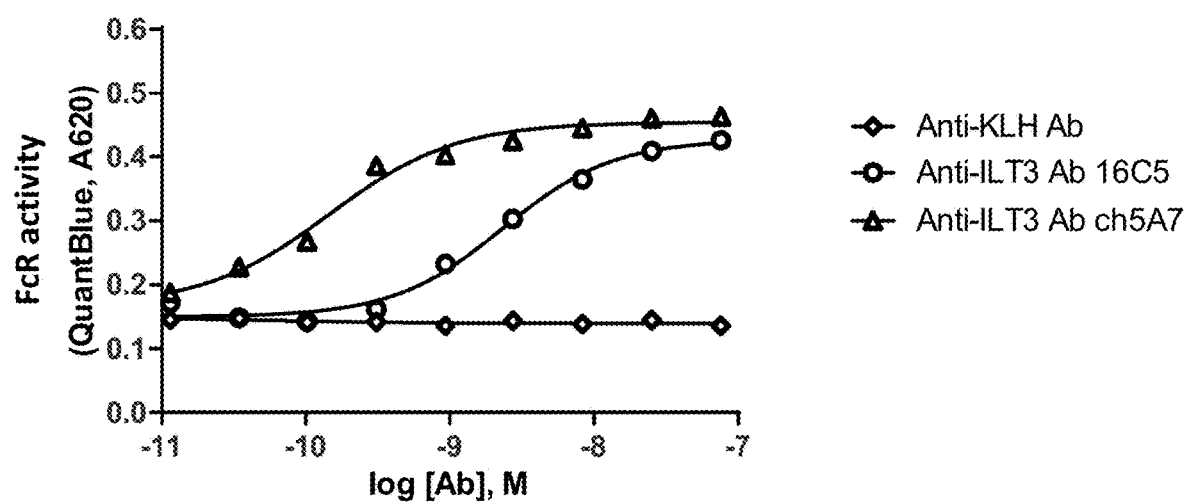
FIG. 13. FcR-induced activation in THP-1 cells. Nunc Maxisorp plates were co-coated with human fibronectin and an anti-KLH antibody for 2 hr at room temperature. Plates were blocked with X-VIVO™ 15 media for 30 minutes prior to the addition of cells and test antibodies. THP-1 Dual™ KI-mSTING reporter cells in X-VIVO™ 15 media ($2 \times 10^6$ cells/mL) were mixed at a 1:1 ratio with a control antibody, anti-ILT3 antibody 16C5, or anti-ILT3 antibody ch5A7. The mixtures were incubated for 30 minutes, seeded onto plates at 100 μL/well, and the plates were incubated overnight. Reporter activity was measured by combining 25 μL of culture supernatant with 100 μL of Quanti-Blue SEAP substrate, incubating the samples at 37° C. for 2 hours, and reading the absorbance at 620 nm.

The reporter is activated by interaction of the anti-KLH antibody and FcR on the surface of THP-1 cells resulting in activation of the FcR signaling pathway and production of secreted embryonic alkaline phosphate (SEAP). When ILT3 on the surface of THP-1 cells interacts with fibronectin, FcR signaling is suppressed and SEAP production is decreased. Anti-ILT3 antibodies 16C5 and ch5A7 blocked the ILT3/fibronectin interaction and reversed the suppression (FIG. 13).

The Detroit 551 cell line is composed of human skin fibroblasts established from normal fetal tissue. These cells have endogenously produced fibronectin bound to receptors on their surface. Detroit 551 cells allow for in vitro assays where fibronectin is naturally on the cell surface and not attached to assay plates. Detroit 551 cells were plated onto poly-D-lysine-coated 384-well plates at $6 \times 10^3$ cells/well (Greiner) and incubated for two days. Monolayers were rinsed with HBSS containing $Mg^{2+}$ and $Ca^{2+}$, leaving approximately 10 µL/well. ILT3-ECD-Fc was added to the wells (final concentration of 1 µg/mL) in the presence of ant-ILT3 antibody 16C5, anti-ILT3 antibody ch5A7, or control anti-KLH antibody. The antibodies were serially diluted 3-fold in media containing the ILT3-ECD-Fc (range of 66 nM to 0.27 nM). Cells were incubated for 1 hr at room temperature and then washed three times with HBSS and fixed with 3.7% formalin for 10 min. Monolayers were rinsed with PBS and blocked with 1% BSA in PBS before staining with Hoechst stain (2.5 µM) and a commercially available polyclonal anti-ILT3 antibody (R&D Systems). An AlexaFluor 647-conjugated rabbit anti-goat Fc secondary antibody (Jackson ImmunoResearch Labs) was added, cells were imaged, and the level of fluorescence was quantified using a CellInsight imaging system.

Figure 14:
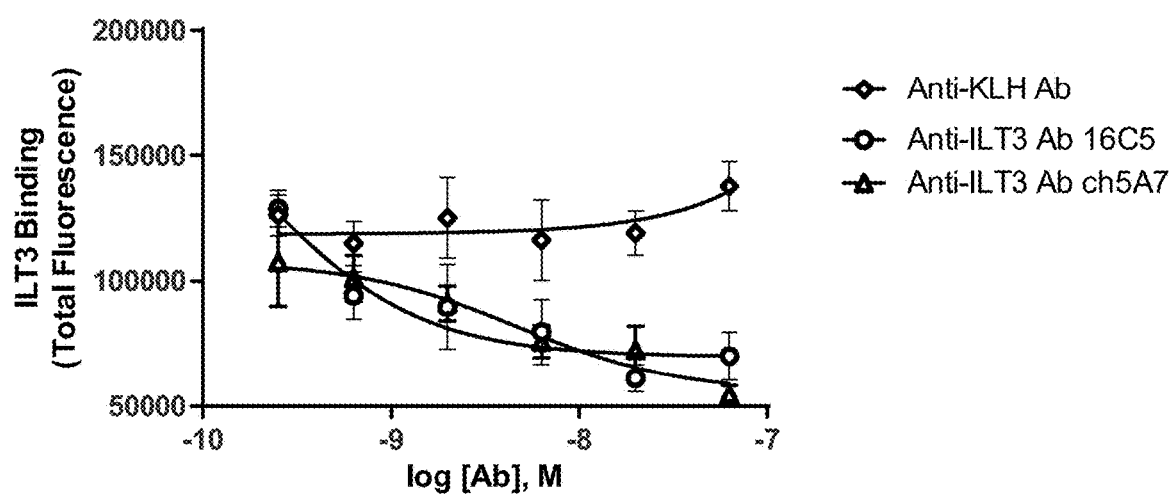
FIG. 14. ILT3 binding to endogenously expressed fibronectin. Detroit 551 cells were plated onto poly-D-lysine-coated 384-well plates at $6 \times 10^3$ cells/well and incubated for two days. Monolayers were rinsed with HBSS containing $Mg^{2+}$ and $Ca^{2+}$. ILT3-ECD-Fc was added to the wells in the presence of ant-ILT3 antibody 16C5, anti-ILT3 antibody ch5A7, or control anti-KLH antibody. The antibodies were serially diluted 3-fold in media containing the ILT3-ECD-Fc (range of 66 nM to 0.27 nM). Cells were incubated for 1 hr at room temperature and then washed three times with HBSS and fixed with 3.7% formalin for 10 min. Monolayers were rinsed with PBS and blocked with 1% BSA in PBS before staining with Hoechst stain and a commercially available polyclonal anti-ILT3 antibody. An AlexaFluor 647-conjugated rabbit anti-goat Fc secondary antibody was added, cells were imaged, and the level of fluorescence was quantified using a CellInsight imaging system.

As shown in FIG. 14, anti-ILT3 antibodies blocked the binding of ILT3-ECD to fibronectin-expressing cells.

Example 11

Effect of Anti-ILT3 Antibody on Chemokine Production by Dendritic Cells

Primary human monocytes were isolated from cryopreserved peripheral blood mononuclear cells by negative selection using a Miltenyi Monocyte Isolation Kit, according to the manufacturer's instructions. For differentiation of macrophages, monocytes were plated at $2 \times 10^6$ cells/mL in X-VIVO™ 15 media (Lonza) containing 100 ng/mL recombinant human M-CSF (Peprotech). After 2-3 days, fresh M-CSF was added to the media. After another 2-3 days, the macrophage cells are washed and harvested by scraping.

Dendritic cell conditioned media (used as the chemoattractant) was produced as follows. To generate dendritic cells, human monocytes were plated at $2 \times 10^6$ cells/mL in X-VIVO™ 15 media (Lonza) containing 50 ng/mL recombinant human GM-CSF and 50 ng/mL recombinant human IL-4 (both from Peprotech) and cultured for 5-7 days. These monocyte-derived dendritic cells were harvested and plated at $1 \times 10^6$ cells/mL onto fibronectin-coated Maxisorp plates (10 µg/mL) in the presence of anti-KLH antibody or anti-ILT3 antibody (10 µg/mL) and incubated for 2 days. The conditioned media was harvested and used in the migration assays described herein.

The macrophage migration assays were performed using an Incucyte® Zoom Live-Cell Analysis system (Sartorius). Membranes of Incucyte Clear-View 96-well chemotaxis plates (Sartorius) were pre-coated with 50 µg/mL of Matrigel® (diluted in X-VIVO™ 15 media with 10% FBS) for 30 minutes at 37° C., followed by 30 minutes at room temperature. Macrophages ($5 \times 10^3$ cells/well) were added to the top chambers of the chemotaxis plates, and the bottom chambers were filled with conditioned media derived from dendritic cells (as described herein). Phase-contrast images were captured every hour for 24 hours and data was analyzed using Incucyte analysis software.

Figure 15:
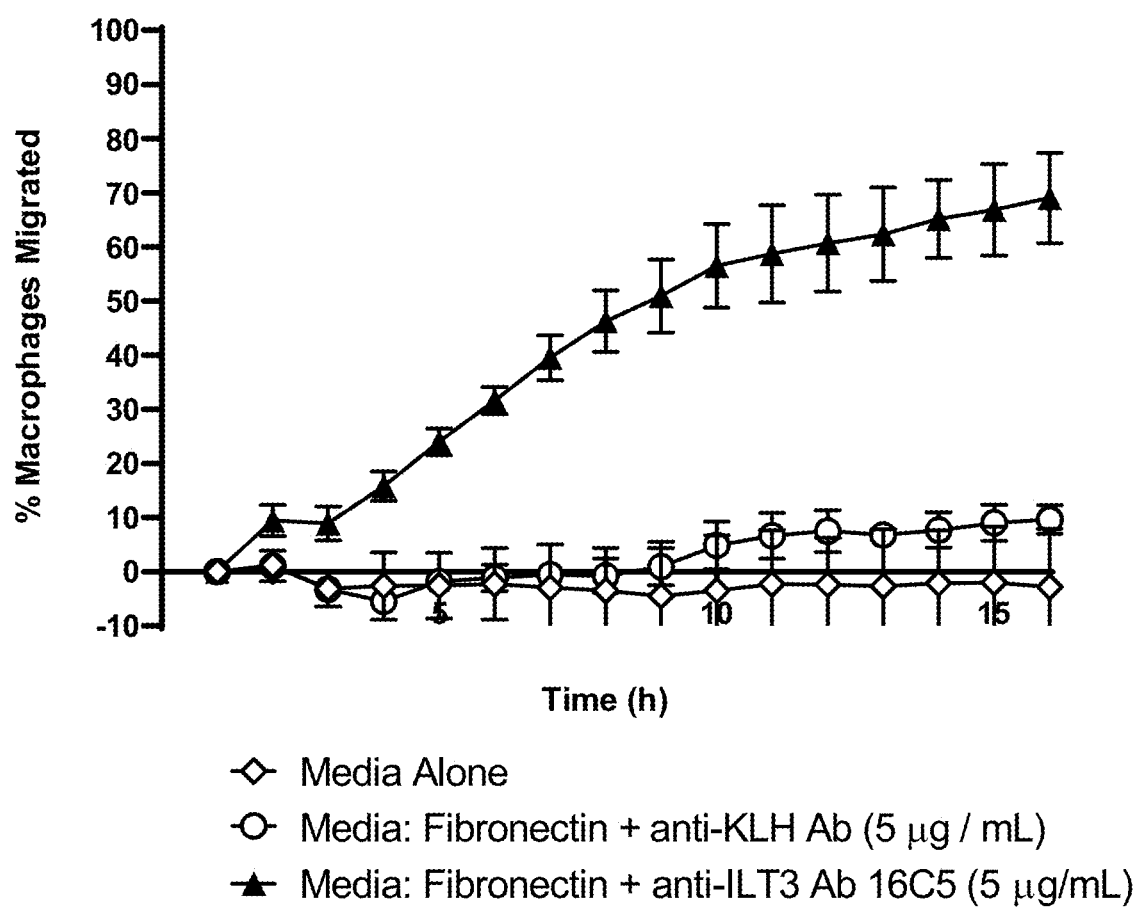
FIG. 15. Effect of anti-ILT3 antibody on chemokine production by dendritic cells. The macrophage migration assays were performed using an Incucyte® Zoom Live-Cell Analysis system. Membranes of Incucyte Clear-View 96-well chemotaxis plates (Sartorius) were pre-coated with 50 μg/mL of Matrigel® (diluted in X-VIVO™ 15 media with 10% FBS) for 30 minutes at 37° C., followed by 30 minutes at room temperature. Macrophages ($5 \times 10^3$ cells/well) were added to the top chambers of the chemotaxis plates, and the bottom chambers were filled with conditioned media derived from dendritic cells. Phase-contrast images were captured every hour for 24 hours and data was analyzed using Incucyte analysis software.

As shown in FIG. 15, macrophages did not migrate in response to conditioned media from fibronectin-treated dendritic cells. In contrast, a high percentage of macrophages migrated in response to conditioned media from dendritic cells treated with fibronectin in the presence of an anti-ILT3 antibody.

These results show that inhibition or blockade of the fibronectin/ILT3 interaction on dendritic cells by anti-ILT3 antibodies increases chemokine/chemoattractant production by the dendritic cells. The increased chemokine production results in an increase in macrophage migration. This suggests that anti-ILT3 antibodies could be effective in enhancing immune responses by helping to increase the recruitment of macrophages and other immune cells to the site of an immune response.

Example 12

Allogeneic Mixed Lymphocyte Reaction (MLR) Assays

Tolerogenic DCs were generated as described herein and resuspended at $4 \times 10^5$ cells/mL. Briefly, to generate tolerogenic DCs (tolDCs), monocytes were treated with GM-CSF and IL-4 for 5 days and then tolerized by treatment with 10 nM dexamethasone and 100 nM vitamin D3 (1α,25-dihydroxyvitamin D3) (both from Sigma-Aldrich) for 2 additional days. LX-2 cells (wild-type or a fibronectin knockout) were treated with 25 µg/mL mitomycin C (Sigma-Aldrich) for 1 hour at 37° C., washed, and resuspended at $1 \times 10^5$ cells/mL. Allogeneic T-cells were purified from peripheral blood monocytes by negative selection using a Miltenyi T-Cell Isolation kit and resuspended at $2 \times 10^6$ cells/mL. Anti-ILT3 antibody 16C5, anti-ILT3 antibody ch5A7, or a control antibody (50 µL) were added to wells of a 96-well, round-bottom plate. Mixed lymphocyte reaction (MLR) assays were set up by adding 50 µL of each cell type (T-cells, tolDCs, and LX-2 cells) for a final T-cell:tolDC:LX-2 cell ratio of 20:2:1. Plates were incubated for 5 days and then cell-free culture supernatants were harvested. Cytokine levels were determined using a Luminex assay (ProcartaPlex system; ThermoFisher Scientific). The media was replaced with fresh media containing tritiated thymidine ($^3$H-thymidine; Perkin-Elmer) at a concentration of 1 µCi/mL. After an additional 18 hrs of incubation, cells were harvested onto filters using a Tomtec cell harvester and $^3$H-thymidine incorporation was counted on a MicroBeta2 microplate reader.

In this assay, the mitomycin C-treated LX-2 cells serve as the source of fibronectin and are not capable of proliferating. In the absence of LX-2 cells (i.e., no fibronectin), the T-cells are activated by the dendritic cells and proliferate. In the presence of LX-2 cells, the activation of T-cells is suppressed and proliferation is reduced or eliminated.

Figure 16A:
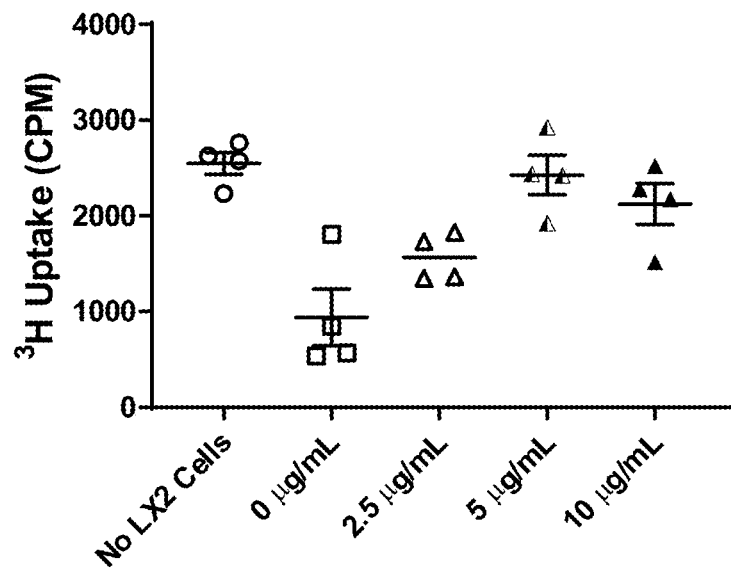
FIG. 16A-16B. Allogeneic MLR assay.
Figure 16B:
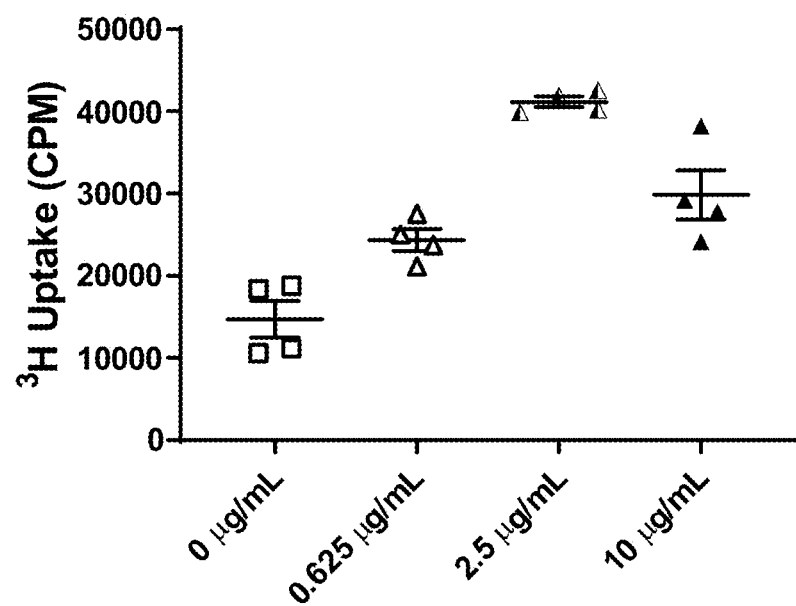

As shown in FIGS. 16A and 16B, anti-ILT3 antibodies 16C5 and ch5A7 reverse the fibronectin-mediated suppression of an allogeneic MLR in a dose-dependent manner. Activity of the anti-ILT3 antibodies is dependent on the presence of fibronectin, i.e., the suppression of MLR activity is not reversed in the presence of the anti-ILT3 antibodies if fibronectin is not present (data not shown).

Example 13

Effect of Anti-ILT3 Antibodies on Dendritic Cells

Dendritic cells were generated as described herein. 96-well Maxisorp plates (Nunc) were coated with fibronectin (5 µg/mL), incubated at room temperature for 1 hour, washed with PBS, and blocked with X-VIVO™ 15 media (Lonza) for 30 minutes. Dendritic cells were plated at $2 \times 10^5$ cells/well in the presence of anti-ILT3 antibody ch5A7, anti-ILT3 antibody Hz5A7.v5, anti-ILT3 antibody 45G10, or control antibody and incubated overnight. Antibody concentrations were 5-fold dilutions from 10 µg/mL to 0.128 ng/mL. Media was harvested for determination of MIP-1α by Luminex assay (ProcartaPlex system; ThermoFisher Scientific) after 48 hours.

Figure 17A:
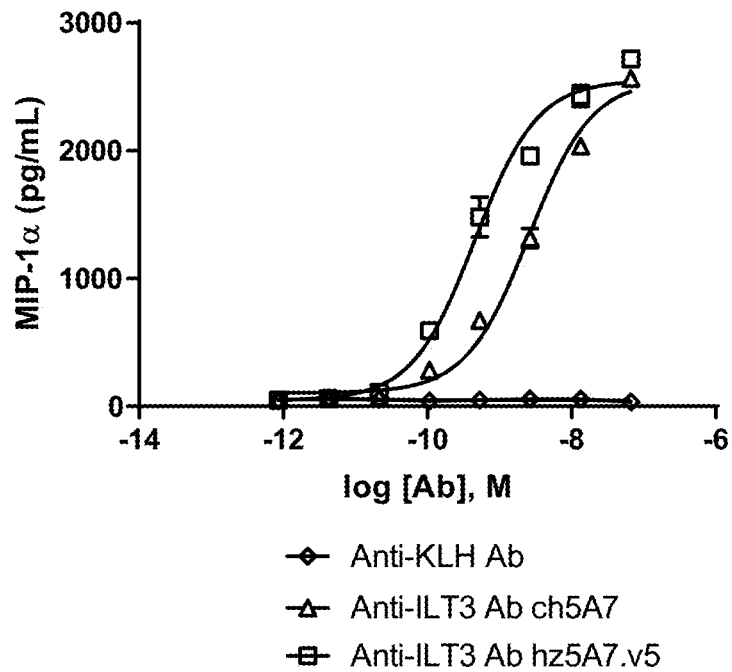
FIG. 17A-17B. Effect of anti-ILT3 antibodies on cytokine production from dendritic cells.
Figure 17B:
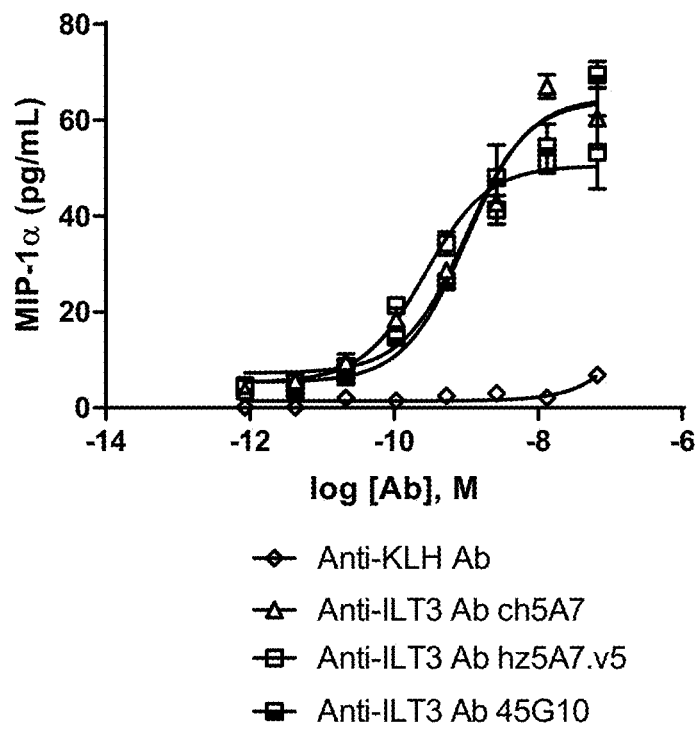

As shown in FIG. 17A, anti-ILT3 antibodies ch5A7 and Hz5A7.v5 increased levels of MIP-1α produced by dendritic cells. FIG. 17B shows similar results with the inclusion of antibody 45G10.

Dendritic cells were generated as described herein. The dendritic cells were tolerized by treatment with 20 ng/mL recombinant human IL-10 (Peprotech). The cells were plated into 96-well, flat-bottom plates at $2 \times 10^5$ cells/well in media containing IL-10 and LPS (2 µg/mL; Sigma-Aldrich) and also in the presence of anti-ILT3 antibody 16C5, anti-ILT3 antibody ch5A7, anti-ILT3 antibody 45G10, or control anti-KLH antibody and incubated for 48 hours. Antibody concentrations were 5-fold dilutions from 5 µg/mL to 1.6 ng/mL. Media was harvested for measurement of TNF-α by Luminex assay (ProcartaPlex system; ThermoFisher Scientific).

Figure 18A:
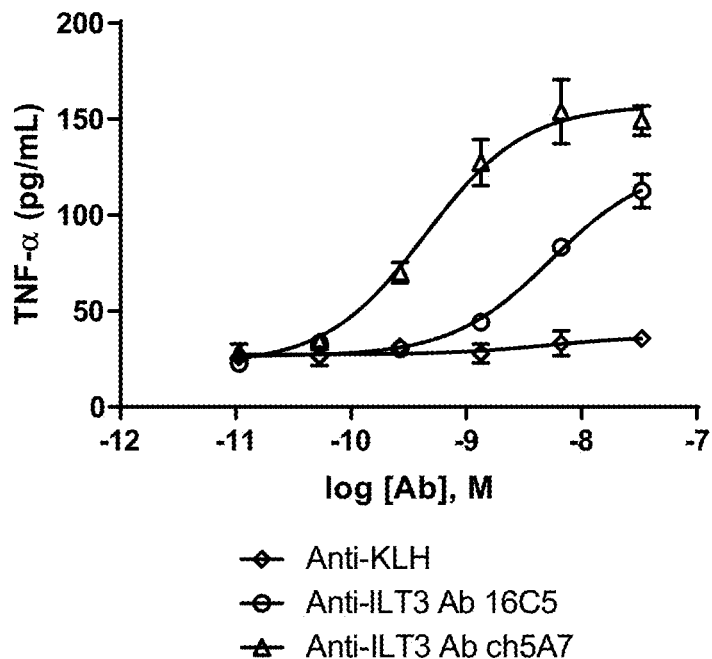
FIG. 18A-18B. Effect of anti-ILT3 antibodies on tolerized dendritic cells.
Figure 18B:
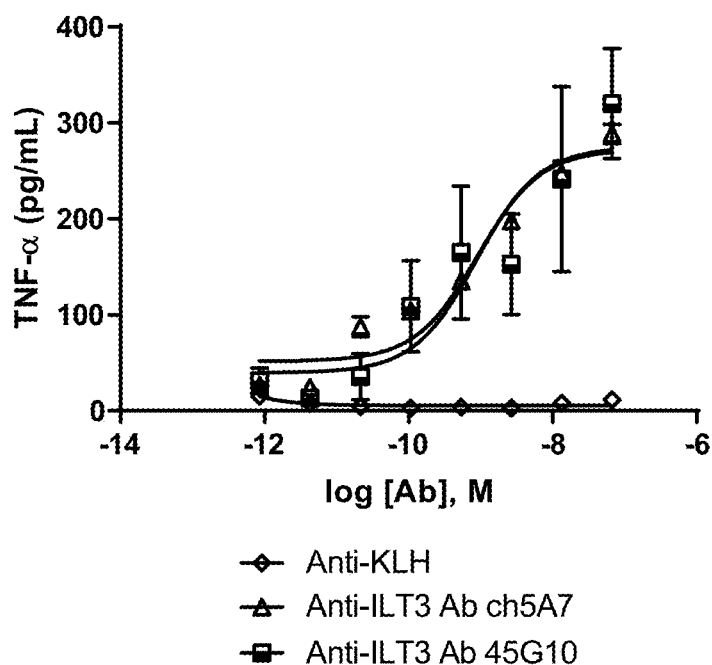

As shown in FIG. 18A, anti-ILT3 antibodies 16C5 and ch5A7 were able to restore the ability of IL-10-tolerized dendritic cells to respond to LPS as evaluated by the production of TNF-α. These results suggest that antibody ch5A7 may be a more potent antibody than 16C5. FIG. 18B shows results from a similar study with anti-ILT3 antibodies ch5A7 and 45G10. Other studies showed that anti-ILT3 antibody ch5A7 was also able to restore the ability of IL-10-tolerized dendritic cells to respond to a second stimulatory molecule, CD40L (data not shown).

Example 14

Allogeneic MLR in the Presence of Anti-ILT3 Antibody in Combination with an Anti-PD-1 Antibody Monocyte-derived dendritic cells were generated from peripheral blood monocytes as described herein. These cells were harvested and tolerized for 48 hours with recombinant human IL-10 (50 ng/mL) in the presence of an anti-KLH antibody or anti-ILT3 antibodies. Allogeneic T-cells were purified from peripheral blood monocytes by negative selection using the Miltenyi T Cell Isolation kit. For the MLR assays, T-cells and tolerized dendritic cells were mixed at a T-cell to lDC ratio of 5:1 in the presence of anti-KLH antibody, anti-ILT3 antibody ch5A7, anti-PD-1 antibody (pembrolizumab), or anti-ILT3 antibody ch5A7 in combination with anti-PD-1 (all antibodies at 1 µg/mL each). Media was harvested for measurement of IFN-γ by Luminex assay (ProcartaPlex system; ThermoFisher Scientific) after 5 days.

Figure 19:
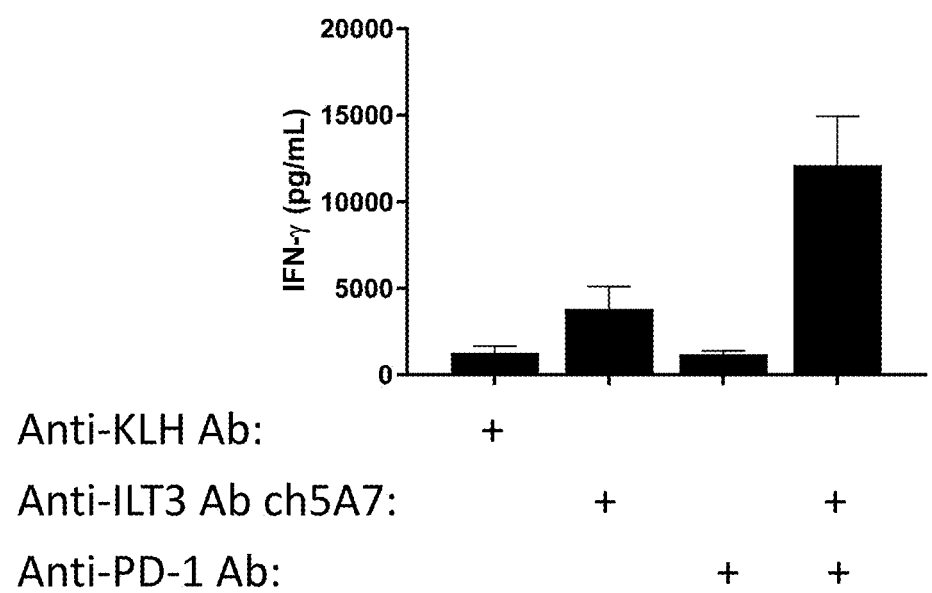
FIG. 19. Allogeneic MLR assay with anti-ILT3 antibody in combination with anti-PD-1 antibody.

As shown in FIG. 19, anti-ILT3 antibody ch5A7 reversed the suppression of response in IL-10-tolerized dendritic cells as demonstrated by an increase in IFN-γ production in T cells. This effect was increased more than 2-fold when the anti-ILT3 antibody was used in combination with an anti-PD-1 antibody.

Example 15

Generation of Humanized Antibody

Based on the antibody characterization data described herein as well as additional studies, antibody 5A7, 48A6, 45G10 were selected for humanization. Antibodies were humanized by methods known to those skilled in the art and humanized antibodies were referred to herein as Hz5A7, Hz48A6 and Hz45G10.

Antibody 5A7 had an undesirable methionine in the heavy chain variable region CDR3, REWR<u>M</u>TLYAMDY (SEQ ID NO:29). During the humanization process, the heavy chain variable region CDR3 was reengineered to remove the methionine and insert a tyrosine resulting in a heavy chain variable region CDR3 comprising REWR<u>Y</u>TLYAMDY (SEQ ID NO:105). In addition, antibody 5A7 was found to have a potential isomerization site in CDR1 of the light chain variable region, RASESV<u>D</u>SYGNSFMH (SEQ ID NO:30) as well as a potential deamidation site in CDR1 of the light chain variable region, RASESVDSYG<u>NS</u>FMH (SEQ ID NO:30). During the humanization process, the light chain variable region CDR1 was reengineered to remove the isomerization site and the deamidation site resulting in a light chain variable region CDR1 comprising RASESV<u>E</u>SYG<u>SS</u>FMH (SEQ ID NO:106). This Hz5A7 variant that comprises all of these modifications is referred to as Hz5A7.v5. The heavy chain variable sequence of Hz5A7.v5 comprises the amino acid sequence SEQ ID NO:123 and the light chain variable sequence of Hz5A7.v5 comprises the amino acid sequence SEQ ID NO:124; CDRs are disclosed in Table 8.

The heavy chain sequence of antibody Hz5A7.v5 comprises an N297G mutation in the constant region that eliminates Fc effector functions. The heavy chain sequence of antibody Hz5A7.v5 is set forth as SEQ ID NO:125 and SEQ ID NO:126 (with and without signal sequence, respectively) and the light chain sequence of antibody Hz5A7.v5 is set forth as SEQ ID NO:127 and SEQ ID NO:128 (with and without signal sequence, respectively).

Several humanized variants of the 48A6 were generated. These include the B0/C2, B1/C2, C0/C2, C1/C2, and C2/C2 Hz48A6 antibodies. Antibody Hz48A6 B0/C2 comprises a heavy chain variable region (B0) with an amino acid sequence SEQ ID NO:156, and a light chain variable region (C2) with an amino acid sequence SEQ ID NO:161; antibody Hz48A6 B1/C2 comprises a heavy chain variable region (B1) with an amino acid sequence SEQ ID NO:157, and a light chain variable region (C2) with an amino acid sequence SEQ ID NO:161; antibody Hz48A6 C0/C2 comprises a heavy chain variable region (C0) with an amino acid sequence SEQ ID NO:158, and a light chain variable region (C2) with an amino acid sequence SEQ ID NO:161; antibody Hz48A6 C1/C2 comprises a heavy chain variable region (C1) with an amino acid sequence SEQ ID NO:159, and a light chain variable region (C2) with an amino acid sequence SEQ ID NO:161; and antibody Hz48A6 C2/C2 comprises a heavy chain variable region (C2) with an amino acid sequence SEQ ID NO:160, and a light chain variable region (C2) with an amino acid sequence SEQ ID NO:161. CDRs of antibody Hz48A6 are the same as the six CDRs of 48A6 and they are shown in Table 6.

Two humanized variants of 45G10 were generated. These include the A2/A4 and B1/A4 Hz45G10 antibodies. Antibody Hz45G10 A2/A4 comprises a heavy chain variable region (A2) with an amino acid sequence SEQ ID NO:162, and a light chain variable region (A4) with an amino acid sequence SEQ ID NO:164; and antibody Hz45G10 B1/A4 comprises a heavy chain variable region (B1) with an amino acid sequence SEQ ID NO:163, and a light chain variable region (A4) with an amino acid sequence SEQ ID NO:164. CDRs of antibody Hz45G10 are the same as the six CDRs of 45G10 and they are shown in Table 5.

Example 16

Characterization of Humanized Antibodies

The binding affinity of Hz5A7.v5 to human ILT3 and cyno ILT3 was determined using a Biacore system as described herein and compared with the binding affinity of the parental chimeric 5A7 (ch5A7) antibody and humanized 5A7 without any CDR modifications (Hz5A7.v1) (see Table 12).

TABLE 12

| | Human ILT3 | | | Cyno ILT3 | | |
|---|---|---|---|---|---|---|
| Antibody | $K_{on}$ [1/Ms] | $K_{off}$ [s$^{-1}$] | $K_D$ M | $K_{on}$ [1/Ms] | $K_{off}$ [s$^{-1}$] | $K_D$ M |
| ch5A7 | $2.9 \times 10^6$ | $1.7 \times 10^{-3}$ | $5.7 \times 10^{-10}$ | $7.5 \times 10^6$ | $1.8 \times 10^{-2}$ | $2.4 \times 10^{-9}$ |
| Hz5A7.v1 | $2.5 \times 10^6$ | $1.2 \times 10^{-3}$ | $4.8 \times 10^{-10}$ | $1.2 \times 10^7$ | $7.7 \times 10^{-3}$ | $6.5 \times 10^{-10}$ |
| Hz5A7.v5 | $2.8 \times 10^6$ | $8.1 \times 10^{-4}$ | $2.8 \times 10^{-10}$ | $1.1 \times 10^7$ | $7.1 \times 10^{-3}$ | $7.0 \times 10^{-10}$ |

Antibody Hz5A7.v5 had a binding affinity to human ILT3 of $2.8 \times 10^{10}$ M at 37° C. as compared to the parental antibody ch5A7 binding affinity of $5.7 \times 10^{10}$ M. In addition, antibody Hz5A7.v5 had a binding affinity to cyno ILT3 of $7.0 \times 10^{10}$ M at 37° C. as compared to the parental antibody ch5A7 binding affinity of $2.4 \times 10^{-9}$ M.

These results demonstrated that the humanization process for antibody 5A7, as well as the removal of a methionine within CDR3 of the heavy chain variable region, a potential isomerization site within CDR1 of the light chain variable region, and a potential deamidation site within CDR1 of the light chain variable region, did not have a significant effect on the binding affinities to human ILT3 or cyno ILT3.

The binding affinities of various Hz48A6 and Hz45G10 antibodies to human ILT3 and cyno ILT3 were also determined using a Biacore system as described herein. Humanized antibodies comprising various combinations of a heavy chain variable region and a light chain variable region and a human Fc domain were tested, and compared with the binding affinity of the parental chimeric antibody (48A6 chimera comprising mouse 48A6 heavy and light variable regions and a human Fc domain, or 45G10 chimera comprising mouse 45G10 heavy and light variable regions and a human Fc domain).

Binding affinities of humanized 48A6 (Hz48A6) antibodies comprising a heavy chain variable region selected from B0 (SEQ ID NO:156), B1 (SEQ ID NO:157), C0 (SEQ ID NO:158), C1 (SEQ ID NO:159) and C2 (SEQ ID NO:160) and a light chain variable region C2 (SEQ ID NO:161) are shown in Table 13.

TABLE 13

| | Human ILT3 | | | Cyno ILT3 | | |
|---|---|---|---|---|---|---|
| Antibody | $K_{on}$ [1/Ms] | $K_{off}$ [s$^{-1}$] | $K_D$ M | $K_{on}$ [1/Ms] | $K_{off}$ [s$^{-1}$] | $K_D$ M |
| 48A6 chimera | $1.31 \times 10^7$ | $8.68 \times 10^{-4}$ | $0.66 \times 10^{-10}$ | $1.99 \times 10^6$ | $11 \times 10^{-2}$ | $54 \times 10^{-9}$ |
| B0-C2 | $2.80 \times 10^6$ | $7.84 \times 10^{-4}$ | $2.8 \times 10^{-10}$ | $2.13 \times 10^5$ | $9.7 \times 10^{-2}$ | $455 \times 10^{-9}$ |
| B1-C2 | $3.05 \times 10^6$ | $7.64 \times 10^{-4}$ | $2.5 \times 10^{-10}$ | $1.74 \times 10^5$ | $9.2 \times 10^{-2}$ | $531 \times 10^{-9}$ |
| C0-C2 | $3.45 \times 10^6$ | $5.41 \times 10^{-4}$ | $1.6 \times 10^{-10}$ | $3.27 \times 10^5$ | $5.8 \times 10^{-2}$ | $177 \times 10^{-9}$ |
| C1-C2 | $2.72 \times 10^6$ | $7.05 \times 10^{-4}$ | $2.6 \times 10^{-10}$ | $1.14 \times 10^5$ | $8.8 \times 10^{-2}$ | $770 \times 10^{-9}$ |
| C2-C2 | $3.06 \times 10^6$ | $7.52 \times 10^{-4}$ | $2.4 \times 10^{-10}$ | $2.17 \times 10^5$ | $8.2 \times 10^{-2}$ | $377 \times 10^{-9}$ |

Binding affinities of humanized 45G10 (Hz45G10) antibodies comprising a heavy chain variable region selected from A2 (SEQ ID NO: 162) and B1 (SEQ ID NO: 163) and a light chain variable region A4 (SEQ ID NO: 164) are shown in Table 14.

TABLE 14

| | Human ILT3 | | | Cyno ILT3 | | |
|---|---|---|---|---|---|---|
| Antibody | $K_{on}$ [1/Ms] | $K_{off}$ [s$^{-1}$] | $K_D$ M | $K_{on}$ [1/Ms] | $K_{off}$ [s$^{-1}$] | $K_D$ M |
| 45G10 chimera | $2.3 \times 10^6$ | $3.4 \times 10^{-4}$ | $1.4 \times 10^{-10}$ | $4.1 \times 10^5$ | $1.5 \times 10^{-2}$ | $37 \times 10^{-9}$ |
| A2-A4 | $1.4 \times 10^6$ | $2.8 \times 10^{-4}$ | $2 \times 10^{-10}$ | $1.9 \times 10^5$ | $2 \times 10^{-2}$ | $113 \times 10^{-9}$ |
| B1-A4 | $1.3 \times 10^6$ | $2.6 \times 10^{-4}$ | $2 \times 10^{-10}$ | $1.2 \times 10^6$ | $9 \times 10^{-2}$ | $76 \times 10^{-9}$ |

Example 17

Effects of Anti-ILT3 Antibodies on Macrophages

Macrophages were generated from primary human monocytes and polarized as described. Maxisorp plates (Nunc) were coated with anti-KLH and human fibronectin (FC0101, Millipore) (each at 5 pg/mL) at room temperature for 1 hour, then washed with PBS and blocked with X-Vivo 15 media for 30 minutes. For assaying anti-ILT3 antibody effects on macrophages, cells were washed, resuspended in X-Vivo 15 media, and incubated with the designated antibodies at room temperature for 20 minutes, then plated on coated wells ($7 \times 10^4$ cells/well in a 100 µL volume) and incubated overnight. Media was harvested for evaluation of cytokine secretion by Luminex assay (ProcartaPlex system; ThermoFisher Scientific) after 24 hours.

Figure 20A:
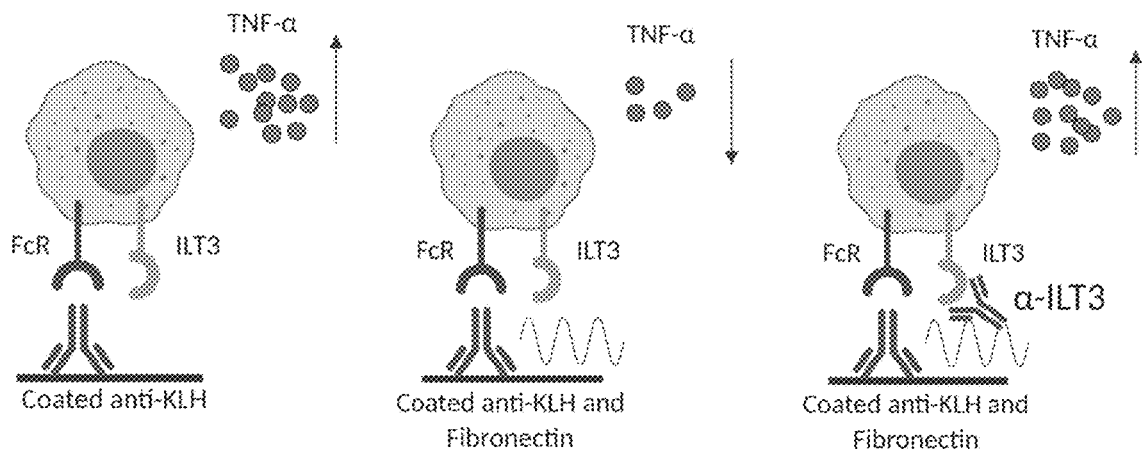
FIG. 20A-20B show that anti-ILT3 antibodies reversed fibronectin-mediated inhibition of FcR signaling and TNF-α production in primary macrophages.
Figure 20B:
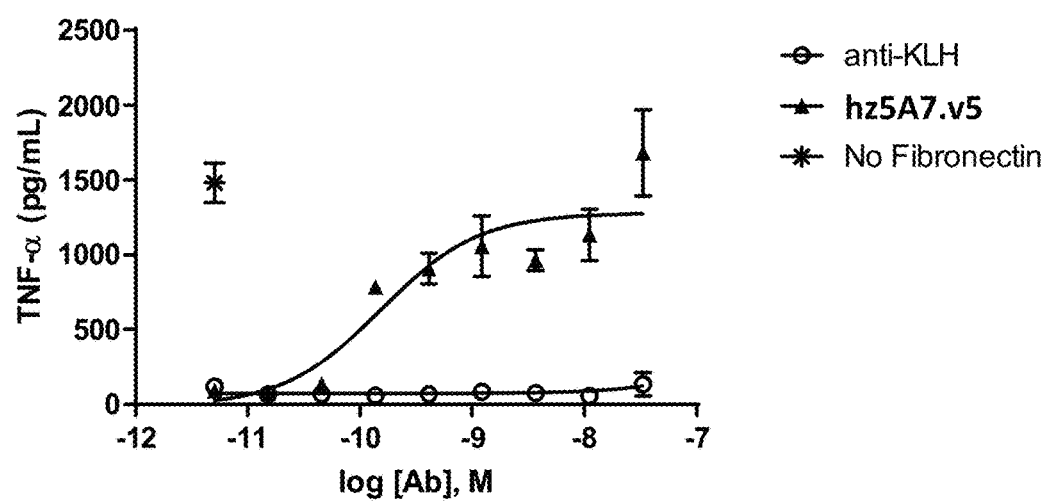

As shown in FIGS. 20A and 20B, unpolarized (MO) macrophages were stimulated with anti-KLH via the Fc receptor (FcR) and secreted TNF-α. In the presence of fibronectin, TNF-α secretion by the macrophages were inhibited. The inhibition of fibronectin induced TNF-α production in macrophages were blocked by an anti-ILT3 antibody (e.g., hz5A7.v5), which blocked interaction between ILT3 and fibronectin, and restored TNF-α secretion. Thus, an anti-ILT3 antibody described herein blocks fibronectin-mediated inhibition of FcR signaling in macrophages and increases FcR-driven cytokine production by macrophages in the presence of fibronectin.

Figure 21A:
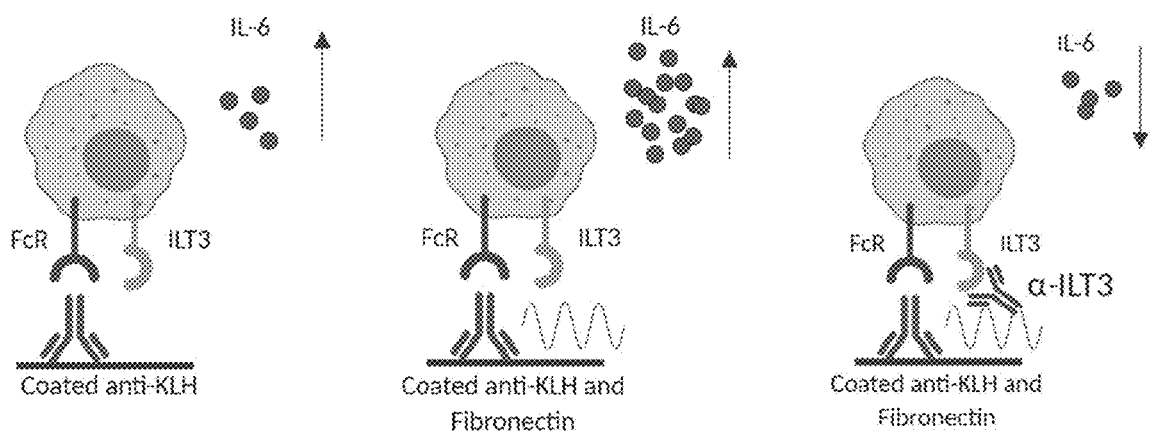
FIG. 21A-21B show that anti-ILT3 antibodies reversed fibronectin-mediated inhibition of FcR signaling and IL-6 production in IL-10 polarized macrophages.
Figure 21B:
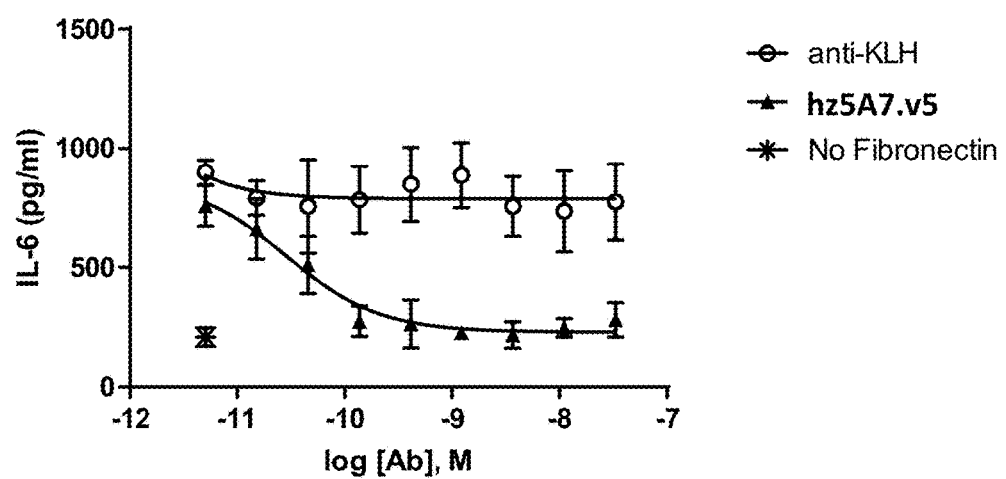

As shown in FIGS. 21A and 21B, IL-10-polarized (M2c) macrophages were stimulated with anti-KLH via the Fc receptor (FcR) and secreted little IL-6. In the presence of fibronectin, IL-6 secretion by the macrophages was increased. The increase of fibronectin induced IL-6 production in macrophages were blocked by an anti-ILT3 antibody (e.g., hz5A7.v5), which blocked interaction between ILT3 and fibronectin, and inhibited IL-6 production. Thus, an anti-ILT3 antibody described herein blocks fibronectin-mediated inhibition of FcR signaling in macrophages.

Example 18

Effects of Anti-ILT3 Antibodies on Cells Expressing Cynomolgus ILT3

A reporter cell line was generated to express cynomolgus ILT3. THP-1 Dual KI-mSTING reporter cells (Invivogen) were used, from which human ILT3 was deleted via CRISPR/Cas9-based gene editing. The cells were then stably infected with retrovirus containing cynomolgus ILT3 in the pBABEpuro vector. Nunc Maxisorp plates were co-coated with human fibronectin and an anti-KLH antibody for 2 hours at room temperature, then blocked with X-Vivo 15 media for 30 minutes at room temperature. The cynomolgus ILT3-expressing reporter cells were resuspended in X-Vivo 15 media ($1.5 \times 10^6$ cells/mL) and mixed at a 1:1 ratio with media containing serial dilutions of a control antibody or the anti-ILT3 antibody ch5A7. The mixtures were incubated for 30 minutes before being seeded onto the plates at 100 µL/well. The mixture was then incubated on the plates overnight before the NF-kB reporter activity from the cells was measured. To measure the reporter activity, 25 µL of culture supernatant was combined with 100 µL of Quanti-Blue SEAP substrate and incubated at 37° C. for 2 hours. Absorbance was read at 620 nm.

Figure 22:
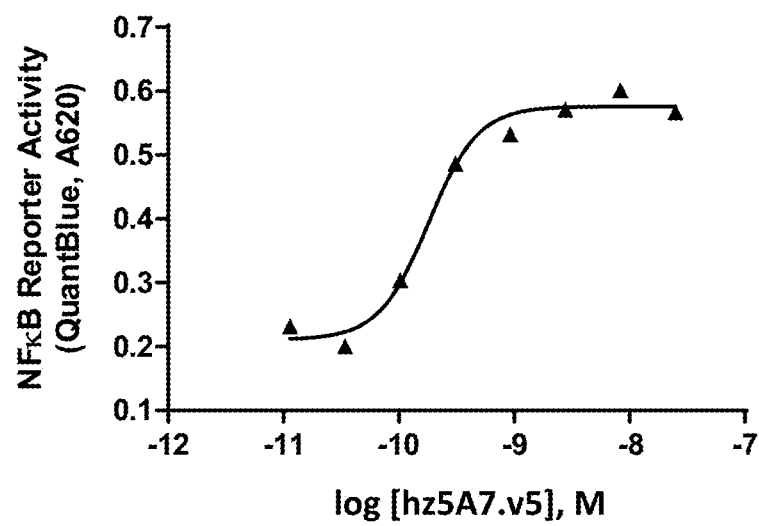
FIG. 22 shows that anti-ILT3 antibodies reversed fibronectin-mediated inhibition of FcR signaling (NF-kB reporter activity) in THP-1 cells expressing cynomolgus ILT3.

As shown in FIG. 22, an anti-ILT3 antibody (e.g., hz5A7.v5) reversed fibronectin-mediated inhibition of NF-kB reporter activity in THP-1 by blocking the interaction between cyno ILT3 and fibronectin.

Example 19

Effects of Anti-ILT3 Antibodies on Primary Cynomolgus Dendritic Cells

Figure 23:
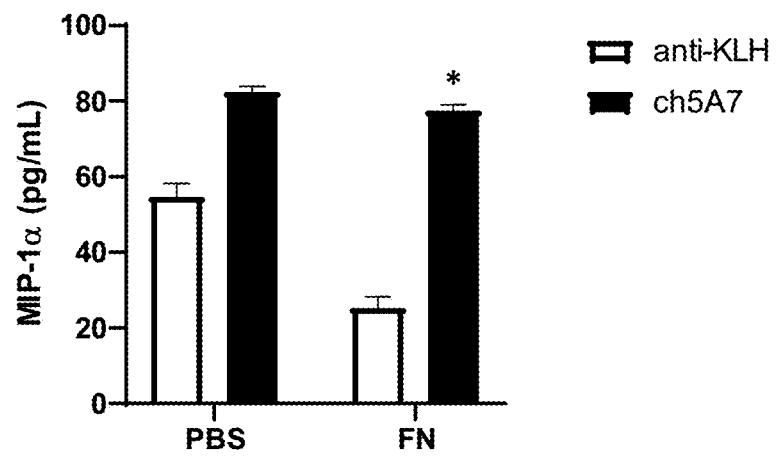
FIG. 23 shows that anti-ILT3 antibodies reversed fibronectin (FN)-mediated inhibition of MIP-1α production in cynomolgus monocyte derived dendritic cells. * indicates P<0.001.

Monocytes were isolated from cryopreserved cynomolgus PBMCs by positive selection using non-human primate CD14 microbeads (Miltenyi Biotec), and differentiated into monocyte-derived dendritic cells (DCs) by 5-day treatment with human GM-CSF and IL-4, as described for human monocyte-derived DCs. Maxisorp plates (Nunc) were coated with PBS or fibronectin (5 µg/mL) for 1 hour at room temperature, then washed with PBS and blocked with X-Vivo 15 media (Lonza) for 30 minutes at room temperature. The dendritic cells were plated at $2 \times 10^5$ cells/well in the presence of 2 µg/mL anti-KLH (control antibody) or anti-ILT3 antibody ch5A7 and cultured overnight. Cell culture media was harvested after 24 hours, and the MIP-1α concentration was determined by Luminex assay using the ProcartaPlex system (ThermoFisher Scientific). As shown in FIG. 23, fibronectin reduced MIP-1α secretion in the cynomolgus monocyte-derived DCs, and this reduction was rescued by ch5A7 which blocked interaction between cyno ILT3 and fibronectin.

Figure 24:
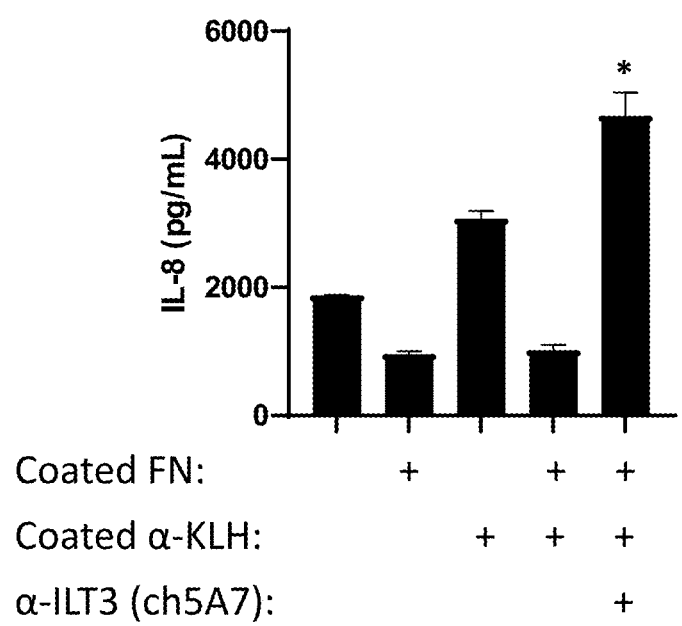
FIG. 24 shows that anti-ILT3 antibodies reversed fibronectin (FN)-mediated inhibition of FcR signaling and IL-8 production in cynomolgus monocyte derived dendritic cells. * indicates P<0.01.

In a separate experiment, DCs were generated from primary cynomolgus monocytes as described herein. Maxisorp plates (Nunc) were coated with anti-KLH and human fibronectin (FC0101, Millipore) (each at 5 µg/mL) at room temperature for 1 hour, then washed with PBS and blocked with X-Vivo 15 media for 30 minutes. The DCs were resuspended in X-Vivo 15 media, incubated with anti-KLH or anti-ILT3 ch5A7 at room temperature for 20 minutes, and then plated on coated wells ($7 \times 10^4$ cells/well in a 100 µL volume) for culturing overnight. After 24 hours of culturing, the culture supernatant was harvested for evaluation of IL-8 secretion by DCs using Luminex assay (ProcartaPlex system; ThermoFisher Scientific). As shown in FIG. 24, fibronectin reduced IL-8 secretion from the cynomolgus monocyte-derived DCs, and this reduction was rescued by ch5A7 which blocked interaction between cyno ILT3 and fibronectin.

Example 20

Anti-Tumor Activity of Anti-ILT3 Antibodies in Humanized Mouse Model

All animal procedures were performed under an Institutional Animal Care and Use Committee (IACUC)-approved animal use protocol (NGM-27-2017). NCI-H2009 lung adenocarcinoma cells (ATCC) were grown in RPMI 1640 containing 10% FBS and 1% penicillin/streptomycin. NSG mice were injected subcutaneously on the left flank with $3 \times 10^6$ NCI-H2009 tumor cells. Seven to 10 days after the implantation of tumor cells, each mouse was injected with $4 \times 10^6$ primary human PBMCs via the tail vein. Tumor growth was measured twice weekly using calipers. Once the tumors reached a volume of approximately 50 mm³, mice were treated twice weekly with 10 mg/kg control anti-KLH antibody or anti-ILT3 antibody 48A6 by intraperitoneal injection (3 doses total). Tumors was monitored and measured twice weekly. Once tumors reached a volume of approximately 2000 mm³, mice were sacrificed.

Figure 25:
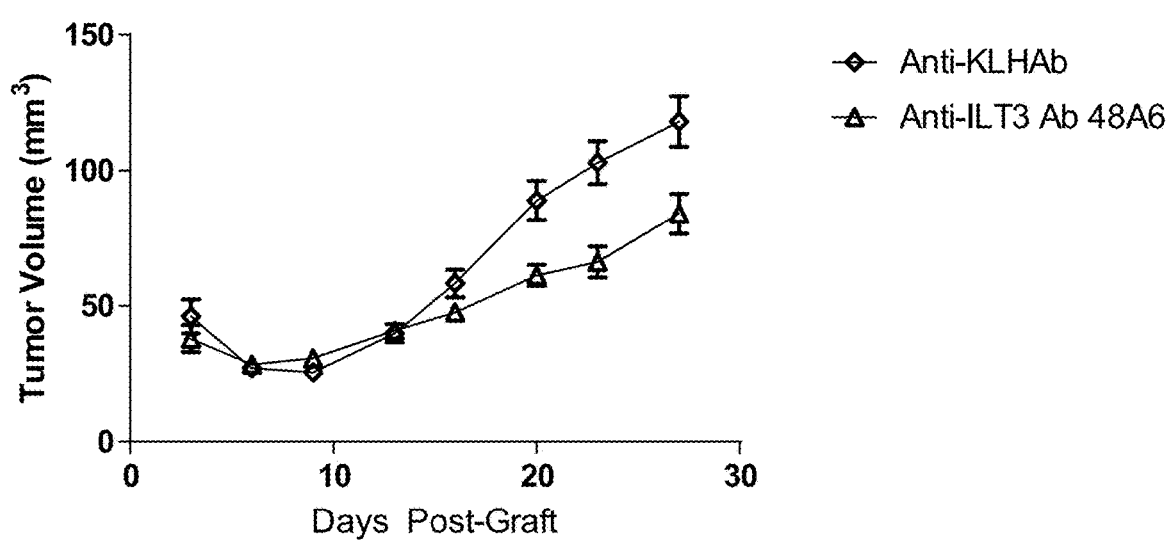
FIG. 25. Anti-tumor activity of anti-ILT3 antibodies in humanized mouse model.

As shown in FIG. 25, the anti-ILT3 antibody 48A6 significantly inhibited tumor growth in this mouse model.

Although the foregoing present disclosure has been described in some detail by way of illustration and example for purposes of clarity of understanding, the descriptions and examples should not be construed as limiting the scope of the present disclosure. The embodiments of the present disclosure described herein are intended to be merely exemplary, and those skilled in the art will recognize numerous equivalents to the specific procedures described herein. All such equivalents are considered to be within the scope of the present disclosure and are covered by the embodiments.

All publications, patents, patent applications, internet sites, and accession numbers/database sequences including both polynucleotide and polypeptide sequences cited herein are hereby incorporated by reference in their entirety for all purposes to the same extent as if each individual publication, patent, patent application, internet site, or accession number/database sequence were specifically and individually indicated to be so incorporated by reference.

Following are sequences disclosed in the application. CDR sequences are listed in Tables 1-4.

```
Human ILT3 amino acid sequence with predicted signal sequence underlined
                                                               (SEQ ID NO: 1)
MIPTFTALLCLGLSLGPRTHMQAGPLPKPTLWAEPGSVISWGNSVTIWCQGTLEAREYR

LDKEESPAPWDRQNPLEPKNKARFSIPSMTEDYAGRYRCYYRSPVGWSQPSDPLELVMT

GAYSKPTLSALPSPLVTSGKSVTLLCQSRSPMDTFLLIKERAAHPLLHLRSEHGAQQHQA

EFPMSPVTSVHGGTYRCFSSHGFSHYLLSHPSDPLELIVSGSLEDPRPSPTRSVSTAAGPE

DQPLMPTGSVPHSGLRRHWEVLIGVLVVSILLLSLLLFLLLQHWRQGKHRTLAQRQADF

QRPPGAAEPEPKDGGLQRRSSPAADVQGENFCAAVKNTQPEDGVEMDTRQSPHDEDPQ

AVTYAKVKHSRPRREMASPPSPLSGEFLDTKDRQAEEDRQMDTEAAASEAPQDVTYAQ

LHSFTLRQKATEPPPSQEGASPAEPSVYATLAIH

Human ILT3 amino acid sequence without predicted signal sequence
                                                               (SEQ ID NO: 2)
QAGPLPKPTLWAEPGSVISWGNSVTIWCQGTLEAREYRLDKEESPAPWDRQNPLEPKNK

ARFSIPSMTEDYAGRYRCYYRSPVGWSQPSDPLELVMTGAYSKPTLSALPSPLVTSGKS

VTLLCQSRSPMDTFLLIKERAAHPLLHLRSEHGAQQHQAEFPMSPVTSVHGGTYRCFSS

HGFSHYLLSHPSDPLELIVSGSLEDPRPSPTRSVSTAAGPEDQPLMPTGSVPHSGLRRHWE

VLIGVLVVSILLLSLLLFLLLQHWRQGKHRTLAQRQADFQRPPGAAEPEPKDGGLQRRS

SPAADVQGENFCAAVKNTQPEDGVEMDTRQSPHDEDPQAVTYAKVKHSRPRREMASP

PSPLSGEFLDTKDRQAEEDRQMDTEAAASEAPQDVTYAQLHSFTLRQKATEPPPSQEGA

SPAEPSVYATLAIH

Human ILT3 Extracellular domain (aa 22-259)
                                                               (SEQ ID NO: 3)
QAGPLPKPTLWAEPGSVISWGNSVTIWCQGTLEAREYRLDKEESPAPWDRQNPLEPKNK

ARFSIPSMTEDYAGRYRCYYRSPVGWSQPSDPLELVMTGAYSKPTLSALPSPLVTSGKS

VTLLCQSRSPMDTFLLIKERAAHPLLHLRSEHGAQQHQAEFPMSPVTSVHGGTYRCFSS

HGFSHYLLSHPSDPLELIVSGSLEDPRPSPTRSVSTAAGPEDQPLMPTGSVPHSGLRRHWE

Human ILT3 Ig-like C2-type Domain 1 amino acid sequence without
N-terminal domain (aa 27-118)
                                                               (SEQ ID NO: 4)
PKPTLWAEPGSVISWGNSVTIWCQGTLEAREYRLDKEESPAPWDRQNPLEPKNKARFSI

PSMTEDYAGRYRCYYRSPVGWSQPSDPLELVMT

Human ILT3 Ig-like C2-type Domain 2 amino acid sequence (aa 124-218)
                                                               (SEQ ID NO: 5)
PTLSALPSPLVTSGKSVTLLCQSRSPMDTFLLIKERAAHPLLHLRSEHGAQQHQAEFPMS

PVTSVHGGTYRCFSSHGFSHYLLSHPSDPLELIVS

Cyno ILT3 amino acid sequence with predicted signal sequence underlined
                                                               (SEQ ID NO: 6)
MTPPLTVLFCLGLSLGPRTCVQAGPLPKPTVWAEPGSVISWGSPVTIWCQGTLDAQEYH

LDKEGSPAPWDTQNPLEPRNKAKFSIPSMTQHYAGRYRCYYHSHPDWSEDSDPLDLVM

TGAYSKPILSVLPSPLVTSGESVTLLCQSQSPMDTFLLFKEGAAHPLPRLRSQHGAQLHW

AEFPMGPVTSVHGGTYRCISSRSFSHYLLSRPSDPVELTVLGSLESPSPSPTRSISAAAGPE
```

-continued

```
DQSLMPTGSDPQSGLRRHWEVLIGVLVVSILLLSLVFFLLLQHWRQGKHRTSAQRQADF

QRPPGAAEPEPKDGGLQRRSRPAADVQGENPNAAMKDTQPEDGVELDSRQRPHDEDPQ

AVTYARVKHSGPRREMASPPSPLSEEFLDTKDTQAEEDRQMDTQAATSEAPQDVTYAQ

LQSLTLRREATEPPPPQKREPSAEPSVYATLAIH
```

Cyno ILT3 amino acid sequence without predicted signal sequence
(SEQ ID NO: 7)
```
QAGPLPKPTVWAEPGSVISWGSPVTIWCQGTLDAQEYHLDKEGSPAPWDTQNPLEPRN

KAKFSIPSMTQHYAGRYRCYYHSHPDWSEDSDPLDLVMTGAYSKPILSVLPSPLVTSGE

SVTLLCQSQSPMDTFLLFKEGAAHPLPRLRSQHGAQLHWAEFPMGPVTSVHGGTYRCIS

SRSFSHYLLSRPSDPVELTVLGSLESPSPSPTRSISAAAGPEDQSLMPTGSDPQSGLRRHW

EVLIGVLVVSILLLSLVFFLLLQHWRQGKHRTSAQRQADFQRPPGAAEPEPKDGGLQRR

SRPAADVQGENPNAAMKDTQPEDGVELDSRQRPHDEDPQAVTYARVKHSGPRREMAS

PPSPLSEEFLDTKDTQAEEDRQMDTQAATSEAPQDVTYAQLQSLTLRREATEPPPPQKRE

PSAEPSVYATLAIH
```

Cyno ILT3 Extracellular domain (aa 22-259)
(SEQ ID NO: 8)
```
QAGPLPKPTVWAEPGSVISWGSPVTIWCQGTLDAQEYHLDKEGSPAPWDTQNPLEPRN

KAKFSIPSMTQHYAGRYRCYYHSHPDWSEDSDPLDLVMTGAYSKPILSVLPSPLVTSGE

SVTLLCQSQSPMDTFLLFKEGAAHPLPRLRSQHGAQLHWAEFPMGPVTSVHGGTYRCIS

SRSFSHYLLSRPSDPVELTVLGSLESPSPSPTRSISAAAGPEDQSLMPTGSDPQSGLRRHW

E
```

Cyno ILT3 Ig-like C2-type Domain 1 amino acid sequence without
N-terminal domain (aa 27-118)
(SEQ ID NO: 9)
```
PKPTVWAEPGSVISWGSPVTIWCQGTLDAQEYHLDKEGSPAPWDTQNPLEPRNKAKFSI

PSMTQHYAGRYRCYYHSHPDWSEDSDPLDLVMT
```

Cyno ILT3 Ig-like C2-type Domain 2 amino acid sequence without
N-terminal domain (aa 124-218)
(SEQ ID NO: 10)
```
PILSVLPSPLVTSGESVTLLCQSQSPMDTFLLFKEGAAHPLPRLRSQHGAQLHWAEFPMG

PVTSVHGGTYRCISSRSFSHYLLSRPSDPVELTVL
```

3A3 Heavy chain variable region amino acid sequence
(SEQ ID NO: 109)
```
QVQLKESGPGLVAPSQSLSITCTVSGFSLTSYGVHWVRQPPGKGLEWLGVIWPGGTINY

NSALMSRLSISKDNSKSQVFLKLNSLQTDDTAMYYCASDKYDGGWFAYWGQGTLVTV

SA
```

3A3 Light chain variable region amino acid sequence
(SEQ ID NO: 110)
```
DIVMTQSQKFMSTSVGDRVSITCKASQNVRTAVAWYQQKPGQSPEALIYLASNRHTGV

PDRFTGSGSGTDFSLSISNVQSEDLADYFCLQHLNYPLTFGSGTKLEIK
```

5A7 Heavy chain variable region amino acid sequence
(SEQ ID NO: 111)
```
EVKLVESGGGLVKPGGSLKLSCAASGFTFSSYGMSWVRQTPEKRLEWVATISGGGSYT

NYPDSVKGRLTISRDNAKKNLYLEMSSLRSEDTALYYCARREWRMTLYAMDYWGQGT

SVTVSS
```

5A7 Light chain variable region amino acid sequence
(SEQ ID NO: 112)
```
NIVLTQSPASLAVSLGQRATISCRASESVDSYGNSFMHWYQQKPGQAPKLLIYLTSNLES

GVPARFSGSGSRTDFTLTIDPVEADDAATYYCQQNNEDPFTFGSGTKLEIK
```

```
12A12 Heavy chain variable region amino acid sequence
                                                      (SEQ ID NO: 113)
EVQLQQSGPELVKPGASVKISCKASGYTFTDYNMDWVKQSHGKSLEWIGYIYPNNGGT
GYNQKFNSKATLTVDKSSSTAYMELHSLTSEDSAVYYCASSPYYDYVGSYAMDYWGQ
GTSVTVSS 12A12 Light chain variable region amino acid sequence
                                                      (SEQ ID NO: 114)
QIVLTQSPAIMSASLGERVTMTCTASSSVSSSYLHWYQQKPGSSPKLWIYSTSNLASGVP
ARFSGSGSGTSYSLTISSMEAEDAATYYCHQYHRSPRTFGGGTKLEIK 16C5 Heavy chain variable region amino acid sequence
                                                      (SEQ ID NO: 115)
EVQLQQSGPELVKPGASVKISCKASGYTFTDYNMDWVKQSHGKSLEWIGYIYPSNGGT
GYNQKFKSKATLTVDKSSNTAYMELHSLTSEDSAVYYCARVPYYDYLYYYAMDYWG
QGTSVTVSS 16C5 Light chain variable region amino acid sequence
                                                      (SEQ ID NO: 116)
QIVLSQSPAILSASPGEKVTMACRASSSVSFMHWYQQKPGSSPQPWIYATSNLASGVPAR
FSGSGSGTSYSLTISRVEAEDAATYYCQQWSTNPYMYTFGGGTKLEIK 45G10 Heavy chain variable region amino acid sequence
                                                      (SEQ ID NO: 117)
EVQLVESGGGLVKPGGSLKLSCAASGFTFSDYGMHWVRQAPEKGLEWVAYIFSGSSTIY
YADTVKGRFTISRDNAKNTLFLQMTSLRSEDTAMYYCARADGRGAMDYWGQGTSVTV
SS 45G10 Light chain variable region amino acid sequence
                                                      (SEQ ID NO: 118)
DVQMTQTTSSLSASLGDRVTISCRASQDISKFLNWYQQKPDGTVTLLIYYTSRLHSGVPS
RFSGSGSGTDYSLTISNLDQEDIATYFCQQGNTLPWTFGGGTKLEIK 48A6 Heavy chain variable region amino acid sequence
                                                      (SEQ ID NO: 119)
EVQLVESGGDLMKPGGSLKLSCAASGFTFSSYGMSWVRQTPDKRLEWVATISSGGTYT
FYPDSVKGRFTISRDNAKNTLYLQMSSLKSEDTAMYYCARRGWLLHYYAMDYWGQG
TSVTVSS 48A6 Light chain variable region amino acid sequence
                                                      (SEQ ID NO: 120)
NIVLTQSPASLAVSLGQRATISCRPSESVDSFGNSFMHWFQQKPGQPPKLLIYLSSKLESG
VPARFSGSGSRTDFTLTIDPVEADDAATYYCQQHNEDPFTFGSGTKLEIK 53F10 Heavy chain variable region amino acid sequence
                                                      (SEQ ID NO: 121)
EVQVVESGGGLVKPGGSLKLSC AASGFTF SDYGMHWVRQAPEKGLEWVAYISTGIITV
YYADTVKGRFTMSRDNAKNTLFLQMTSLRSEDTAIYYCARADGRGAMDYWGQGTSVI
VSS 53F10 Light chain variable region amino acid sequence
                                                      (SEQ ID NO: 122)
DIQMTQTTSSLSASLGDRVTISCRASQDISNFLNWYQQKPDGTVTLLIYYTSRLHSGVPS
RFSGSGSGTDYSLTISNLEQEDFATYFCQQGNTLPWTFGGGTKLEIK Hz5A7.v5 Heavy chain variable region amino acid sequence
                                                      (SEQ ID NO: 123)
EVQLVESGGGLVQPGGSLRLSCAASGFTFSSYGMSWVRQAPGKGLEWVATISGGGSYT
NYPDSVKGRFTISRDNAKNSLYLQMNSLRAEDTAVYYCARREWRYTLYAMDYWGQG
TTVTVSS
```

-continued

Hz5A7.v5 Light chain variable region amino acid sequence
(SEQ ID NO: 124)
DIQLTQSPSFLSASVGDRVTITCRASESVESYGSSFMHWYQQKPGKAPKLLIYLTSNLES

GVPSRFSGSGSGTEFTLTISSLQPEDFATYYCQQNNEDPFTFGQGTKLEIK

Hz5A7.v5 Heavy chain amino acid sequence with signal sequence underlined
(SEQ ID NO: 125)
<u>MDMRVPAQLLGLLLLWLRGARC</u>EVQLVESGGGLVQPGGSLRLSCAASGFTFSSYGMS

WVRQAPGKGLEWVATISGGGSYTNYPDSVKGRFTISRDNAKNSLYLQMNSLRAEDTAV

YYCARREWRYTLYAMDYWGQGTTVTVSSASTKGPSVFPLAPSSKSTSGGTAALGCLVK

DYFPEPVTVSWNSGALTSGVHTFPAVLQSSGLYSLSSVVTVPSSSLGTQTYICNVNHKPS

NTKVDKKVEPKSCDKTHTCPPCPAPELLGGPSVFLFPPKPKDTLMISRTPEVTCVVVDVS

HEDPEVKFNWYVDGVEVHNAKTKPREEQYGSTYRVVSVLTVLHQDWLNGKEYKCKV

SNKALPAPIEKTISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEALHNHYTQKSL

SLSPGK

Hz5A7.v5 Heavy chain amino acid sequence without signal sequence
(SEQ ID NO: 126)
EVQLVESGGGLVQPGGSLRLSCAASGFTFSSYGMSWVRQAPGKGLEWVATISGGGSYT

NYPDSVKGRFTISRDNAKNSLYLQMNSLRAEDTAVYYCARREWRYTLYAMDYWGQG

TTVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVDGVEVHNAKT

KPREEQYGSTYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPVLDSDGSFFL

YSKLTVDKSRWQQGNVFSCSVMHEALHNHYTQKSLSLSPGK

Hz5A7.v5 Light chain amino acid sequence with signal sequence underlined
(SEQ ID NO: 127)
<u>MDMRVPAQLLGLLLLWLRGARC</u>DIQLTQSPSFLSASVGDRVTITCRASESVESYGSSFM

HWYQQKPGKAPKLLIYLTSNLESGVPSRFSGSGSGTEFTLTISSLQPEDFATYYCQQNNE

DPFTFGQGTKLEIKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLSSPVTKSFNR

GEC

Hz5A7.v5 Light chain amino acid sequence without signal sequence
(SEQ ID NO: 128)
DIQLTQSPSFLSASVGDRVTITCRASESVESYGSSFMHWYQQKPGKAPKLLIYLTSNLES

GVPSRFSGSGSGTEFTLTISSLQPEDFATYYCQQNNEDPFTFGQGTKLEIKRTVAAPSVFIF

PPSDEQLKSGTASVVCLLNNFYPREAKVQWKVDNALQSGNSQESVTEQDSKDSTYSLSS

TLTLSKADYEKHKVYACEVTHQGLSSPVTKSFNRGEC

Human IgG1 constant region
(SEQ ID NO: 129)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK

Human IgG1 constant region E233A/L235A
(SEQ ID NO: 130)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPALAG

GPSVFLFPPKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFFLYSKLTVD

KSRWQQGNVFSCSVMHEALHNHYTQKSLSLSPGK

Human IgG1 constant region L234A/L235A
(SEQ ID NO: 131)
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCP

PCPAPEAAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAPIEK

TISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSL

SPGK

Human IgG1 constant region L234A/L235A/P329G
(SEQ ID NO: 132)
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCP

PCPAPEAAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALGAPIEK

TISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSL

SPGK

Human IgG1 constant region N297G
(SEQ ID NO: 133)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQY

GSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK

Human IgG1 constant region N297G/H310A
(SEQ ID NO: 134)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQY

GSTYRVVSVLTVLAQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK

Human Kappa light chain constant region
(SEQ ID NO: 135)
RTVAAPSVFIFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC

```
Human Lambda light chain constant region
                                                           (SEQ ID NO: 136)
GQPKAAPSVTLFPPSSEELQANKATLVCLISDFYPGAVTVAWKADSSPVKAGVETTTPS

KQSNNKYAASSYLSLTPEQWKSHRSYSCQVTHEGSTVEKTVAPTECS

Human ILT3 Ig-like C2-type D1 and D2 amino acid sequence without
N-terminal domain (aa 27-218)
                                                           (SEQ ID NO: 137)
QAGPLPKPTLWAEPGSVISWGNSVTIWCQGTLEAREYRLDKEESPAPWDRQNPLEPKNK

ARFSIPSMTEDYAGRYRCYYRSPVGWSQPSDPLELVMTGAYSKPTLSALPSPLVTSGKS

VTLLCQSRSPMDTFLLIKERAAHPLLHLRSEHGAQQHQAEFPMSPVTSVHGGTYRCFSS

HGFSHYLLSHPSDPLELIVS

Human Fibronectin with predicted signal sequence underlined
                                                           (SEQ ID NO: 138)
MLRGPGPGLLLLAVQCLGTAVPSTGASKSKRQAQQMVQPQSPVAVSQSKPGCYDNGK

HYQINQQWERTYLGNALVCTCYGGSRGFNCESKPEAEETCFDKYTGNTYRVGDTYERP

KDSMIWDCTCIGAGRGRISCTIANRCHEGGQSYKIGDTWRRPHETGGYMLECVCLGNG

KGEWTCKPIAEKCFDHAAGTSYVVGETWEKPYQGWMMVDCTCLGEGSGRITCTSRNR

CNDQDTRTSYRIGDTWSKKDNRGNLLQCICTGNGRGEWKCERHTSVQTTSSGSGPFTD

VRAAVYQPQPHPQPPPYGHCVTDSGVVYSVGMQWLKTQGNKQMLCTCLGNGVSCQE

TAVTQTYGGNSNGEPCVLPFTYNGRTFYSCTTEGRQDGHLWCSTTSNYEQDQKYSFCT

DHTVLVQTRGGNSNGALCHFPFLYNNHNYTDCTSEGRRDNMKWCGTTQNYDADQKF

GFCPMAAHEEICTTNEGVMYRIGDQWDKQHDMGHMMRCTCVGNGRGEWTCIAYSQL

RDQCIVDDITYNVNDTFHKRHEEGHMLNCTCFGQGRGRWKCDPVDQCQDSETGTFYQI

GDSWEKYVHGVRYQCYCYGRGIGEWHCQPLQTYPSSSGPVEVFITETPSQPNSHPIQWN

APQPSHISKYILRWRPKNSVGRWKEATIPGHLNSYTIKGLKPGVVYEGQLISIQQYGHQE

VTRFDFTTTSTSTPVTSNTVTGETTPFSPLVATSESVTEITASSFVVSWVSASDTVSGFRVE

YELSEEGDEPQYLDLPSTATSVNIPDLLPGRKYIVNVYQISEDGEQSLILSTSQTTAPDAPP

DTTVDQVDDTSIVVRWSRPQAPITGYRIVYSPSVEGSSTELNLPETANSVTLSDLQPGVQ

YNITIYAVEENQESTPVVIQQETTGTPRSDTVPSPRDLQFVEVTDVKVTIMWTPPESAVT

GYRVDVIPVNLPGEHGQRLPISRNTFAEVTGLSPGVTYYFKVFAVSHGRESKPLTAQQTT

KLDAPTNLQFVNETDSTVLVRWTPPRAQITGYRLTVGLTRRGQPRQYNVGPSVSKYPLR

NLQPASEYTVSLVAIKGNQESPKATGVFTTLQPGSSIPPYNTEVTETTIVITWTPAPRIGFK

LGVRPSQGGEAPREVTSDSGSIVVSGLTPGVEYVYTIQVLRDGQERDAPIVNKVVTPLSP

PTNLHLEANPDTGVLTVSWERSTTPDITGYRITTTPTNGQQGNSLEEVVHADQSSCTFDN

LSPGLEYNVSVYTVKDDKESVPISDTIIPEVPQLTDLSFVDITDSSIGLRWTPLNSSTIIGYR

ITVVAAGEGIPIFEDFVDSSVGYYTVTGLEPGIDYDISVITLINGGESAPTTLTQQTAVPPPT

DLRFTNIGPDTMRVTWAPPPSIDLTNFLVRYSPVKNEEDVAELSISPSDNAVVLTNLLPG

TEYVVSVSSVYEQHESTPLRGRQKTGLDSPTGIDFSDITANSFTVHWIAPRATITGYRIRH

HPEHFSGRPREDRVPHSRNSITLTNLTPGTEYVVSIVALNGREESPLLIGQQSTVSDVPRD

LEVVAATPTSLLISWDAPAVTVRYYRITYGETGGNSPVQEFTVPGSKSTATISGLKPGVD

YTITVYAVTGRGDSPASSKPISINYRTEIDKPSQMQVTDVQDNSISVKWLPSSSPVTGYRV

TTTPKNGPGPTKTKTAGPDQTEMTIEGLQPTVEYVVSVYAQNPSGESQPLVQTAVTNID

RPKGLAFTDVDVDSIKIAWESPQGQVSRYRVTYSSPEDGIHELFPAPDGEEDTAELQGLR

PGSEYTVSVVALHDDMESQPLIGTQSTAIPAPTDLKFTQVTPTSLSAQWTPPNVQLTGYR
```

-continued

VRVTPKEKTGPMKEINLAPDSSSVVVSGLMVATKYEVSVYALKDTLTSRPAQGVVTTL

ENVSPPRRARVTDATETTITISWRTKTETITGFQVDAVPANGQTPIQRTIKPDVRSYTITGL

QPGTDYKIYLYTLNDNARSSPVVIDASTAIDAPSNLRFLATTPNSLLVSWQPPRARITGYII

KYEKPGSPPREVVPRPRPGVTEATITGLEPGTEYTIYVIALKNNQKSEPLIGRKKTDELPQ

LVTLPHPNLHGPEILDVPSTVQKTPFVTHPGYDTGNGIQLPGTSGQQPSVGQQMIFEEHG

FRRTTPPTTATPIRHRPRPYPPNVGEEIQIGHIPREDVDYHLYPHGPGLNPNASTGQEALS

QTTISWAPFQDTSEYIISCHPVGTDEEPLQFRVPGTSTSATLTGLTRGATYNVIVEALKDQ

QRHKVREEVVTVGNSVNEGLNQPTDDSCFDPYTVSHYAVGDEWERMSESGFKLLCQC

LGFGSGHFRCDSSRWCHDNGVNYKIGEKWDRQGENGQMMSCTCLGNGKGEFKCDPH

EATCYDDGKTYHVGEQWQKEYLGAICSCTCFGGQRGWRCDNCRRPGGEPSPEGTTGQ

SYNQYSQRYHQRTNTNVNCPIECFMPLDVQADREDSRE

Human Fibronectin with predicted signal sequence
(SEQ ID NO: 139)
QAQQMVQPQSPVAVSQSKPGCYDNGKHYQINQQWERTYLGNALVCTCYGGSRGFNCE

SKPEAEETCFDKYTGNTYRVGDTYERPKDSMIWDCTCIGAGRGRISCTIANRCHEGGQS

YKIGDTWRRPHETGGYMLECVCLGNGKGEWTCKPIAEKCFDHAAGTSYVVGETWEKP

YQGWMMVDCTCLGEGSGRITCTSRNRCNDQDTRTSYRIGDTWSKKDNRGNLLQCICTG

NGRGEWKCERHTSVQTTSSGSGPFTDVRAAVYQPQPHPQPPPYGHCVTDSGVVYSVGM

QWLKTQGNKQMLCTCLGNGVSCQETAVTQTYGGNSNGEPCVLPFTYNGRTFYSCTTEG

RQDGHLWCSTTSNYEQDQKYSFCTDHTVLVQTRGGNSNGALCHFPFLYNNHNYTDCTS

EGRRDNMKWCGTTQNYDADQKFGFCPMAAHEEICTTNEGVMYRIGDQWDKQHDMG

HMMRCTCVGNGRGEWTCIAYSQLRDQCIVDDITYNVNDTFHKRHEEGHMLNCTCFGQ

GRGRWKCDPVDQCQDSETGTFYQIGDSWEKYVHGVRYQCYCYGRGIGEWHCQPLQTY

PSSSGPVEVFITETPSQPNSHPIQWNAPQPSHISKYILRWRPKNSVGRWKEATIPGHLNSY

TIKGLKPGVVYEGQLISIQQYGHQEVTRFDFTTTSTSTPVTSNTVTGETTPFSPLVATSES

VTEITASSFVVSWVSASDTVSGFRVEYELSEEGDEPQYLDLPSTATSVNIPDLLPGRKYIV

NVYQISEDGEQSLILSTSQTTAPDAPPDTTVDQVDDTSIVVRWSRPQAPITGYRIVYSPSV

EGSSTELNLPETANSVTLSDLQPGVQYNITIYAVEENQESTPVVIQQETTGTPRSDTVPSP

RDLQFVEVTDVKVTIMWTPPESAVTGYRVDVIPVNLPGEHGQRLPISRNTFAEVTGLSPG

VTYYFKVFAVSHGRESKPLTAQQTTKLDAPTNLQFVNETDSTVLVRWTPPRAQITGYRL

TVGLTRRGQPRQYNVGPSVSKYPLRNLQPASEYTVSLVAIKGNQESPKATGVFTTLQPG

SSIPPYNTEVTETTIVITWTPAPRIGFKLGVRPSQGGEAPREVTSDSGSIVVSGLTPGVEYV

YTIQVLRDGQERDAPIVNKVVTPLSPPTNLHLEANPDTGVLTVSWERSTTPDITGYRITTT

PTNGQQGNSLEEVVHADQSSCTFDNLSPGLEYNVSVYTVKDDKESVPISDTIIPEVPQLT

DLSFVDITDSSIGLRWTPLNSSTIIGYRITVVAAGEGIPIFEDFVDSSVGYYTVTGLEPGIDY

DISVITLINGGESAPTTLTQQTAVPPPTDLRFTNIGPDTMRVTWAPPPSIDLTNFLVRYSPV

KNEEDVAELSISPSDNAVVLTNLLPGTEYVVSVSSVYEQHESTPLRGRQKTGLDSPTGID

FSDITANSFTVHWIAPRATITGYRIRHHPEHFSGRPREDRVPHSRNSITLTNLTPGTEYVVS

IVALNGREESPLLIGQQSTVSDVPRDLEVVAATPTSLLISWDAPAVTVRYYRITYGETGG

NSPVQEFTVPGSKSTATISGLKPGVDYTITVYAVTGRGDSPASSKPISINYRTEIDKPSQM

QVTDVQDNSISVKWLPSSSPVTGYRVTTTPKNGPGPTKTKTAGPDQTEMTIEGLQPTVE

```
-continued
YVVSVYAQNPSGESQPLVQTAVTNIDRPKGLAFTDVDVDSIKIAWESPQGQVSRYRVTY

SSPEDGIHELFPAPDGEEDTAELQGLRPGSEYTVSVVALHDDMESQPLIGTQSTAIPAPTD

LKFTQVTPTSLSAQWTPPNVQLTGYRVRVTPKEKTGPMKEINLAPDSSSVVVSGLMVAT

KYEVSVYALKDTLTSRPAQGVVTTLENVSPPRRARVTDATETTITISWRTKTETITGFQV

DAVPANGQTPIQRTIKPDVRSYTITGLQPGTDYKIYLYTLNDNARSSPVVIDASTAIDAPS

NLRFLATTPNSLLVSWQPPRARITGYIIKYEKPGSPPREVVPRPRPGVTEATITGLEPGTEY

TIYVIALKNNQKSEPLIGRKKTDELPQLVTLPHPNLHGPEILDVPSTVQKTPFVTHPGYDT

GNGIQLPGTSGQQPSVGQQMIFEEHGFRRTTPPTTATPIRHRPRPYPPNVGEEIQIGHIPRE

DVDYHLYPHGPGLNPNASTGQEALSQTTISWAPFQDTSEYIISCHPVGTDEEPLQFRVPG

TSTSATLTGLTRGATYNVIVEALKDQQRHKVREEVVTVGNSVNEGLNQPTDDSCFDPYT

VSHYAVGDEWERMSESGFKLLCQCLGFGSGHFRCDSSRWCHDNGVNYKIGEKWDRQG

ENGQMMSCTCLGNGKGEFKCDPHEATCYDDGKTYHVGEQWQKEYLGAICSCTCFGGQ

RGWRCDNCRRPGGEPSPEGTTGQSYNQYSQRYHQRTNTNVNCPIECFMPLDVQADRED

SRE

Human Fibronectin fragment containing heparin-binding and
collagen-binding domains (~70 kDa fragment)
                                                  (SEQ ID NO: 140)
QAQQMVQPQSPVAVSQSKPGCYDNGKHYQINQQWERTYLGNALVCTCYGGSRGFNCE

SKPEAEETCFDKYTGNTYRVGDTYERPKDSMIWDCTCIGAGRGRISCTIANRCHEGGQS

YKIGDTWRRPHETGGYMLECVCLGNGKGEWTCKPIAEKCFDHAAGTSYVVGETWEKP

YQGWMMVDCTCLGEGSGRITCTSRNRCNDQDTRTSYRIGDTWSKKDNRGNLLQCICTG

NGRGEWKCERHTSVQTTSSGSGPFTDVRAAVYQPQPHPQPPPYGHCVTDSGVVYSVGM

QWLKTQGNKQMLCTCLGNGVSCQETAVTQTYGGNSNGEPCVLPFTYNGRTFYSCTTEG

RQDGHLWCSTTSNYEQDQKYSFCTDHTVLVQTRGGNSNGALCHFPFLYNNHNYTDCTS

EGRRDNMKWCGTTQNYDADQKFGFCPMAAHEEICTTNEGVMYRIGDQWDKQHDMG

HMMRCTCVGNGRGEWTCIAYSQLRDQCIVDDITYNVNDTFHKRHEEGHMLNCTCFGQ

GRGRWKCDPVDQCQDSETGTFYQIGDSWEKYVHGVRYQCYCYGRGIGEWHCQPLQTY

PSS

Human Fibronectin fragment containing heparin-binding domain
(~30 kDa fragment)
                                                  (SEQ ID NO: 141)
QAQQMVQPQSPVAVSQSKPGCYDNGKHYQINQQWERTYLGNALVCTCYGGSRGFNCE

SKPEAEETCFDKYTGNTYRVGDTYERPKDSMIWDCTCIGAGRGRISCTIANRCHEGGQS

YKIGDTWRRPHETGGYMLECVCLGNGKGEWTCKPIAEKCFDHAAGTSYVVGETWEKP

YQGWMMVDCTCLGEGSGRITCTSRNRCNDQDTRTSYRIGDTWSKKDNRGNLLQCICTG

NGRGEWKCER

Human Fibronectin fragment containing collagen-binding domain
(~45 kDa fragment)
                                                  (SEQ ID NO: 142)
HTSVQTTSSGSGPFTDVRAAVYQPQPHPQPPPYGHCVTDSGVVYSVGMQWLKTQGNK

QMLCTCLGNGVSCQETAVTQTYGGNSNGEPCVLPFTYNGRTFYSCTTEGRQDGHLWCS

TTSNYEQDQKYSFCTDHTVLVQTRGGNSNGALCHFPFLYNNHNYTDCTSEGRRDNMK

WCGTTQNYDADQKFGFCPMAAHEEICTTNEGVMYRIGDQWDKQHDMGHMMRCTCV

GNGRGEWTCIAYSQLRDQCIVDDITYNVNDTFHKRHEEGHMLNCTCFGQGRGRWKCD

PVDQCQDSETGTFYQIGDSWEKYVHGVRYQCYCYGRGIGEWHCQPLQTYPSS
```

-continued

Human Fibronectin fragment containing type I repeat 1
(SEQ ID NO: 143)
PGCYDNGKHYQINQQWERTYLGNALVCTCYGGSRGFNCESKPEA Human Fibronectin fragment containing type I repeat 2
(SEQ ID NO: 144)
ETCFDKYTGNTYRVGDTYERPKDSMIWDCTCIGAGRGRISCTIA Human Fibronectin fragment containing type I repeat 3
(SEQ ID NO: 145)
NRCHEGGQSYKIGDTWRRPHETGGYMLECVCLGNGKGEWTCKPI Human Fibronectin fragment containing type I repeat 4
(SEQ ID NO: 146)
AEKCFDHAAGTSYVVGETWEKPYQGWMMVDCTCLGEGSGRITCTSR Human Fibronectin fragment containing type I repeat 5
(SEQ ID NO: 147)
NRCNDQDTRTSYRIGDTWSKKDNRGNLLQCICTGNGRGEWKCERH Human CNTFR-alpha with predicted signal sequence underlined
(SEQ ID NO: 148)
MAAPVPWACCAVLAAAAAVVYAQRHSPQEAPHVQYERLGSDVTLPCGTANWDAAVT

WRVNGTDLAPDLLNGSQLVLHGLELGHSGLYACFHRDSWHLRHQVLLHVGLPPREPVL

SCRSNTYPKGFYCSWHLPTPTYIPNTFNVTVLHGSKIMVCEKDPALKNRCHIRYMHLFST

IKYKVSISVSNALGHNATAITFDEFTIVKPDPPENVVARPVPSNPRRLEVTWQTPSTWPDP

ESFPLKFFLRYRPLILDQWQHVELSDGTAHTITDAYAGKEYIIQVAAKDNEIGTWSDWSV

AAHATPWTEEPRHLTTEAQAAETTTSTTSSLAPPPTTKICDPGELGSGGGPSAPFLVSVPI

TLALAAAAATASSLLI

Human CNTFR-alpha without predicted signal sequence
(SEQ ID NO: 149)
QRHSPQEAPHVQYERLGSDVTLPCGTANWDAAVTWRVNGTDLAPDLLNGSQLVLHGL

ELGHSGLYACFHRDSWHLRHQVLLHVGLPPREPVLSCRSNTYPKGFYCSWHLPTPTYIP

NTFNVTVLHGSKIMVCEKDPALKNRCHIRYMHLFSTIKYKVSISVSNALGHNATAITFDE

FTIVKPDPPENVVARPVPSNPRRLEVTWQTPSTWPDPESFPLKFFLRYRPLILDQWQHVE

LSDGTAHTITDAYAGKEYIIQVAAKDNEIGTWSDWSVAAHATPWTEEPRHLTTEAQAA

ETTTSTTSSLAPPPTTKICDPGELGSGGGPSAPFLVSVPITLALAAAAATASSLLI

Human CNTFR-alpha - mature form
(SEQ ID NO: 150)
QRHSPQEAPHVQYERLGSDVTLPCGTANWDAAVTWRVNGTDLAPDLLNGSQLVLHGL

ELGHSGLYACFHRDSWHLRHQVLLHVGLPPREPVLSCRSNTYPKGFYCSWHLPTPTYIP

NTFNVTVLHGSKIMVCEKDPALKNRCHIRYMHLFSTIKYKVSISVSNALGHNATAITFDE

FTIVKPDPPENVVARPVPSNPRRLEVTWQTPSTWPDPESFPLKFFLRYRPLILDQWQHVE

LSDGTAHTITDAYAGKEYIIQVAAKDNEIGTWSDWSVAAHATPWTEEPRHLTTEAQAA

ETTTSTTSSLAPPPTTKICDPGELGS

Human CNTFR-alpha fragment containing Ig-like C2 type domain
(SEQ ID NO: 151)
QRHSPQEAPHVQYERLGSDVTLPCGTANWDAAVTWRVNGTDLAPDLLNGSQLVLHGL

ELGHSGLYACFHRDSWHLRHQVLLH

Human CNTFR-alpha fragment containing FN type III domain 1
(SEQ ID NO: 152)
PPREPVLSCRSNTYPKGFYCSWHLPTPTYIPNTFNVTVLHGSKIMVCEKDPALKNRCHIR

YMHLFSTIKYKVSISVSNALGHNATAITFDEFTIVKPDPPENVVARPVPSNPRRLEVT

Human CNTFR-alpha fragment containing FN type III domain 2
(SEQ ID NO: 153)
WQTPSTWPDPESFPLKFFLRYRPLILDQWQHVELSDGTAHTITDAYAGKEYIIQVAAKD

NEIGTWSDWSVAAHATPWTEEP

-continued

Hexahistidine peptide tag
(SEQ ID NO: 154)
HHHHHH

Human ILT3 Domain 2 with stem amino acid sequence (aa 124-259)
(SEQ ID NO: 155)
PTLSALPSPLVTSGKSVTLLCQSRSPMDTFLLIKERAAHPLLHLRSEHGAQQHQAEFPMS

PVTSVHGGTYRCFSSHGFSHYLLSHPSDPLELIVSGSLEDPRPSPTRSVSTAAGPEDQPLM

PTGSVPHSGLRRHWE

Hz48A6 heavy chain variable region amino acid sequences
HC-B0
(SEQ ID NO: 156)
EVQLVESGGGLVQPGGSLRLSCAASGFTFSSYGMSWVRQAPGKGLEWVATISSGGTYT

FYPDSVKGRFTISRDNAKNSLYLQMNSLRAEDTAVYYCARRGWLLHYYAMDYWGQG

TSVTVSS

HC-B1
(SEQ ID NO: 157)
EVQLVESGGGLMQPGGSLRLSCAASGFTFSSYGMSWVRQAPGKGLEWVATISSGGTYT

FYPDSVKGRFTISRDNAKNSLYLQMNSLRAEDTAVYYCARRGWLLHYYAMDYWGQG

TSVTVSS

HC-C0
(SEQ ID NO: 158)
EVQLVESGGGLVQPGGSLRLSCAASGFTFSSYGMSWVRQAPGKGLEWVGTISSGGTYT

FYPDSVKGRFTISRDNSKNTLYLQMNSLRAEDTAVYYCARRGWLLHYYAMDYWGQGT

LVTVSS

HC-C1
(SEQ ID NO: 159)
EVQLVESGGGLVQPGGSLRLSCAASGFTFSSYGMSWVRQAPGKGLEWVATISSGGTYT

FYPDSVKGRFTISRDNSKNTLYLQMNSLRAEDTAVYYCARRGWLLHYYAMDYWGQGT

LVTVSSHC-C2
(SEQ ID NO: 160)
EVQLVESGGGLMQPGGSLRLSCAASGFTFSSYGMSWVRQAPGKGLEWVATISSGGTYT

FYPDSVKGRFTISRDNSKNTLYLQMNSLRAEDTAVYYCARRGWLLHYYAMDYWGQGT

LVTVSS

Hz48A6 light chain variable region amino acid sequence
LC-C2
(SEQ ID NO: 161)
DIQLTQSPSFLSASVGDRVTITCRPSESVDSFGNSFMHWFQQKPGKAPKLLIYLSSKLESG

VPSRFSGSGSGTEFTLTISSLQPEDFATYYCQQHNEDPFTFGQGTKVEIK

Hz45G10 heavy chain variable region amino acid sequence
HC-A2
(SEQ ID NO: 162)
EVQLVESGGGLVQPGGSLRLSCAASGFTFSDYGMHWVRQAPGKGLEWVAYIFSGSSTI

YYADTVKGRFTISRDNAKNSLYLQMNSLRAEDTAVYYCARADGRGAMDYWGQTTV

TVSS

HC-B1
(SEQ ID NO: 163)
EVQLVESGGGLVKPGGSLRLSCAASGFTFSDYGMHWVRQAPGKGLEWVSYIFSGSSTIY

YADTVKGRFTISRDNAKNSLYLQMNSLRAEDTAVYYCARADGRGAMDYWGQGTLVT

VSS

Hz45G10 light chain variable region amino acid sequence
LC-A4

(SEQ ID NO: 164)

DIQMTQSPSSLSASVGDRVTITCRASQDISKFLNWYQQKPGKAPKLLIYYTSRLHSGVPS

RFSGSGSGTDFTFTISSLQPEDIATYFCQQGNTLPWTFGGGTKLEIK

---

What is claimed:

1. An antibody that specifically binds human immunoglobulin-like transcript 3 (ILT3), wherein the antibody comprises:
   (a) a heavy chain variable region (VH) comprising a VH-complementarity determining region (CDR)1, a VH-CDR2, and a VH-CDR3 from the amino acid sequence of SEQ ID NO:111; and a light chain variable region (VL) comprising a VL-complementarity determining region (CDR)1, a VL-CDR2, and a VL-CDR3 from the amino acid sequence of SEQ ID NO:112; or
   (b) a VH comprising a VH-CDR1, a VH-CDR2, and a VH-CDR3 from the amino acid sequence of SEQ ID NO:123; and a VL comprising a VL-CDR1, a VL-CDR2, and a VL-CDR3 from the amino acid sequence of SEQ ID NO:124.

2. The antibody of claim 1, wherein:
   (a) the VH-CDR1 comprises the amino acid sequence GFTFSSYGMS (SEQ ID NO:27), the VH-CDR2 comprises the amino acid sequence TISGGGSYTNYPDSVKG (SEQ ID NO:28), the VH-CDR3 comprises the amino acid sequence REWRYTLYAMDY (SEQ ID NO:105), the VL-CDR1 comprises the amino acid sequence RASESVESYGSSFMH (SEQ ID NO:106), the VL-CDR2 comprises the amino acid sequence LTSNLES (SEQ ID NO:31), and the VL-CDR3 comprises the amino acid sequence QQNNEDPFT (SEQ ID NO:32);
   (b) the VH-CDR1 comprises the amino acid sequence GFTFSSY (SEQ ID NO:33), the VH-CDR2 comprises the amino acid sequence SGGGSY (SEQ ID NO:34), the VH CDR3 comprises the amino acid sequence REWRYTLYAMDY (SEQ ID NO:105), the VL-CDR1 comprises the amino acid sequence RASESVESYGSSFMH (SEQ ID NO:106), the VL-CDR2 comprises the amino acid sequence LTSNLES (SEQ ID NO:31), and the VL-CDR3 comprises the amino acid sequence QQNNEDPFT (SEQ ID NO:32);
   (c) the VH-CDR1 comprises the amino acid sequence GFTFSSYGMS (SEQ ID NO:27), the VH-CDR2 comprises the amino acid sequence TISGGGSYTN (SEQ ID NO:35), the VH-CDR3 comprises the amino acid sequence REWRYTLYAMDY (SEQ ID NO:105), the VL-CDR1 comprises the amino acid sequence RASESVESYGSSFMH (SEQ ID NO:106), the VL-CDR2 comprises the amino acid sequence LTSNLES (SEQ ID NO:31), and the VL-CDR3 comprises the amino acid sequence QQNNEDPFT (SEQ ID NO:32);
   (d) the VH CDR1 comprises the amino acid sequence SYGMS (SEQ ID NO:36), the VH-CDR2 comprises the amino acid sequence TISGGGSYTNYPDSVKG (SEQ ID NO:28), the VH-CDR3 comprises the amino acid sequence REWRYTLYAMDY (SEQ ID NO:105), the VL-CDR1 comprises the amino acid sequence RASESVESYGSSFMH (SEQ ID NO:106), the VL-CDR2 comprises the amino acid sequence LTSNLES (SEQ ID NO:31), and the VL-CDR3 comprises the amino acid sequence QQNNEDPFT (SEQ ID NO:32);
   (e) the VH-CDR1 comprises the amino acid sequence SSYGMS (SEQ ID NO:37), the VH-CDR2 comprises the amino acid sequence WVATISGGGSYTN (SEQ ID NO:38), the VH-CDR3 comprises the amino acid sequence ARREWRYTLYAMD (SEQ ID NO:107), the VL-CDR1 comprises the amino acid sequence ESYGSSFMHWY (SEQ ID NO:108), the VL-CDR2 comprises the amino acid sequence LLIYLTSNLE (SEQ ID NO:41), and the VL-CDR3 comprises the amino acid sequence QQNNEDPF (SEQ ID NO:42),
   (f) the VH-CDR1 comprises the amino acid sequence GFTFSSYGMS (SEQ ID NO:27), the VH-CDR2 comprises the amino acid sequence TISGGGSYTNYPDSVKG (SEQ ID NO:28), the VH-CDR3 comprises the amino acid sequence REWRYTLYAMDY (SEQ ID NO:29), the VL-CDR1 comprises the amino acid sequence RASESVESYGSSFMH (SEQ ID NO:30), the VL-CDR2 comprises the amino acid sequence LTSNLES (SEQ ID NO:31), and the VL-CDR3 comprises the amino acid sequence QQNNEDPFT (SEQ ID NO:32);
   (g) the VH-CDR1 comprises the amino acid sequence GFTFSSY (SEQ ID NO:33), the VH-CDR2 comprises the amino acid sequence SGGGSY (SEQ ID NO:34), the VH CDR3 comprises the amino acid sequence REWRYTLYAMDY (SEQ ID NO:29), the VL-CDR1 comprises the amino acid sequence RASESVESYGSSFMH (SEQ ID NO:30), the VL-CDR2 comprises the amino acid sequence LTSNLES (SEQ ID NO:31), and the VL-CDR3 comprises the amino acid sequence QQNNEDPFT (SEQ ID NO:32);
   (h) the VH-CDR1 comprises the amino acid sequence GFTFSSYGMS (SEQ ID NO:27), the VH-CDR2 comprises the amino acid sequence TISGGGSYTN (SEQ ID NO:35), the VH-CDR3 comprises the amino acid sequence REWRYTLYAMDY (SEQ ID NO:29), the VL-CDR1 comprises the amino acid sequence RASESVESYGSSFMH (SEQ ID NO:30), the VL-CDR2 comprises the amino acid sequence LTSNLES (SEQ ID NO:31), and the VL-CDR3 comprises the amino acid sequence QQNNEDPFT (SEQ ID NO:32);
(i) the VH CDR1 comprises the amino acid sequence SYGMS (SEQ ID NO:36), the VH-CDR2 comprises the amino acid sequence TISGGGSYTNYPDSVKG (SEQ ID NO:28), the VH-CDR3 comprises the amino acid sequence REWRYTLYAMDY (SEQ ID NO:29), the VL-CDR1 comprises the amino acid sequence RASESVESYGSSFMH (SEQ ID NO:30), the VL-CDR2 comprises the amino acid sequence LTSNLES (SEQ ID NO:31), and the VL-CDR3 comprises the amino acid sequence QQNNEDPFT (SEQ ID NO:32); or
(j) the VH-CDR1 comprises the amino acid sequence SSYGMS (SEQ ID NO:37), the VH-CDR2 comprises the amino acid sequence WVATISGGGSYTN (SEQ ID NO:38), the VH-CDR3 comprises the amino acid sequence ARREWRMTLYAMD (SEQ ID NO:39), the VL-CDR1 comprises the amino acid sequence DSYGNSFMHWY (SEQ ID NO:40), a VL-CDR2 comprises the amino acid sequence LLIYLTSNLE (SEQ ID NO:41), and the VL-CDR3 comprises the amino acid sequence QQNNEDPF (SEQ ID NO:42).

3. The antibody of claim 1, wherein:
(a) the VH comprises the amino acid sequence of SEQ ID NO:123 and/or the VL comprises the amino acid sequence of SEQ ID NO:124; or
(b) the VH comprises the amino acid sequence of SEQ ID NO:111 and/or the VL comprises the amino acid sequence of SEQ ID NO:112.

4. The antibody of claim 1, wherein the antibody is a chimeric antibody, a recombinant antibody, a humanized antibody, a bispecific antibody, or a multispecific antibody.

5. The antibody of claim 1, wherein the antibody is an antibody fragment comprising at least one antigen-binding site.

6. The antibody of claim 5, wherein the antibody fragment is a Fab, a Fab', a F(ab')$_2$, a Fv, an scFv, an (scFv)$_2$, a single chain antibody, a dual variable region antibody, a diabody, or a nanobody.

7. The antibody of claim 1, wherein the antibody is an IgG1 antibody, an IgG2 antibody, or an IgG4 antibody.

8. The antibody of claim 1, comprising a kappa light chain constant region or a lambda light chain constant region.

9. The antibody of claim 1, comprising a human IgG1 constant region and a human kappa light chain constant region.

10. The antibody of claim 9, wherein the human IgG1 constant region comprises one or more mutations that reduce or eliminate effector functions.

11. The antibody of claim 1, wherein the antibody is attached to a half-life extending moiety.

12. The antibody of claim 1, wherein the antibody has one or more of the following properties:
(i) binding cynomolgus ILT3;
(ii) binding human and cynomolgus ILT3;
(iii) not binding ILT2, ILT4, ILT5, and or LILRB5;
(iv) not binding LILRA1, LILRA2, LILRA4, LILRA5, and or LILRA6;
(v) being an ILT3 antagonist;
(vi) inhibiting ILT3 activity;
(vii) inhibiting ILT3 signaling in cells that express ILT3;
(viii) inhibiting binding of ILT3 to APOE;
(ix) inhibiting binding of ILT3 to fibronectin;
(x) inhibiting binding of ILT3 to CNTFR;
(xi) inhibiting ILT3-induced suppression of myeloid cells;
(xii) inhibiting ILT3-induced suppression of myeloid cell activity;
(xiii) restoring FcR activation in myeloid cells that express ILT3; and
(xiv) restoring chemokine production in myeloid cells that express ILT3.

13. The antibody of claim 12, wherein the antibody has a $K_D$ for human ILT3 of from 1 µM to 1 µM as assessed by Surface Plasmon Resonance (SPR).

14. The antibody of claim 1, comprising a heavy chain comprising the amino acid sequence of SEQ ID NO:126 and/or a light chain comprising the amino acid sequence of SEQ ID NO:128.

15. A pharmaceutical composition comprising the antibody of claim 1 and a pharmaceutically acceptable carrier.

16. An isolated polynucleotide or polynucleotides encoding the antibody of claim 1.

17. A vector or vectors comprising the polynucleotide or polynucleotides of claim 16.

18. An isolated cell comprising the polynucleotide or polynucleotides of claim 16, or a vector or vectors comprising the polynucleotide or polynucleotides of claim 16.

19. A method of making an antibody that specifically binds human ILT3, the method comprising:
(a) culturing the cell of claim 18 under conditions that result in the expression of the antibody, and
(b) isolating the antibody.

20. The method of claim 19, further comprising formulating the antibody as a sterile pharmaceutical composition.

21. A method of disrupting, inhibiting, or blocking the binding of ILT3 to fibronectin or fibronectin-induced ILT3 activity in a mixture of cells, the method comprising contacting the cells with the antibody of claim 1.

22. A method of disrupting, inhibiting, or blocking ILT3-induced suppression of myeloid cells or ILT3-induced suppression of myeloid cell activity, the method comprising contacting the myeloid cells with the antibody of claim 1.

23. A method of disrupting, inhibiting, or blocking the binding of ILT3 to fibronectin or fibronectin-induced ILT3 activity in a subject, the method comprising administering to the subject a therapeutically effective amount of the antibody of claim 1.

24. A method of disrupting, inhibiting, or blocking ILT3-induced suppression of myeloid cells or ILT3-induced suppression of myeloid cell activity in a subject, the method comprising administering to the subject the antibody of claim 1 in an amount sufficient to activate the myeloid cells.

25. A method of treating cancer, or inhibiting tumor growth, tumor relapse, or tumor regrowth in a subject, the method comprising administering to the subject a therapeutically effective amount of the antibody of claim 1.

26. A method of increasing or enhancing an immune response to a tumor or tumor cells in a subject, the method comprising administering to the subject a therapeutically effective amount of the antibody of claim 1.

27. A method of activating myeloid cells in the tumor microenvironment in a subject with a tumor, the method comprising administering to the subject a therapeutically effective amount of the antibody of claim 1.

28. The method of claim 25, wherein (i) the cancer is pancreatic cancer, breast cancer, lung cancer, head and neck cancer, colorectal cancer, prostate cancer, skin cancer, melanoma, stomach cancer, gastric cancer, intestinal cancer, ovarian cancer, cervical cancer, uterine cancer, endometrial cancer, urinary bladder cancer, brain cancer, esophageal cancer, liver cancer, kidney cancer, sarcoma, or testicular cancer; and/or (ii) the tumor is a pancreatic tumor, a breast tumor, a lung tumor, a head and neck tumor, a colorectal tumor, a prostate tumor, a skin tumor, a melanoma tumor, a stomach tumor, a gastric tumor, an intestinal tumor, an ovarian tumor, a cervical tumor, an uterine tumor, an endometrial tumor, a bladder tumor, a brain tumor, an esophageal tumor, a liver tumor, a kidney tumor, a sarcoma, or a testicular tumor.

29. The method of claim 25, wherein the cancer is hematologic cancer.

30. The method of claim 29, wherein the hematologic cancer is myelogenous leukemia, acute myeloid leukemia (AML), chronic myeloid leukemia, or myelodysplastic syndrome.

31. The method of claim 26, wherein the tumor is a pancreatic tumor, a breast tumor, a lung tumor, a head and neck tumor, a colorectal tumor, a prostate tumor, a skin tumor, a melanoma tumor, a stomach tumor, a gastric tumor, an intestinal tumor, an ovarian tumor, a cervical tumor, an uterine tumor, an endometrial tumor, a bladder tumor, a brain tumor, an esophageal tumor, a liver tumor, a kidney tumor, a sarcoma, or a testicular tumor.

32. The method of claim 27, wherein the tumor is a pancreatic tumor, a breast tumor, a lung tumor, a head and neck tumor, a colorectal tumor, a prostate tumor, a skin tumor, a melanoma tumor, a stomach tumor, a gastric tumor, an intestinal tumor, an ovarian tumor, a cervical tumor, an uterine tumor, an endometrial tumor, a bladder tumor, a brain tumor, an esophageal tumor, a liver tumor, a kidney tumor, a sarcoma, or a testicular tumor.

33. The method of claim 23, wherein the antibody is administered as part of a combination therapy comprising a PD-1 antagonist.

34. The method of claim 24, wherein the antibody is administered as part of a combination therapy comprising a PD-1 antagonist.

35. The method of claim 25, wherein the antibody is administered as part of a combination therapy comprising a PD-1 antagonist.

36. The method of claim 26, wherein the antibody is administered as part of a combination therapy comprising a PD-1 antagonist.

37. The method of claim 27, wherein the antibody is administered as part of a combination therapy comprising a PD-1 antagonist.

38. The method of claim 33, wherein the PD-1 antagonist is pembrolizumab.

39. The method of claim 34, wherein the PD-1 antagonist is pembrolizumab.

40. The method of claim 35, wherein the PD-1 antagonist is pembrolizumab.

41. The method of claim 36, wherein the PD-1 antagonist is pembrolizumab.

42. The method of claim 37, wherein the PD-1 antagonist is pembrolizumab.

43. An antibody that specifically binds human ILT3, wherein the antibody comprises a VH comprising a VH-CDR1, a VH-CDR2, and a VH-CDR3 from the amino acid sequence of SEQ ID NO:123; and a VL comprising a VL-CDR1, a VL-CDR2, and a VL-CDR3 from the amino acid sequence of SEQ ID NO:124.

44. The antibody of claim 43, wherein:
(a) the VH-CDR1 comprises the amino acid sequence GFTFSSYGMS (SEQ ID NO:27), the VH-CDR2 comprises the amino acid sequence TISGGGSYTNYPDSVKG (SEQ ID NO:28), the VH-CDR3 comprises the amino acid sequence REWRYTLYAMDY (SEQ ID NO:105), the VL-CDR1 comprises the amino acid sequence RASESVESYGSSFMH (SEQ ID NO:106), the VL-CDR2 comprises the amino acid sequence LTSNLES (SEQ ID NO:31), and the VL-CDR3 comprises the amino acid sequence QQNNEDPFT (SEQ ID NO:32);
(b) the VH-CDR1 comprises the amino acid sequence GFTFSSY (SEQ ID NO:33), the VH-CDR2 comprises the amino acid sequence SGGGSY (SEQ ID NO:34), the VH-CDR3 comprises the amino acid sequence REWRYTLYAMDY (SEQ ID NO:105), VL-CDR1 comprises the amino acid sequence RASESVESYGSSFMH (SEQ ID NO:106), the VL-CDR2 comprises the amino acid sequence LTSNLES (SEQ ID NO:31), and the VL-CDR3 comprises the amino acid sequence QQNNEDPFT (SEQ ID NO:32);
(c) the VH-CDR1 comprises the amino acid sequence GFTFSSYGMS (SEQ ID NO:27), the VH-CDR2 comprises the amino acid sequence TISGGGSYTN (SEQ ID NO:35), the VH-CDR3 comprises the amino acid sequence REWRYTLYAMDY (SEQ ID NO:105), the VL-CDR1 comprises the amino acid sequence RASESVESYGSSFMH (SEQ ID NO:106), the VL-CDR2 comprises the amino acid sequence LTSNLES (SEQ ID NO:31), and the VL-CDR3 comprises the amino acid sequence QQNNEDPFT (SEQ ID NO:32);
(d) the VH-CDR1 comprises the amino acid sequence SYGMS (SEQ ID NO:36), the VH-CDR2 comprises the amino acid sequence TISGGGSYTNYPDSVKG (SEQ ID NO:28), the VH-CDR3 comprises the amino acid sequence REWRYTLYAMDY (SEQ ID NO:105), the VL-CDR1 comprises the amino acid sequence RASESVESYGSSFMH (SEQ ID NO:106), the VL-CDR2 comprises the amino acid sequence LTSNLES (SEQ ID NO:31), and the VL-CDR3 comprises the amino acid sequence QQNNEDPFT (SEQ ID NO:32); or
(e) the VH-CDR1 comprises the amino acid sequence SSYGMS (SEQ ID NO:37), the VH-CDR2 comprises the amino acid sequence WVATISGGGSYTN (SEQ ID NO:38), the VH-CDR3 comprises the amino acid sequence ARREWRYTLYAMD (SEQ ID NO:107), the VL-CDR1 comprises the amino acid sequence ESYGSSFMHWY (SEQ ID NO:108), the VL-CDR2 comprises the amino acid sequence LLIYLTSNLE (SEQ ID NO:41), and the VL-CDR3 comprises the amino acid sequence QQNNEDPF (SEQ ID NO:42).

45. The antibody of claim 43, wherein the VH comprises the amino acid sequence of SEQ ID NO:123 and the VL comprises the amino acid sequence of SEQ ID NO:124.

46. The antibody of claim 43, comprising a heavy chain comprising the amino acid sequence of SEQ ID NO:126 and a light chain comprising the amino acid sequence of SEQ ID NO:128.

47. A method of treating cancer, or inhibiting tumor growth, tumor relapse, or tumor regrowth in a subject, comprising administering to the subject a therapeutically effective amount of the antibody of claim 43.

48. The method of claim 47, wherein (i) the cancer is pancreatic cancer, breast cancer, lung cancer, head and neck cancer, colorectal cancer, prostate cancer, skin cancer, melanoma, stomach cancer, gastric cancer, intestinal cancer, ovarian cancer, cervical cancer, uterine cancer, endometrial cancer, urinary bladder cancer, brain cancer, esophageal cancer, liver cancer, kidney cancer, sarcoma, or testicular cancer; and/or (ii) the tumor is a pancreatic tumor, a breast tumor, a lung tumor, a head and neck tumor, a colorectal tumor, a prostate tumor, a skin tumor, a melanoma tumor, a stomach tumor, a gastric tumor, an intestinal tumor, an ovarian tumor, a cervical tumor, an uterine tumor, an endometrial tumor, a bladder tumor, a brain tumor, an esophageal tumor, a liver tumor, a kidney tumor, a sarcoma, or a testicular tumor.

49. The method of claim 47, wherein the cancer is hematologic cancer.

50. The method of claim 49, wherein the hematologic cancer is myelogenous leukemia, acute myeloid leukemia (AML), chronic myeloid leukemia, or myelodysplastic syndrome.

51. The method of claim 47, wherein the antibody is administered as part of a combination therapy comprising a PD-1 antagonist.

52. The method of claim 51, wherein the PD-1 antagonist is pembrolizumab.

53. An isolated cell comprising a polynucleotide or polynucleotides encoding the antibody of claim 43 or a vector or vector comprising a polynucleotide or polynucleotides encoding the antibody of claim 43.

* * * * *

UNITED STATES PATENT AND TRADEMARK OFFICE
CERTIFICATE OF CORRECTION

| | |
|---|---|
| PATENT NO. | : 11,760,802 B2 |
| APPLICATION NO. | : 17/125734 |
| DATED | : September 19, 2023 |
| INVENTOR(S) | : Crawley et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 208 days.

Signed and Sealed this
Twelfth Day of November, 2024

*Katherine Kelly Vidal*

Katherine Kelly Vidal
*Director of the United States Patent and Trademark Office*